US011591331B2

(12) United States Patent
Trzoss et al.

(10) Patent No.: US 11,591,331 B2
(45) Date of Patent: Feb. 28, 2023

(54) PARP1 INHIBITORS AND USES THEREOF

(71) Applicant: Xinthera, Inc., San Diego, CA (US)

(72) Inventors: Lynnie Trzoss, San Diego, CA (US);
Qing Dong, San Diego, CA (US);
Stephen W. Kaldor, San Diego, CA (US)

(73) Assignee: XINTHERA, INC., San Diego, CA (US)

( * ) Notice: Subject to any disclaimer, the term of this patent is extended or adjusted under 35 U.S.C. 154(b) by 0 days.

(21) Appl. No.: 17/723,929

(22) Filed: Apr. 19, 2022

(65) Prior Publication Data

US 2022/0348574 A1 Nov. 3, 2022

Related U.S. Application Data

(60) Provisional application No. 63/254,832, filed on Oct. 12, 2021, provisional application No. 63/183,563, filed on May 3, 2021, provisional application No. 63/176,610, filed on Apr. 19, 2021.

(51) Int. Cl.
*C07D 471/04* (2006.01)
*C07D 491/048* (2006.01)
*C07D 498/14* (2006.01)
*A61P 35/00* (2006.01)
*C07D 519/00* (2006.01)
*C07D 513/04* (2006.01)
*C07D 491/147* (2006.01)

(52) U.S. Cl.
CPC ............ *C07D 471/04* (2013.01); *A61P 35/00* (2018.01); *C07D 491/048* (2013.01); *C07D 491/147* (2013.01); *C07D 498/14* (2013.01); *C07D 513/04* (2013.01); *C07D 519/00* (2013.01)

(58) Field of Classification Search
CPC .............. C07D 471/04; C07D 491/048; C07D 491/147; C07D 498/14; C07D 513/04; A61P 35/00
USPC ........................................................ 514/429
See application file for complete search history.

(56) References Cited

U.S. PATENT DOCUMENTS

| | | | |
|---|---|---|---|
| 8,404,713 B2 | 3/2013 | Angibaud et al. | |
| 10,464,919 B2 | 11/2019 | Lee et al. | |
| 11,325,906 B2 * | 5/2022 | Johannes | ............. C07D 471/04 |
| 2021/0040084 A1 | 2/2021 | Johannes et al. | |

FOREIGN PATENT DOCUMENTS

| | | |
|---|---|---|
| CN | 115232129 A | 10/2022 |
| WO | WO-03080581 A1 | 10/2003 |
| WO | WO-2009053373 A1 | 4/2009 |
| WO | WO-2010085570 A1 | 7/2010 |
| WO | WO-2011014681 A1 | 2/2011 |
| WO | WO-2014064149 A1 | 5/2014 |
| WO | WO-2021013735 A1 | 1/2021 |
| WO | WO-2021260092 A1 | 12/2021 |
| WO | WO-2022222921 A1 | 10/2022 |
| WO | WO-2022222964 A1 | 10/2022 |
| WO | WO-2022222965 A1 | 10/2022 |
| WO | WO-2022222966 A1 | 10/2022 |
| WO | WO-2022222995 A1 | 10/2022 |
| WO | WO-2022223025 A1 | 10/2022 |
| WO | WO-2022225934 A1 | 10/2022 |
| WO | WO-2022228387 A1 | 11/2022 |

OTHER PUBLICATIONS

Boehler et al. Poly(ADP-ribose) polymerase 3 (PARP3), a newcomer in cellular response to DNA damage and mitotic progression. PNAS USA 108(7):2783-2788 (2011).
Gill et al. The novel PARP1-selective inhibitor AZD5305 has reduced haematological toxicity when compared to PARP1/2 inhibitors in pre-clinical models. Poster # 1374 AACR 2021 Annual Apr. 10-19, 2020.
Gozgit et al. PARP7 negatively regulates the type I interferon response in cancer cells and its inhibition triggers antitumor immunity. Cancer Cell 39(9):1214-1226 (2021).
Hande et al. Structure-based and property-based drug design of AZD5305, a highly selective PARP1 inhibitor and trapper. Poster #296 AACR 2021. Apr. 10-15, 2021.
Illuzzi et al. In vitro cellular profiling of AZD5305, novel PARP1-selective inhibitor and trapper. Poster #1272 AACR2021, Apr. 10-15, 2021.
Johannes et al. Discovery and first structural disclosure of AZD5305, a next generation, highly selective PARP1 inhibitor and trapper. AstraZeneca—AZD5305—a best in class highly selective PARP1 inhibitor. Presentation at AACR 2021 Apr. 10, 2021.
Kulak et al. Disruption of Wnt/I3-Catenin Signaling and Telomeric Shortening Are Inextricable Consequences of Tankyrase Inhibition in Human Cells. Mol Cell Biol. 35(14):2425-2435 (2015).
Staniszewska et al. The novel PARP1-selective inhibitor, AZD5305, is efficacious as monotherapy and in combination with standard of care chemotherapy in in vivo preclinical models. Poster #1270 AACR 2021. Apr. 10-15, 2021 and May 17-21.
Vermehren-Schmaedick et al. Characterization of PARP6 Function in Knockout Mice and Patients with Developmental Delay. Cells 10(6):1289 (2021).
Vyas et al. A Systematic Analysis of the PARP Protein Family Identifies New Functions Critical for Cell Physiology. Nat. Commun. 4(1):2240 (2013).
Yu et al. PARP-10, a novel Myc-interacting protein with poly(ADP-ribose) polymerase activity, inhibits transformation. Oncogene 24:1982-1993 (2005).
PCT/US2022/025357 International Search Report and Written Opinion dated Jun. 30, 2022.
Co-pending U.S. Appl. No. 17/957,584, inventors Hoffman; Robert L. et al., filed Sep. 30, 2022.

(Continued)

*Primary Examiner* — Kahsay Habte
(74) *Attorney, Agent, or Firm* — Wilson Sonsini Goodrich & Rosati

(57) ABSTRACT

Described herein are PARP1 inhibitors and pharmaceutical compositions comprising said inhibitors. The subject compounds and compositions are useful for the treatment of cancer.

21 Claims, No Drawings

(56) References Cited

OTHER PUBLICATIONS

Ren et al. Synthesis and in vitro biological evaluation of 3-ethyl-1,5-naphthyridin-2 (1H)-one derivatives as potent PARP-1 selective inhibitors and PARP-1 DNA trappers. Bioorg Med Chem Lett. 129046 (2022).

* cited by examiner

PARP1 INHIBITORS AND USES THEREOF

CROSS-REFERENCE

This application claims the benefit of U.S. Provisional Application Ser. No. 63/176,610 filed Apr. 19, 2021, U.S. Provisional Application Ser. No. 63/183,563 filed May 3, 2021, and U.S. Provisional Application Ser. No. 63/254,832 filed Oct. 12, 2021 which are hereby incorporated by reference in their entirety.

BACKGROUND OF THE INVENTION

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytotoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut and skeletal muscle. Inhibitors have been efficacious in inflammatory diseases such as arthritis, gout, inflammatory bowel disease, CNS inflammation such as MS and allergic encephalitis, sepsis, septic shock, hemorrhagic shock, pulmonary fibrosis, and uveitis. PARP inhibitors have also shown benefit in several models of degenerative disease including diabetes (as well as complications) and Parkinson's disease. PARP inhibitors can ameliorate the liver toxicity following acetaminophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing cell death of cancer cells, limiting tumor growth, decreasing metastasis, and prolonging the survival of tumor-bearing animals.

PARP1 and PARP2 are the most extensively studied PARPs for their role in DNA damage repair. PARP1 is activated by DNA damage breaks and functions to catalyze the addition of poly (ADP-ribose) (PAR) chains to target proteins. This post-translational modification, known as PARylation, mediates the recruitment of additional DNA repair factors to DNA lesions.

Following completion of this recruitment role, PARP auto-PARylation triggers the release of bound PARP from DNA to allow access to other DNA repair proteins to complete repair. Thus, the binding of PARP to damaged sites, its catalytic activity, and its eventual release from DNA are all important steps for a cancer cell to respond to DNA damage caused by chemotherapeutic agents and radiation therapy.

Inhibition of PARP family enzymes has been exploited as a strategy to selectively kill cancer cells by inactivating complementary DNA repair pathways. A number of pre-clinical and clinical studies have demonstrated that tumor cells bearing deleterious alterations of BRCA1 or BRCA2, key tumor suppressor proteins involved in double-strand DNA break (DSB) repair by homologous recombination (HR), are selectively sensitive to small molecule inhibitors of the PARP family of DNA repair enzymes. Such tumors have deficient homologous recombination repair (HRR) pathways and are dependent on PARP enzymes function for survival. Although PARP inhibitor therapy has predominantly targeted SRCA-mutated cancers, PARP inhibitors have been tested clinically in non-SRCA-mutant tumors, those which exhibit homologous recombination deficiency (HRD).

It is believed that PARP inhibitors having improved selectivity for PARP1 may possess improved efficacy and reduced toxicity compared to other clinical PARP1/2 inhibitors. It is believed also that selective strong inhibition of PARP1 would lead to trapping of PARP1 on DNA, resulting in DNA double strand breaks (DSBs) through collapse of replication forks in S-phase. It is believed also that PARP1-DNA trapping is an effective mechanism for selectively killing tumor cells having HRD. An unmet medical need therefore exists for effective and safe PARP inhibitors. Especially PARP inhibitors having selectivity for PARP1.

SUMMARY OF THE INVENTION

Disclosed herein is a compound of Formula (III″), or a pharmaceutically acceptable salt, solvate, or stereoisomer thereof:

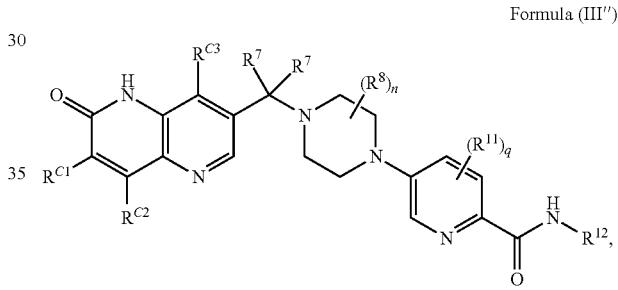

Formula (III″)

wherein:
$R^{C1}$ is hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more R$^{Ca}$;

each R$^{Ca}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{Ca}$ on the same atom are taken together to form an oxo;

$R^{C2}$ is hydrogen, deuterium, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^{C3}$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

each $R^7$ is independently hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or two $R^7$ are taken together to form a cycloalkyl or a heterocycloalkyl; each optionally substituted with deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^8$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^8$ on the same carbon are taken together to form an oxo;

or two $R^8$ on the same carbon, adjacent carbons, or opposite carbons are taken together to form a cycloalkyl or heterocycloalkyl; each optionally substituted with one or more deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

n is 0-6;

$R^{12}$ is $C_1$-$C_6$alkyl, $C_1$-$C_6$deuteroalkyl, cycloalkyl, or heterocycloalkyl; wherein the alkyl, cycloalkyl, and heterocycloalkyl is optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^{11}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

q is 0-3;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Also disclosed herein is a pharmaceutical composition comprising a compound disclosed herein, or a pharmaceutically acceptable salt, solvate, or stereoisomer thereof, and a pharmaceutically acceptable excipient.

Also disclosed herein is a method of treating cancer in a subject in need thereof, the method comprising administering a compound disclosed herein, or a pharmaceutically acceptable salt, solvate, or stereoisomer thereof. In some embodiments, the cancer is breast cancer, ovarian cancer, pancreatic cancer, prostate cancer, a hematological cancer, gastrointestinal cancer, or lung cancer.

Also disclosed herein is method of treating a cancer comprising a BRCA1 and/or a BRCA2 mutation in a subject in need thereof, the method comprising administering a compound of any one of claims 1-70, or a pharmaceutically acceptable salt, solvate, or stereoisomer thereof. In some embodiments, the cancer the cancer is bladder cancer, brain & CNS cancers, breast cancer, cervical cancer, colorectal cancer, esophagus cancer, Hodgkin lymphoma, non-Hodgkin lymphoma, kidney cancer, leukemia, lung cancer, melanoma, myeloma, oral cavity cancer, ovarian cancer, pancreatic cancer, prostate cancer, skin cancer, stomach cancer, thyroid cancer, or uterus cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.
"Carboxyl" refers to —COOH.
"Cyano" refers to —CN.
"Alkyl" refers to a straight-chain or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to a straight-chain or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic or polycyclic carbocyclic ring, which may include fused (when fused with an aryl or a heteroaryl ring, the cycloalkyl is bonded through a non-aromatic ring atom) or bridged ring systems. In some embodiments, the cycloalkyl is fully saturated. Representative cycloalkyls include, but are not limited to, cycloalkyls having from three to fifteen carbon atoms (C$_3$-C$_{15}$ cycloalkyl or C$_3$-C$_{15}$ cycloalkenyl), from three to ten carbon atoms (C$_3$-C$_{10}$ cycloalkyl or C$_3$-C$_{10}$ cycloalkenyl), from three to eight carbon atoms (C$_3$-C$_8$ cycloalkyl or C$_3$-C$_8$ cycloalkenyl), from three to six carbon atoms (C$_3$-C$_6$ cycloalkyl or C$_3$-C$_6$ cycloalkenyl), from three to five carbon atoms (C$_3$-C$_5$ cycloalkyl or C$_3$-C$_5$ cycloalkenyl), or three to four carbon atoms (C$_3$-C$_4$ cycloalkyl or C$_3$-C$_4$ cycloalkenyl). In some embodiments, the cycloalkyl is a 3- to 10-membered cycloalkyl or a 3- to 10-membered cycloalkenyl. In some embodiments, the cycloalkyl is a 3- to 6-membered cycloalkyl or a 3- to 6-membered cycloalkenyl. In some embodiments, the cycloalkyl is a 5- to 6-membered cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Cyanoalkyl" refers to an alkyl radical, as defined above, that is substituted by one or more cyano group. In some embodiments, the alkyl is substituted with one cyano. In some embodiments, the alkyl is substituted with one or two cyanos. Cyanoalkyls include, for example, cyanomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl include, for example, CD$_3$, CH$_2$D, CHD$_2$, CH$_2$CD$_3$, CD$_2$CD$_3$, CHDCD$_3$, CH$_2$CH$_2$D, or CH$_2$CHD$_2$. In some embodiments, the deuteroalkyl is CD$_3$.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl or $C_2$-$C_{15}$ heterocycloalkenyl), from two to ten carbon atoms ($C_2$-$C_{10}$ heterocycloalkyl or $C_2$-$C_{10}$ heterocycloalkenyl), from two to eight carbon atoms ($C_2$-$C_8$ heterocycloalkyl or $C_2$-$C_8$ heterocycloalkenyl), from two to seven carbon atoms ($C_2$-$C_7$ heterocycloalkyl or $C_2$-$C_7$ heterocycloalkenyl), from two to six carbon atoms ($C_2$-$C_6$ heterocycloalkyl or $C_2$-$C_7$ heterocycloalkenyl), from two to five carbon atoms ($C_2$-$C_5$ heterocycloalkyl or $C_2$-$C_5$ heterocycloalkenyl), or two to four carbon atoms ($C_2$-$C_4$ heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

"Synergy" or "synergize" refers to an effect of a combination that is greater than additive of the effects of each component alone at the same doses.

As used herein, a "disease or disorder associated with PARP" or, alternatively, "a PARP-mediated disease or disorder" means any disease or other deleterious condition in which PARP, or a mutant thereof, is known or suspected to play a role.

As used herein, a "disease or disorder associated with PARP1" or, alternatively, "a PARP1-mediated disease or disorder" means any disease or other deleterious condition in which PARP, or a mutant thereof, is known or suspected to play a role.

Compounds

Described herein are compounds of Formula (I), (I'), (II), (III), (III'), (III"), (IV), and (V), or a pharmaceutically acceptable salt, solvate, or stereoisomer thereof useful in the treatment of cancer.

Disclosed herein is a compound of Formula (I'), or a pharmaceutically acceptable salt, solvate, or stereoisomer thereof:

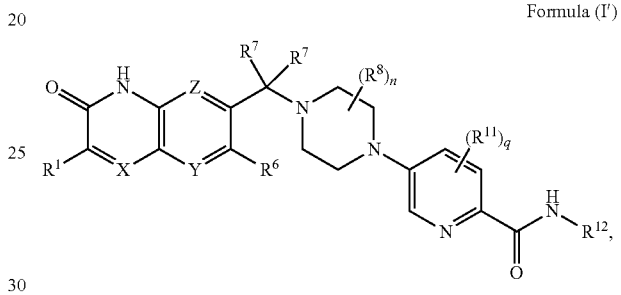

Formula (I')

wherein:

$R^1$ is hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$cyanoalkyl, C$_1$-C$_6$heteroalkyl, C$_2$-C$_6$alkenyl, C$_2$-C$_6$alkynyl, cycloalkyl, or heterocycloalkyl;

X is N or CR$^2$;

$R^2$ is hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$cyanoalkyl, C$_1$-C$_6$heteroalkyl, C$_2$-C$_6$alkenyl, C$_2$-C$_6$alkynyl, cycloalkyl, or heterocycloalkyl;

Z is N or CR$^4$;

$R^4$ is hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$cyanoalkyl, C$_1$-C$_6$heteroalkyl, C$_2$-C$_6$alkenyl, C$_2$-C$_6$alkynyl, cycloalkyl, or heterocycloalkyl;

Y is N or CR$^5$;

$R^5$ is hydrogen, deuterium, halogen, —CN, —NO$_2$, —OH, —OR$^a$, —OC(=O)R$^a$, —OC(=O)OR$^b$, —OC(=O)

$NR^cR^d$, —SH, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —$NR^bC(=O)OR^b$, —$NR^bS(=O)_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —$NR^bC(=O)OR^b$, —$NR^bS(=O)_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;

each $R^7$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or two $R^7$ are taken together to form a cycloalkyl or a heterocycloalkyl; each optionally substituted with deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^8$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —$NR^bC(=O)OR^b$, —$NR^bS(=O)_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^8$ on the same carbon are taken together to form an oxo;

or two $R^8$ on the same carbon, adjacent carbons, or opposite carbons are taken together to form a cycloalkyl or heterocycloalkyl; each optionally substituted with one or more deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

n is 0-6;

$R^{12}$ is cycloalkyl or heterocycloalkyl; wherein the cycloalkyl and heterocycloalkyl is optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^{11}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —$NR^bC(=O)OR^b$, —$NR^bS(=O)_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

q is 0-3;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Disclosed herein is a compound of Formula (I), or a pharmaceutically acceptable salt, solvate, or stereoisomer thereof:

Formula (I)

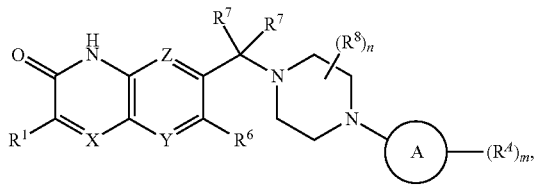

wherein:
R¹ is hydrogen, deuterium, halogen, —CN, —NO₂, —ORᵃ, —OC(=O)Rᵃ, —OC(=O)ORᵇ, —OC(=O)NRᶜRᵈ, —SH, —SRᵃ, —S(=O)Rᵃ, —S(=O)₂Rᵃ, —S(=O)₂NRᶜRᵈ, —NRᶜRᵈ, —NRᵇC(=O)NRᶜRᵈ, —NRᵇC(=O)Rᵃ, —NRᵇC(=O)ORᵇ, —NRᵇS(=O)₂Rᵃ, —C(=O)Rᵃ, —C(=O)ORᵇ, —C(=O)NRᶜRᵈ, C₁-C₆alkyl, C₁-C₆haloalkyl, C₁-C₆deuteroalkyl, C₁-C₆hydroxyalkyl, C₁-C₆aminoalkyl, C₁-C₆cyanoalkyl, C₁-C₆heteroalkyl, C₂-C₆alkenyl, C₂-C₆alkynyl, cycloalkyl, or heterocycloalkyl;

X is N or CR²;

R² is hydrogen, deuterium, halogen, —CN, —NO₂, —OH, —ORᵃ, —OC(=O)Rᵃ, —OC(=O)ORᵇ, —OC(=O)NRᶜRᵈ, —SH, —SRᵃ, —S(=O)Rᵃ, —S(=O)₂Rᵃ, —S(=O)₂NRᶜRᵈ, —NRᶜRᵈ, —NRᵇC(=O)NRᶜRᵈ, —NRᵇC(=O)Rᵃ, —NRᵇC(=O)ORᵇ, —NRᵇS(=O)₂Rᵃ, —C(=O)Rᵃ, —C(=O)ORᵇ, —C(=O)NRᶜRᵈ, C₁-C₆alkyl, C₁-C₆haloalkyl, C₁-C₆deuteroalkyl, C₁-C₆hydroxyalkyl, C₁-C₆aminoalkyl, C₁-C₆cyanoalkyl, C₁-C₆heteroalkyl, C₂-C₆alkenyl, C₂-C₆alkynyl, cycloalkyl, or heterocycloalkyl;

or R¹ and R² are taken together to form a cycloalkyl, heterocycloalkyl, aryl, or heteroaryl; each optionally substituted with deuterium, halogen, —CN, —OH, —ORᵃ, —NRᶜRᵈ, C₁-C₆alkyl, C₁-C₆haloalkyl, C₁-C₆deuteroalkyl, C₁-C₆hydroxyalkyl, C₁-C₆aminoalkyl, C₁-C₆heteroalkyl, cycloalkyl, or heterocycloalkyl;

Z is N or CR⁴;

R⁴ is hydrogen, deuterium, halogen, —CN, —NO₂, —OH, —ORᵃ, —OC(=O)Rᵃ, —OC(=O)ORᵇ, —OC(=O)NRᶜRᵈ, —SH, —SRᵃ, —S(=O)Rᵃ, —S(=O)₂Rᵃ, —S(=O)₂NRᶜRᵈ, —NRᶜRᵈ, —NRᵇC(=O)NRᶜRᵈ, —NRᵇC(=O)Rᵃ, —NRᵇC(=O)ORᵇ, —NRᵇS(=O)₂Rᵃ, —C(=O)Rᵃ, —C(=O)ORᵇ, —C(=O)NRᶜRᵈ, C₁-C₆alkyl, C₁-C₆haloalkyl, C₁-C₆deuteroalkyl, C₁-C₆hydroxyalkyl, C₁-C₆aminoalkyl, C₁-C₆cyanoalkyl, C₁-C₆heteroalkyl, C₂-C₆alkenyl, C₂-C₆alkynyl, cycloalkyl, or heterocycloalkyl;

Y is N or CR⁵;

R⁵ is hydrogen, deuterium, halogen, —CN, —NO₂, —OH, —ORᵃ, —OC(=O)Rᵃ, —OC(=O)ORᵇ, —OC(=O)NRᶜRᵈ, —SH, —SRᵃ, —S(=O)Rᵃ, —S(=O)₂Rᵃ, —S(=O)₂NRᶜRᵈ, —NRᶜRᵈ, —NRᵇC(=O)NRᶜRᵈ, —NRᵇC(=O)Rᵃ, —NRᵇC(=O)ORᵇ, —NRᵇS(=O)₂Rᵃ, —C(=O)Rᵃ, —C(=O)ORᵇ, —C(=O)NRᶜRᵈ, C₁-C₆alkyl, C₁-C₆haloalkyl, C₁-C₆deuteroalkyl, C₁-C₆hydroxyalkyl, C₁-C₆aminoalkyl, C₁-C₆cyanoalkyl, C₁-C₆heteroalkyl, C₂-C₆alkenyl, C₂-C₆alkynyl, cycloalkyl, or heterocycloalkyl;

R⁶ is hydrogen, deuterium, halogen, —CN, —NO₂, —OH, —ORᵃ, —OC(=O)Rᵃ, —OC(=O)ORᵇ, —OC(=O)NRᶜRᵈ, —SH, —SRᵃ, —S(=O)Rᵃ, —S(=O)₂Rᵃ, —S(=O)₂NRᶜRᵈ, —NRᶜRᵈ, —NRᵇC(=O)NRᶜRᵈ, —NRᵇC(=O)Rᵃ, —NRᵇC(=O)ORᵇ, —NRᵇS(=O)₂Rᵃ, —C(=O)Rᵃ, —C(=O)ORᵇ, —C(=O)NRᶜRᵈ, C₁-C₆alkyl, C₁-C₆haloalkyl, C₁-C₆deuteroalkyl, C₁-C₆hydroxyalkyl, C₁-C₆aminoalkyl, C₁-C₆cyanoalkyl, C₁-C₆heteroalkyl, C₂-C₆alkenyl, C₂-C₆alkynyl, cycloalkyl, or heterocycloalkyl;

each R⁷ is independently hydrogen, deuterium, halogen, —CN, —OH, —ORᵃ, —NRᶜRᵈ, C₁-C₆alkyl, C₁-C₆haloalkyl, C₁-C₆deuteroalkyl, C₁-C₆hydroxyalkyl, C₁-C₆aminoalkyl, C₁-C₆heteroalkyl, cycloalkyl, or heterocycloalkyl;

or two R⁷ are taken together to form a cycloalkyl or a heterocycloalkyl; each optionally substituted with deuterium, halogen, —CN, —OH, —ORᵃ, —NRᶜRᵈ, C₁-C₆alkyl, C₁-C₆haloalkyl, C₁-C₆deuteroalkyl, C₁-C₆hydroxyalkyl, C₁-C₆aminoalkyl, or C₁-C₆heteroalkyl;

each R⁸ is independently deuterium, halogen, —CN, —NO₂, —OH, —ORᵃ, —OC(=O)Rᵃ, —OC(=O)ORᵇ, —OC(=O)NRᶜRᵈ, —SH, —SRᵃ, —S(=O)Rᵃ, —S(=O)₂Rᵃ, —S(=O)₂NRᶜRᵈ, —NRᶜRᵈ, —NRᵇC(=O)NRᶜRᵈ, —NRᵇC(=O)Rᵃ, —NRᵇC(=O)ORᵇ, —NRᵇS(=O)₂Rᵃ, —C(=O)Rᵃ, —C(=O)ORᵇ, —C(=O)NRᶜRᵈ, C₁-C₆alkyl, C₁-C₆haloalkyl, C₁-C₆deuteroalkyl, C₁-C₆hydroxyalkyl, C₁-C₆aminoalkyl, C₁-C₆heteroalkyl, C₂-C₆alkenyl, C₂-C₆alkynyl, cycloalkyl, heterocycloalkyl, aryl, or heteroaryl;

or two R⁸ on the same carbon are taken together to form an oxo;

or two R⁸ on the same carbon, adjacent carbons, or opposite carbons are taken together to form a cycloalkyl or heterocycloalkyl; each optionally substituted with one or more deuterium, halogen, —CN, —OH, —ORᵃ, —NRᶜRᵈ, C₁-C₆alkyl, C₁-C₆haloalkyl, C₁-C₆deuteroalkyl, C₁-C₆hydroxyalkyl, C₁-C₆aminoalkyl, or C₁-C₆heteroalkyl;

n is 0-6;

Ring A is 3- to 16-membered monocyclic, bicyclic, or tricyclic ring, optionally comprising 1 to 5 heteroatoms selected from the group consisting of O, N, S, P, or B;

each Rᴬ is independently deuterium, halogen, —CN, —NO₂, —OH, —ORᵃ, —OC(=O)Rᵃ, —OC(=O)ORᵇ, —OC(=O)NRᶜRᵈ, —SH, —SRᵃ, —S(=O)Rᵃ, —S(=O)₂Rᵃ, —S(=O)₂NRᶜRᵈ, —NRᶜRᵈ, —NRᵇC(=O)NRᶜRᵈ, —NRᵇC(=O)Rᵃ, —NRᵇC(=O)ORᵇ, —NRᵇS(=O)₂Rᵃ, —C(=O)Rᵃ, —C(=O)ORᵇ, —C(=O)NRᶜRᵈ, C₁-C₆alkyl, C₁-C₆haloalkyl, C₁-C₆deuteroalkyl, C₁-C₆hydroxyalkyl, C₁-C₆aminoalkyl, C₁-C₆heteroalkyl, C₂-C₆alkenyl, C₂-C₆alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more Rᴬᵃ;

or two Rᴬ on the same atom are taken together to form an oxo;

each Rᴬᵃ is independently deuterium, halogen, —CN, —NO₂, —OH, —ORᵃ, —OC(=O)Rᵃ, —OC(=O)ORᵇ, —OC(=O)NRᶜRᵈ, —SH, —SRᵃ, —S(=O)Rᵃ, —S(=O)₂Rᵃ, —S(=O)₂NRᶜRᵈ, —NRᶜRᵈ, —NRᵇC(=O)NRᶜRᵈ, —NRᵇC(=O)Rᵃ, —NRᵇC(=O)ORᵇ, —NRᵇS(=O)₂Rᵃ, —C(=O)Rᵃ, —C(=O)ORᵇ, —C(=O)NRᶜRᵈ, C₁-C₆alkyl, C₁-C₆haloalkyl, C₁-C₆deuteroalkyl, C₁-C₆hydroxyalkyl, C₁-C₆aminoalkyl, C₁-C₆heteroalkyl, C₂-C₆alkenyl, C₂-C₆alkynyl, cycloalkyl, heterocycloalkyl, aryl, or heteroaryl;

or two $R^{Aa}$ on the same atom are taken together to form an oxo;

m is 0-6;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

provided that at least one of X or Y is N; and provided that when n is 0 then

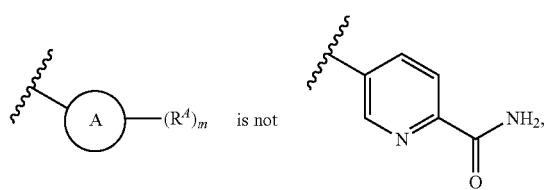

-continued

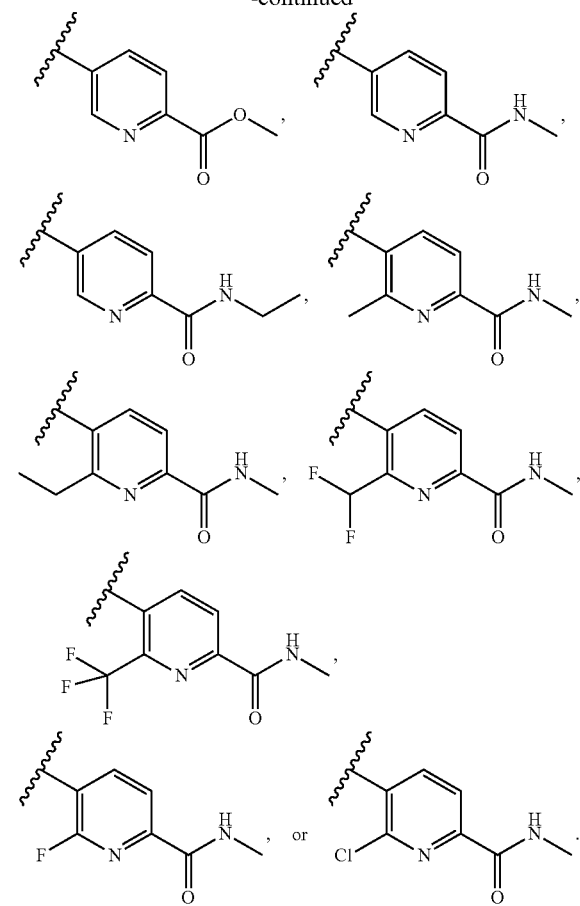

In some embodiments of a compound of Formula (I) or (I'), $R^1$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkynyl, or cycloalkyl.

In some embodiments of a compound of Formula (I) or (I'), $R^1$ is halogen or cycloalkyl.

In some embodiments of a compound of Formula (I) or (I'), $R^1$ is cycloalkyl.

In some embodiments of a compound of Formula (I) or (I'), $R^1$ is $C_1$-$C_6$alkyl.

In some embodiments of a compound of Formula (I) or (I'), X is N and Y is $CR^5$.

In some embodiments of a compound of Formula (I) or (I'), $R^5$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (I) or (I'), $R^5$ is hydrogen, deuterium, halogen, or $C_1$-$C_6$alkyl. In some embodiments of a compound of Formula (I) or (I'), $R^5$ is hydrogen.

In some embodiments of a compound of Formula (I) or (I'), X is $CR^2$ and Y is N.

In some embodiments of a compound of Formula (I) or (I'), $R^2$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (I) or (I'), $R^2$ is hydrogen, deuterium, halogen, or $C_1$-$C_6$alkyl. In some embodiments of a compound of Formula (I) or (I'), $R^2$ is hydrogen. In some embodiments of a compound of Formula (I) or (I'), $R^2$ is hydrogen or $C_1$-$C_6$alkyl. In some embodiments of a compound of Formula (I) or (I'), $R^2$ is $C_1$-$C_6$alkyl.

In some embodiments of a compound of Formula (I) or (I'), X is N and Y is N.

In some embodiments of a compound of Formula (I) or (I'), Z is N. In some embodiments of a compound of Formula (I) or (I'), Z is $CR^4$.

In some embodiments of a compound of Formula (I) or (I'), $R^4$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (I) or (I'), $R^4$ is hydrogen, deuterium, halogen, or $C_1$-$C_6$alkyl. In some embodiments of a compound of Formula (I) or (I'), $R^4$ is hydrogen.

In some embodiments of a compound of Formula (I) or (I'), $R^6$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (I) or (I'), $R^6$ is hydrogen, deuterium, halogen, or $C_1$-$C_6$alkyl. In some embodiments of a compound of Formula (I) or (I'), $R^6$ is hydrogen.

In some embodiments of a compound of Formula (I) or (I'), each $R^7$ is independently hydrogen, deuterium, halogen, $C_1$-$C_6$alkyl, or $C_1$-$C_6$haloalkyl. In some embodiments of a compound of Formula (I) or (I'), each $R^7$ is hydrogen. In some embodiments of a compound of Formula (I) or (I'), two $R^7$ are taken together to form a cycloalkyl.

In some embodiments of a compound of Formula (I) or (I'), each $R^8$ is $C_1$-$C_6$alkyl; or two $R^8$ on the same carbon are taken together to form an oxo. In some embodiments of a compound of Formula (I) or (I'), two $R^8$ on opposite carbons are taken together to form a cycloalkyl. In some embodiments of a compound of Formula (I) or (I'), two $R^8$ on the same carbon are taken together to form a cycloalkyl. In some embodiments of a compound of Formula (I) or (I'), two $R^8$ on adjacent carbons are taken together to form a cycloalkyl.

In some embodiments of a compound of Formula (I) or (I'), n is 0. In some embodiments of a compound of Formula (I) or (I'), n is 1. In some embodiments of a compound of Formula (I) or (I'), n is 2. In some embodiments of a compound of Formula (I) or (I'), n is 3. In some embodiments of a compound of Formula (I) or (I'), n is 4. In some embodiments of a compound of Formula (I) or (I'), n is 5. In some embodiments of a compound of Formula (I) or (I'), n is 6. In some embodiments of a compound of Formula (I) or (I'), n is 0-3. In some embodiments of a compound of Formula (I) or (I'), n is 1-3. In some embodiments of a compound of Formula (I) or (I'), n is 1 or 2. In some embodiments of a compound of Formula (I) or (I'), n is 1-4. In some embodiments of a compound of Formula (I) or (I'), n is 2-4.

In some embodiments of a compound of Formula (I), Ring A is 3- to 7-membered monocyclic ring, optionally comprising 1 to 3 heteroatoms selected from the group consisting of O, N, or S.

In some embodiments of a compound of Formula (I), Ring A is phenyl.

In some embodiments of a compound of Formula (I), Ring A is 5- to 6-membered heteroaryl, comprising 1 to 3 heteroatoms selected from the group consisting of O, N, or S.

In some embodiments of a compound of Formula (I), Ring A is 5-membered heteroaryl, comprising 1 to 3 heteroatoms selected from the group consisting of O, N, or S.

In some embodiments of a compound of Formula (I), Ring A is 6-membered heteroaryl, comprising 1 to 3 heteroatoms that are N.

In some embodiments of a compound of Formula (I), Ring A is pyridinyl.

In some embodiments of a compound of Formula (I), Ring A is not pyridinyl.

The compound of any one of claims 1-26, or a pharmaceutically acceptable salt, solvate, or stereoisomer thereof, wherein Ring A is 3- to 7-membered cycloalkyl.

In some embodiments of a compound of Formula (I), Ring A is 3- to 7-membered heterocycloalkyl, comprising 1 to 3 heteroatoms selected from the group consisting of O, N, or S.

In some embodiments of a compound of Formula (I), Ring A is 6- to 12-membered bicyclic ring, optionally comprising 1 to 3 heteroatoms selected from the group consisting of O, N, or S.

In some embodiments of a compound of Formula (I), Ring A is 6- to 12-membered bicyclic heterocycloalkyl, comprising 1 to 3 heteroatoms selected from the group consisting of O, N, or S.

In some embodiments of a compound of Formula (I), Ring A is 6- to 12-membered bicyclic heteroaryl, comprising 1 to 3 heteroatoms selected from the group consisting of O, N, or S.

In some embodiments of a compound of Formula (I), Ring A is 6- to 12-membered bicyclic partially saturated ring, optionally comprising 1 to 3 heteroatoms selected from the group consisting of 0, N, or S.

In some embodiments of a compound of Formula (I), each $R^A$ is independently deuterium, halogen, —CN, —OH, —$OR^a$, —$S(=O)_2R^a$, —$S(=O)_2NR^cR^d$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein the alkyl, cycloalkyl, heterocycloalkyl, aryl, and heteroaryl is optionally and independently substituted with one or more $R^{Aa}$; or two $R^A$ on the same atom are taken together to form an oxo. In some embodiments of a compound of Formula (I), each $R^A$ is independently deuterium, halogen, —$S(=O)_2R^a$, —$S(=O)_2NR^cR^d$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, cycloalkyl, heterocycloalkyl, aryl, or heteroaryl; wherein the alkyl, cycloalkyl, heterocycloalkyl, aryl, and heteroaryl is optionally and independently substituted with one or more $R^{Aa}$; or two $R^A$ on the same atom are taken together to form an oxo. In some embodiments of a compound of Formula (I), each $R^A$ is independently halogen, —$C(=O)NR^cR^d$, or $C_1$-$C_6$alkyl. In some embodiments of a compound of Formula (I), each $R^A$ is independently —$C(=O)NR^cR^d$. In some embodiments of a compound of Formula (I), $R^A$ is not —$C(=O)NR^cR^d$. In some embodiments of a compound of Formula (I), each $R^A$ is independently heteroaryl optionally and independently substituted with one or more $R^{Aa}$.

In some embodiments of a compound of Formula (I), each $R^{Aa}$ is independently deuterium, halogen, —CN, —OH, —$OR^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; or two $R^{Aa}$ on the same atom are taken together to form an oxo. In some embodiments of a compound of Formula (I), each $R^{Aa}$ is independently deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl; or two $R^{Aa}$ on the same atom are taken together to form an oxo.

In some embodiments of a compound of Formula (I), m is 0-4. In some embodiments of a compound of Formula (I), m is 0 or 1. In some embodiments of a compound of Formula (I), m is 2 or 3. In some embodiments of a compound of Formula (I), m is 1 or 2. In some embodiments of a compound of Formula (I), m is 0. In some embodiments of a compound of Formula (I), m is 1. In some embodiments of a compound of Formula (I), m is 2. In some embodiments of a compound of Formula (I), m is 3. In some embodiments of a compound of Formula (I), m is 4. In some embodiments of a compound of Formula (I), m is 5. In some embodiments of a compound of Formula (I), m is 6.

In some embodiments of a compound of Formula (I),

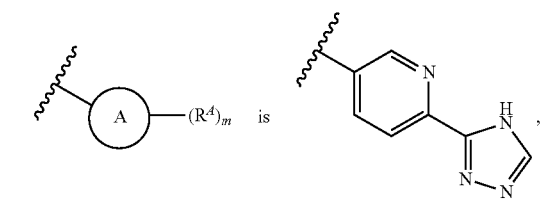

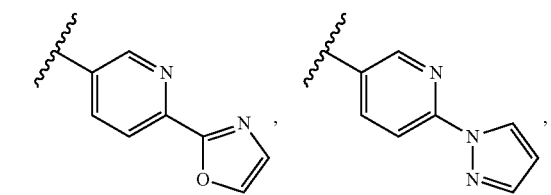

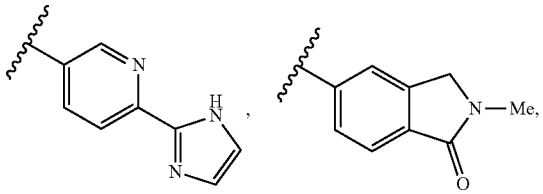

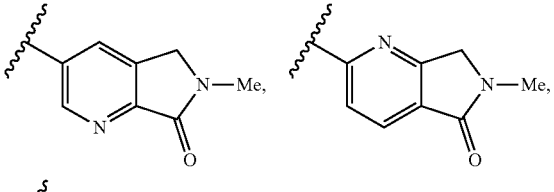

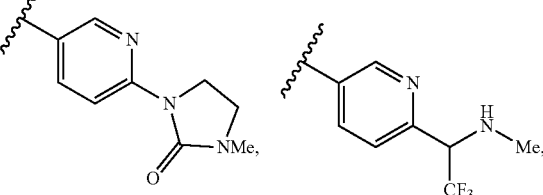

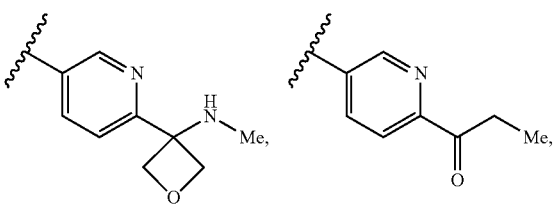

-continued

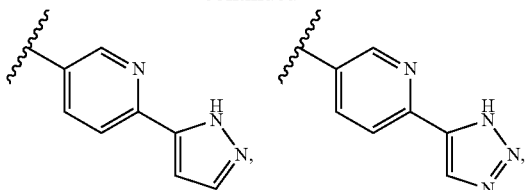

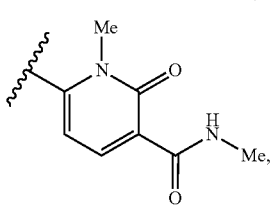
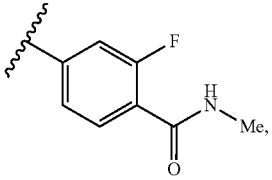

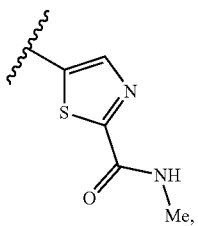
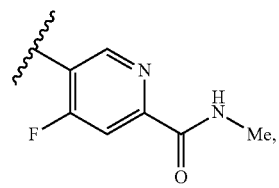

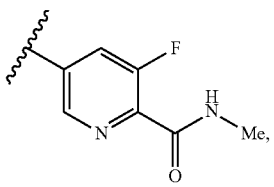
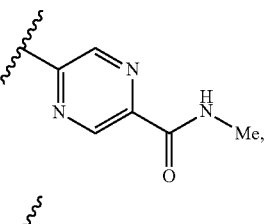

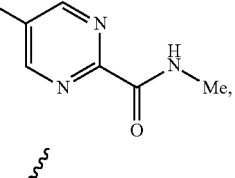
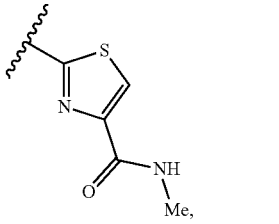

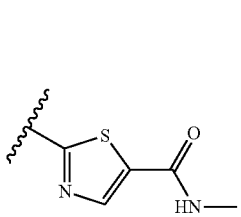
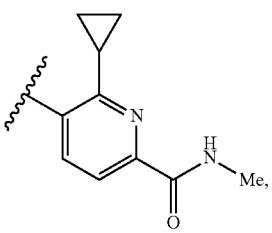

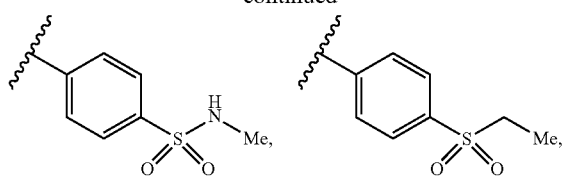
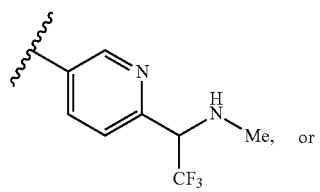
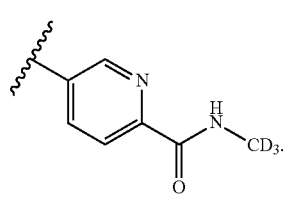
In some embodiments of a compound of Formula (I), 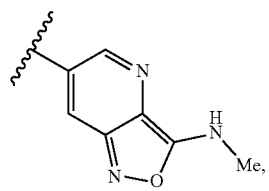 is
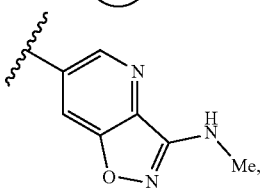 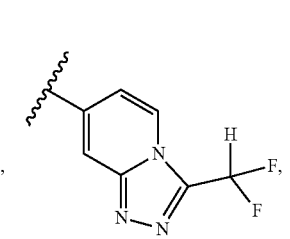 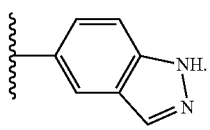
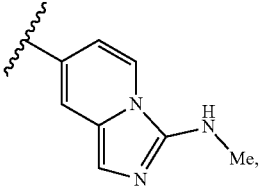 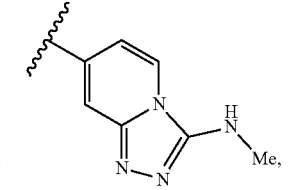
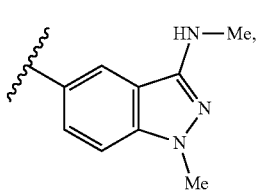 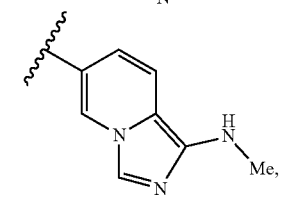
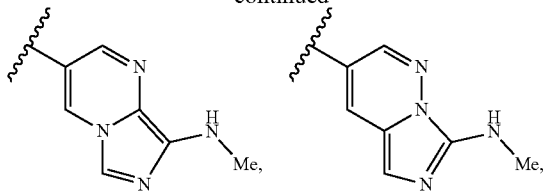
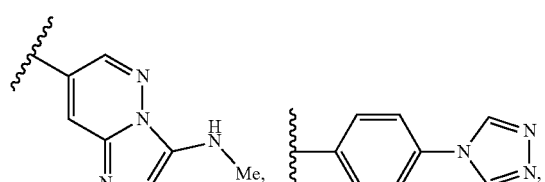
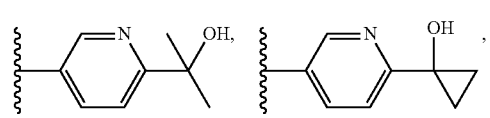
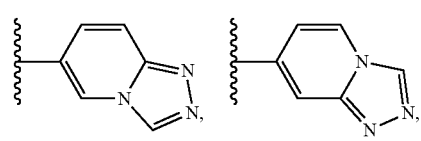
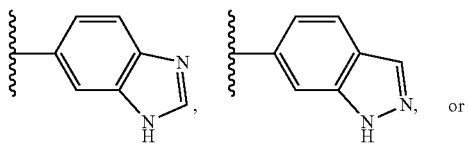
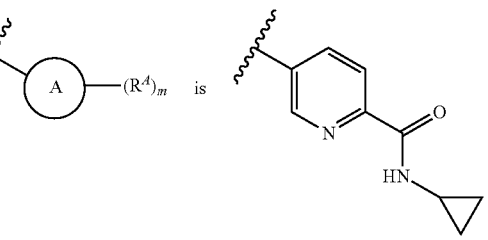
In some embodiments of a compound of Formula (I),
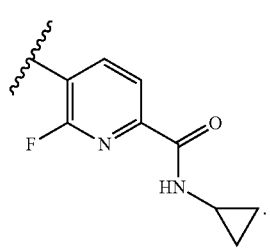

In some embodiments of a compound of Formula (I),

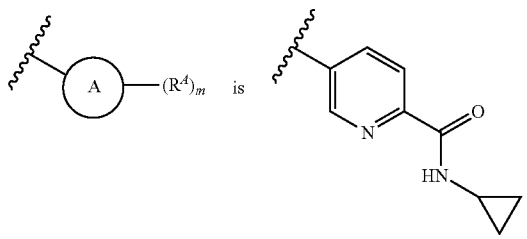 is

In some embodiments of a compound of Formula (I),

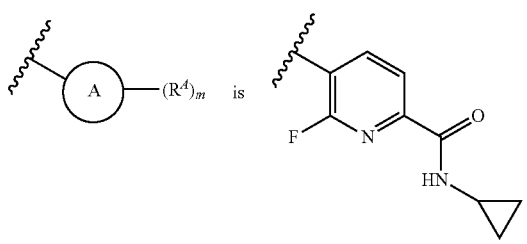 is

In some embodiments of a compound of Formula (I'), each $R^{11}$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I'), each $R^{11}$ is independently deuterium, halogen, $C_1$-$C_6$alkyl, $C_1$-$C_6$haloalkyl, or $C_1$-$C_6$deuteroalkyl. In some embodiments of a compound of Formula (I'), each $R^{11}$ is independently halogen or $C_1$-$C_6$alkyl. In some embodiments of a compound of Formula (I'), each $R^{11}$ is independently halogen.

In some embodiments of a compound of Formula (I'), q is 0 or 1. In some embodiments of a compound of Formula (I'), q is 1 or 2. In some embodiments of a compound of Formula (I'), q is 0. In some embodiments of a compound of Formula (I'), q is 1. In some embodiments of a compound of Formula (I'), q is 2. In some embodiments of a compound of Formula (I'), q is 3.

In some embodiments of a compound of Formula (I'), $R^{12}$ is cycloalkyl. In some embodiments of a compound of Formula (I'), $R^{12}$ is cycloalkyl.

In some embodiments of a compound of Formula (I), the compound is a compound of formula:

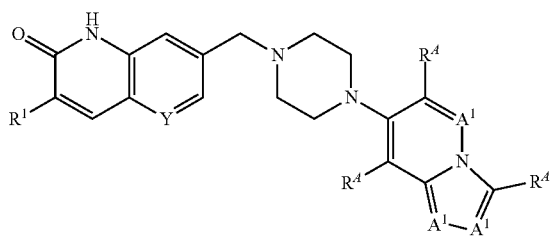

wherein $R^1$ is $C_1$-$C_6$alkyl, $C_1$-$C_6$haloalkyl, or $C_1$-$C_6$deuteroalkyl; Y is N, CH, or CF; each $A^1$ is independently CH, CD, CMe, $CCF_3$, CCl, CF, or N; each $R^4$ is independently hydrogen, deuterium, halogen, $C_1$-$C_6$alkyl, $C_1$-$C_6$haloalkyl, $C_1$-$C_6$deuteroalkyl, NHMe, or $NHCD_3$.

In some embodiments of a compound of Formula (I), the compound is a compound of formula:

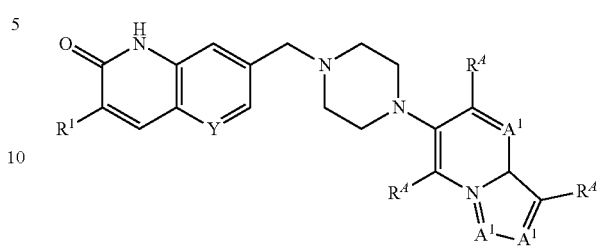

wherein $R^1$ is $C_1$-$C_6$alkyl, $C_1$-$C_6$haloalkyl, or $C_1$-$C_6$deuteroalkyl; Y is N, CH, or CF; each $A^1$ is independently CH, CD, CMe, $CCF_3$, CCl, CF, or N; each $R^4$ is independently hydrogen, deuterium, halogen, $C_1$-$C_6$alkyl, $C_1$-$C_6$haloalkyl, $C_1$-$C_6$deuteroalkyl, NHMe, or $NHCD_3$.

In some embodiments of a compound of Formula (I), the compound is a compound of formula:

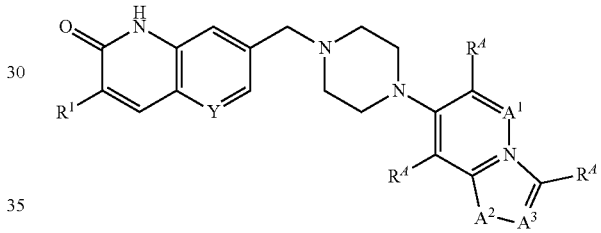

wherein $R^1$ is $C_1$-$C_6$alkyl, $C_1$-$C_6$haloalkyl, or $C_1$-$C_6$deuteroalkyl; Y is N, CH, or CF; each $A^1$ is independently CH, CD, CMe, $CCF_3$, CCl, CF, or N; each $R^4$ is independently hydrogen, deuterium, halogen, $C_1$-$C_6$alkyl, $C_1$-$C_6$haloalkyl, $C_1$-$C_6$deuteroalkyl, NHMe, or $NHCD_3$; $A^2$ is O, NH, NMe, or $NCD_3$; and $A^3$ is N, CH, CF, or CD.

In some embodiments of a compound of Formula (I), the compound is a compound of formula:

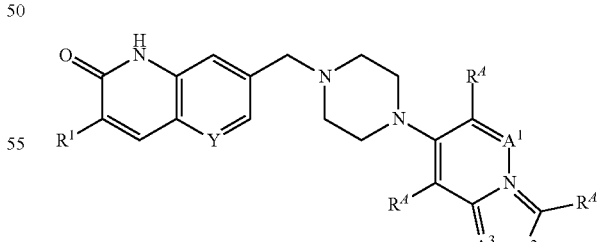

wherein $R^1$ is $C_1$-$C_6$alkyl, $C_1$-$C_6$haloalkyl, or $C_1$-$C_6$deuteroalkyl; Y is N, CH, or CF; each $A^1$ is independently CH, CD, CMe, $CCF_3$, CCl, CF, or N; each $R^4$ is independently hydrogen, deuterium, halogen, $C_1$-$C_6$alkyl, $C_1$-$C_6$haloalkyl, $C_1$-$C_6$deuteroalkyl, NHMe, or $NHCD_3$; $A^2$ is O, NH, NMe, or $NCD_3$; and $A^3$ is N, CH, CF, or CD.

In some embodiments of a compound of Formula (I), the compound is a compound of formula:

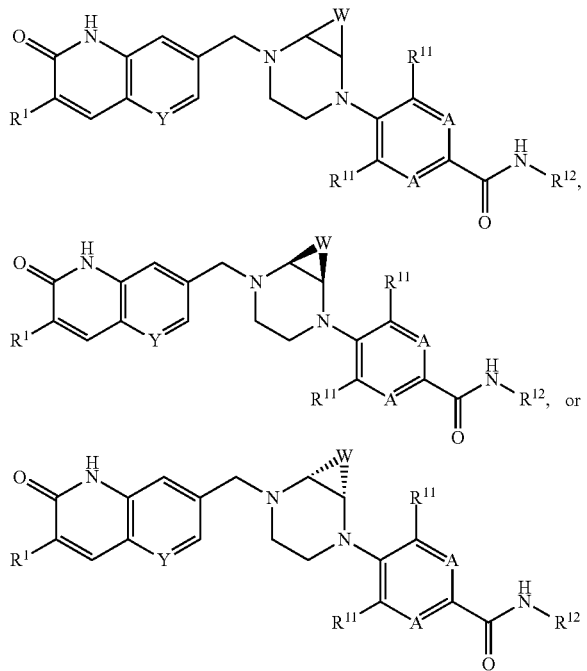

wherein R¹ is $C_1$-$C_6$alkyl, $C_1$-$C_6$haloalkyl, or $C_1$-$C_6$deuteroalkyl; Y is N, CH, or CF; each A is independently CH, CD, CMe, $CCF_3$, CCl, CF, or N; W is $CH_2$, $CF_2$, $CD_2$, CHF, CHD; each $R^{11}$ is independently hydrogen, deuterium, or halogen; and $R^{12}$ is $C_1$-$C_6$alkyl or $C_1$-$C_6$deuteroalkyl.

Also disclosed herein is a compound of Formula (II), or a pharmaceutically acceptable salt, solvate, or stereoisomer thereof:

Formula (II)

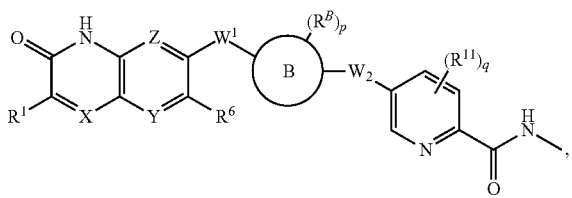

wherein:
R¹ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, or $C_2$-$C_6$alkynyl, cycloalkyl, or heterocycloalkyl;
X is N or $CR^2$;
R² is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
or R¹ and R² are taken together to form a cycloalkyl, heterocycloalkyl, aryl, or heteroaryl; each optionally substituted with deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
Z is N or $CR^4$;
$R^4$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
Y is N or $CR^5$;
$R^5$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
$R^6$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^WC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
$W^1$ is absent, —C($R^7$)$_2$—, —O—, —S—, —$NR^{W1}$—, —C($R^7$)$_2$C($R^7$)$_2$—, —C($R^7$)$_2NR^{W1}$—, —$NR^{W1}$C($R^7$)$_2$—, —C($R^7$)$_2$O—, —OC($R^7$)$_2$—, —C($R^7$)$_2$S—, or —SC($R^7$)$_2$—;
each $R^7$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
or two $R^7$ are taken together to form a cycloalkyl or a heterocycloalkyl; each optionally substituted with deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
$R^{W1}$ is hydrogen, $C_1$-$C_6$alkyl, $C_1$-$C_6$haloalkyl, or $C_1$-$C_6$deuteroalkyl;
Ring B is 3- to 16-membered monocyclic, bicyclic, or tricyclic ring, optionally comprising 1 to 5 heteroatoms selected from the group consisting of O, N, S, P, or B;
each $R^B$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ba}$;

or two $R^B$ on the same atom are taken together to form an oxo;

each $R^{Ba}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ba}$ on the same atom are taken together to form an oxo;

p is 0-6;

$W^2$ is absent, —C(R$^9$)$_2$—, —O—, —S—, —NR$^{W2}$—, —C(R$^9$)$_2$C(R$^9$)$_2$—, —C(R$^9$)$_2$NR$^{W2}$—, —NR$^{W2}$C(R$^9$)$_2$—, —C(R$^9$)$_2$O—, —OC(R$^9$)$_2$—, —C(R$^9$)$_2$S—, or —SC(R$^9$)$_2$—;

each $R^9$ is independently hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or two $R^9$ are taken together to form a cycloalkyl or a heterocycloalkyl; each optionally substituted with deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

$R^{W2}$ is hydrogen, $C_1$-$C_6$alkyl, $C_1$-$C_6$haloalkyl, or $C_1$-$C_6$deuteroalkyl;

each $R^{11}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

q is 0-3;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

provided that

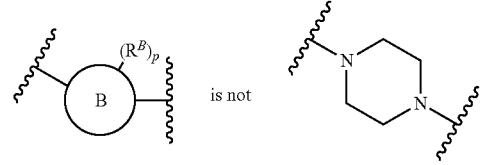

In some embodiments of a compound of Formula (II), $R^1$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, or cycloalkyl. In some embodiments of a compound of Formula (II), $R^1$ is $C_1$-$C_6$alkyl.

In some embodiments of a compound of Formula (II), X is CR$^2$ and Y is CR$^5$.

In some embodiments of a compound of Formula (II), X is N and Y is CR$^5$.

In some embodiments of a compound of Formula (II), $R^5$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (II), $R^5$ is hydrogen, deuterium, halogen, or $C_1$-$C_6$alkyl. In some embodiments of a compound of Formula (II), $R^5$ is hydrogen.

In some embodiments of a compound of Formula (II), X is CR$^2$ and Y is N.

In some embodiments of a compound of Formula (II), $R^2$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (II), $R^2$ is hydrogen, deuterium, halogen, or $C_1$-$C_6$alkyl. In some embodiments of a compound of Formula (II), $R^2$ is hydrogen.

In some embodiments of a compound of Formula (II), X is N and Y is N.

In some embodiments of a compound of Formula (II), Z is N. In some embodiments of a compound of Formula (II), Z is $CR^4$.

In some embodiments of a compound of Formula (II), $R^4$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (II), $R^4$ is hydrogen, deuterium, halogen, or $C_1$-$C_6$alkyl. In some embodiments of a compound of Formula (II), $R^4$ is hydrogen.

In some embodiments of a compound of Formula (II), $R^6$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (II), $R^6$ is hydrogen, deuterium, halogen, or $C_1$-$C_6$alkyl. In some embodiments of a compound of Formula (II), $R^6$ is hydrogen.

In some embodiments of a compound of Formula (II), $W^1$ is —$C(R^7)_2$—, —$NR^{W1}$—, —$C(R^7)_2C(R^7)_2$—, —$C(R^7)_2NR^{W1}$—, or —$NR^{W1}C(R^7)_2$—. In some embodiments of a compound of Formula (II), $W^1$ is —$C(R^7)_2$—, —$NR^{W1}$—, or —$C(R^7)_2NR^{W1}$—. In some embodiments of a compound of Formula (II), $W^1$ is —$C(R^7)_2$—.

In some embodiments of a compound of Formula (II), each $R^7$ is independently hydrogen, deuterium, halogen, $C_1$-$C_6$alkyl, or $C_1$-$C_6$haloalkyl. In some embodiments of a compound of Formula (II), each $R^7$ is hydrogen. In some embodiments of a compound of Formula (II), two $R^7$ are taken together to form a cycloalkyl.

In some embodiments of a compound of Formula (II), $R^{W1}$ is hydrogen or $C_1$-$C_6$alkyl. In some embodiments of a compound of Formula (II), $R^{W1}$ is hydrogen.

In some embodiments of a compound of Formula (II), $W^2$ is absent, —$C(R^9)_2$—, —$NR^{W2}$—, —$C(R^9)_2C(R^9)_2$—, —$C(R^9)_2NR^{W2}$—, or —$NR^{W2}C(R^9)_2$—.

In some embodiments of a compound of Formula (II), $W^1$ is absent or —$NR^{W2}$—. In some embodiments of a compound of Formula (II), $W^2$ is absent. In some embodiments of a compound of Formula (II), $W^2$ is —O—.

In some embodiments of a compound of Formula (II), each $R^9$ is independently hydrogen, deuterium, halogen, $C_1$-$C_6$alkyl, or $C_1$-$C_6$haloalkyl. In some embodiments of a compound of Formula (II), each $R^9$ is hydrogen. In some embodiments of a compound of Formula (II), two $R^{799}$ are taken together to form a cycloalkyl.

In some embodiments of a compound of Formula (II), $R^{W2}$ is hydrogen or $C_1$-$C_6$alkyl. In some embodiments of a compound of Formula (II), $R^{W2}$ is hydrogen.

The compound of any one of claims 50-81, or a pharmaceutically acceptable salt, solvate, or stereoisomer thereof, wherein Ring B is 3- to 7-membered monocyclic ring, optionally comprising 1 to 3 heteroatoms selected from the group consisting of O, N, or S.

In some embodiments of a compound of Formula (II), Ring B is 3- to 7-membered cycloalkyl.

In some embodiments of a compound of Formula (II), Ring B is 3- to 7-membered heterocycloalkyl, comprising 1 to 3 heteroatoms selected from the group consisting of O, N, or S.

In some embodiments of a compound of Formula (II), Ring B is piperazinyl.

In some embodiments of a compound of Formula (II), Ring B is not piperazinyl.

In some embodiments of a compound of Formula (II), Ring B is 6- to 12-membered bicyclic ring, optionally comprising 1 to 3 heteroatoms selected from the group consisting of O, N, or S.

In some embodiments of a compound of Formula (II), Ring B is 6- to 12-membered bicyclic heterocycloalkyl, comprising 1 to 3 heteroatoms selected from the group consisting of O, N, or S.

In some embodiments of a compound of Formula (II), Ring B is 6- to 12-membered bicyclic heterocycloalkyl, comprising 1 to 3 heteroatoms that are N.

In some embodiments of a compound of Formula (II), Ring B is 6- to 16-membered tricyclic ring, optionally comprising 1 to 3 heteroatoms selected from the group consisting of O, N, or S.

In some embodiments of a compound of Formula (II), Ring B is 6- to 16-membered tricyclic heterocycloalkyl, comprising 1 to 3 heteroatoms selected from the group consisting of O, N, or S.

In some embodiments of a compound of Formula (II), Ring B is 6- to 16-membered tricyclic heterocycloalkyl, comprising 1 to 3 heteroatoms that are N.

In some embodiments of a compound of Formula (II), each $R^B$ is independently deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl; or two $R^B$ on the same atom are taken together to form an oxo.

In some embodiments of a compound of Formula (II), each $R^B$ is independently deuterium, halogen, $C_1$-$C_6$alkyl, $C_1$-$C_6$haloalkyl, or $C_1$-$C_6$deuteroalkyl; or two $R^B$ on the same atom are taken together to form an oxo.

In some embodiments of a compound of Formula (II), p is 0-4. In some embodiments of a compound of Formula (II), p is 0 or 1. In some embodiments of a compound of Formula (II), p is 1 or 2. In some embodiments of a compound of Formula (II), p is 1. In some embodiments of a compound of Formula (II), p is 2. In some embodiments of a compound of Formula (II), p is 3. In some embodiments of a compound of Formula (II), p is 4.

In some embodiments of a compound of Formula (II),

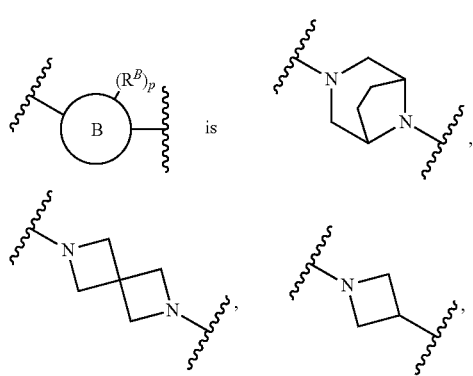

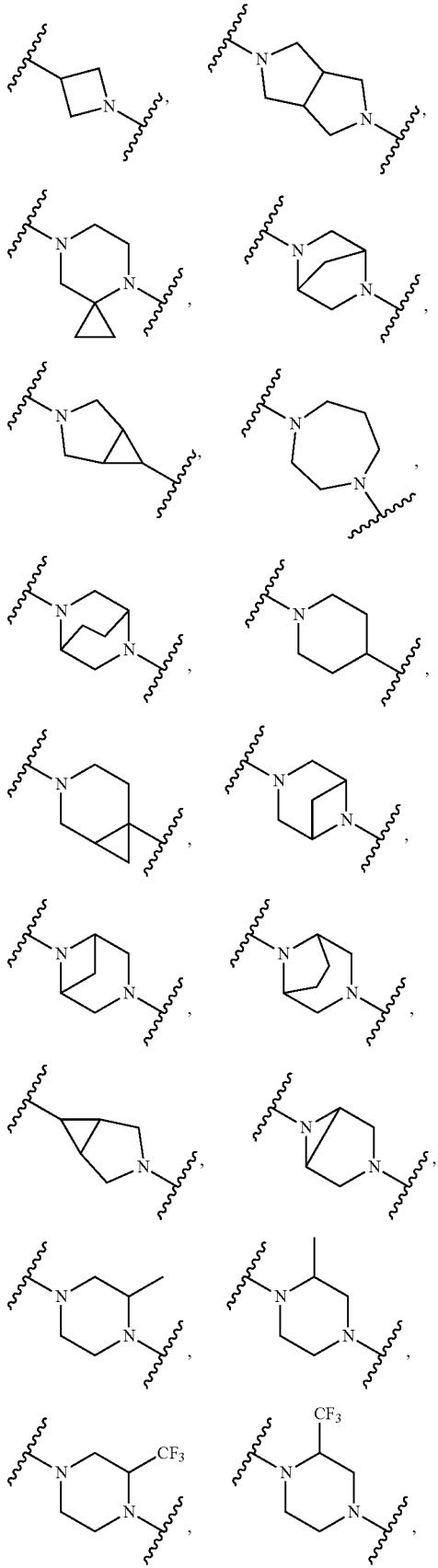

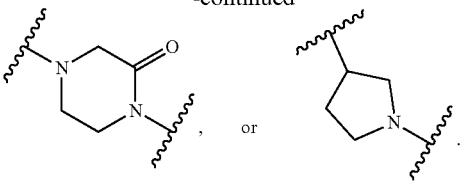

In some embodiments of a compound of Formula (II),

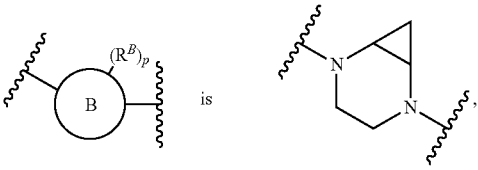 is 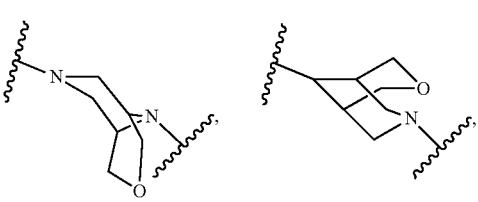

In some embodiments of a compound of Formula (II), each $R^{11}$ is independently deuterium, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (II), each $R^{11}$ is independently deuterium, halogen, $C_1$-$C_6$alkyl, $C_1$-$C_6$haloalkyl, or $C_1$-$C_6$deuteroalkyl. In some embodiments of a compound of Formula (II), each $R^{11}$ is independently halogen or $C_1$-$C_6$alkyl.

In some embodiments of a compound of Formula (II), q is 0 or 1. In some embodiments of a compound of Formula (II), q is 1 or 2. In some embodiments of a compound of Formula (II), q is 1. In some embodiments of a compound of Formula (II), q is 0. In some embodiments of a compound of Formula (II), q is 2. In some embodiments of a compound of Formula (II), q is 3.

Also disclosed herein is a compound of Formula (III"), or a pharmaceutically acceptable salt, solvate, or stereoisomer thereof:

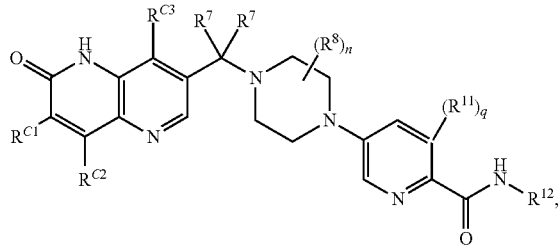

Formula (III″)

wherein:
$R^{C1}$ is hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ca}$;

each $R^{Ca}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{Ca}$ on the same atom are taken together to form an oxo;

$R^{C2}$ is hydrogen, deuterium, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

$R^{C3}$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;

each $R^7$ is independently hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or two $R^7$ are taken together to form a cycloalkyl or a heterocycloalkyl; each optionally substituted with deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^8$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^8$ on the same carbon are taken together to form an oxo;

or two $R^8$ on the same carbon, adjacent carbons, or opposite carbons are taken together to form a cycloalkyl or heterocycloalkyl; each optionally substituted with one or more deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

n is 0-6;

$R^{12}$ is $C_1$-$C_6$alkyl, $C_1$-$C_6$deuteroalkyl, cycloalkyl, or heterocycloalkyl; wherein the alkyl, cycloalkyl, and heterocycloalkyl is optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^{11}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

q is 0-3;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each R$^c$ and R$^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or R$^c$ and R$^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

In some embodiments of a compound of Formula (III"), R$^{C1}$ is deuterium, halogen, —CN, —OH, —OR$^a$, —NR$^c$R$^d$, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl; wherein the alkyl, alkenyl, alkynyl, cycloalkyl, and heterocycloalkyl is optionally and independently substituted with one or more R$^{Ca}$. In some embodiments of a compound of Formula (III"), R$^{C1}$ is halogen, C$_1$-C$_6$haloalkyl, C$_1$-C$_6$deuteroalkyl, cycloalkyl, or heterocycloalkyl. In some embodiments of a compound of Formula (III"), R$^{C1}$ is halogen, cycloalkyl, or heterocycloalkyl. In some embodiments of a compound of Formula (III"), R$^{C1}$ is halogen or cycloalkyl. In some embodiments of a compound of Formula (III"), R$^{C1}$ is halogen. In some embodiments of a compound of Formula (III"), R$^{C1}$ is cycloalkyl.

In some embodiments of a compound of Formula (III"), each R$^{Ca}$ is independently deuterium, halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl. In some embodiments of a compound of Formula (III"), each R$^{Ca}$ is independently deuterium, halogen, —CN, —OH, —OR$^a$, —NR$^c$R$^d$, C$_1$-C$_6$alkyl, or C$_1$-C$_6$haloalkyl.

In some embodiments of a compound of Formula (III"), R$^{C2}$ is hydrogen, deuterium, halogen, —CN, —OH, —OR$^a$, —NR$^c$R$^d$, C$_1$-C$_6$alkyl, or C$_1$-C$_6$haloalkyl. In some embodiments of a compound of Formula (III"), R$^{C2}$ is hydrogen, deuterium, halogen, C$_1$-C$_6$alkyl, or C$_1$-C$_6$haloalkyl. In some embodiments of a compound of Formula (III"), R$^{C2}$ is hydrogen, C$_1$-C$_6$alkyl, or C$_1$-C$_6$haloalkyl. In some embodiments of a compound of Formula (III"), R$^{C2}$ is hydrogen or C$_1$-C$_6$alkyl. In some embodiments of a compound of Formula (III"), R$^{C2}$ is hydrogen. In some embodiments of a compound of Formula (III"), R$^{C2}$ is C$_1$-C$_6$alkyl.

In some embodiments of a compound of Formula (III"), R$^{C3}$ is hydrogen, deuterium, halogen, —CN, —OH, —OR$^a$, —NR$^c$R$^d$, C$_1$-C$_6$alkyl, or C$_1$-C$_6$haloalkyl. In some embodiments of a compound of Formula (III"), R$^{C3}$ is hydrogen, deuterium, halogen, C$_1$-C$_6$alkyl, or C$_1$-C$_6$haloalkyl. In some embodiments of a compound of Formula (III"), R$^{C3}$ is hydrogen, C$_1$-C$_6$alkyl, or C$_1$-C$_6$haloalkyl. In some embodiments of a compound of Formula (III"), R$^{C3}$ is hydrogen or C$_1$-C$_6$alkyl. In some embodiments of a compound of Formula (III"), R$^{C3}$ is hydrogen. In some embodiments of a compound of Formula (III"), R$^{C3}$ is C$_1$-C$_6$alkyl.

In some embodiments of a compound of Formula (III"),

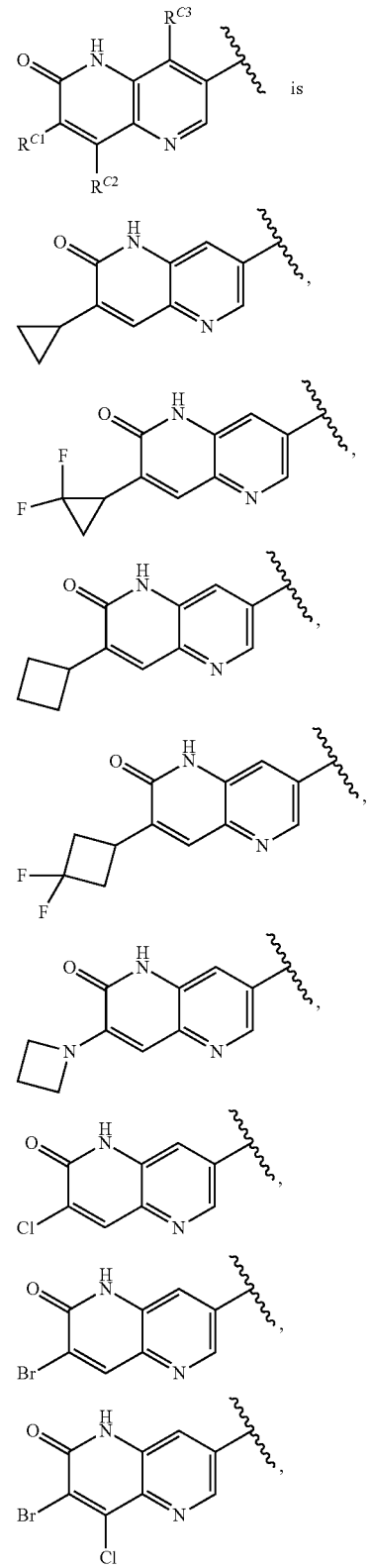

-continued
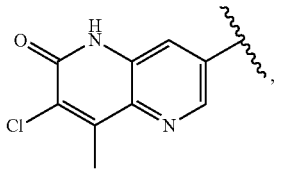,
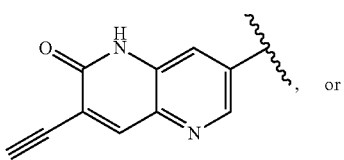, or
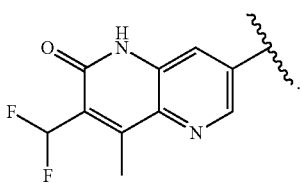.
In some embodiments of a compound of Formula (III″),
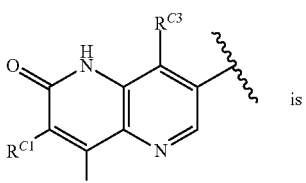 is
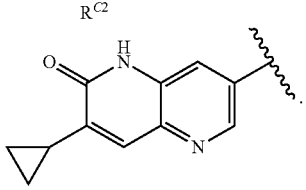.
In some embodiments of a compound of Formula (III″),
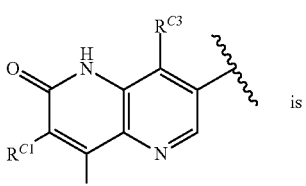 is
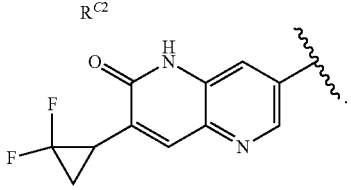.
In some embodiments of a compound of Formula (III″),
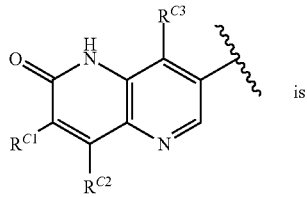 is
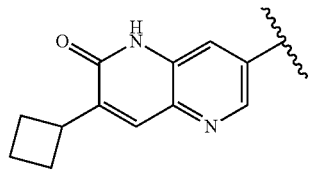.
In some embodiments of a compound of Formula (III″),
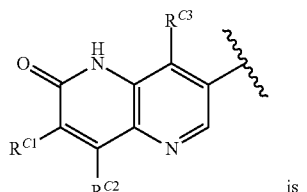 is
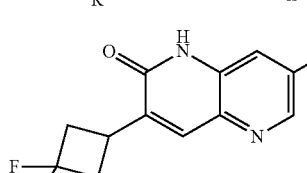.
In some embodiments of a compound of Formula (III″),
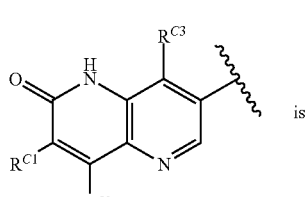 is
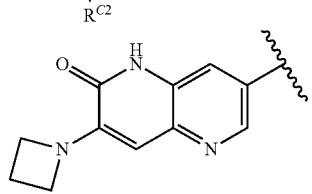.
In some embodiments of a compound of Formula (III″),
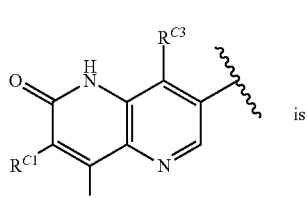 is -continued

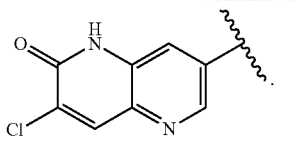

In some embodiments of a compound of Formula (III″),

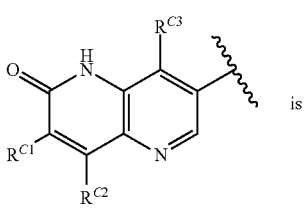
is

In some embodiments of a compound of Formula (III″),

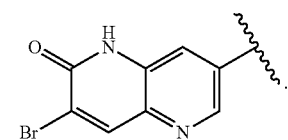

In some embodiments of a compound of Formula (III″),

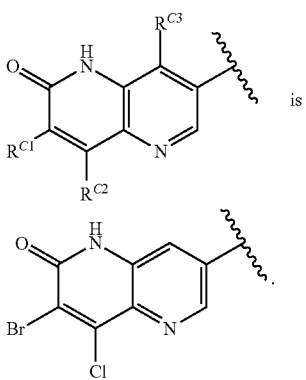
is

In some embodiments of a compound of Formula (III″),

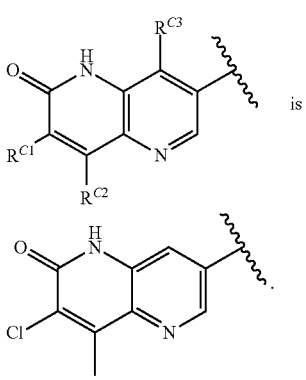
is

In some embodiments of a compound of Formula (III″),

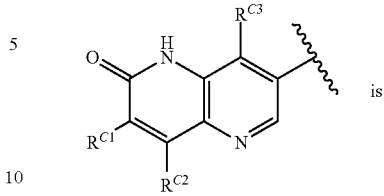
is

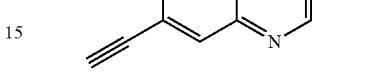

In some embodiments of a compound of Formula (III″),

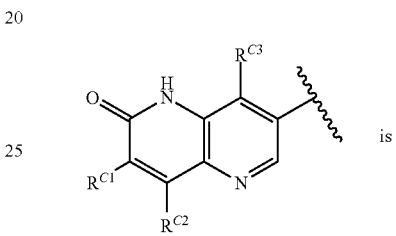
is

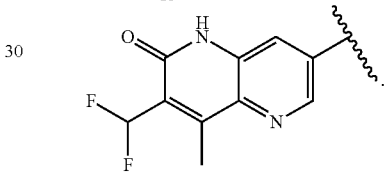

In some embodiments of a compound of Formula (III″), each $R^7$ is independently hydrogen, deuterium, halogen, $C_1$-$C_6$alkyl, or $C_1$-$C_6$haloalkyl. In some embodiments of a compound of Formula (III″), each $R^7$ is hydrogen. In some embodiments of a compound of Formula (III″), two $R^7$ are taken together to form a cycloalkyl.

In some embodiments of a compound of Formula (III″), each $R^8$ is $C_1$-$C_6$alkyl; or two $R^8$ on the same carbon are taken together to form an oxo. In some embodiments of a compound of Formula (III″), two $R^8$ on opposite carbons are taken together to form a cycloalkyl. In some embodiments of a compound of Formula (III″), two $R^8$ on the same carbon are taken together to form a cycloalkyl. In some embodiments of a compound of Formula (III″), two $R^8$ on adjacent carbons are taken together to form a cycloalkyl.

In some embodiments of a compound of Formula (III″), n is 0. In some embodiments of a compound of Formula (III″), n is 1. In some embodiments of a compound of Formula (III″), n is 2. In some embodiments of a compound of Formula (III″), n is 3. In some embodiments of a compound of Formula (III″), n is 4. In some embodiments of a compound of Formula (III″), n is 5. In some embodiments of a compound of Formula (III″), n is 6. In some embodiments of a compound of Formula (III″), n is 0-3. In some embodiments of a compound of Formula (III″), n is 1-3. In some embodiments of a compound of Formula (III″), n is 1 or 2. In some embodiments of a compound of Formula (III″), n is 1-4. In some embodiments of a compound of Formula (III″), n is 2-4.

In some embodiments of a compound of Formula (III″), each $R^{11}$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (III"), each $R^{11}$ is independently deuterium, halogen, $C_1$-$C_6$alkyl, $C_1$-$C_6$haloalkyl, or $C_1$-$C_6$deuteroalkyl. In some embodiments of a compound of Formula (III"), each $R^{11}$ is independently halogen or $C_1$-$C_6$alkyl. In some embodiments of a compound of Formula (III"), each $R^{11}$ is independently halogen.

In some embodiments of a compound of Formula (III"), q is 0 or 1. In some embodiments of a compound of Formula (III"), q is 1 or 2. In some embodiments of a compound of Formula (III"), q is 0. In some embodiments of a compound of Formula (III"), q is 1. In some embodiments of a compound of Formula (III"), q is 2. In some embodiments of a compound of Formula (III"), q is 3.

In some embodiments of a compound of Formula (III"), $R^{12}$ is $C_1$-$C_6$alkyl or cycloalkyl. In some embodiments of a compound of Formula (III"), $R^{12}$ is $C_1$-$C_6$alkyl. In some embodiments of a compound of Formula (III"), $R^{12}$ is cycloalkyl.

Also disclosed herein is a compound of Formula (III'), or a pharmaceutically acceptable salt, solvate, or stereoisomer thereof:

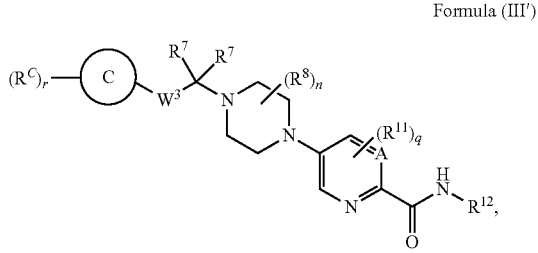

Formula (III')

wherein:
Ring C is 3- to 16-membered monocyclic, bicyclic, or tricyclic ring, optionally comprising 1 to 5 heteroatoms selected from the group consisting of O, N, S, P, or B;
each $R^C$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{Ca}$;
or two $R^C$ on the same atom are taken together to form an oxo;
each $R^{Ca}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;
or two $R^{Ca}$ on the same atom are taken together to form an oxo;
r is 0-6;
$W^3$ is absent, —C(R$^7$)$_2$—, or $C_2$ alkynylene;
each $R^7$ is independently hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
or two $R^7$ are taken together to form a cycloalkyl or a heterocycloalkyl; each optionally substituted with deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
each $R^8$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;
or two $R^8$ on the same carbon are taken together to form an oxo;
or two $R^8$ on the same carbon, adjacent carbons, or opposite carbons are taken together to form a cycloalkyl or heterocycloalkyl; each optionally substituted with one or more deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
n is 0-6;
A is N or CR$^{11}$ or CH;
$R^{12}$ is $C_1$-$C_6$alkyl or $C_1$-$C_6$deuteroalkyl;
each $R^{11}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
q is 0-3;
each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

provided that when n is 0 then $(R^C)_r$—C is not

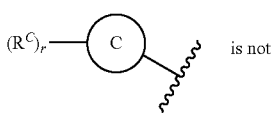,

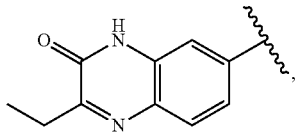,

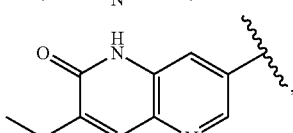,

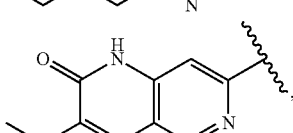,

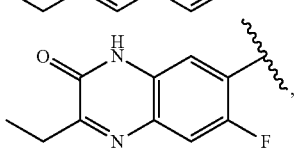,

-continued

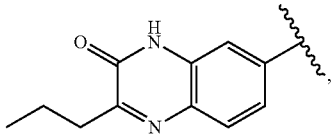,

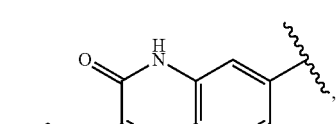,

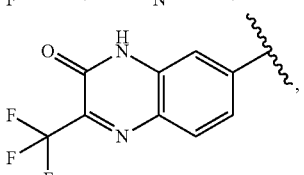,

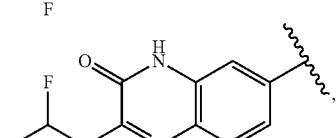,

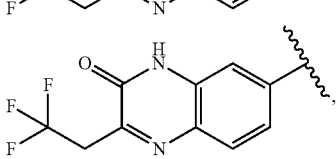,

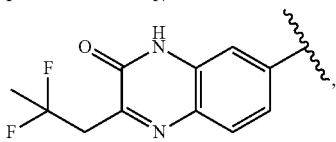,

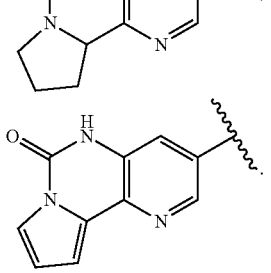, or

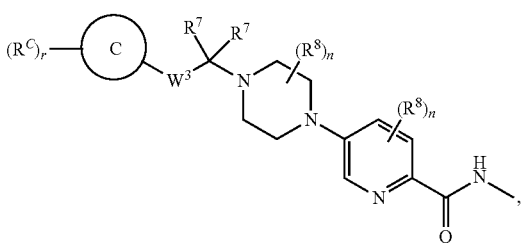.

Also disclosed herein is a compound of Formula (III), or a pharmaceutically acceptable salt, solvate, or stereoisomer thereof:

Formula (III)

wherein:

Ring C is 3- to 16-membered monocyclic, bicyclic, or tricyclic ring, optionally comprising 1 to 5 heteroatoms selected from the group consisting of O, N, S, P, or B;

each $R^C$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more R$^{Ca}$;

or two $R^C$ on the same atom are taken together to form an oxo;

each $R^{Ca}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two $R^{Ca}$ on the same atom are taken together to form an oxo;

r is 0-6;

$W^3$ is absent, —C(R$^7$)$_2$—, or C$_2$ alkynylene;

each $R^7$ is independently hydrogen, deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

or two $R^7$ are taken together to form a cycloalkyl or a heterocycloalkyl; each optionally substituted with deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each $R^8$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two $R^8$ on the same carbon are taken together to form an oxo;

or two $R^8$ on the same carbon, adjacent carbons, or opposite carbons are taken together to form a cycloalkyl or heterocycloalkyl; each optionally substituted with one or more deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

n is 0-6;

each $R^{11}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

q is 0-3;

each $R^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each $R^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each $R^c$ and $R^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

provided that when n is 0 then

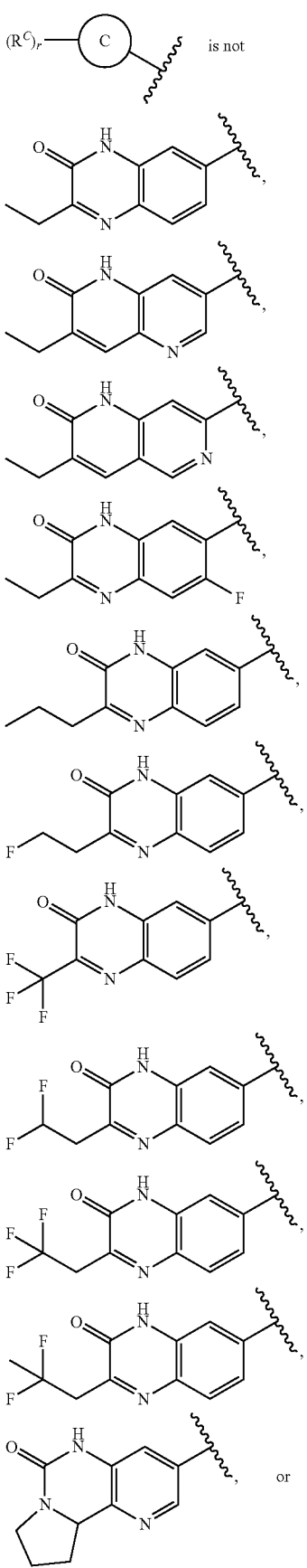

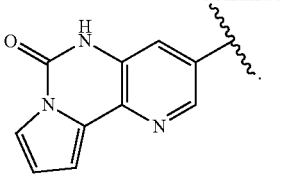

In some embodiments of a compound of Formula (III) or (III'), Ring C is 3- to 7-membered monocyclic ring, optionally comprising 1 to 3 heteroatoms selected from the group consisting of O, N, or S.

In some embodiments of a compound of Formula (III) or (III'), Ring C is phenyl.

In some embodiments of a compound of Formula (III) or (III'), Ring C is 5- to 6-membered heteroaryl, comprising 1 to 3 heteroatoms selected from the group consisting of O, N, or S.

In some embodiments of a compound of Formula (III) or (III'), Ring C is 5-membered heteroaryl, comprising 1 to 3 heteroatoms selected from the group consisting of O, N, or S.

In some embodiments of a compound of Formula (III) or (III'), Ring C is 6-membered heteroaryl, comprising 1 to 3 heteroatoms that are N.

In some embodiments of a compound of Formula (III) or (III'), Ring C is 3- to 7-membered cycloalkyl.

In some embodiments of a compound of Formula (III) or (III'), Ring C is 3- to 7-membered heterocycloalkyl, comprising 1 to 3 heteroatoms selected from the group consisting of O, N, or S.

In some embodiments of a compound of Formula (III) or (III'), Ring C is 6- to 12-membered bicyclic ring, optionally comprising 1 to 3 heteroatoms selected from the group consisting of O, N, or S.

In some embodiments of a compound of Formula (III) or (III'), Ring C is 6- to 12-membered bicyclic heterocycloalkyl, comprising 1 to 3 heteroatoms selected from the group consisting of O, N, or S.

In some embodiments of a compound of Formula (III) or (III'), Ring C is 6- to 12-membered bicyclic heteroaryl, comprising 1 to 3 heteroatoms selected from the group consisting of O, N, or S.

In some embodiments of a compound of Formula (III) or (III'), Ring C is 8- to 16-membered tricyclic ring, optionally comprising 1 to 3 heteroatoms selected from the group consisting of O, N, or S.

In some embodiments of a compound of Formula (III) or (III'), Ring C is 8- to 16-membered tricyclic heterocycloalkyl, comprising 1 to 3 heteroatoms selected from the group consisting of O, N, or S.

In some embodiments of a compound of Formula (III) or (III'), each $R^C$ is independently deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, cycloalkyl, or heterocycloalkyl; or two $R^C$ on the same atom are taken together to form an oxo. In some embodiments of a compound of Formula (III) or (III'), each $R^C$ is independently deuterium, halogen, —CN, $C_1$-$C_6$alkyl, $C_1$-$C_6$haloalkyl, or $C_1$-$C_6$deuteroalkyl; or two $R^C$ on the same atom are taken together to form an oxo. In some embodiments of a compound of Formula (III) or (III'), each $R^C$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkynyl, or cycloalkyl. In some embodiments of a compound of Formula (III) or (III'), each $R^C$ is independently $C_1$-$C_6$alkyl. In some embodiments of a compound of Formula (III) or (III'), $R^C$ is not $C_1$-$C_6$alkyl. In some embodiments of a compound of Formula (III) or (III'), $R^C$ is not $C_1$-$C_6$haloalkyl.

In some embodiments of a compound of Formula (III) or (III'), r is 0-4. In some embodiments of a compound of Formula (III) or (III'), r is 1-3. In some embodiments of a compound of Formula (III) or (III'), r is 0 or 1. In some embodiments of a compound of Formula (III) or (III'), r is 0-3. In some embodiments of a compound of Formula (III) or (III'), r is 1 or 2. In some embodiments of a compound of Formula (III) or (III'), r is 1 or 2. In some embodiments of a compound of Formula (III) or (III'), r is 1. In some embodiments of a compound of Formula (III) or (III'), r is 2. In some embodiments of a compound of Formula (III) or (III'), r is 3. In some embodiments of a compound of Formula (III) or (III'), r is 4.

In some embodiments of a compound of Formula (III) or (III'),

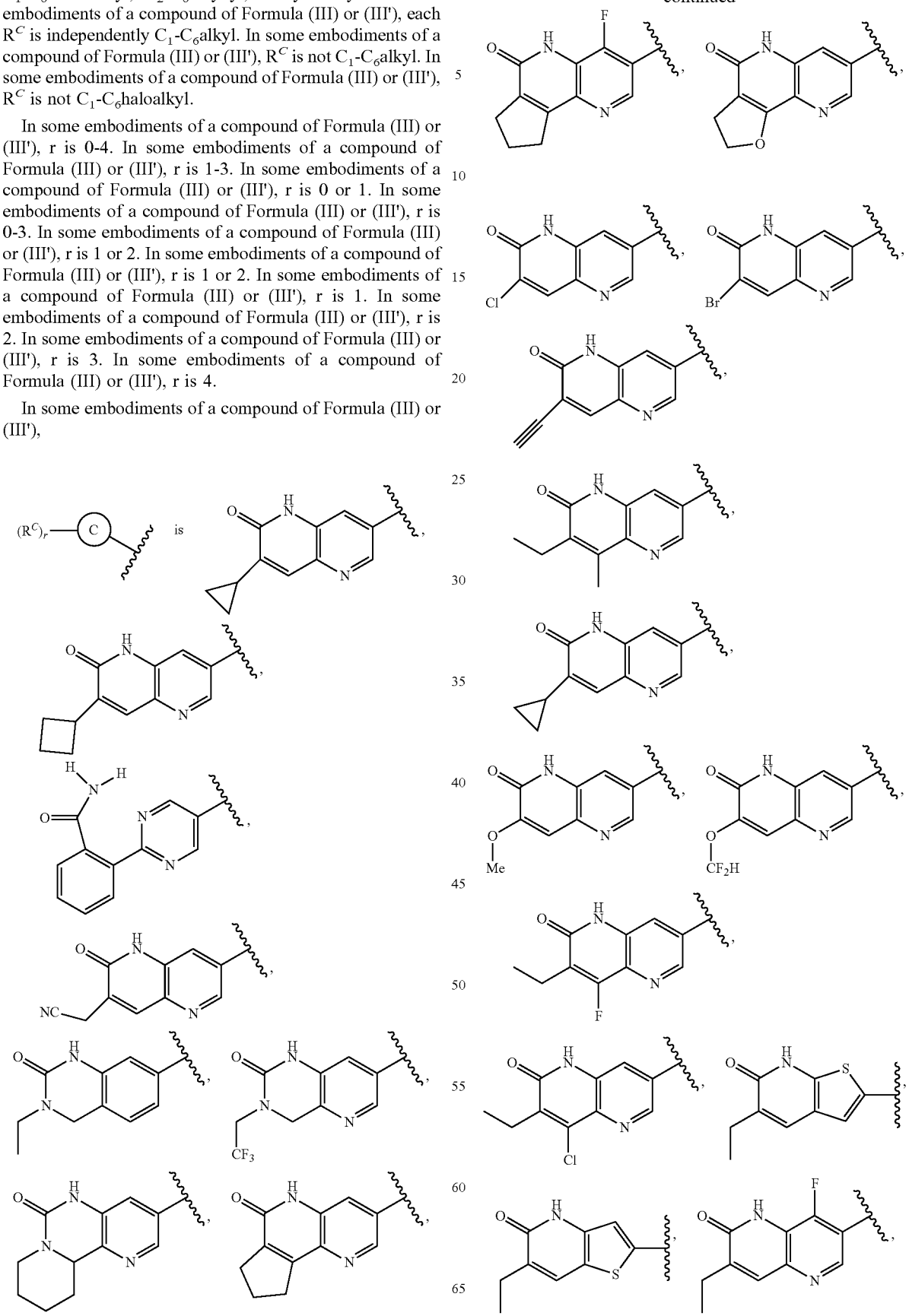

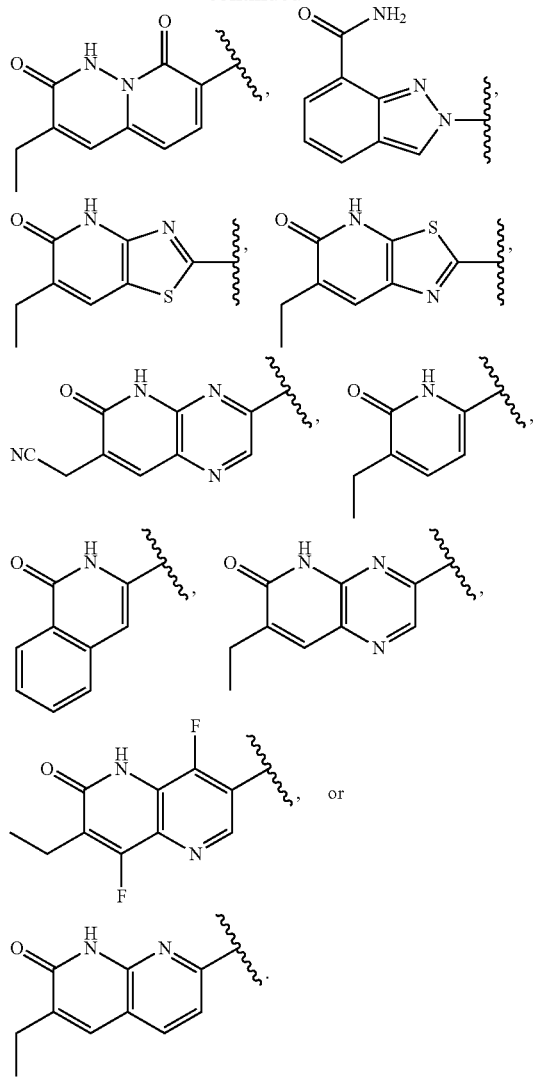
In some embodiments of a compound of Formula (III) or (III'),
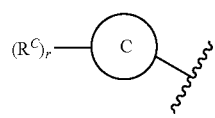 is
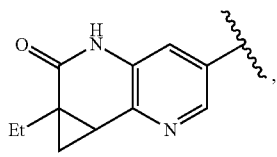
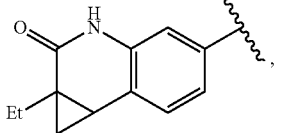
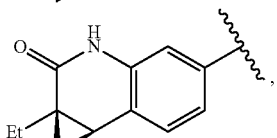
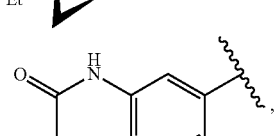
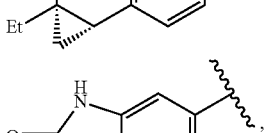
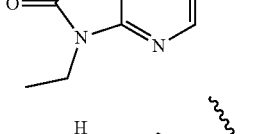
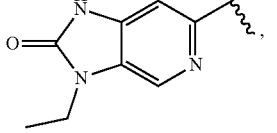
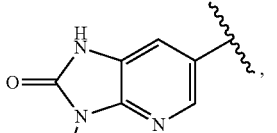
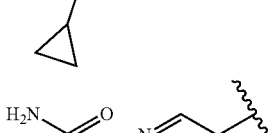
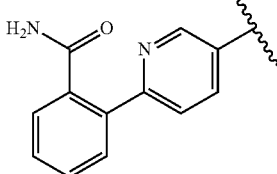
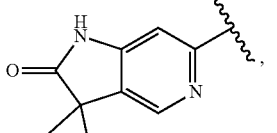
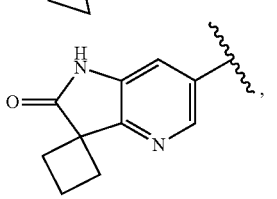

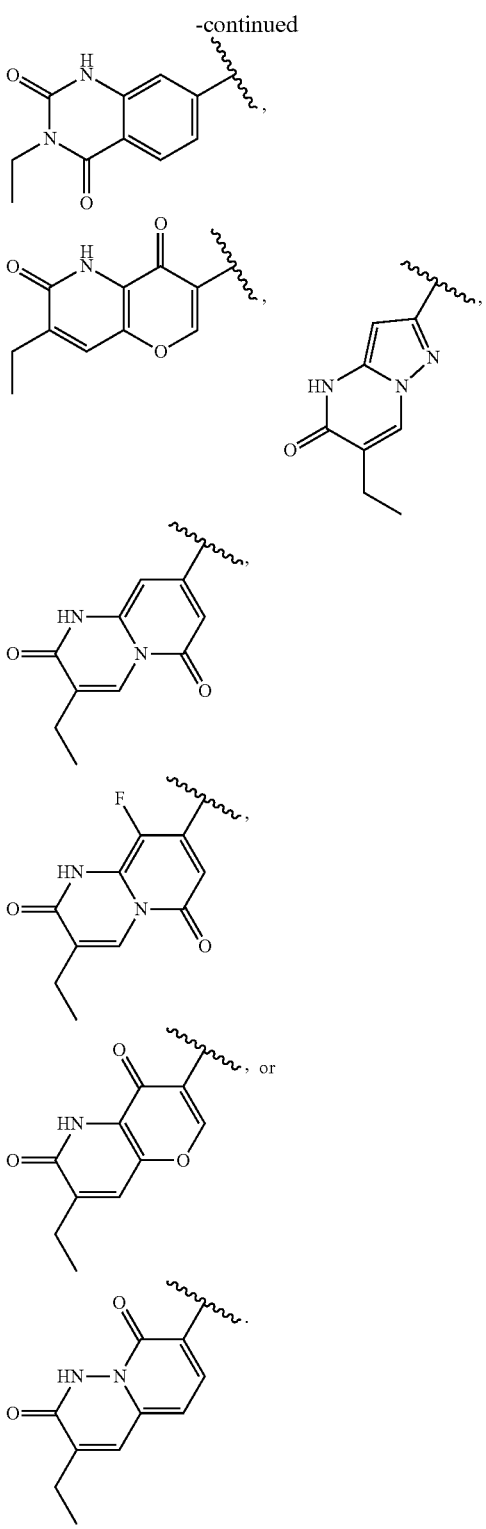

In some embodiments of a compound of Formula (III) or (III'), W³ is absent. In some embodiments of a compound of Formula (III) or (III'), W³ is C₂ alkynylene. In some embodiments of a compound of Formula (III) or (III'), W³ is —C($R^7$)₂—.

In some embodiments of a compound of Formula (III) or (III'), each $R^7$ is independently hydrogen, deuterium, halogen, $C_1$-$C_6$alkyl, or $C_1$-$C_6$haloalkyl. In some embodiments of a compound of Formula (III) or (III'), each $R^7$ is hydrogen. In some embodiments of a compound of Formula (III) or (III'), two $R^7$ are taken together to form a cycloalkyl.

In some embodiments of a compound of Formula (III) or (III'), each $R^8$ is $C_1$-$C_6$alkyl; or two $R^8$ on the same carbon are taken together to form an oxo. In some embodiments of a compound of Formula (III) or (III'), two $R^8$ on opposite carbons are taken together to form a cycloalkyl. In some embodiments of a compound of Formula (III) or (III'), two $R^8$ on the same carbon are taken together to form a cycloalkyl. In some embodiments of a compound of Formula (III) or (III'), two $R^8$ on adjacent carbons are taken together to form a cycloalkyl.

In some embodiments of a compound of Formula (III) or (III'), n is 0. In some embodiments of a compound of Formula (III) or (III'), n is 1. In some embodiments of a compound of Formula (III) or (III'), n is 2. In some embodiments of a compound of Formula (III) or (III'), n is 3. In some embodiments of a compound of Formula (III) or (III'), n is 4. In some embodiments of a compound of Formula (III) or (III'), n is 5. In some embodiments of a compound of Formula (III) or (III'), n is 6. In some embodiments of a compound of Formula (III) or (III'), n is 0-3. In some embodiments of a compound of Formula (III) or (III'), n is 1-3. In some embodiments of a compound of Formula (III) or (III'), n is 1 or 2. In some embodiments of a compound of Formula (III) or (III'), n is 1-4. In some embodiments of a compound of Formula (III) or (III'), n is 2-4.

In some embodiments of a compound of Formula (III) or (III'), each $R^{11}$ is independently deuterium, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (III) or (III'), each $R^{11}$ is independently deuterium, halogen, $C_1$-$C_6$alkyl, $C_1$-$C_6$haloalkyl, or $C_1$-$C_6$deuteroalkyl. In some embodiments of a compound of Formula (III) or (III'), each $R^{11}$ is independently halogen or $C_1$-$C_6$alkyl.

In some embodiments of a compound of Formula (III) or (III'), q is 0 or 1. In some embodiments of a compound of Formula (III) or (III'), q is 1 or 2. In some embodiments of a compound of Formula (III) or (III'), q is 0. In some embodiments of a compound of Formula (III) or (III'), q is 1. In some embodiments of a compound of Formula (III) or (III'), q is 2. In some embodiments of a compound of Formula (III) or (III'), q is 3.

In some embodiments of a compound of Formula (III) or (III'), the compound is a compound of formula:

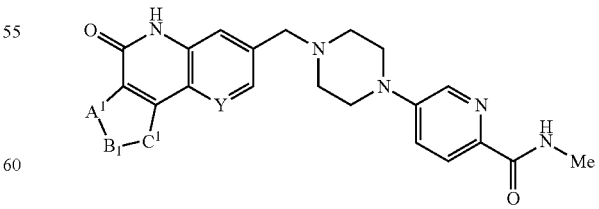

wherein Y is N, CH, or CF; $A^1$ is $CH_2$, $CF_2$, CHF, $CHCH_3$, $C(CH_3)_2$; $B^1$ is $CH_2$, $CF_2$, CHF, $CHCH_3$, $C(CH_3)_2$; and $C^1$ is O or S; or a pharmaceutically acceptable salt, solvate, or stereoisomer thereof.

In some embodiments of a compound of Formula (III) or (III'), the compound is a compound of formula:

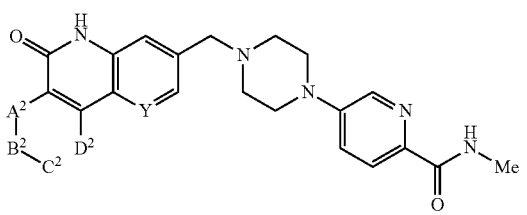

wherein Y is N, CH, or CF; $A^2$ is $CH_2$, $CF_2$, CHF, $CHCH_3$, $C(CH_3)_2$; $B^2$ is $CH_2$, $CF_2$, CHF, $CHCH_3$, $C(CH_3)_2$; and $C^2$ is $CH_2$, $CF_2$, CHF, $CHCH_3$, $C(CH_3)_2$; and $D^2$ is O or S; or a pharmaceutically acceptable salt, solvate, or stereoisomer thereof.

In some embodiments of a compound of Formula (III) or (III'), the compound is a compound of formula:

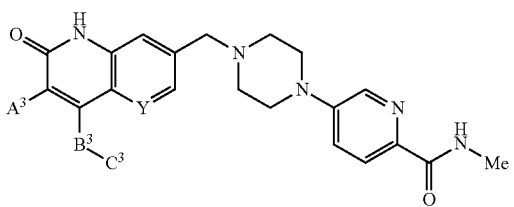

wherein Y is N, CH, or CF; $A^3$ is hydrogen, halogen, $C_1$-$C_6$alkyl, $C_1$-$C_6$haloalkyl, or cycloalkyl optionally substituted with halogen; $B^3$ is O or S; and $C^3$ is hydrogen, $C_1$-$C_6$alkyl, $C_1$-$C_6$haloalkyl, or cycloalkyl optionally substituted with halogen; or a pharmaceutically acceptable salt, solvate, or stereoisomer thereof.

In some embodiments of a compound of Formula (III) or (III'), the compound is a compound of formula:

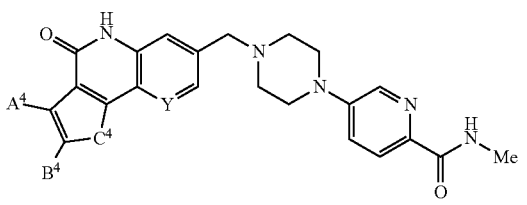

wherein Y is N, CH, or CF; $A^4$ is hydrogen, $C_1$-$C_6$alkyl, or $C_1$-$C_6$haloalkyl; $B^4$ is hydrogen, $C_1$-$C_6$alkyl, $C_1$-$C_6$haloalkyl; and $C^4$ is O or S; or a pharmaceutically acceptable salt, solvate, or stereoisomer thereof.

In some embodiments of a compound of Formula (III) or (III'), the compound is a compound of formula:

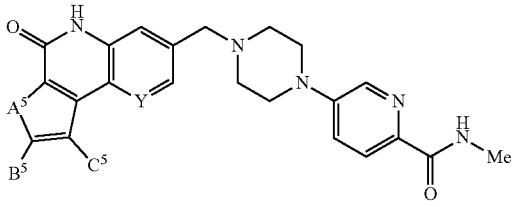

wherein Y is N, CH, or CF; $A^5$ is O or S; $B^5$ is hydrogen, $C_1$-$C_6$alkyl, or $C_1$-$C_6$haloalkyl; and $C^5$ is hydrogen, $C_1$-$C_6$alkyl, $C_1$-$C_6$haloalkyl; or a pharmaceutically acceptable salt, solvate, or stereoisomer thereof.

In some embodiments of a compound of Formula (III) or (III'), the compound is a compound of formula:

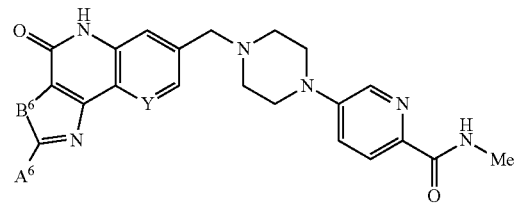

wherein Y is N, CH, or CF; $A^6$ is hydrogen, $C_1$-$C_6$alkyl, or $C_1$-$C_6$haloalkyl; and $B^6$ is O or S; or a pharmaceutically acceptable salt, solvate, or stereoisomer thereof.

In some embodiments of a compound of Formula (III) or (III'), the compound is a compound of formula:

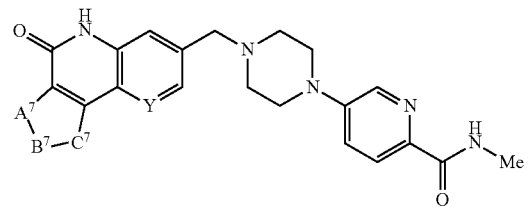

wherein Y is N, CH, or CF; $A^7$ is O or S; $B^7$ is $CH_2$, $CF_2$, CHF, $CHCH_3$, $C(CH_3)_2$; and $C^7$ is $CH_2$, $CF_2$, CHF, $CHCH_3$, $C(CH_3)_2$; or a pharmaceutically acceptable salt, solvate, or stereoisomer thereof.

In some embodiments of a compound of Formula (III) or (III'), the compound is a compound of formula:

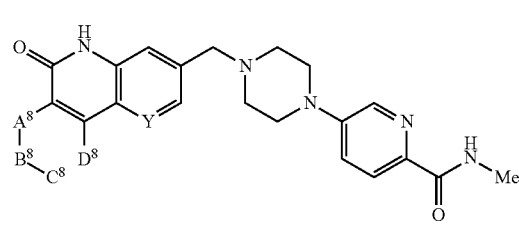

wherein Y is N, CH, or CF; $A^8$ is O or S; $B^8$ is $CH_2$, $CF_2$, CHF, $CHCH_3$, $C(CH_3)_2$; $C^7$ is $CH_2$, $CF_2$, CHF, $CHCH_3$, $C(CH_3)_2$; and $D^8$ is $CH_2$, $CF_2$, CHF, $CHCH_3$, $C(CH_3)_2$; or a pharmaceutically acceptable salt, solvate, or stereoisomer thereof.

In some embodiments of a compound of Formula (III) or (III'), the compound is a compound of formula:

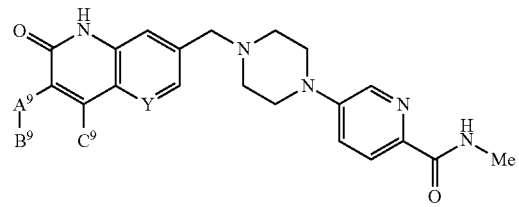

wherein Y is N, CH, or CF; $A^9$ is O or S; $B^9$ is hydrogen, $C_1$-$C_6$alkyl, $C_1$-$C_6$haloalkyl, or cycloalkyl optionally substituted with halogen; and $C^9$ is hydrogen, halogen, $C_1$-$C_6$alkyl, $C_1$-$C_6$haloalkyl, or cycloalkyl optionally substituted with halogen; or a pharmaceutically acceptable salt, solvate, or stereoisomer thereof.

In some embodiments of a compound of Formula (III) or (III'), the compound is a compound of formula:

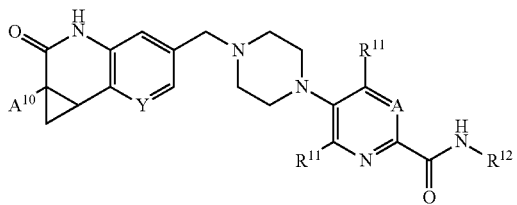

wherein Y is N, CH, or CF; A is CH, CMe, $CCF_3$, CCl, CF, or N; $R^{12}$ is $C_1$-$C_6$alkyl, $C_1$-$C_6$deuteroalkyl; each $R^{11}$ is independently hydrogen, deuterium, or halogen; $A^{10}$ is $C_1$-$C_6$alkyl, $C_1$-$C_6$haloalkyl, or $C_1$-$C_6$deuteroalkyl.

Disclosed herein is a compound of Formula (IV), or a pharmaceutically acceptable salt, solvate, or stereoisomer thereof:

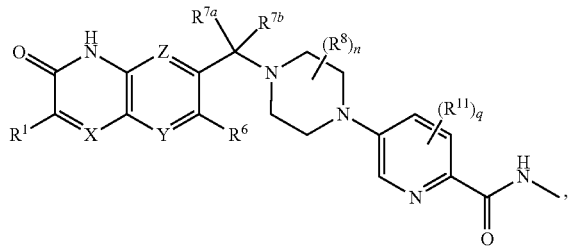

Formula (IV)

wherein:

$R^1$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;

X is N or $CR^2$;

$R^2$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;

or $R^1$ and $R^2$ are taken together to form a cycloalkyl, heterocycloalkyl, aryl, or heteroaryl; each optionally substituted with deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

Z is N or $CR^4$;

$R^4$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;

Y is N or $CR^5$;

$R^5$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;

$R^6$ is hydrogen, deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;

$R^{7a}$ is deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^{7b}$ is hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or $R^{7a}$ and $R^{7b}$ are taken together to form a cycloalkyl or a heterocycloalkyl; each optionally substituted with deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^8$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^8$ on the same carbon are taken together to form an oxo;

or two $R^8$ on the same carbon, adjacent carbons, or opposite carbons are taken together to form a cycloalkyl or heterocycloalkyl; each optionally substituted with one or more deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

n is 0-6;

each $R^{11}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

q is 0-3;

each $R^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each $R^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each $R^c$ and $R^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

In some embodiments of a compound of Formula (IV), $R^1$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$cyanoalkyl, C$_1$-C$_6$heteroalkyl, C$_2$-C$_6$alkenyl, C$_2$-C$_6$alkynyl, or cycloalkyl. In some embodiments of a compound of Formula (IV), $R^1$ is C$_1$-C$_6$alkyl.

In some embodiments of a compound of Formula (IV), X is CR$^2$ and Y is CR$^5$.

In some embodiments of a compound of Formula (IV), X is N and Y is CR$^5$.

In some embodiments of a compound of Formula (IV), $R^5$ is hydrogen, deuterium, halogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$cyanoalkyl, C$_1$-C$_6$heteroalkyl, or cycloalkyl. In some embodiments of a compound of Formula (IV), $R^5$ is hydrogen, deuterium, halogen, or C$_1$-C$_6$alkyl. In some embodiments of a compound of Formula (IV), $R^5$ is hydrogen.

In some embodiments of a compound of Formula (IV), X is CR$^2$ and Y is N.

In some embodiments of a compound of Formula (IV), $R^2$ is hydrogen, deuterium, halogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$cyanoalkyl, C$_1$-C$_6$heteroalkyl, or cycloalkyl. In some embodiments of a compound of Formula (IV), $R^2$ is hydrogen, deuterium, halogen, or C$_1$-C$_6$alkyl. In some embodiments of a compound of Formula (IV), $R^2$ is hydrogen.

In some embodiments of a compound of Formula (IV), X is N and Y is N.

In some embodiments of a compound of Formula (IV), Z is N. In some embodiments of a compound of Formula (IV), Z is CR$^4$.

In some embodiments of a compound of Formula (IV), $R^4$ is hydrogen, deuterium, halogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$cyanoalkyl, C$_1$-C$_6$heteroalkyl, or cycloalkyl. In some embodiments of a compound of Formula (IV), $R^4$ is hydrogen, deuterium, halogen, or C$_1$-C$_6$alkyl. In some embodiments of a compound of Formula (IV), $R^4$ is hydrogen.

In some embodiments of a compound of Formula (IV), $R^6$ is hydrogen, deuterium, halogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$cyanoalkyl, C$_1$-C$_6$heteroalkyl, or cycloalkyl. In some embodiments of a compound of Formula (IV), $R^6$ is hydrogen, deuterium, halogen, or C$_1$-C$_6$alkyl. In some embodiments of a compound of Formula (IV), $R^6$ is hydrogen.

In some embodiments of a compound of Formula (IV), $R^{7a}$ is deuterium, halogen, C$_1$-C$_6$alkyl, C$_1$-C$_6$haloalkyl, or C$_1$-C$_6$deuteroalkyl. In some embodiments of a compound of Formula (IV), $R^{7a}$ is deuterium or C$_1$-C$_6$alkyl. In some embodiments of a compound of Formula (IV), $R^{7a}$ is deuterium.

In some embodiments of a compound of Formula (IV), $R^{7b}$ is hydrogen, deuterium, halogen, C$_1$-C$_6$alkyl, C$_1$-C$_6$haloalkyl, or C$_1$-C$_6$deuteroalkyl. In some embodiments of a compound of Formula (IV), $R^{7b}$ is hydrogen, deuterium, or C$_1$-C$_6$alkyl.

In some embodiments of a compound of Formula (IV), $R^{7a}$ and $R^{7b}$ are taken together to form a cycloalkyl. In some embodiments of a compound of Formula (IV), $R^{7a}$ and $R^{7b}$ are deuterium.

In some embodiments of a compound of Formula (IV), each $R^8$ is C$_1$-C$_6$alkyl; or two $R^8$ on the same carbon are taken together to form an oxo. In some embodiments of a compound of Formula (IV), two $R^8$ on opposite carbons are taken together to form a cycloalkyl. In some embodiments of a compound of Formula (IV), two $R^8$ on the same carbon are taken together to form a cycloalkyl. In some embodiments of a compound of Formula (IV), two $R^8$ on adjacent carbons are taken together to form a cycloalkyl.

In some embodiments of a compound of Formula (IV), n is 0. In some embodiments of a compound of Formula (IV), n is 1. In some embodiments of a compound of Formula (IV), n is 2. In some embodiments of a compound of Formula (IV), n is 3. In some embodiments of a compound of Formula (IV), n is 4. In some embodiments of a compound of Formula (IV), n is 5. In some embodiments of a compound of Formula (IV), n is 6. In some embodiments of a compound of Formula (IV), n is 0-3. In some embodiments of a compound of Formula (IV), n is 1-3. In some embodiments of a compound of Formula (IV), n is 1 or 2. In some embodiments of a compound of Formula (IV), n is 1-4. In some embodiments of a compound of Formula (IV), n is 2-4.

In some embodiments of a compound of Formula (IV), each $R^{11}$ is independently deuterium, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (IV), each $R^{11}$ is independently deuterium, halogen, $C_1$-$C_6$alkyl, $C_1$-$C_6$haloalkyl, or $C_1$-$C_6$deuteroalkyl. In some embodiments of a compound of Formula (IV), each $R^{11}$ is independently halogen or $C_1$-$C_6$alkyl.

In some embodiments of a compound of Formula (IV), q is 0 or 1. In some embodiments of a compound of Formula (IV), q is 1 or 2. In some embodiments of a compound of Formula (IV), q is 0. In some embodiments of a compound of Formula (IV), q is 1. In some embodiments of a compound of Formula (IV), q is 2. In some embodiments of a compound of Formula (IV), q is 3.

Disclosed herein is a compound of Formula (V), or a pharmaceutically acceptable salt, solvate, or stereoisomer thereof:

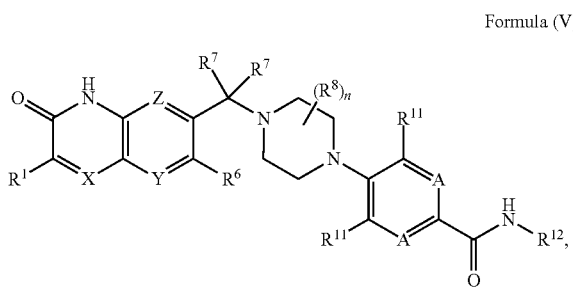

Formula (V)

wherein:
$R^1$ is hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SW, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;
X is N or CR$^2$;
$R^2$ is hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;
or $R^1$ and $R^2$ are taken together to form a cycloalkyl, heterocycloalkyl, aryl, or heteroaryl; each optionally substituted with deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
Z is N or CR$^4$;
$R^4$ is hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;
Y is N or CR$^5$;
$R^5$ is hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;
$R^6$ is hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;
each $R^7$ is independently hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
or two $R^7$ are taken together to form a cycloalkyl or a heterocycloalkyl; each optionally substituted with deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
each $R^8$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^8$ on the same carbon are taken together to form an oxo;

or two $R^8$ on the same carbon, adjacent carbons, or opposite carbons are taken together to form a cycloalkyl or heterocycloalkyl; each optionally substituted with one or more deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

n is 1-6;

each $R^{11}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

provided that one $R^{11}$ and one $R^8$ are taken together to form a cycloalkyl, heterocycloalkyl, aryl, or heteroaryl; each optionally substituted with one or more deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each A is independently N or CR$^{11}$;

$R^{12}$ is $C_1$-$C_6$alkyl or $C_1$-$C_6$deuteroalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound of Formula (V), $R^1$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkynyl, or cycloalkyl.

In some embodiments of a compound of Formula (V), $R^1$ is $C_1$-$C_6$alkyl.

In some embodiments of a compound of Formula (V), X is N and Y is CR$^5$.

In some embodiments of a compound of Formula (V), $R^5$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (V), $R^5$ is hydrogen, deuterium, halogen, or $C_1$-$C_6$alkyl. In some embodiments of a compound of Formula (V), $R^5$ is hydrogen.

In some embodiments of a compound of Formula (V), X is CR$^2$ and Y is N.

In some embodiments of a compound of Formula (V), $R^2$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (V), $R^2$ is hydrogen, deuterium, halogen, or $C_1$-$C_6$alkyl. In some embodiments of a compound of Formula (V), $R^2$ is hydrogen.

In some embodiments of a compound of Formula (V), X is N and Y is N.

In some embodiments of a compound of Formula (V), Z is N. In some embodiments of a compound of Formula (V), Z is CR$^4$.

In some embodiments of a compound of Formula (V), $R^4$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (V), $R^4$ is hydrogen, deuterium, halogen, or $C_1$-$C_6$alkyl. In some embodiments of a compound of Formula (V), $R^4$ is hydrogen.

In some embodiments of a compound of Formula (V), $R^6$ is hydrogen, deuterium, halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, or cycloalkyl. In some embodiments of a compound of Formula (V), $R^6$ is hydrogen, deuterium, halogen, or $C_1$-$C_6$alkyl. In some embodiments of a compound of Formula (V), $R^6$ is hydrogen.

In some embodiments of a compound of Formula (V), each $R^7$ is independently hydrogen, deuterium, halogen, $C_1$-$C_6$alkyl, or $C_1$-$C_6$haloalkyl. In some embodiments of a compound of Formula (V), each $R^7$ is hydrogen. In some embodiments of a compound of Formula (V), two $R^7$ are taken together to form a cycloalkyl.

In some embodiments of a compound of Formula (V), each $R^8$ is $C_1$-$C_6$alkyl; or two $R^8$ on the same carbon are taken together to form an oxo. In some embodiments of a compound of Formula (V), two $R^8$ on opposite carbons are taken together to form a cycloalkyl. In some embodiments of a compound of Formula (V), two $R^8$ on the same carbon are taken together to form a cycloalkyl. In some embodiments of a compound of Formula (V), two $R^8$ on adjacent carbons are taken together to form a cycloalkyl.

In some embodiments of a compound of Formula (V), n is 0. In some embodiments of a compound of Formula (V), n is 1. In some embodiments of a compound of Formula (V), n is 2. In some embodiments of a compound of Formula (V), n is 3. In some embodiments of a compound of Formula (V), n is 4. In some embodiments of a compound of Formula (V), n is 5. In some embodiments of a compound of Formula (V), n is 6. In some embodiments of a compound of Formula (V), n is 0-3. In some embodiments of a compound of Formula (V), n is 1-3. In some embodiments of a compound of Formula (V), n is 1 or 2. In some embodiments of a compound of Formula (V), n is 1-4. In some embodiments of a compound of Formula (V), n is 2-4.

In some embodiments of a compound of Formula (V), each $R^{11}$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (V), each $R^{11}$ is independently deuterium, halogen, $C_1$-$C_6$alkyl, $C_1$-$C_6$haloalkyl, or $C_1$-$C_6$deuteroalkyl. In some embodiments of a compound of Formula (V), each $R^{11}$ is independently halogen or $C_1$-$C_6$alkyl.

In some embodiments of a compound of Formula (V), one A is $CR^{11}$ and one is N. In some embodiments of a compound of Formula (V), both A are $CR^{11}$. In some embodiments of a compound of Formula (V), both A are N.

In some embodiments of a compound of Formula (V), $R^{12}$ is $C_1$-$C_6$alkyl. In some embodiments of a compound of Formula (V), $R^{12}$ is $C_1$-$C_6$deuteroalkyl.

In some embodiments of a compound of Formula (V), one $R^{11}$ and one $R^8$ are taken together to form a cycloalkyl or heterocycloalkyl; each optionally substituted with one or more deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound of Formula (V), one $R^{11}$ and one $R^8$ are taken together to form a heterocycloalkyl optionally substituted with one or more deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound of Formula (V), one $R^{11}$ and one $R^8$ are taken together to form a 5- or 6-membered heterocycloalkyl optionally substituted with one or more deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound of Formula (V), one $R^{11}$ and one $R^8$ are taken together to form a 6-membered heterocycloalkyl optionally substituted with one or more deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound of Formula (V), one $R^{11}$ and one $R^8$ are taken together to form a 5-membered heterocycloalkyl optionally substituted with one or more deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound of Formula (V), the compound has the following formula:

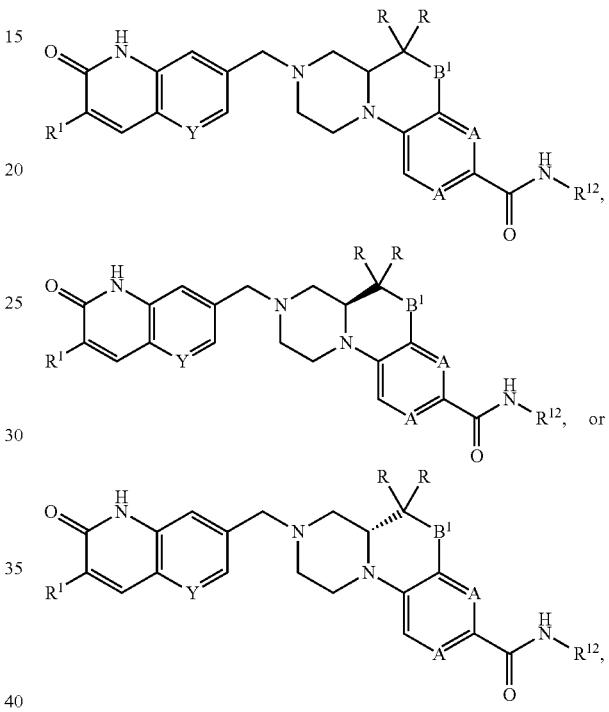

wherein $R^1$ is $C_1$-$C_6$alkyl, $C_1$-$C_6$haloalkyl, or $C_1$-$C_6$deuteroalkyl; Y is N, CH, or CF; each A is independently CH, CD, CMe, $CCF_3$, CCl, CF, or N; $B^1$ is O, S, NH, NMe, $NCD_3$, $CH_2$, CHF, $CD_2$, or CDH; R is hydrogen, deuterium, or halogen; and $R^{12}$ is $C_1$-$C_6$alkyl or $C_1$-$C_6$deuteroalkyl.

In some embodiments of a compound disclosed herein, each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^a$ is independently $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —$OCH_3$, —S(=O)$CH_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl. In some embodiments of a compound disclosed herein, each R$^a$ is independently C$_1$-C$_6$alkyl, C$_1$-C$_6$haloalkyl, cycloalkyl, or heterocycloalkyl. In some embodiments of a compound disclosed herein, each R$^a$ is independently C$_1$-C$_6$alkyl or C$_1$-C$_6$haloalkyl. In some embodiments of a compound disclosed herein, each R$^a$ is independently C$_1$-C$_6$alkyl.

In some embodiments of a compound disclosed herein, each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl. In some embodiments of a compound disclosed herein, each R$^b$ is independently hydrogen, C$_1$-C$_6$alkyl, C$_1$-C$_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl. In some embodiments of a compound disclosed herein, each R$^b$ is independently hydrogen, C$_1$-C$_6$alkyl, C$_1$-C$_6$haloalkyl, cycloalkyl, or heterocycloalkyl. In some embodiments of a compound disclosed herein, each R$^b$ is independently hydrogen, C$_1$-C$_6$alkyl, or C$_1$-C$_6$haloalkyl. In some embodiments of a compound disclosed herein, each R$^b$ is independently hydrogen or C$_1$-C$_6$alkyl.

In some embodiments of a compound disclosed herein, each R$^c$ and R$^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl. In some embodiments of a compound disclosed herein, each R$^c$ and R$^d$ are independently hydrogen, C$_1$-C$_6$alkyl, C$_1$-C$_6$haloalkyl, cycloalkyl, or heterocycloalkyl. In some embodiments of a compound disclosed herein, each R$^c$ and R$^d$ are independently hydrogen, C$_1$-C$_6$alkyl, or C$_1$-C$_6$haloalkyl. In some embodiments of a compound disclosed herein, each R$^c$ and R$^d$ are independently hydrogen or C$_1$-C$_6$alkyl.

In some embodiments of a compound disclosed herein, R$^c$ and R$^d$ are taken together with the atom to which they are attached to form a heterocycloalkyl optionally substituted with one or more oxo, deuterium, halogen, —CN, —OH, —OCH$_3$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

In some embodiments of a compound disclosed herein, each R$^A$, R$^B$, R$^C$, R$^a$, R$^b$, R$^c$, R$^d$, the cycloalkyl or heterocycloalkyl formed when 2 R$^7$ are taken together, the cycloalkyl or heterocycloalkyl formed when 2 R$^8$ are taken together, and the heterocycloalkyl formed when R$^c$ and R$^d$ are taken together, is independently substituted with one, two, three, or four substituents as defined herein. In some embodiments of a compound disclosed herein, each R$^A$, R$^B$, R$^C$, R$^a$, R$^b$, R$^c$, R$^d$, the cycloalkyl or heterocycloalkyl formed when 2 R$^7$ are taken together, the cycloalkyl or heterocycloalkyl formed when 2 R$^8$ are taken together, and the heterocycloalkyl formed when R$^c$ and R$^d$ are taken together, is independently substituted with one, two, or three substituents as defined herein. In some embodiments of a compound disclosed herein, each R$^A$, R$^B$, R$^C$, R$^a$, R$^b$, R$^c$, R$^d$, the cycloalkyl or heterocycloalkyl formed when 2 R$^7$ are taken together, the cycloalkyl or heterocycloalkyl formed when 2 R$^8$ are taken together, and the heterocycloalkyl formed when R$^c$ and R$^d$ are taken together, is independently substituted with one or two substituents as defined herein. In some embodiments of a compound disclosed herein, each R$^A$, R$^B$, R$^C$, R$^a$, R$^b$, R$^c$, R$^d$, the cycloalkyl or heterocycloalkyl formed when 2 R$^7$ are taken together, the cycloalkyl or heterocycloalkyl formed when 2 R$^8$ are taken together, and the heterocycloalkyl formed when R$^c$ and R$^d$ are taken together, is independently substituted with one substituent as defined herein.

Any combination of the groups described above for the various variables is contemplated herein. Throughout the specification, groups and substituents thereof are chosen by one skilled in the field to provide stable moieties and compounds.

In some embodiments, the compound disclosed herein, or a pharmaceutically acceptable salt, solvate, or stereoisomer thereof, is selected from a compound of Table 1.

TABLE 1
| Ex. | Structure |
|---|---|
| 1 | 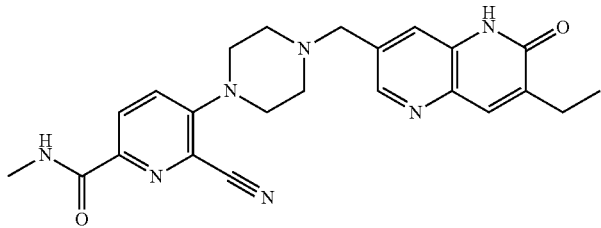 [SMILES: CCc1cc2ncc(CN3CCN(c4ccc(C(=O)NC)nc4C#N)CC3)cc2[nH]c1=O] |
| 2 | 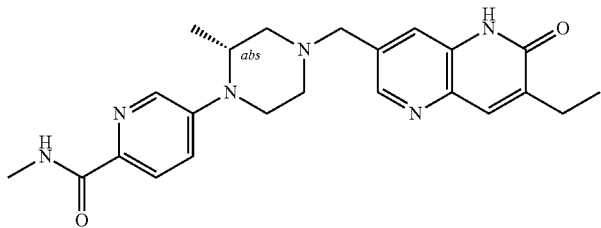 [SMILES: CCc1cc2ncc(CN3CCN(c4ccc(C(=O)NC)nc4)[C@H](C)C3)cc2[nH]c1=O] |
| 3A | 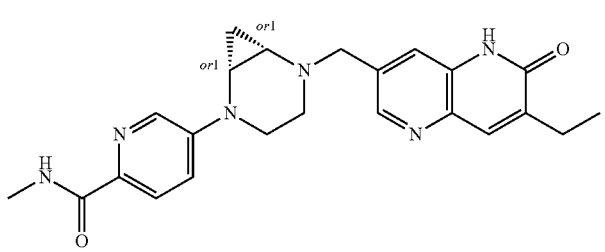 [SMILES: CCc1cc2ncc(CN3CCN(c4ccc(C(=O)NC)nc4)[C@@H]4C[C@@H]43)cc2[nH]c1=O] |
| 3B | 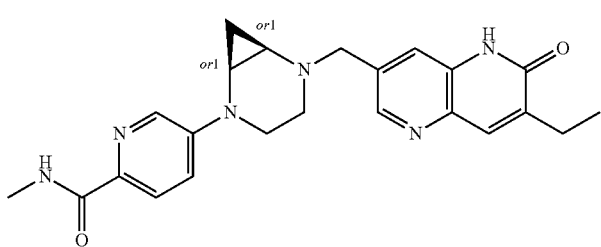 [SMILES: CCc1cc2ncc(CN3CCN(c4ccc(C(=O)NC)nc4)[C@H]4C[C@H]43)cc2[nH]c1=O] |
| 4 | 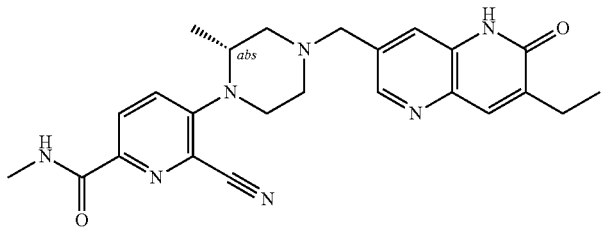 [SMILES: CCc1cc2ncc(CN3CCN(c4ccc(C(=O)NC)nc4C#N)[C@H](C)C3)cc2[nH]c1=O] |
| 5 | 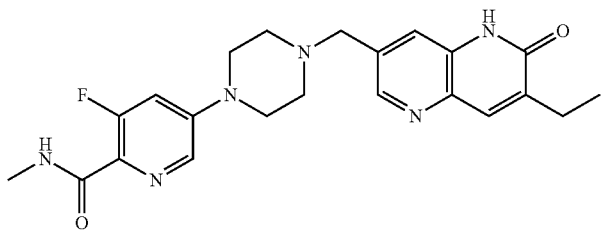 [SMILES: CCc1cc2ncc(CN3CCN(c4cnc(C(=O)NC)c(F)c4)CC3)cc2[nH]c1=O] |

TABLE 1-continued
| Ex. | Structure |
|---|---|
| 6 | 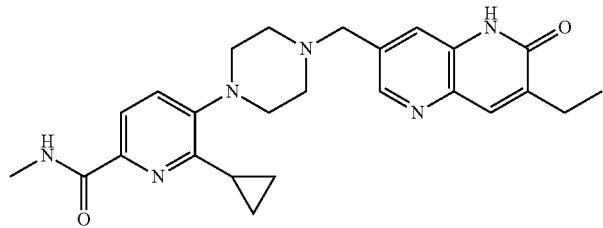 [SMILES: CCc1cc2ncc(CN3CCN(c4ccc(C(=O)NC)nc4C4CC4)CC3)cc2[nH]c1=O] |
| 7 | 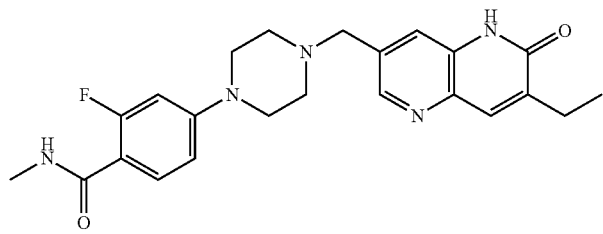 [SMILES: CCc1cc2ncc(CN3CCN(c4ccc(C(=O)NC)c(F)c4)CC3)cc2[nH]c1=O] |
| 8 | 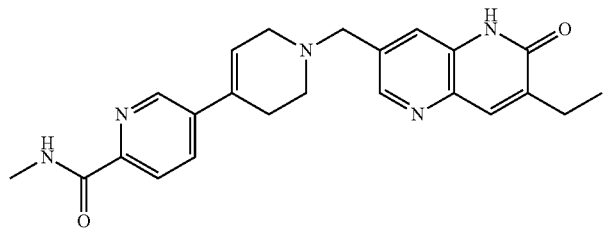 [SMILES: CCc1cc2ncc(CN3CC=C(c4ccc(C(=O)NC)nc4)CC3)cc2[nH]c1=O] |
| 9 | 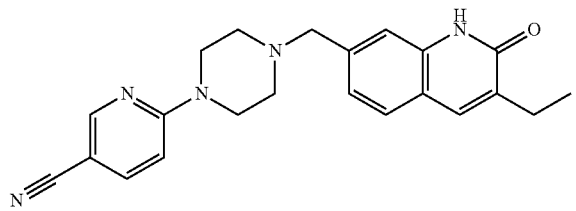 [SMILES: CCc1cc2ccc(CN3CCN(c4ccc(C#N)cn4)CC3)cc2[nH]c1=O] |
| 10 | 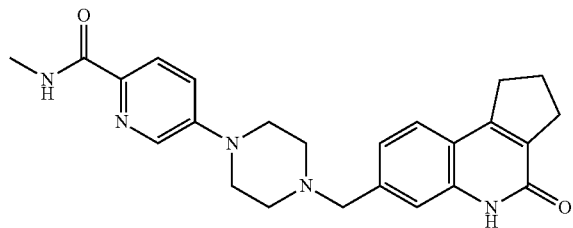 [SMILES: CNC(=O)c1ccc(N2CCN(Cc3ccc4c5c(c(=O)[nH]c4c3)CCC5)CC2)cn1] |
| 11 | 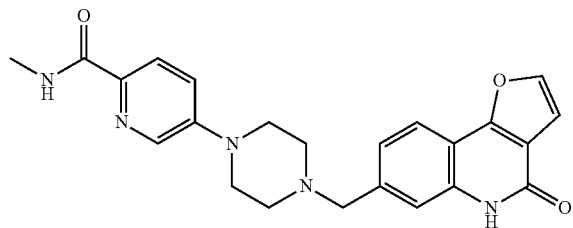 [SMILES: CNC(=O)c1ccc(N2CCN(Cc3ccc4c(c3)[nH]c(=O)c3ccoc34)CC2)cn1] |

TABLE 1-continued
| Ex. | Structure |
|---|---|
| 12 | 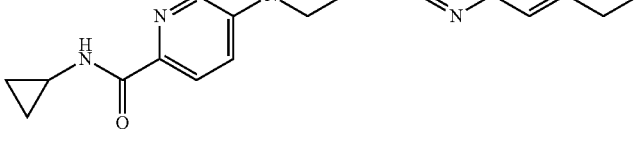 |
| 13 | 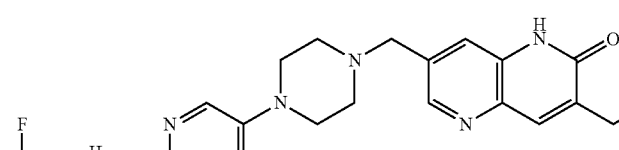 |
| 14 | 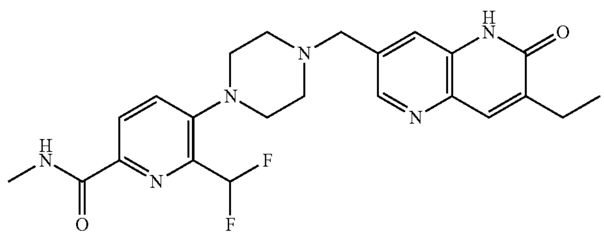 [SMILES: CCc1cc2ncc(CN3CCN(c4ccc(C(=O)NC)nc4C(F)F)CC3)cc2[nH]c1=O] |
| 15 | 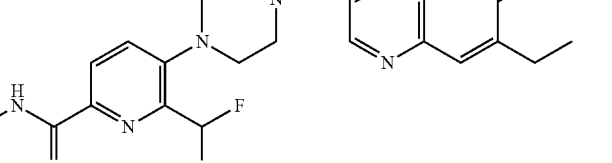 |
| 16 | 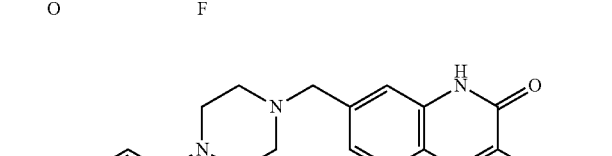 |
| 17 | 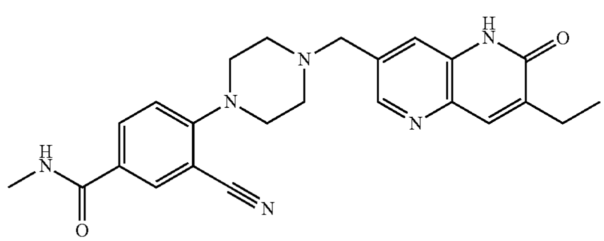 [SMILES: CCc1cc2ncc(CN3CCN(c4ccc(C(=O)NC)cc4C#N)CC3)cc2[nH]c1=O] |

TABLE 1-continued
| Ex. | Structure |
|---|---|
| 18 | 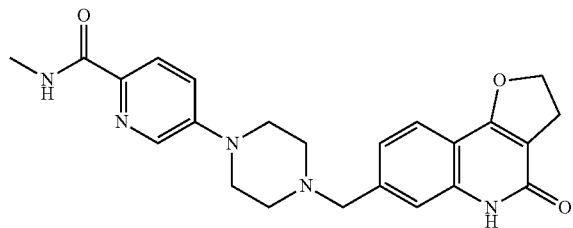 |
| 19 | 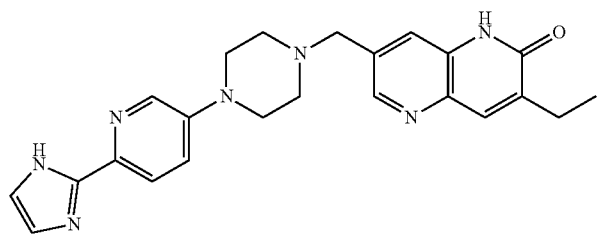 [SMILES: CCc1cc2ncc(CN3CCN(c4ccc(-c5ncc[nH]5)nc4)CC3)cc2[nH]c1=O] |
| 20 | 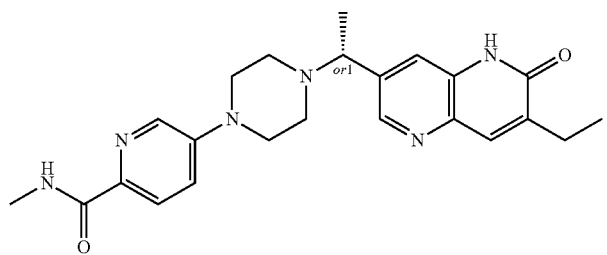 [SMILES: CCc1cc2ncc([C@@H](C)N3CCN(c4ccc(C(=O)NC)nc4)CC3)cc2[nH]c1=O] |
| 21 | 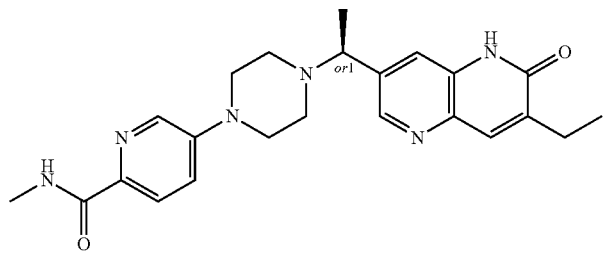 [SMILES: CCc1cc2ncc([C@H](C)N3CCN(c4ccc(C(=O)NC)nc4)CC3)cc2[nH]c1=O] |
| 22A | 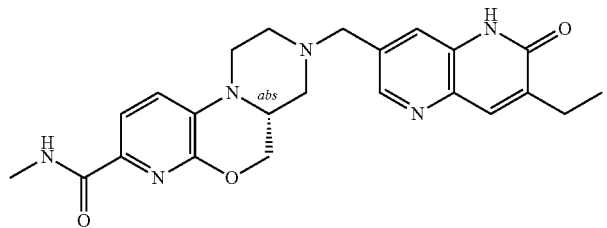 [SMILES: CCc1cc2ncc(CN3CCN4c5ccc(C(=O)NC)nc5OC[C@H]4C3)cc2[nH]c1=O] |
| 22B | 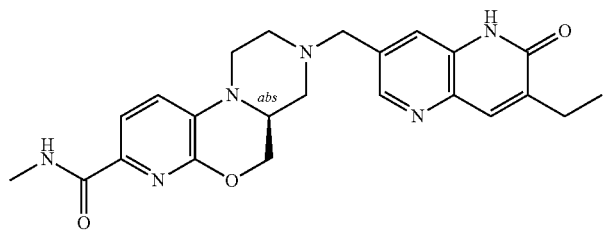 [SMILES: CCc1cc2ncc(CN3CCN4c5ccc(C(=O)NC)nc5OC[C@@H]4C3)cc2[nH]c1=O] |

TABLE 1-continued
| Ex. | Structure |
|---|---|
| 23 | 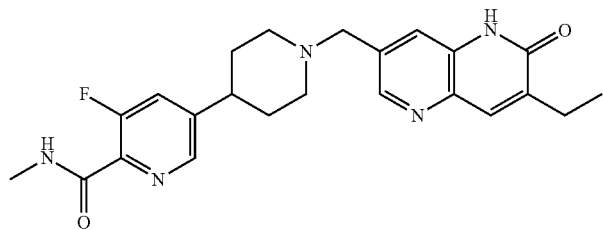 [SMILES: CCc1cc2ncc(CN3CCC(c4cnc(C(=O)NC)c(F)c4)CC3)cc2[nH]c1=O] |
| 24 | 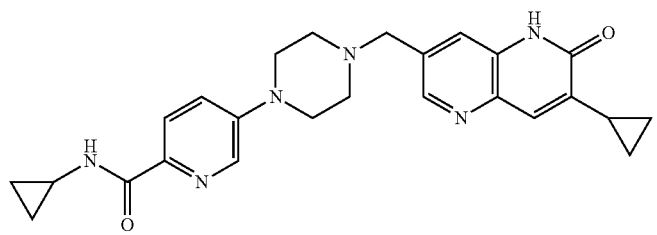 [SMILES: O=C(NC1CC1)c1ccc(N2CCN(Cc3cnc4cc(C5CC5)c(=O)[nH]c4c3)CC2)cn1] |
| 25 | 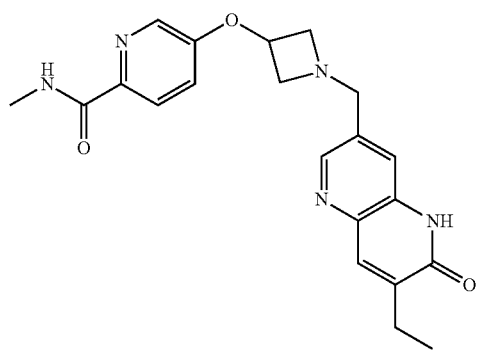 [SMILES: CCc1cc2ncc(CN3CC(Oc4ccc(C(=O)NC)nc4)C3)cc2[nH]c1=O] |
| 26 | 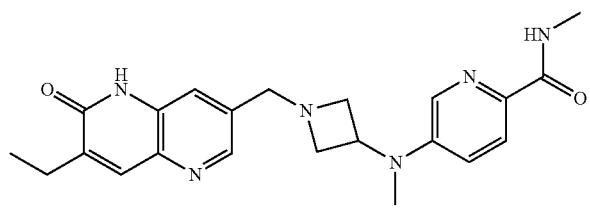 [SMILES: CCc1cc2ncc(CN3CC(N(C)c4ccc(C(=O)NC)nc4)C3)cc2[nH]c1=O] |
| 27 | 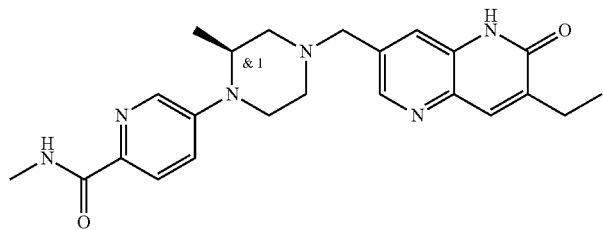 [SMILES: CCc1cc2ncc(CN3CCN(c4ccc(C(=O)NC)nc4)[C@@H](C)C3)cc2[nH]c1=O] |
| 28 | 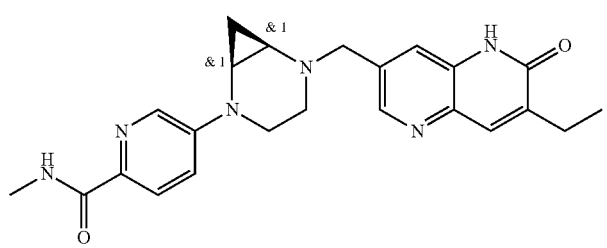 [SMILES: CCc1cc2ncc(CN3CCN(c4ccc(C(=O)NC)nc4)[C@H]4C[C@H]43)cc2[nH]c1=O] |

TABLE 1-continued
| Ex. | Structure |
|---|---|
| 29 | 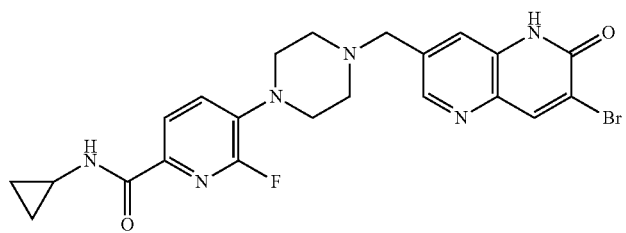 [SMILES: O=C(NC1CC1)c1ccc(N2CCN(Cc3cnc4cc(Br)c(=O)[nH]c4c3)CC2)c(F)n1] |
| 30 | 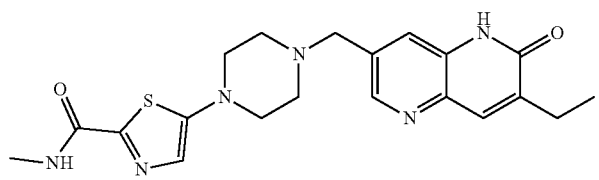 [SMILES: CCc1cc2ncc(CN3CCN(c4cnc(C(=O)NC)s4)CC3)cc2[nH]c1=O] |
| 31 | 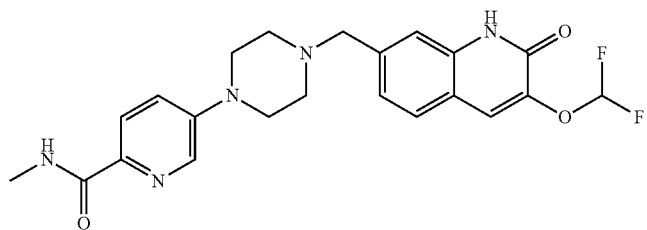 [SMILES: CNC(=O)c1ccc(N2CCN(Cc3ccc4cc(OC(F)F)c(=O)[nH]c4c3)CC2)cn1] |
| 32 | 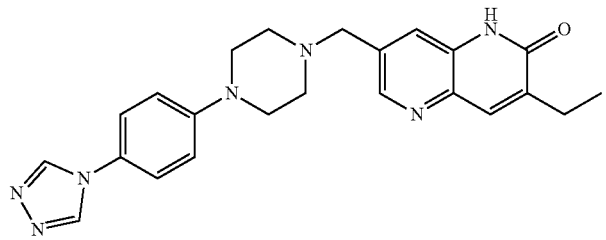 [SMILES: CCc1cc2ncc(CN3CCN(c4ccc(-n5cnnc5)cc4)CC3)cc2[nH]c1=O] |
| 33 | 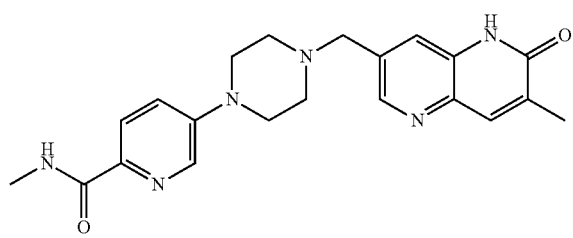 |
| 34 | 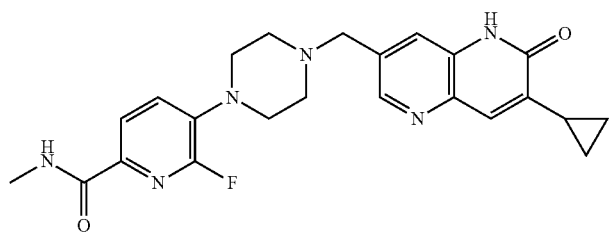 [SMILES: CNC(=O)c1ccc(N2CCN(Cc3cnc4cc(C5CC5)c(=O)[nH]c4c3)CC2)c(F)n1] |

TABLE 1-continued
| Ex. | Structure |
|---|---|
| 35 | 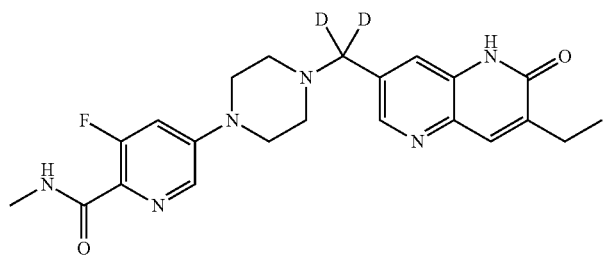 [SMILES: [2H]C([2H])(c1cnc2cc(CC)c(=O)[nH]c2c1)N1CCN(c2cnc(C(=O)NC)c(F)c2)CC1] |
| 36 | 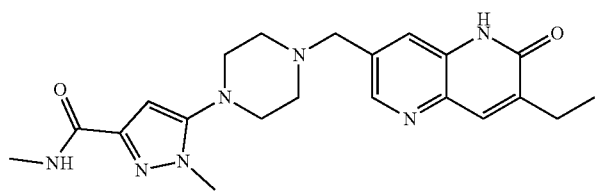 [SMILES: CCc1cc2ncc(CN3CCN(c4cc(C(=O)NC)nn4C)CC3)cc2[nH]c1=O] |
| 37 | 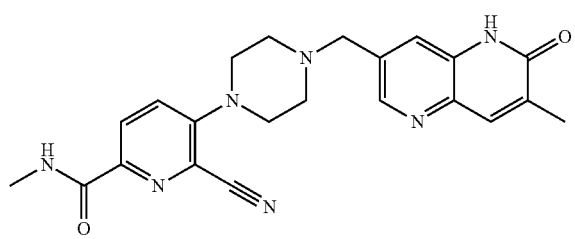 |
| 38 | 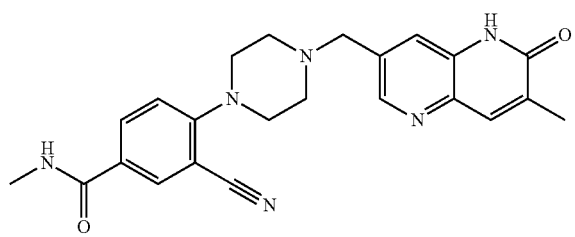 |
| 39 | 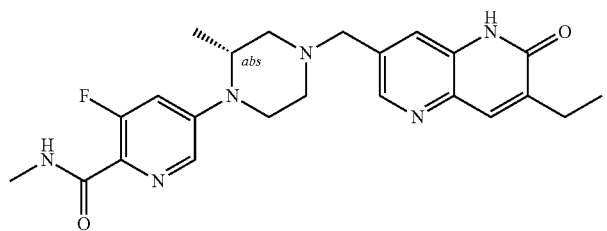 [SMILES: CCc1cc2ncc(CN3CCN(c4cnc(C(=O)NC)c(F)c4)[C@H](C)C3)cc2[nH]c1=O] |
| 40 | 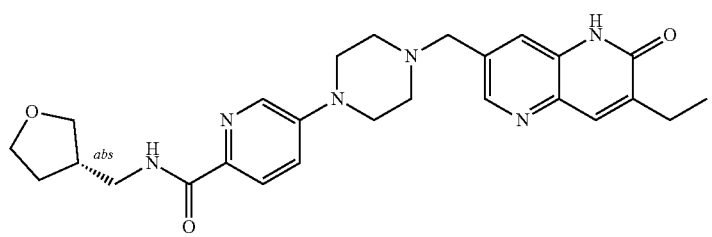 [SMILES: CCc1cc2ncc(CN3CCN(c4ccc(C(=O)NC[C@@H]5CCOC5)nc4)CC3)cc2[nH]c1=O] |

TABLE 1-continued
| Ex. | Structure |
|---|---|
| 41 | 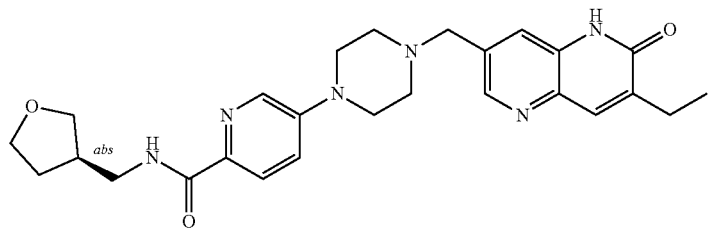 [SMILES: CCc1cc2ncc(CN3CCN(c4ccc(C(=O)NC[C@H]5CCOC5)nc4)CC3)cc2[nH]c1=O] |
| 42 | 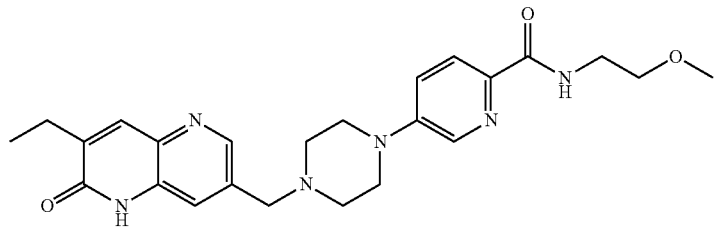 [SMILES: CCc1cc2ncc(CN3CCN(c4ccc(C(=O)NCCOC)nc4)CC3)cc2[nH]c1=O] |
| 43 | 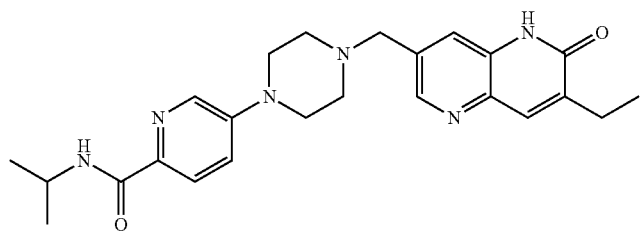 [SMILES: CCc1cc2ncc(CN3CCN(c4ccc(C(=O)NC(C)C)nc4)CC3)cc2[nH]c1=O] |
| 44 | 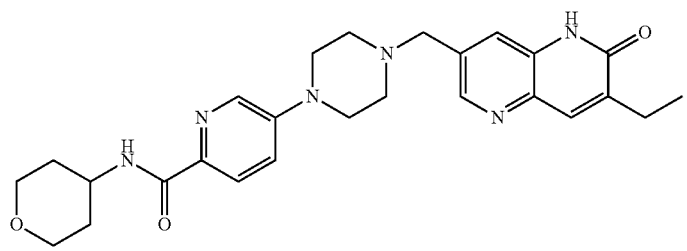 [SMILES: CCc1cc2ncc(CN3CCN(c4ccc(C(=O)NC5CCOCC5)nc4)CC3)cc2[nH]c1=O] |
| 45 | 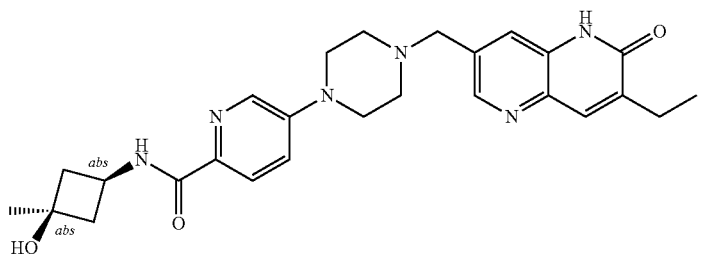 [SMILES: CCc1cc2ncc(CN3CCN(c4ccc(C(=O)N[C@H]5C[C@@](C)(O)C5)nc4)CC3)cc2[nH]c1=O] |
| 46 | 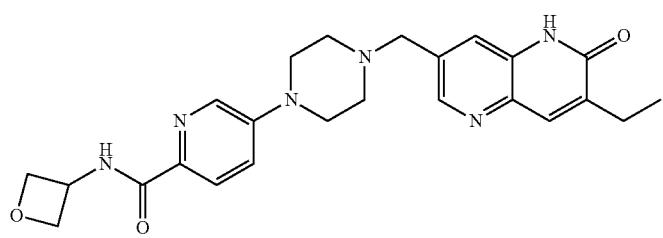 [SMILES: CCc1cc2ncc(CN3CCN(c4ccc(C(=O)NC5COC5)nc4)CC3)cc2[nH]c1=O] |

TABLE 1-continued
| Ex. | Structure |
|---|---|
| 47 | 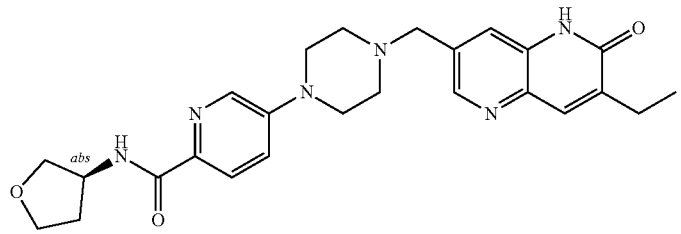 [SMILES: CCc1cc2ncc(CN3CCN(c4ccc(C(=O)N[C@H]5CCOC5)nc4)CC3)cc2[nH]c1=O] |
| 48 | 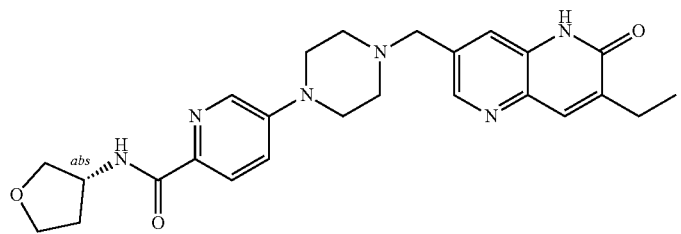 [SMILES: CCc1cc2ncc(CN3CCN(c4ccc(C(=O)N[C@@H]5CCOC5)nc4)CC3)cc2[nH]c1=O] |
| 49 | 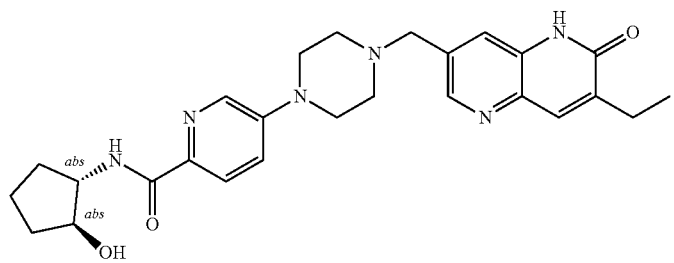 [SMILES: CCc1cc2ncc(CN3CCN(c4ccc(C(=O)N[C@H]5CCC[C@@H]5O)nc4)CC3)cc2[nH]c1=O] |
| 50 | 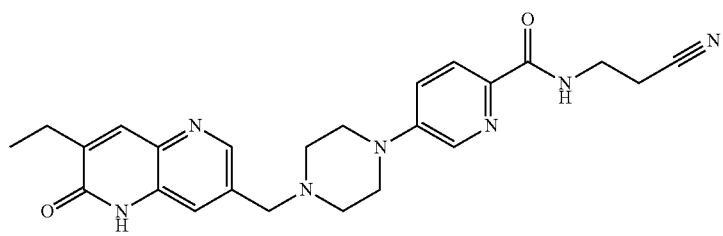 [SMILES: CCc1cc2ncc(CN3CCN(c4ccc(C(=O)NCCC#N)nc4)CC3)cc2[nH]c1=O] |
| 51 | 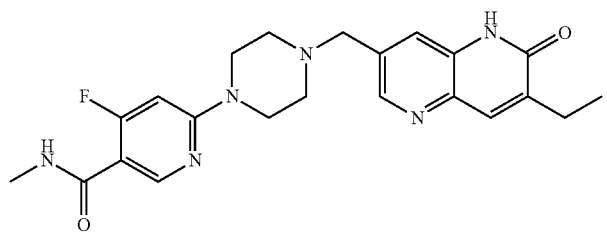 [SMILES: CCc1cc2ncc(CN3CCN(c4cc(F)c(C(=O)NC)cn4)CC3)cc2[nH]c1=O] |
| 52 | 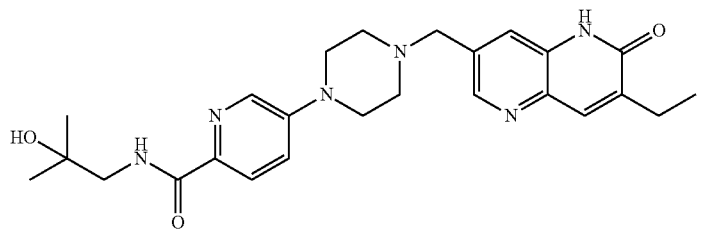 [SMILES: CCc1cc2ncc(CN3CCN(c4ccc(C(=O)NCC(C)(C)O)nc4)CC3)cc2[nH]c1=O] |

TABLE 1-continued
| Ex. | Structure |
|---|---|
| 53 | 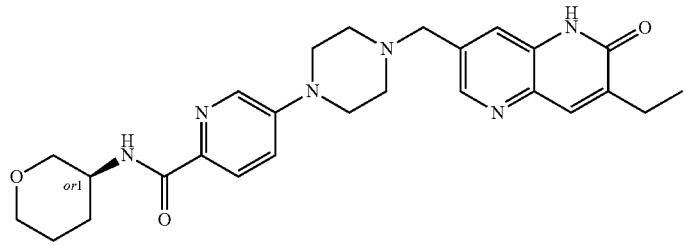 [SMILES: CCc1cc2ncc(CN3CCN(c4ccc(C(=O)N[C@H]5CCCOC5)nc4)CC3)cc2[nH]c1=O] |
| 54 | 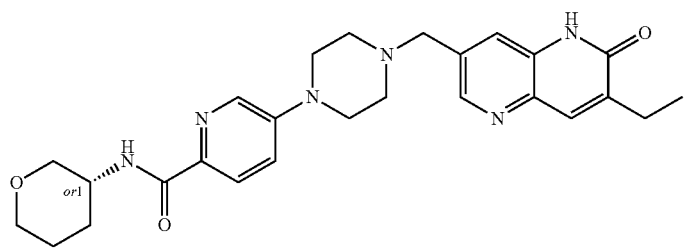 [SMILES: CCc1cc2ncc(CN3CCN(c4ccc(C(=O)N[C@@H]5CCCOC5)nc4)CC3)cc2[nH]c1=O] |
| 55 | 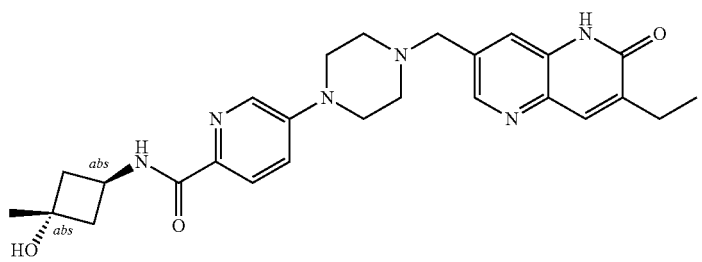 [SMILES: CCc1cc2ncc(CN3CCN(c4ccc(C(=O)N[C@H]5C[C@](C)(O)C5)nc4)CC3)cc2[nH]c1=O] |
| 56 | 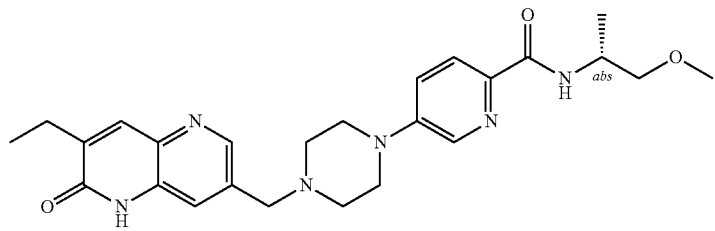 [SMILES: CCc1cc2ncc(CN3CCN(c4ccc(C(=O)N[C@H](C)COC)nc4)CC3)cc2[nH]c1=O] |
| 57 | 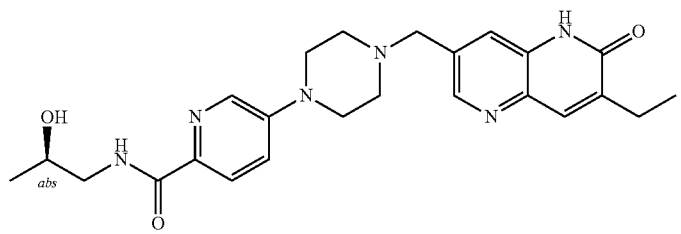 [SMILES: CCc1cc2ncc(CN3CCN(c4ccc(C(=O)NC[C@@H](C)O)nc4)CC3)cc2[nH]c1=O] |
| 58 | 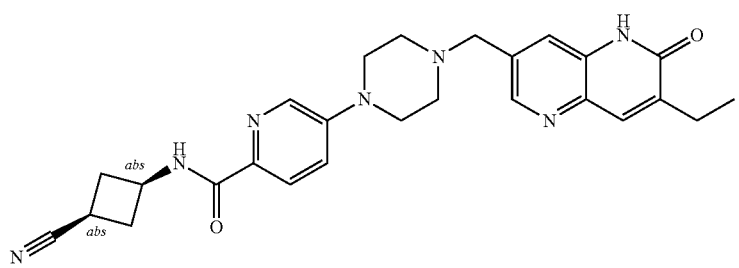 [SMILES: CCc1cc2ncc(CN3CCN(c4ccc(C(=O)N[C@H]5C[C@@H](C#N)C5)nc4)CC3)cc2[nH]c1=O] |

TABLE 1-continued
| Ex. | Structure |
|---|---|
| 59 | 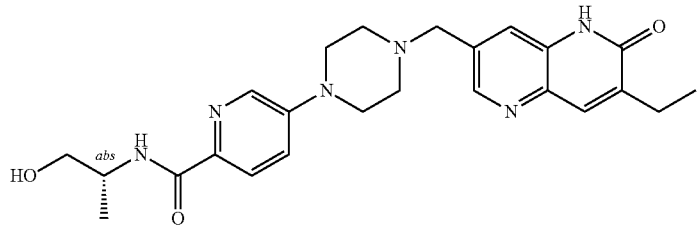 [SMILES: CCc1cc2ncc(CN3CCN(c4ccc(C(=O)N[C@H](C)CO)nc4)CC3)cc2[nH]c1=O] |
| 60 | 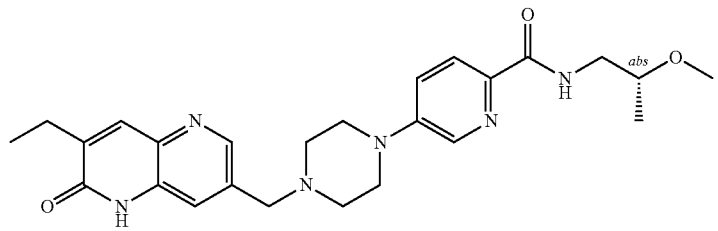 [SMILES: CCc1cc2ncc(CN3CCN(c4ccc(C(=O)NC[C@@H](C)OC)nc4)CC3)cc2[nH]c1=O] |
| 61 | 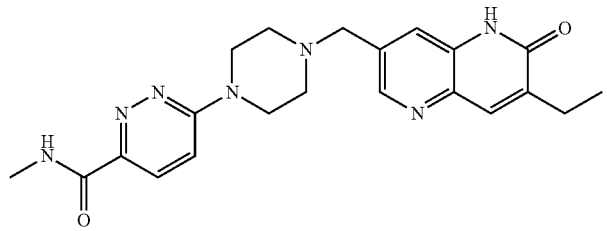 [SMILES: CCc1cc2ncc(CN3CCN(c4ccc(C(=O)NC)nn4)CC3)cc2[nH]c1=O] |
| 62 | 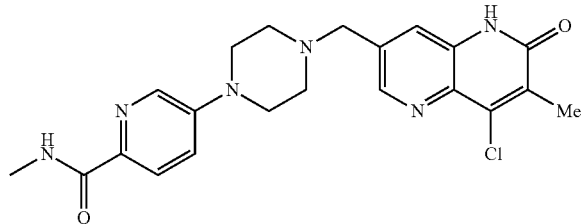 [SMILES: CNC(=O)c1ccc(N2CCN(Cc3cnc4c(Cl)c(C)c(=O)[nH]c4c3)CC2)cn1] |
| 63 | 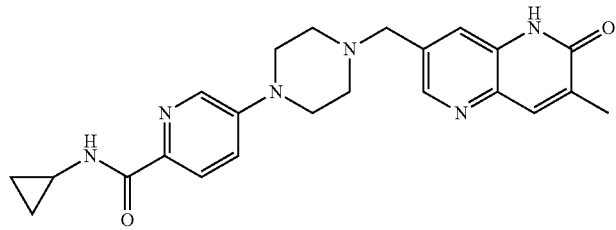 [SMILES: Cc1cc2ncc(CN3CCN(c4ccc(C(=O)NC5CC5)nc4)CC3)cc2[nH]c1=O] |
| 64 | 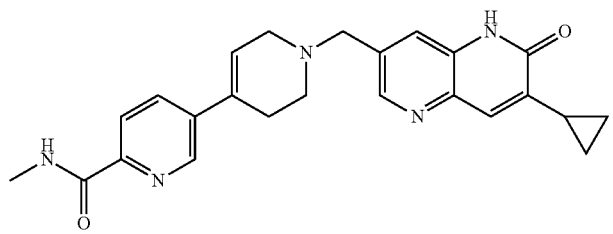 [SMILES: CNC(=O)c1ccc(C2=CCN(Cc3cnc4cc(C5CC5)c(=O)[nH]c4c3)CC2)cn1] |

TABLE 1-continued
| Ex. | Structure |
|---|---|
| 65 | 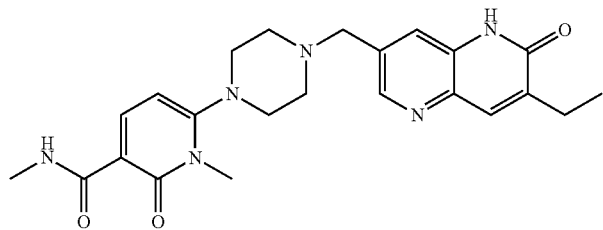 [SMILES: CCc1cc2ncc(CN3CCN(c4ccc(C(=O)NC)c(=O)n4C)CC3)cc2[nH]c1=O] |
| 66 | 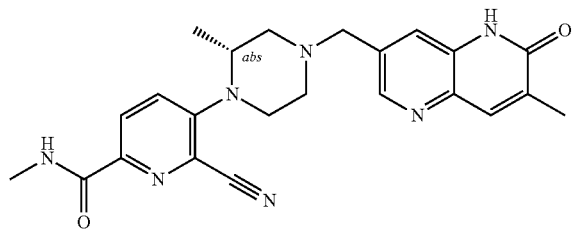 |
| 67 | 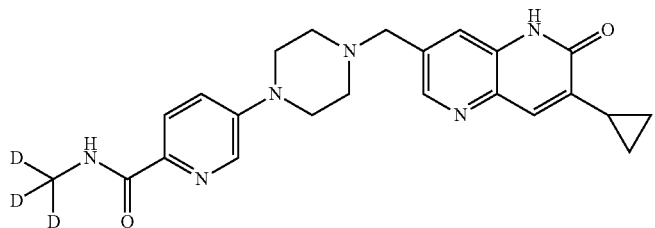 [SMILES: [2H]C([2H])([2H])NC(=O)c1ccc(N2CCN(Cc3cnc4cc(C5CC5)c(=O)[nH]c4c3)CC2)cn1] |
| 68 | 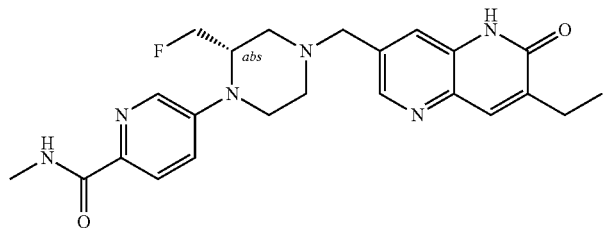 [SMILES: CCc1cc2ncc(CN3CCN(c4ccc(C(=O)NC)nc4)[C@H](CF)C3)cc2[nH]c1=O] |
| 69 | 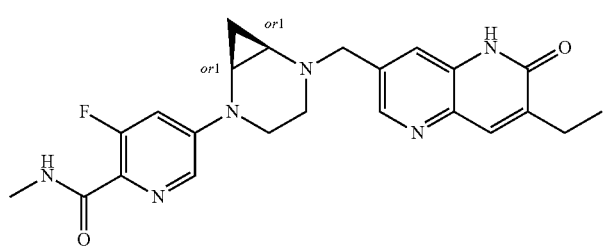 [SMILES: CCc1cc2ncc(CN3CCN(c4cnc(C(=O)NC)c(F)c4)[C@H]4C[C@H]43)cc2[nH]c1=O] |
| 70 | 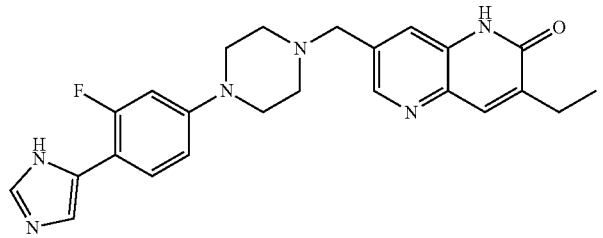 [SMILES: CCc1cc2ncc(CN3CCN(c4ccc(-c5cnc[nH]5)c(F)c4)CC3)cc2[nH]c1=O] |

TABLE 1-continued

| Ex. | Structure |
|---|---|
| 71 | 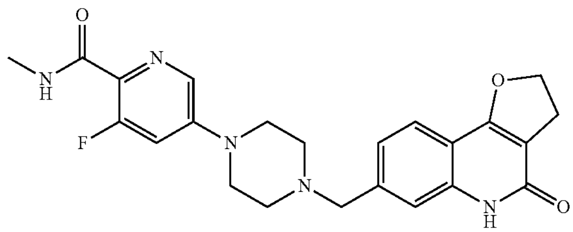 [SMILES: CNC(=O)c1ncc(N2CCN(Cc3ccc4c5c(c(=O)[nH]c4c3)CCO5)CC2)cc1F] |
| 72 | 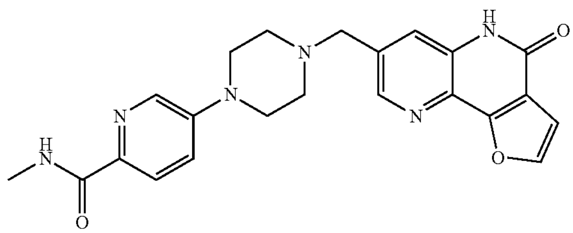 [SMILES: CNC(=O)c1ccc(N2CCN(Cc3cnc4c(c3)[nH]c(=O)c3ccoc34)CC2)cn1] |
| 73 | 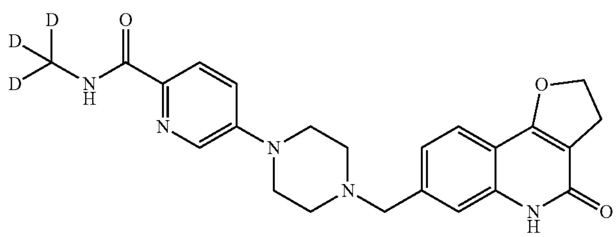 [SMILES: [2H]C([2H])([2H])NC(=O)c1ccc(N2CCN(Cc3ccc4c5c(c(=O)[nH]c4c3)CCO5)CC2)cn1] |
| 74 | 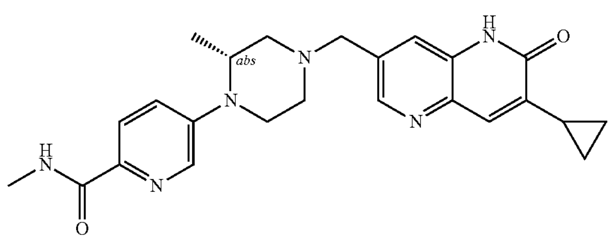 [SMILES: CNC(=O)c1ccc(N2CCN(Cc3cnc4cc(C5CC5)c(=O)[nH]c4c3)C[C@H]2C)cn1] |
| 75 | 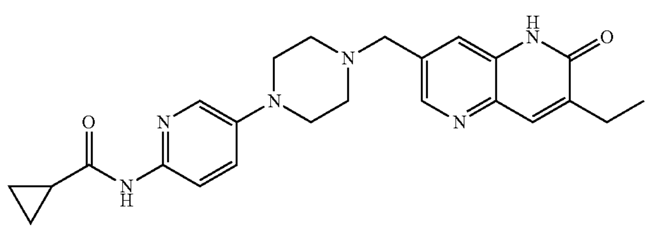 [SMILES: CCc1cc2ncc(CN3CCN(c4ccc(NC(=O)C5CC5)nc4)CC3)cc2[nH]c1=O] |
| 76 | 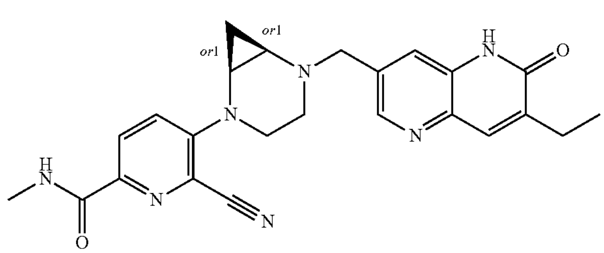 [SMILES: CCc1cc2ncc(CN3CCN(c4ccc(C(=O)NC)nc4C#N)[C@H]4C[C@H]43)cc2[nH]c1=O] |

TABLE 1-continued
| Ex. | Structure |
|---|---|
| 77 | 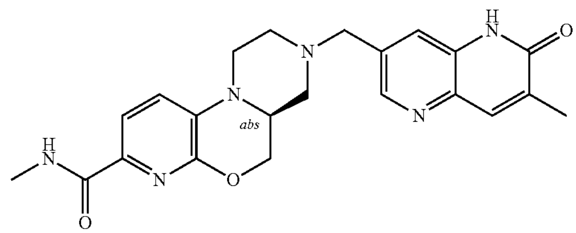 |
| 78 | 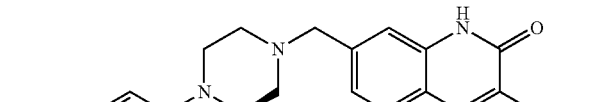 |
| 79 | 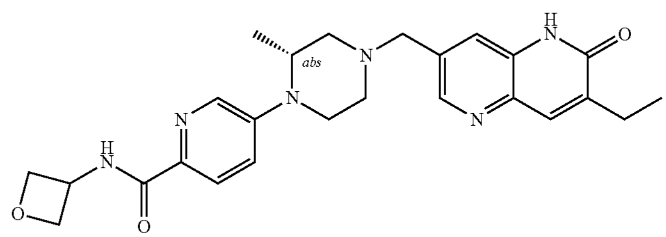 [SMILES: CCc1cc2ncc(CN3CCN(c4ccc(C(=O)NC5COC5)nc4)[C@H](C)C3)cc2[nH]c1=O] |
| 80 | 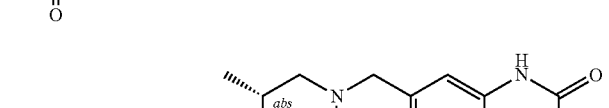 |
| 81 | 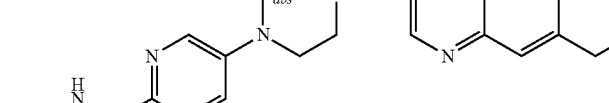 |
| 82 | 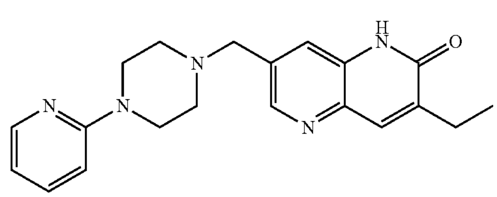 [SMILES: CCc1cc2ncc(CN3CCN(c4ccccn4)CC3)cc2[nH]c1=O] |
| 83 | 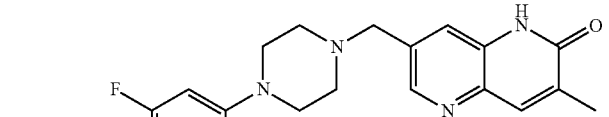 |

TABLE 1-continued
| Ex. | Structure |
|---|---|
| 84 | 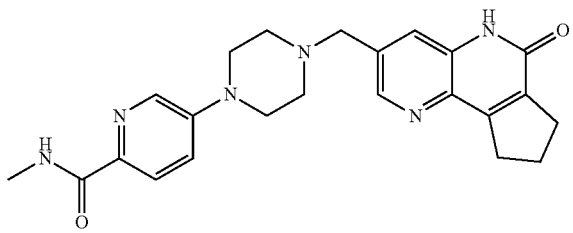 [SMILES: CNC(=O)c1ccc(N2CCN(Cc3cnc4c5c(c(=O)[nH]c4c3)CCC5)CC2)cn1] |
| 85 | 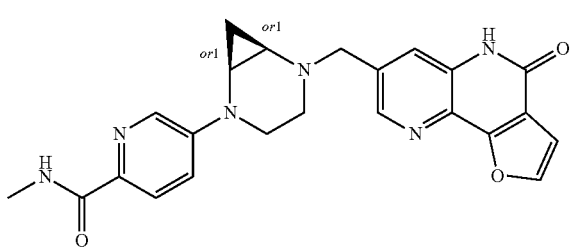 [SMILES: CNC(=O)c1ccc(N2CCN(Cc3cnc4c(c3)[nH]c(=O)c3ccoc34)[C@@H]3C[C@@H]32)cn1] |
| 86 | 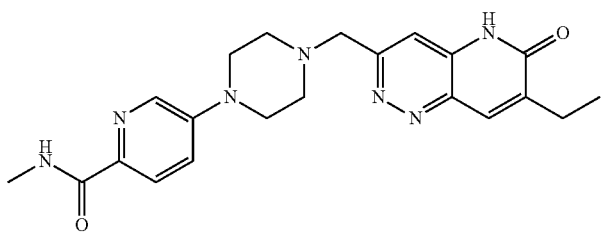 [SMILES: CCc1cc2nnc(CN3CCN(c4ccc(C(=O)NC)nc4)CC3)cc2[nH]c1=O] |
| 87 | 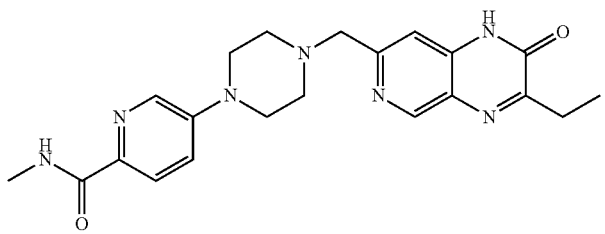 [SMILES: CCc1nc2cnc(CN3CCN(c4ccc(C(=O)NC)nc4)CC3)cc2[nH]c1=O] |
| 88 | 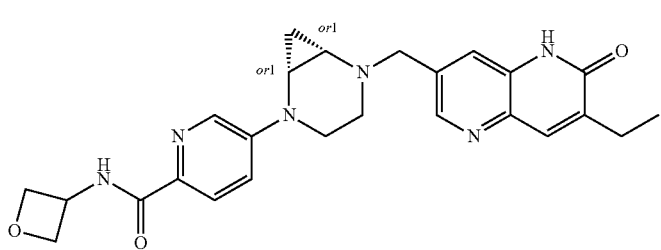 [SMILES: CCc1cc2ncc(CN3CCN(c4ccc(C(=O)NC5COC5)nc4)[C@@H]4C[C@@H]43)cc2[nH]c1=O] |
| 89 | 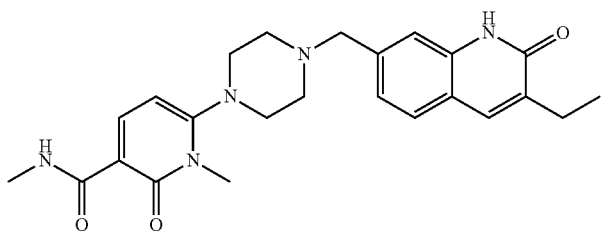 [SMILES: CCc1cc2ccc(CN3CCN(c4ccc(C(=O)NC)c(=O)n4C)CC3)cc2[nH]c1=O] |

TABLE 1-continued
| Ex. | Structure |
|---|---|
| 90 | 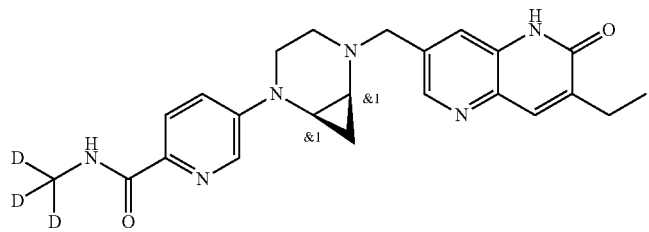 [SMILES: [2H]C([2H])([2H])NC(=O)c1ccc(N2CCN(Cc3cnc4cc(CC)c(=O)[nH]c4c3)[C@H]3C[C@H]32)cn1] |
| 91 | 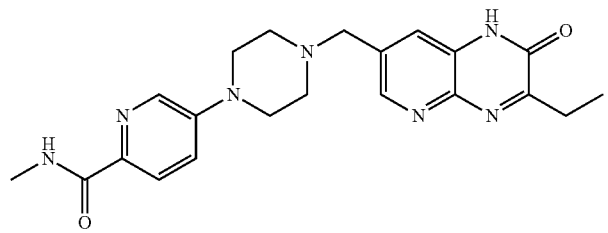 [SMILES: CCc1nc2ncc(CN3CCN(c4ccc(C(=O)NC)nc4)CC3)cc2[nH]c1=O] |
| 92 | 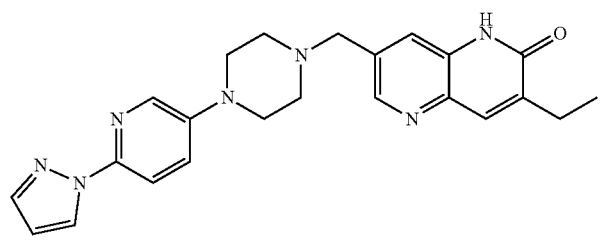 [SMILES: CCc1cc2ncc(CN3CCN(c4ccc(-n5cccn5)nc4)CC3)cc2[nH]c1=O] |
| 93 | 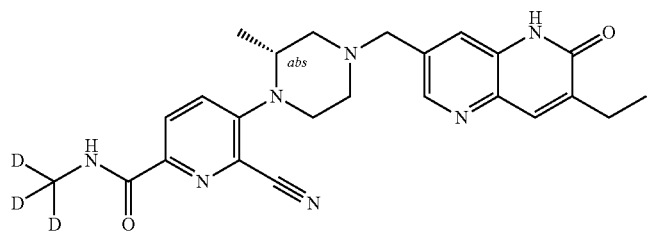 [SMILES: [2H]C([2H])([2H])NC(=O)c1ccc(N2CCN(Cc3cnc4cc(CC)c(=O)[nH]c4c3)C[C@H]2C)c(C#N)n1] |
| 94 | 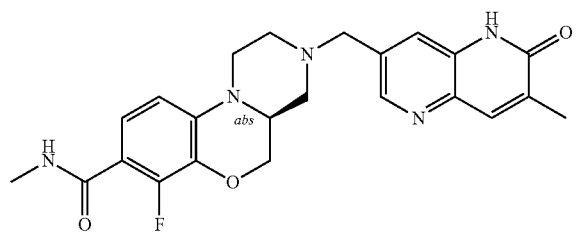 |
| 95 | 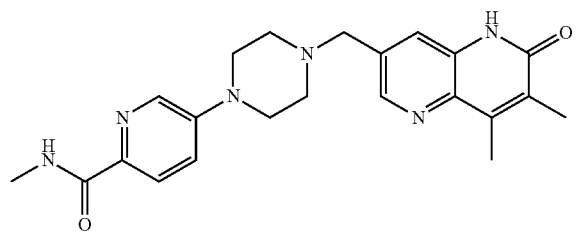 |

TABLE 1-continued
| Ex. | Structure |
|---|---|
| 96 | 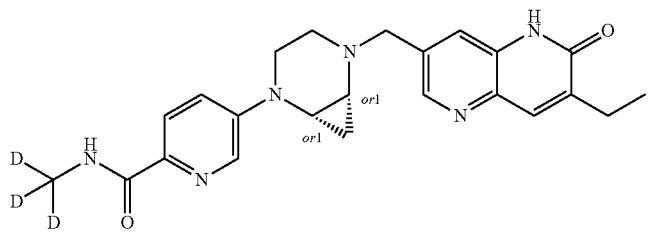 [SMILES: [2H]C([2H])([2H])NC(=O)c1ccc(N2CCN(Cc3cnc4cc(CC)c(=O)[nH]c4c3)[C@@H]3C[C@@H]32)cn1] |
| 97 | 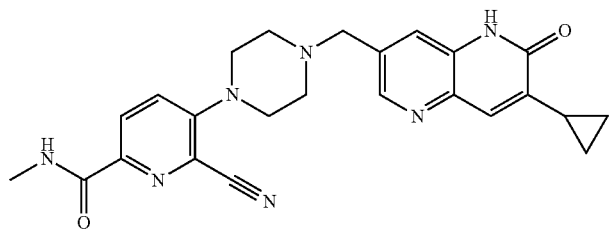 [SMILES: CNC(=O)c1ccc(N2CCN(Cc3cnc4cc(C5CC5)c(=O)[nH]c4c3)CC2)c(C#N)n1] |
| 98 | 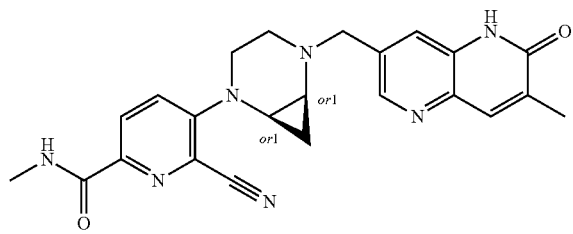 |
| 99 | 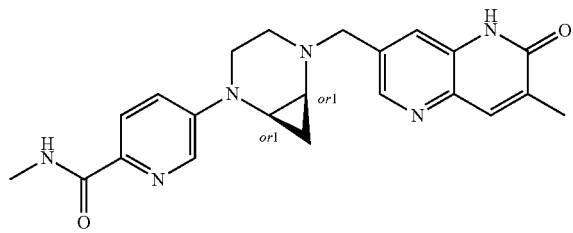 |
| 100 | 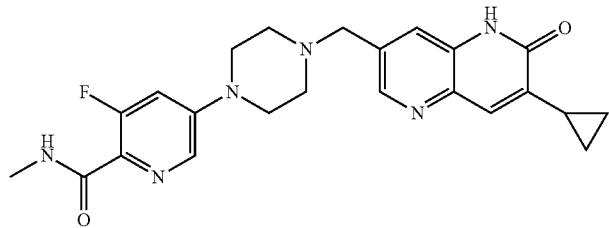 [SMILES: CNC(=O)c1ncc(N2CCN(Cc3cnc4cc(C5CC5)c(=O)[nH]c4c3)CC2)cc1F] |
| 101 | 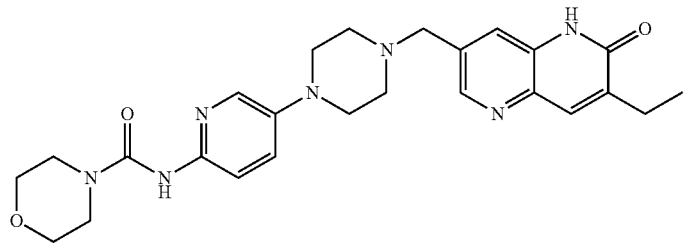 [SMILES: CCc1cc2ncc(CN3CCN(c4ccc(NC(=O)N5CCOCC5)nc4)CC3)cc2[nH]c1=O] |

TABLE 1-continued
| Ex. | Structure |
|---|---|
| 102 | 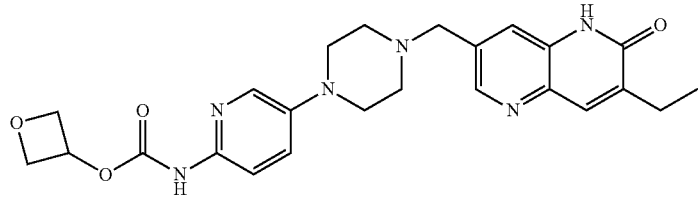 [SMILES: CCc1cc2ncc(CN3CCN(c4ccc(NC(=O)OC5COC5)nc4)CC3)cc2[nH]c1=O] |
| 103 | 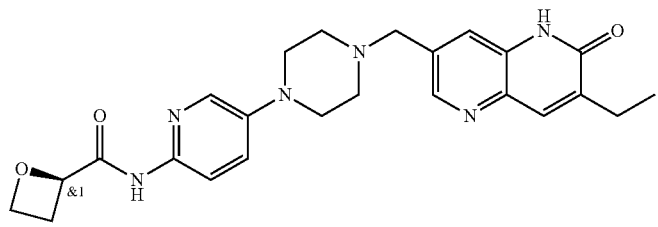 [SMILES: CCc1cc2ncc(CN3CCN(c4ccc(NC(=O)[C@H]5CCO5)nc4)CC3)cc2[nH]c1=O] |
| 104 | 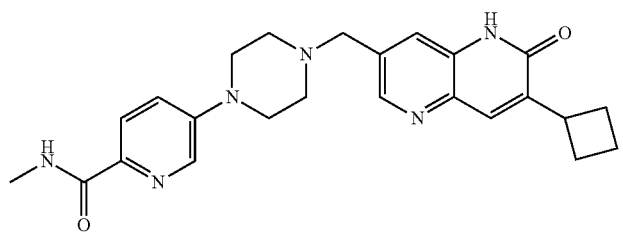 [SMILES: CNC(=O)c1ccc(N2CCN(Cc3cnc4cc(C5CCC5)c(=O)[nH]c4c3)CC2)cn1] |
| 105 | 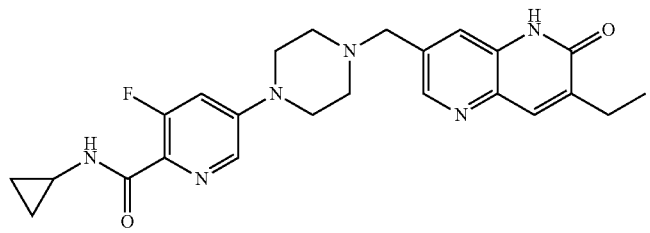 |
| 106 | 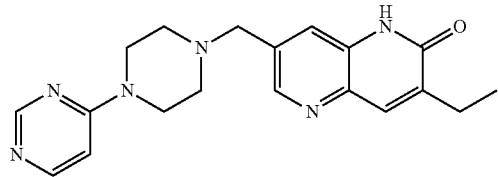 [SMILES: CCc1cc2ncc(CN3CCN(c4ccncn4)CC3)cc2[nH]c1=O] |
| 107 | 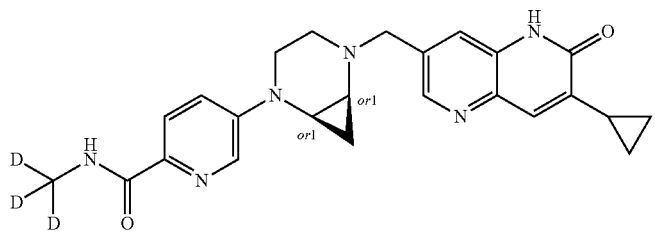 [SMILES: [2H]C([2H])([2H])NC(=O)c1ccc(N2CCN(Cc3cnc4cc(C5CC5)c(=O)[nH]c4c3)[C@H]3C[C@H]32)cn1] |
| 108 | 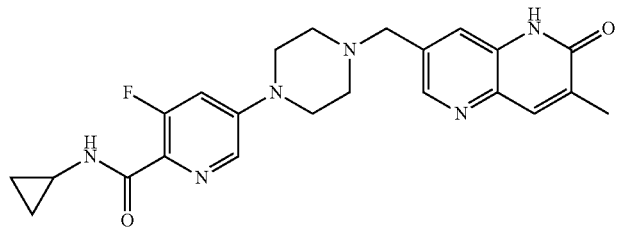 [SMILES: Cc1cc2ncc(CN3CCN(c4cnc(C(=O)NC5CC5)c(F)c4)CC3)cc2[nH]c1=O] |

TABLE 1-continued
| Ex. | Structure |
|---|---|
| 109 | 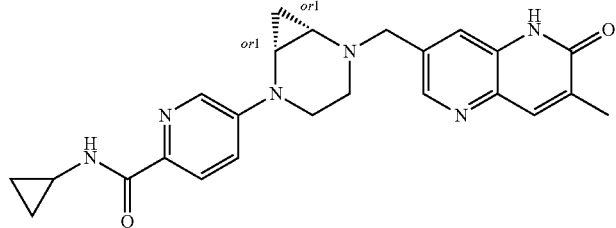 [SMILES: Cc1cc2ncc(CN3CCN(c4ccc(C(=O)NC5CC5)nc4)[C@@H]4C[C@@H]43)cc2[nH]c1=O] |
| 110 | 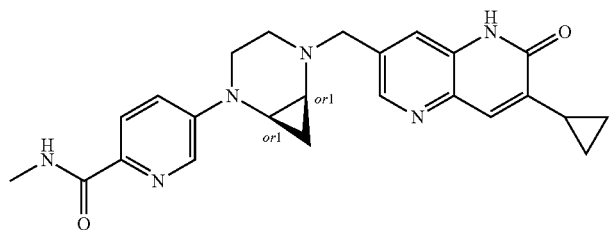 [SMILES: CNC(=O)c1ccc(N2CCN(Cc3cnc4cc(C5CC5)c(=O)[nH]c4c3)[C@H]3C[C@H]32)cn1] |
| 111 | 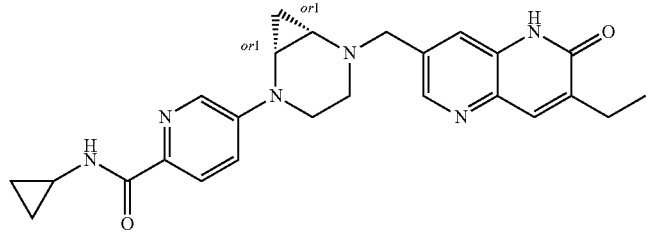 [SMILES: CCc1cc2ncc(CN3CCN(c4ccc(C(=O)NC5CC5)nc4)[C@@H]4C[C@@H]43)cc2[nH]c1=O] |
| 112 | 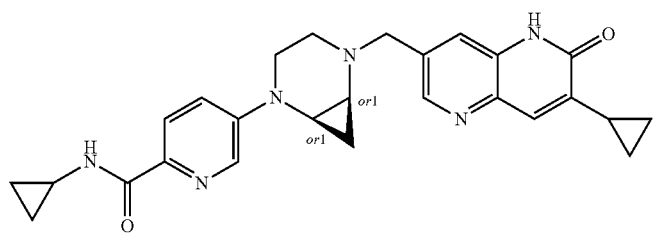 [SMILES: O=C(NC1CC1)c1ccc(N2CCN(Cc3cnc4cc(C5CC5)c(=O)[nH]c4c3)[C@H]3C[C@H]32)cn1] |
| 113 | 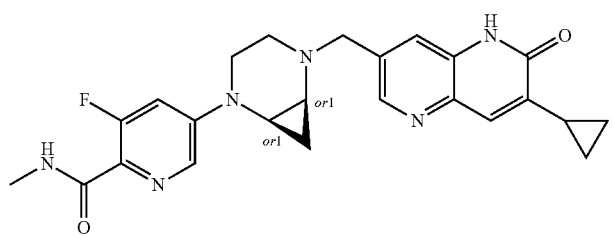 [SMILES: CNC(=O)c1ncc(N2CCN(Cc3cnc4cc(C5CC5)c(=O)[nH]c4c3)[C@H]3C[C@H]32)cc1F] |
| 114 | 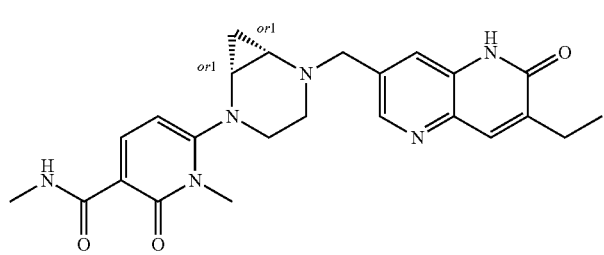 [SMILES: CCc1cc2ncc(CN3CCN(c4ccc(C(=O)NC)c(=O)n4C)[C@@H]4C[C@@H]43)cc2[nH]c1=O] |

TABLE 1-continued
| Ex. | Structure |
|---|---|
| 115 | 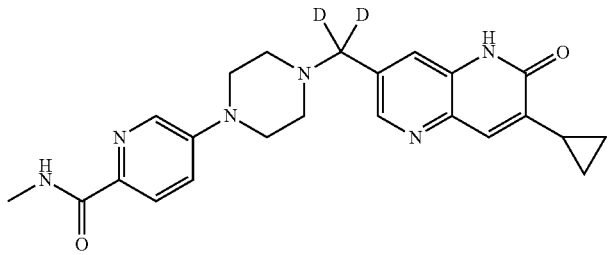 [SMILES: [2H]C([2H])(c1cnc2cc(C3CC3)c(=O)[nH]c2c1)N1CCN(c2ccc(C(=O)NC)nc2)CC1] |
| 116 | 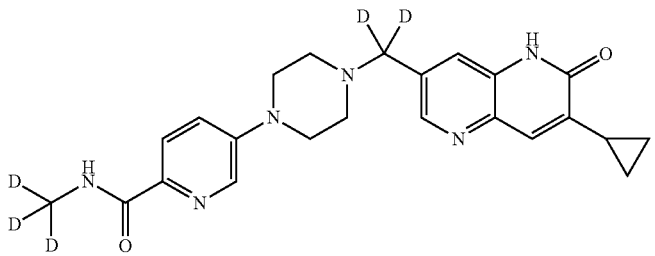 [SMILES: [2H]C([2H])([2H])NC(=O)c1ccc(N2CCN(C([2H])([2H])c3cnc4cc(C5CC5)c(=O)[nH]c4c3)CC2)cn1] |
| 117 | 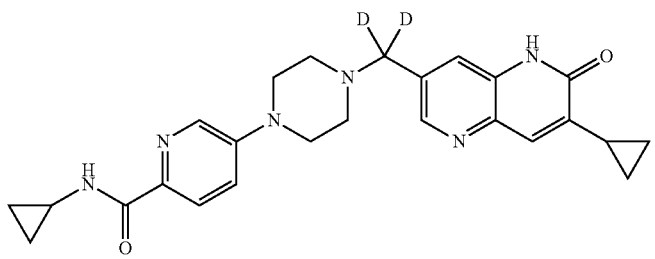 [SMILES: [2H]C([2H])(c1cnc2cc(C3CC3)c(=O)[nH]c2c1)N1CCN(c2ccc(C(=O)NC3CC3)nc2)CC1] |
| 118 | 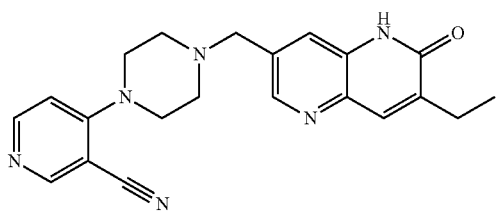 [SMILES: CCc1cc2ncc(CN3CCN(c4ccncc4C#N)CC3)cc2[nH]c1=O] |
| 119 | 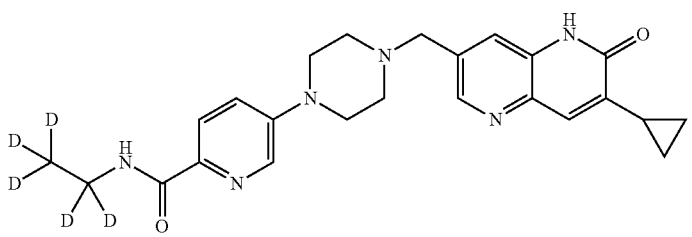 [SMILES: [2H]C([2H])([2H])C([2H])([2H])NC(=O)c1ccc(N2CCN(Cc3cnc4cc(C5CC5)c(=O)[nH]c4c3)CC2)cn1] |
| 120 | 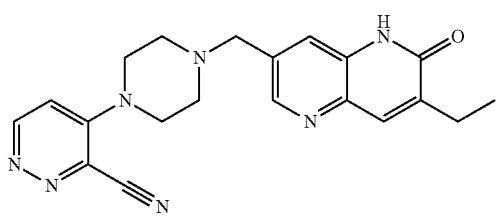 [SMILES: CCc1cc2ncc(CN3CCN(c4ccnnc4C#N)CC3)cc2[nH]c1=O] |

TABLE 1-continued
| Ex. | Structure |
|---|---|
| 121 | 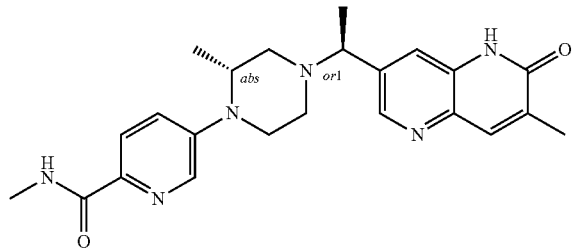 |
| 122 | 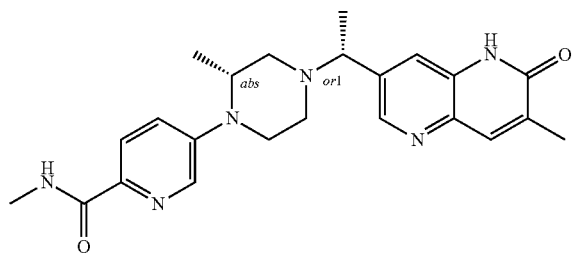 |
| 123 | 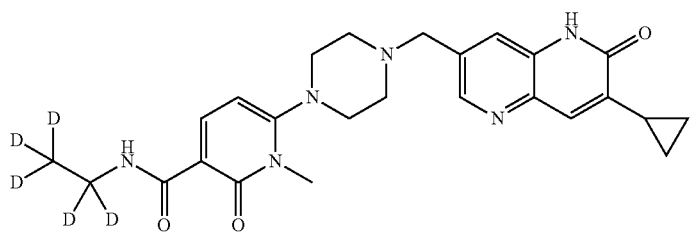 [SMILES: [2H]C([2H])([2H])C([2H])([2H])NC(=O)c1ccc(N2CCN(Cc3cnc4cc(C5CC5)c(=O)[nH]c4c3)CC2)n(C)c1=O] |
| 124 | 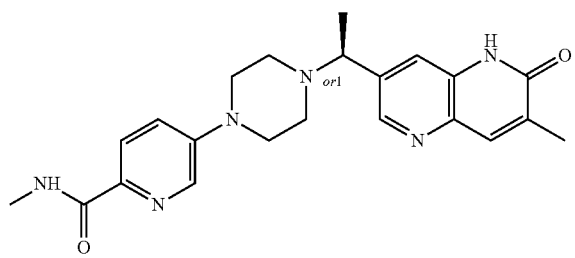 |
| 125 | 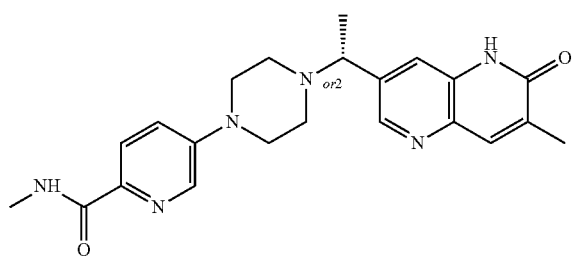 |
| 126 | 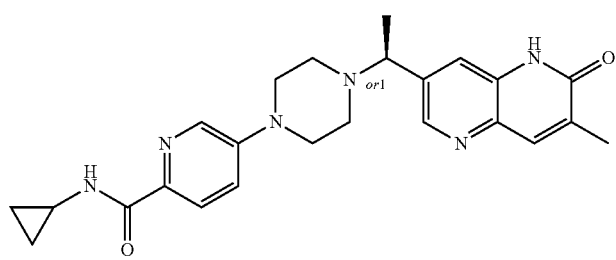 [SMILES: Cc1cc2ncc([C@@H](C)N3CCN(c4ccc(C(=O)NC5CC5)nc4)CC3)cc2[nH]c1=O] |

TABLE 1-continued
| Ex. | Structure |
|---|---|
| 127 | 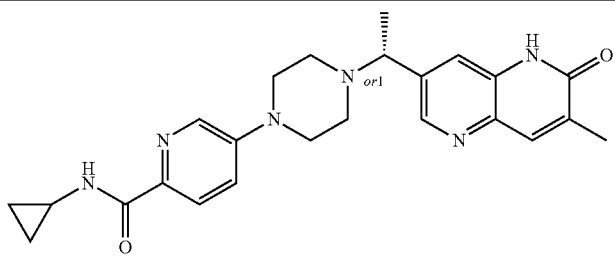 |
| 128 | 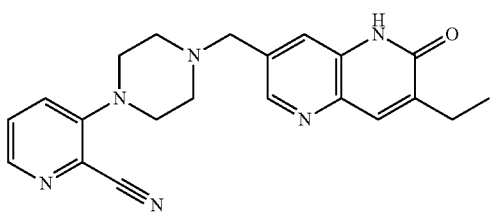 [SMILES: CCc1cc2ncc(CN3CCN(c4cccnc4C#N)CC3)cc2[nH]c1=O] |
| 129 | 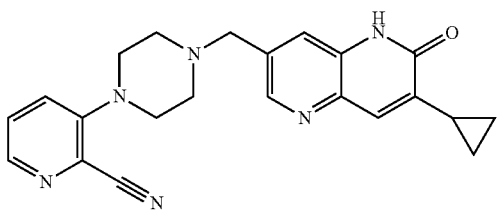 [SMILES: N#Cc1ncccc1N1CCN(Cc2cnc3cc(C4CC4)c(=O)[nH]c3c2)CC1] |
| 130 | 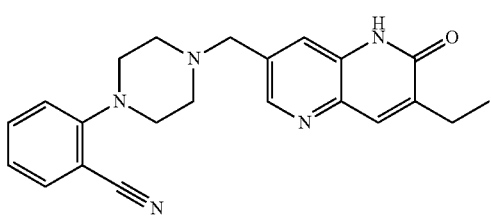 [SMILES: CCc1cc2ncc(CN3CCN(c4ccccc4C#N)CC3)cc2[nH]c1=O] |
| 131 | 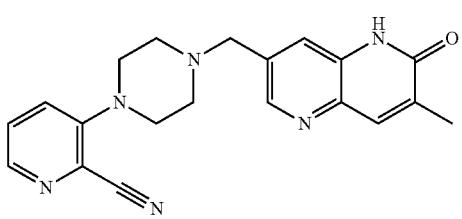 [SMILES: Cc1cc2ncc(CN3CCN(c4cccnc4C#N)CC3)cc2[nH]c1=O] |
| 132 | 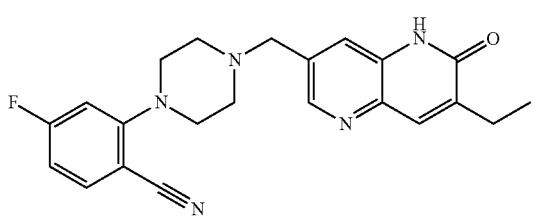 [SMILES: CCc1cc2ncc(CN3CCN(c4cc(F)ccc4C#N)CC3)cc2[nH]c1=O] |
| 133 | 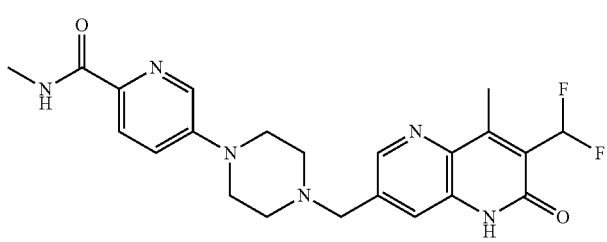 [SMILES: CNC(=O)c1ccc(N2CCN(Cc3cnc4c(C)c(C(F)F)c(=O)[nH]c4c3)CC2)cn1] |

TABLE 1-continued
| Ex. | Structure |
|---|---|
| 134 | 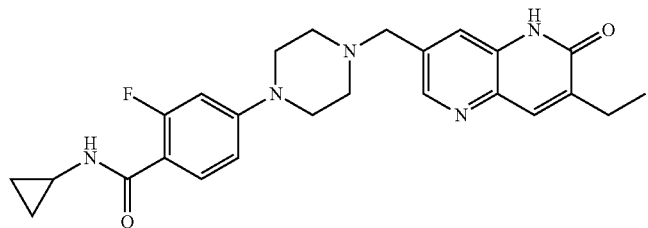 [SMILES: CCc1cc2ncc(CN3CCN(c4ccc(C(=O)NC5CC5)c(F)c4)CC3)cc2[nH]c1=O] |
| 135 | 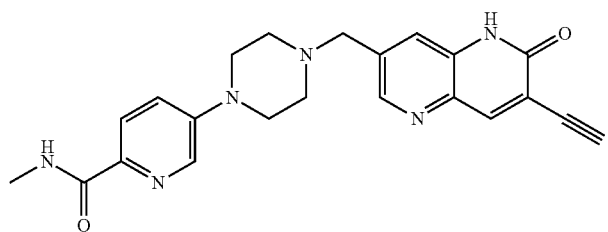 [SMILES: C#Cc1cc2ncc(CN3CCN(c4ccc(C(=O)NC)nc4)CC3)cc2[nH]c1=O] |
| 136 | 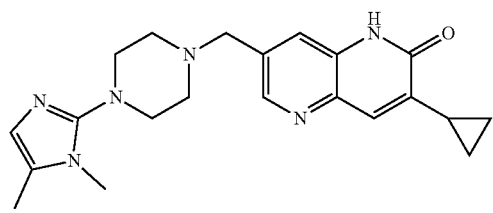 [SMILES: Cc1cnc(N2CCN(Cc3cnc4cc(C5CC5)c(=O)[nH]c4c3)CC2)n1C] |
| 137 | 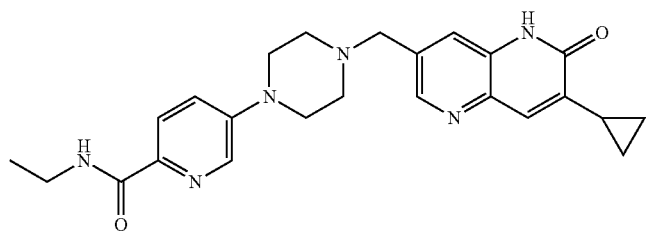 [SMILES: CCNC(=O)c1ccc(N2CCN(Cc3cnc4cc(C5CC5)c(=O)[nH]c4c3)CC2)cn1] |
| 138 | 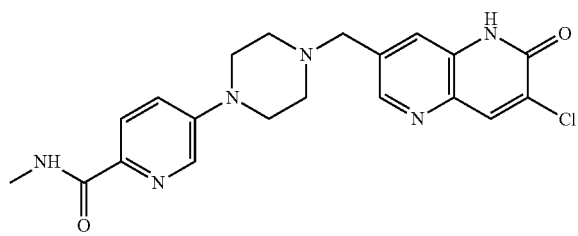 [SMILES: CNC(=O)c1ccc(N2CCN(Cc3cnc4cc(Cl)c(=O)[nH]c4c3)CC2)cn1] |
| 139 | 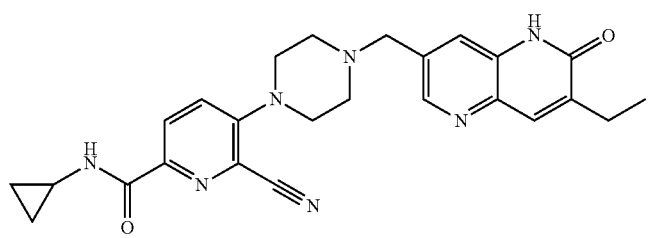 [SMILES: CCc1cc2ncc(CN3CCN(c4ccc(C(=O)NC5CC5)nc4C#N)CC3)cc2[nH]c1=O] |

TABLE 1-continued

| Ex. | Structure |
|---|---|
| 140 | 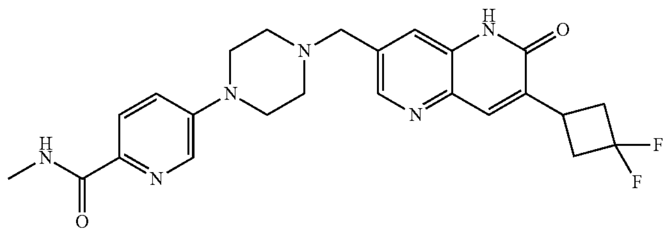 [SMILES: CNC(=O)c1ccc(N2CCN(Cc3cnc4cc(C5CC(F)(F)C5)c(=O)[nH]c4c3)CC2)cn1] |
| 141 | 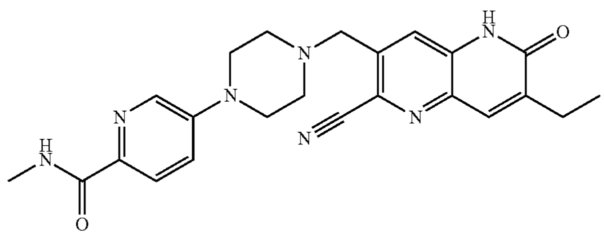 [SMILES: CCc1cc2nc(C#N)c(CN3CCN(c4ccc(C(=O)NC)nc4)CC3)cc2[nH]c1=O] |
| 142 | 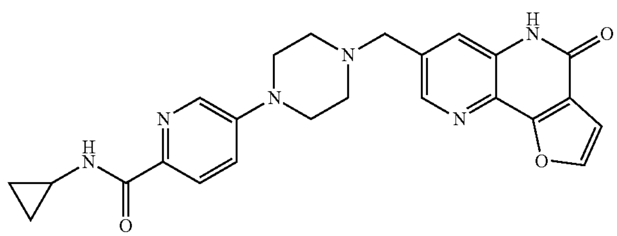 [SMILES: O=C(NC1CC1)c1ccc(N2CCN(Cc3cnc4c(c3)[nH]c(=O)c3ccoc34)CC2)cn1] |
| 143 | 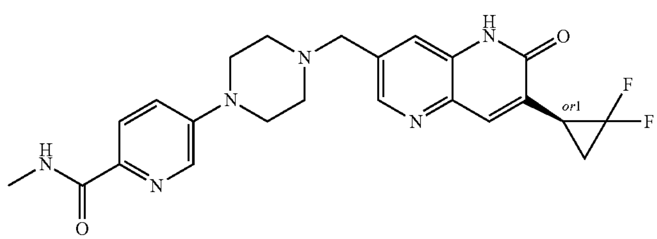 [SMILES: CNC(=O)c1ccc(N2CCN(Cc3cnc4cc([C@@H]5CC5(F)F)c(=O)[nH]c4c3)CC2)cn1] |
| 144 | 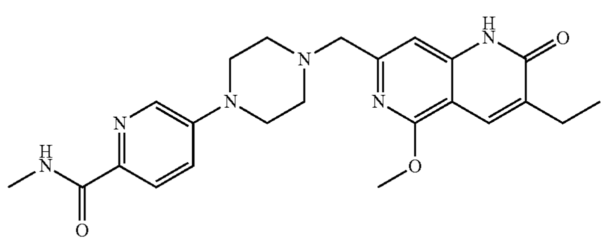 [SMILES: CCc1cc2c(OC)nc(CN3CCN(c4ccc(C(=O)NC)nc4)CC3)cc2[nH]c1=O] |
| 145 | 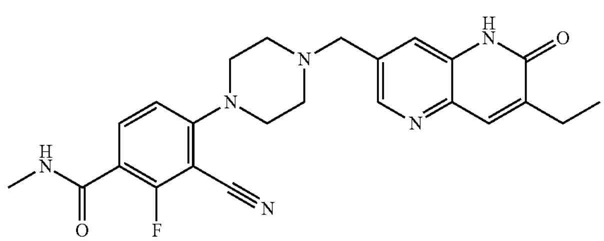 [SMILES: CCc1cc2ncc(CN3CCN(c4ccc(C(=O)NC)c(F)c4C#N)CC3)cc2[nH]c1=O] |

TABLE 1-continued
| Ex. | Structure |
|---|---|
| 146 | 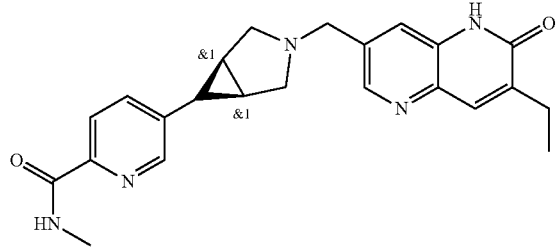 |
| 147 | 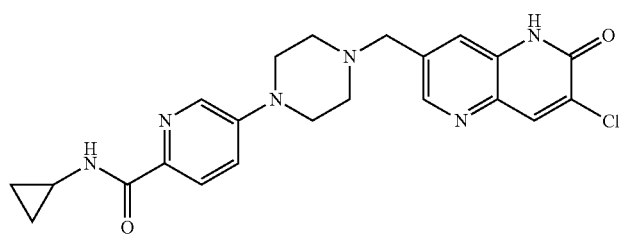 [SMILES: O=C(NC1CC1)c1ccc(N2CCN(Cc3cnc4cc(Cl)c(=O)[nH]c4c3)CC2)cn1] |
| 148 | 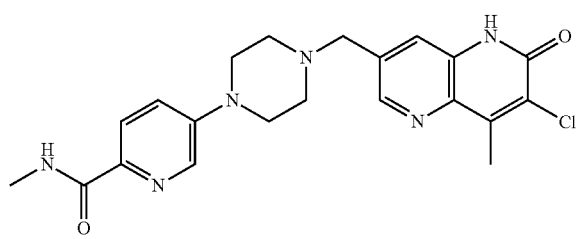 [SMILES: CNC(=O)c1ccc(N2CCN(Cc3cnc4c(C)c(Cl)c(=O)[nH]c4c3)CC2)cn1] |
| 149 | 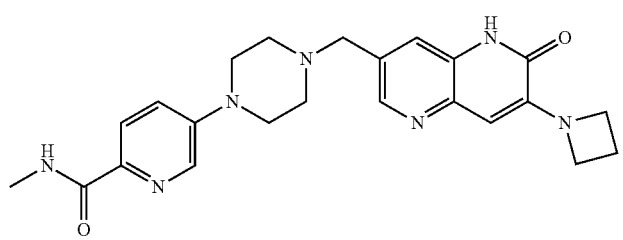 |
| 150 | 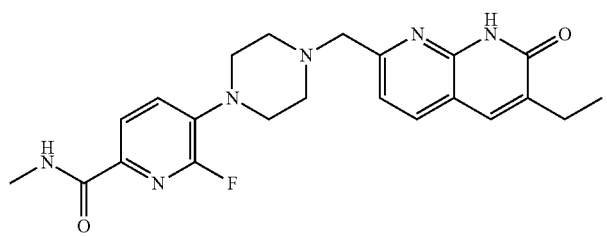 [SMILES: CCc1cc2ccc(CN3CCN(c4ccc(C(=O)NC)nc4F)CC3)nc2[nH]c1=O] |
| 151 | 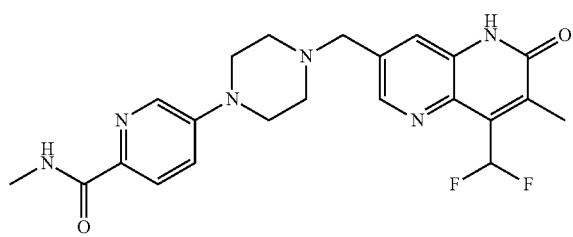 |

TABLE 1-continued
| Ex. | Structure |
|---|---|
| 152 | 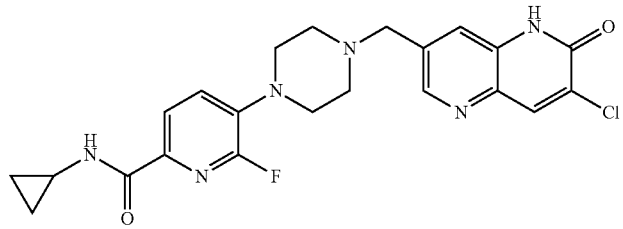 [SMILES: O=C(NC1CC1)c1ccc(N2CCN(Cc3cnc4cc(Cl)c(=O)[nH]c4c3)CC2)c(F)n1] |
| 153 | 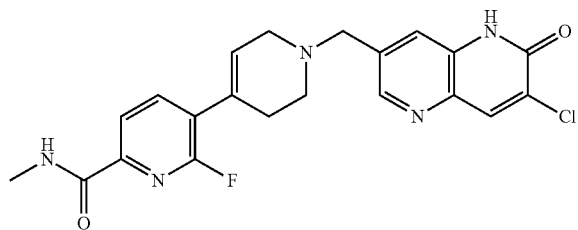 [SMILES: CNC(=O)c1ccc(C2=CCN(Cc3cnc4cc(Cl)c(=O)[nH]c4c3)CC2)c(F)n1] |
| 154 | 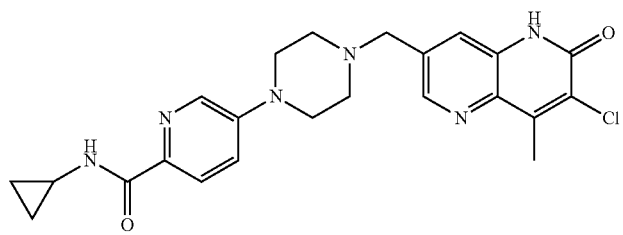 [SMILES: Cc1c(Cl)c(=O)[nH]c2cc(CN3CCN(c4ccc(C(=O)NC5CC5)nc4)CC3)cnc12] |
| 155 | 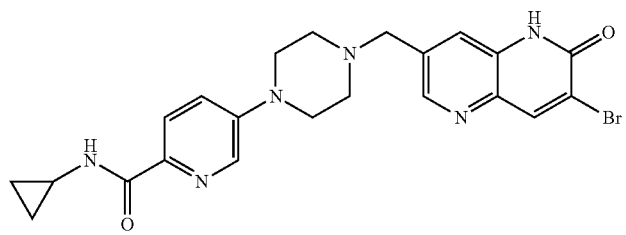 [SMILES: O=C(NC1CC1)c1ccc(N2CCN(Cc3cnc4cc(Br)c(=O)[nH]c4c3)CC2)cn1] |
| 156 | 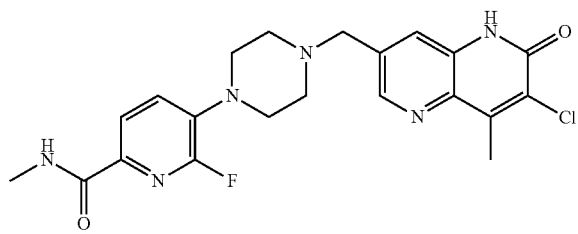 [SMILES: CNC(=O)c1ccc(N2CCN(Cc3cnc4c(C)c(Cl)c(=O)[nH]c4c3)CC2)c(F)n1] |
| 157 | 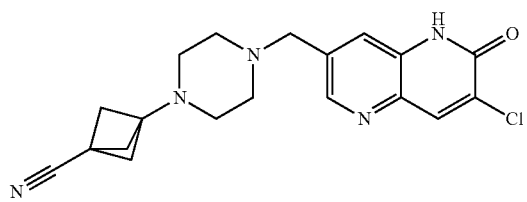 [SMILES: N#CC12CC(N3CCN(Cc4cnc5cc(Cl)c(=O)[nH]c5c4)CC3)(C1)C2] |

TABLE 1-continued
| Ex. | Structure |
|---|---|
| 158 | 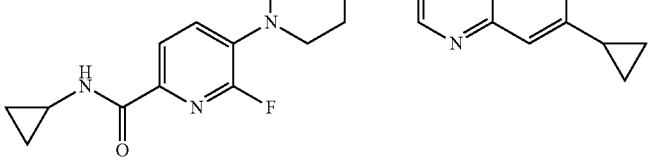 |
| 159 | 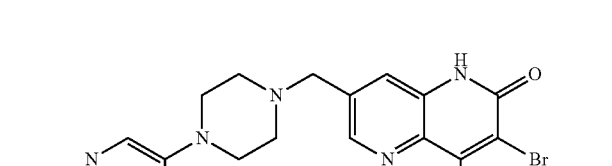 |
| 160 | 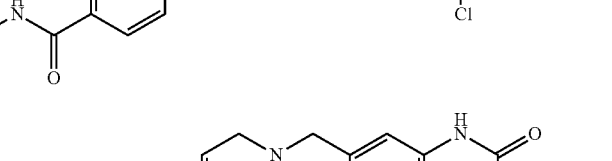 |
| 161 | 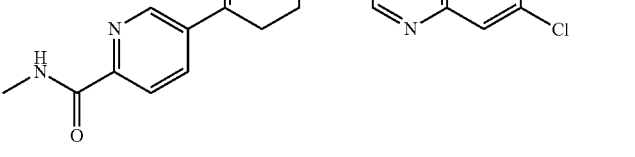 |
In some embodiments, the compound is selected from the group consisting of:
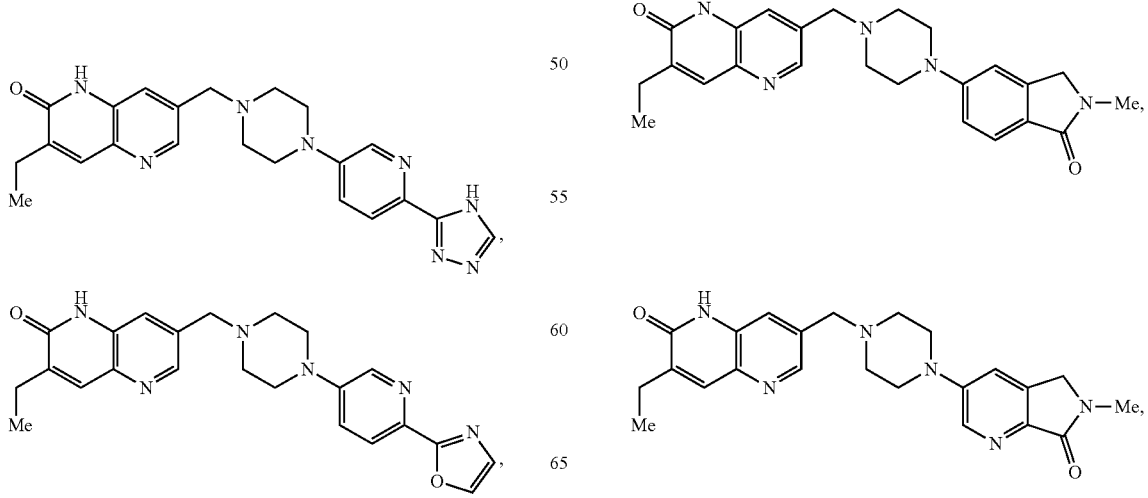

125
-continued
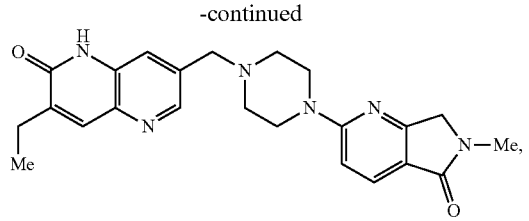
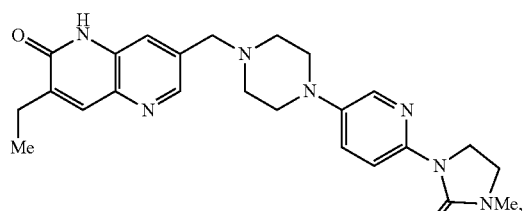
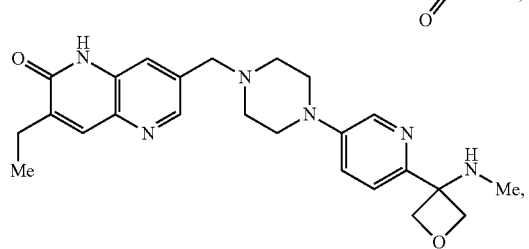
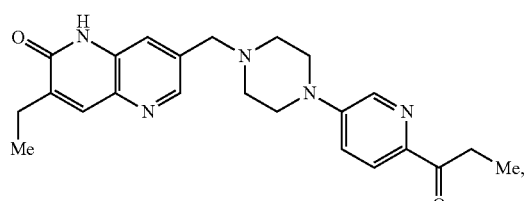
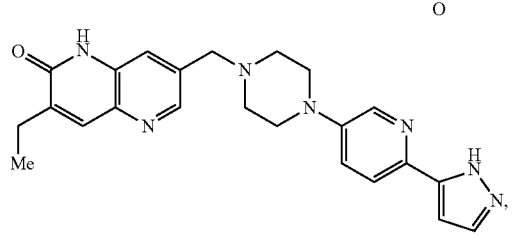
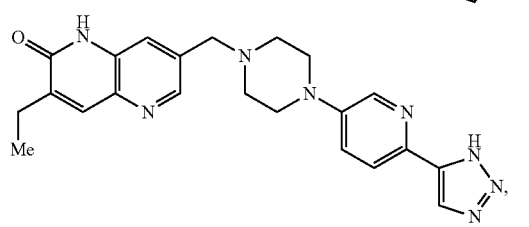
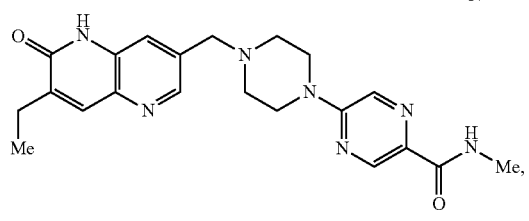
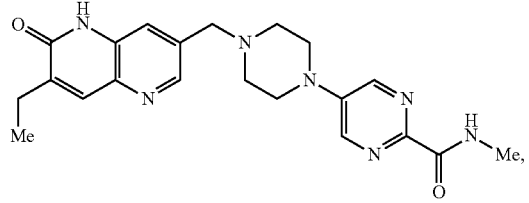
126
-continued
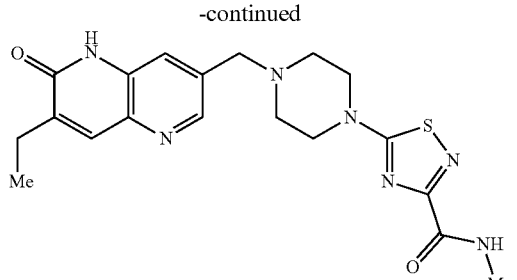
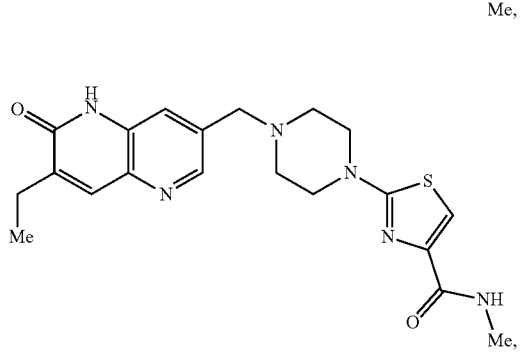
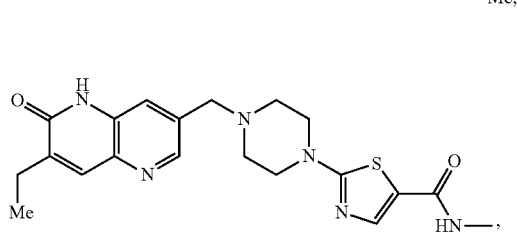
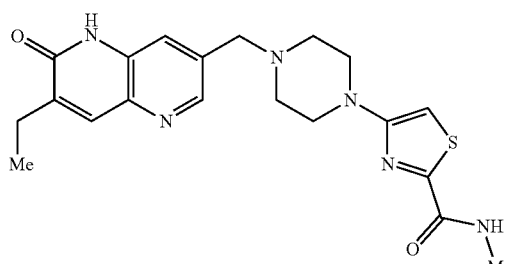
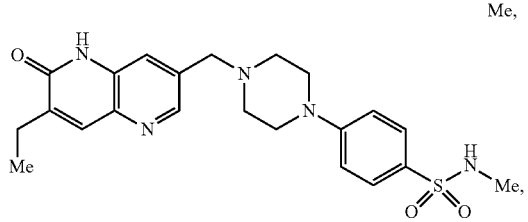
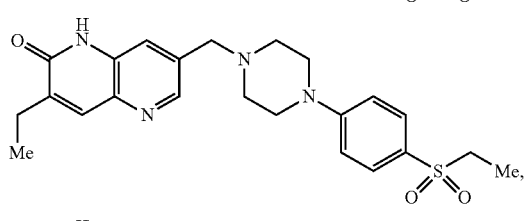
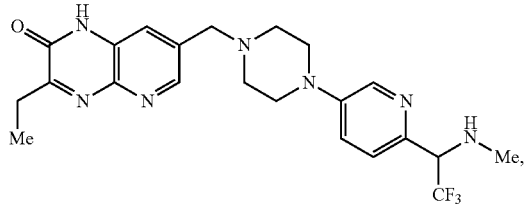

127
-continued
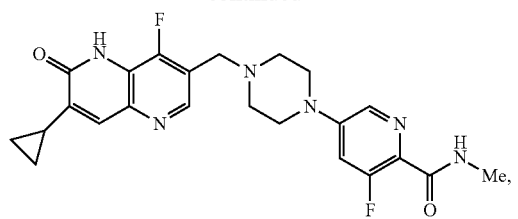
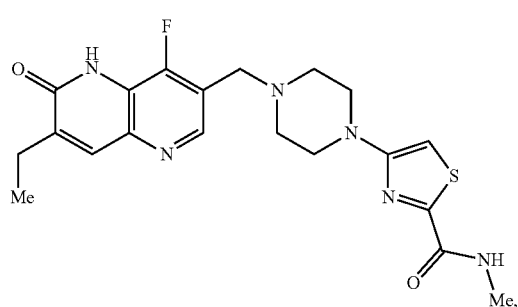
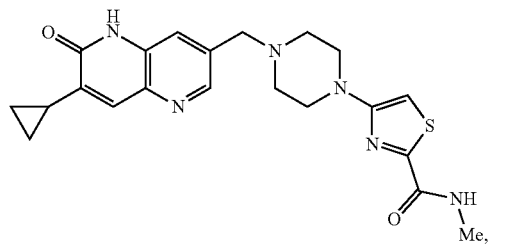
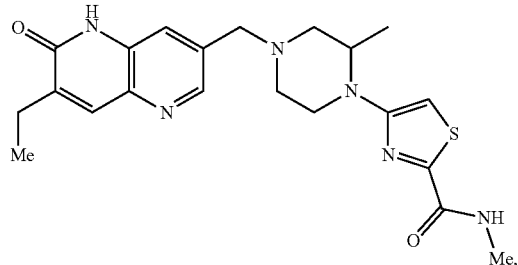
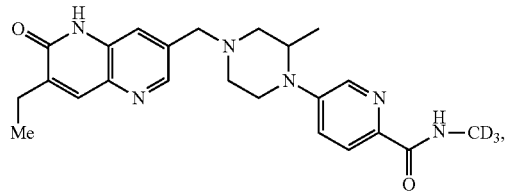
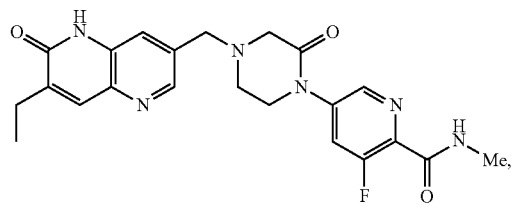
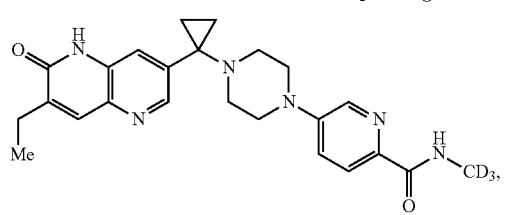
128
-continued
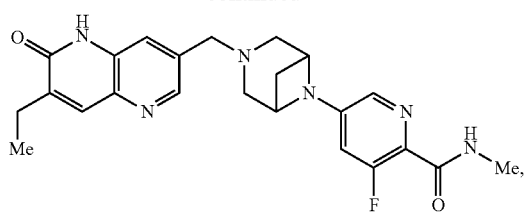
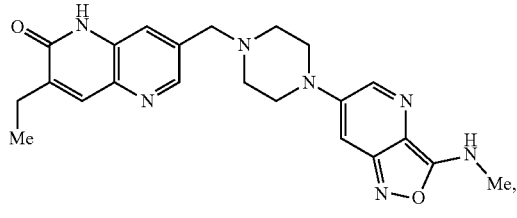
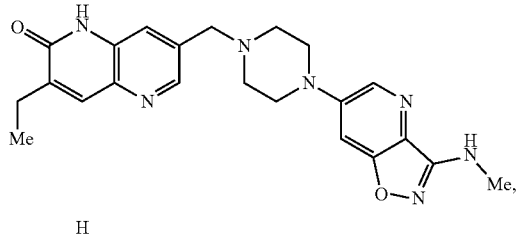
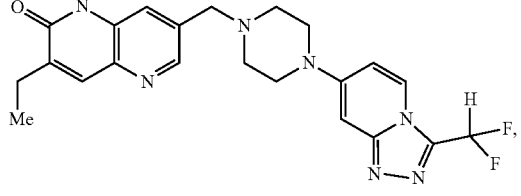
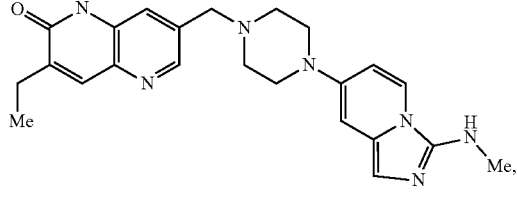
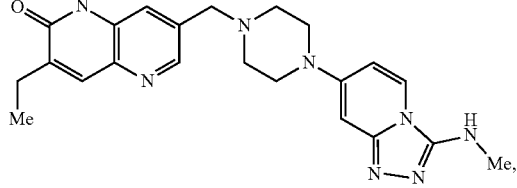
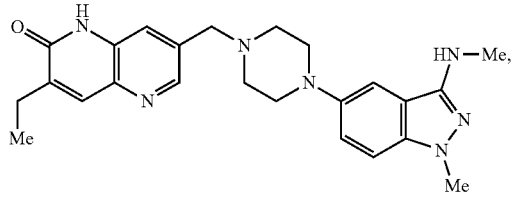
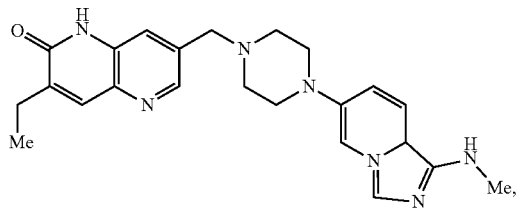

129
-continued
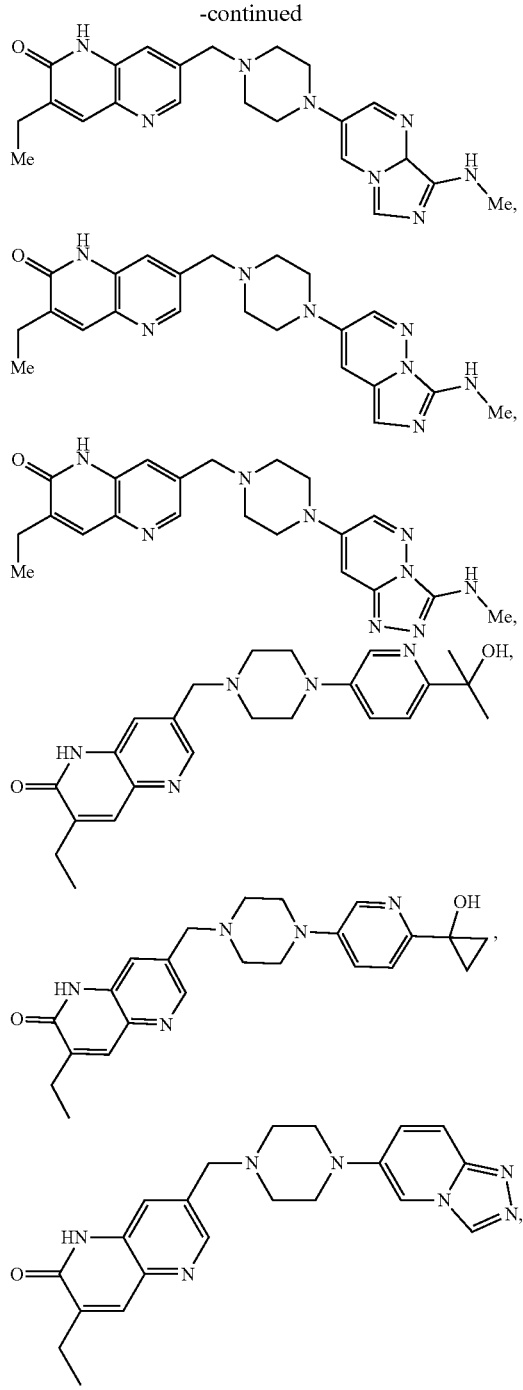
130
-continued
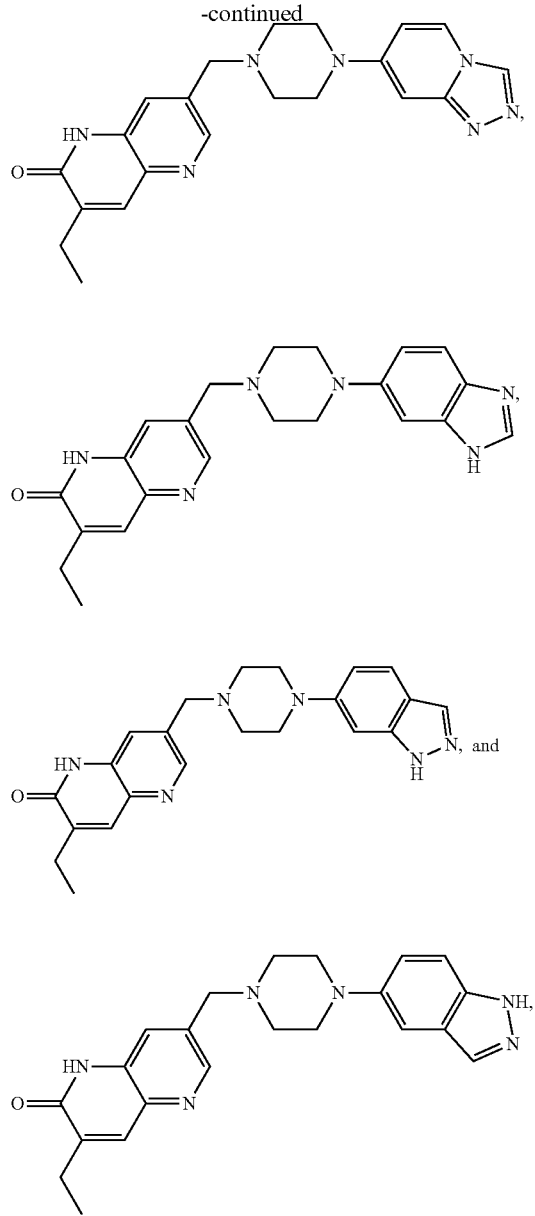
or a pharmaceutically acceptable salt, solvate, or stereoisomer thereof.
In some embodiments, the compound is selected from the group consisting of:
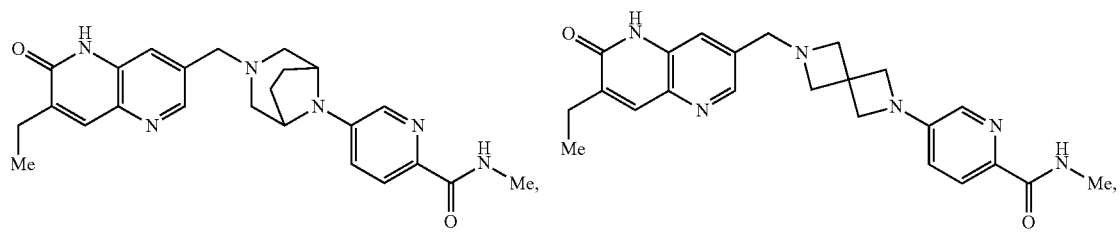

131
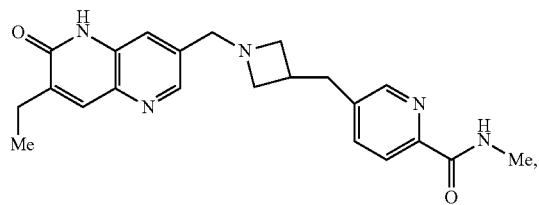
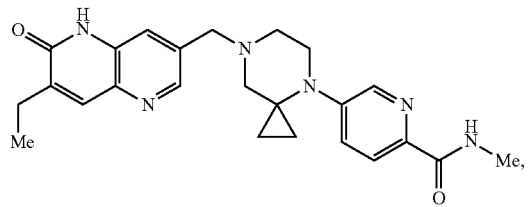
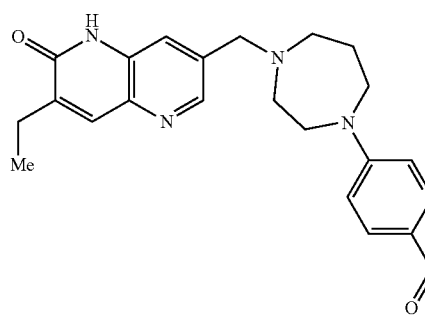
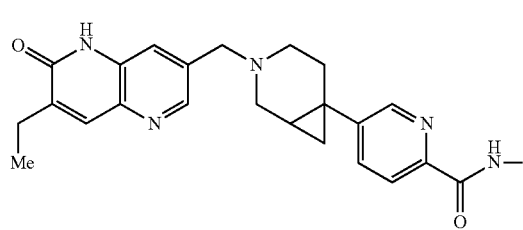
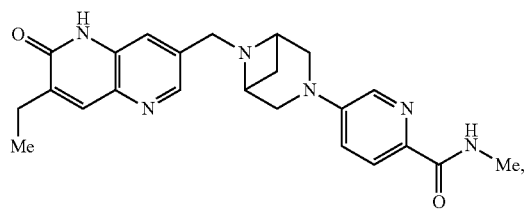
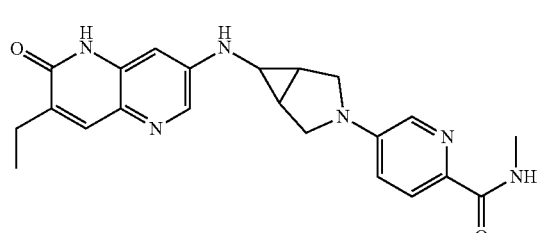
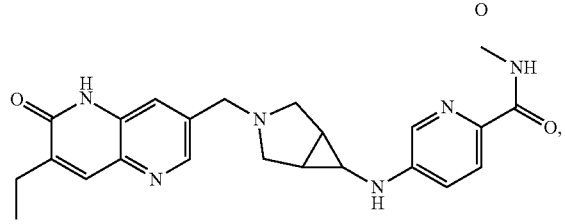
-continued
132
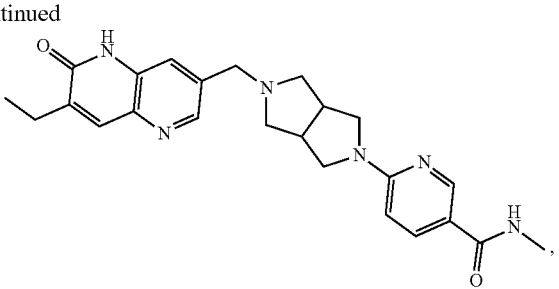
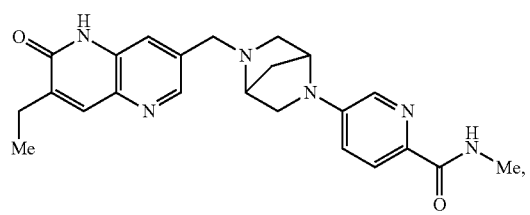
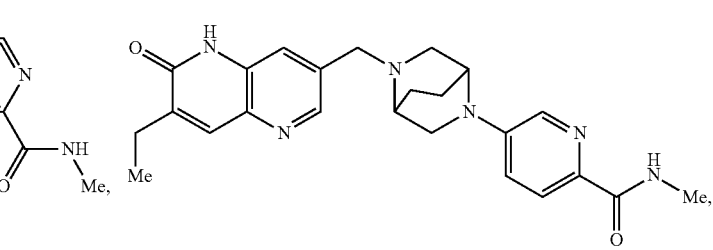
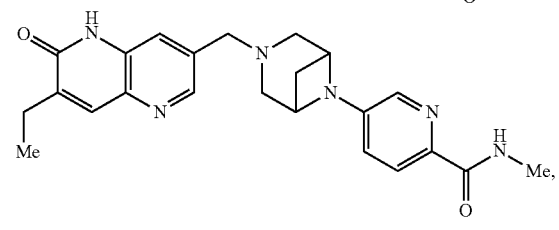
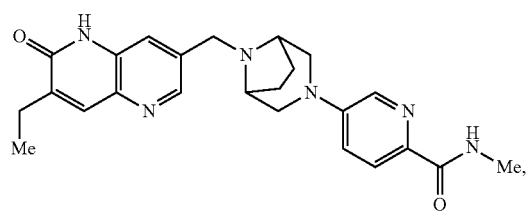
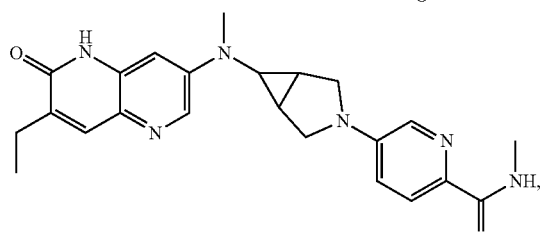
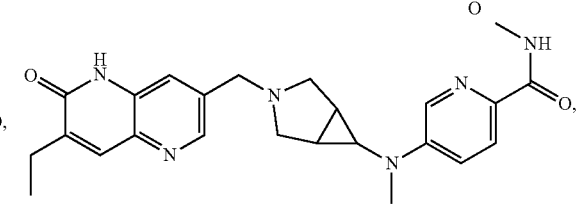

133  134
-continued
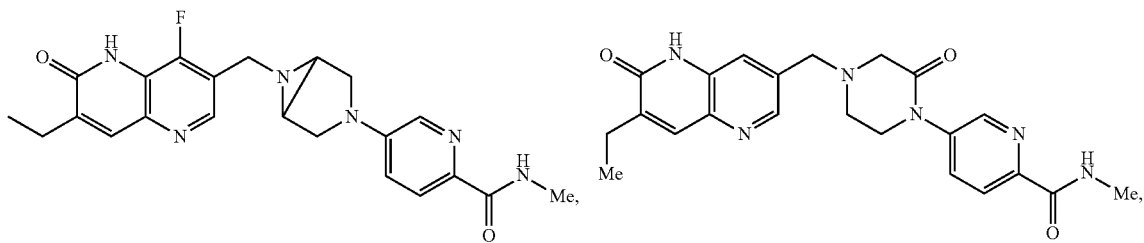
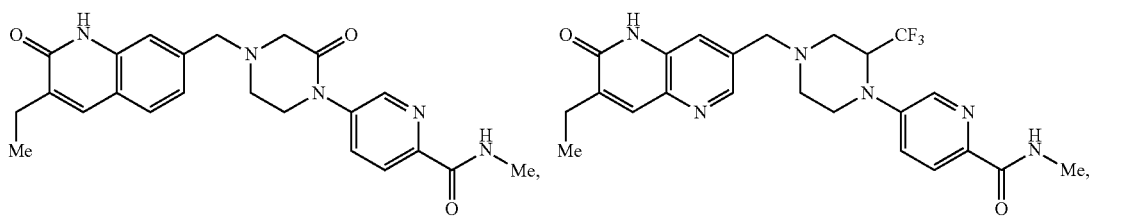
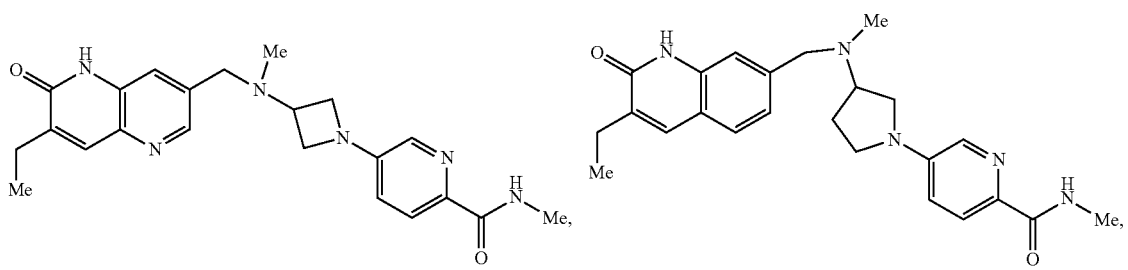
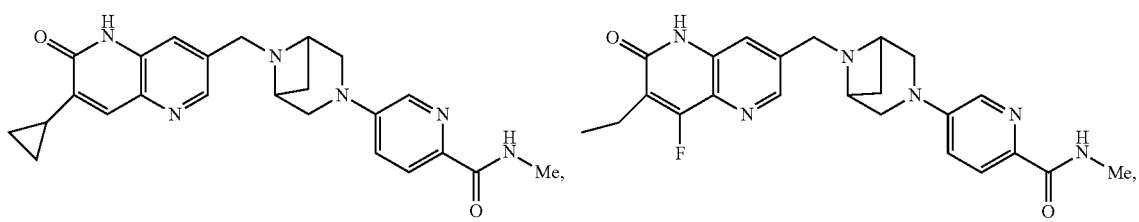
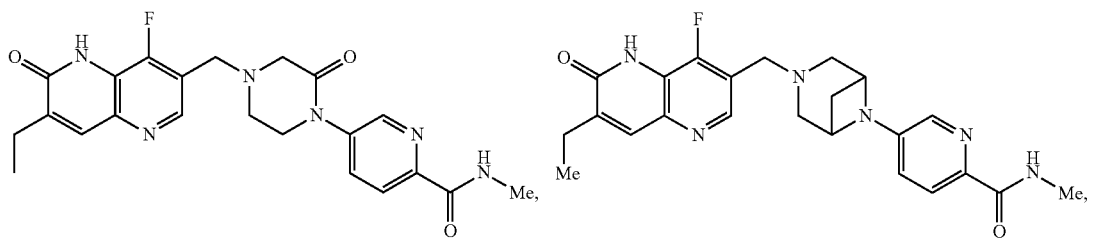
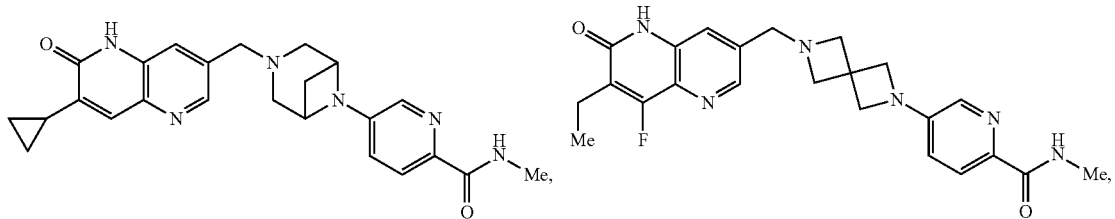
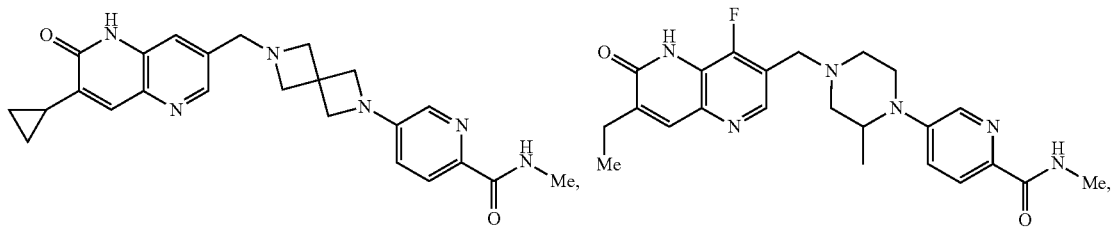

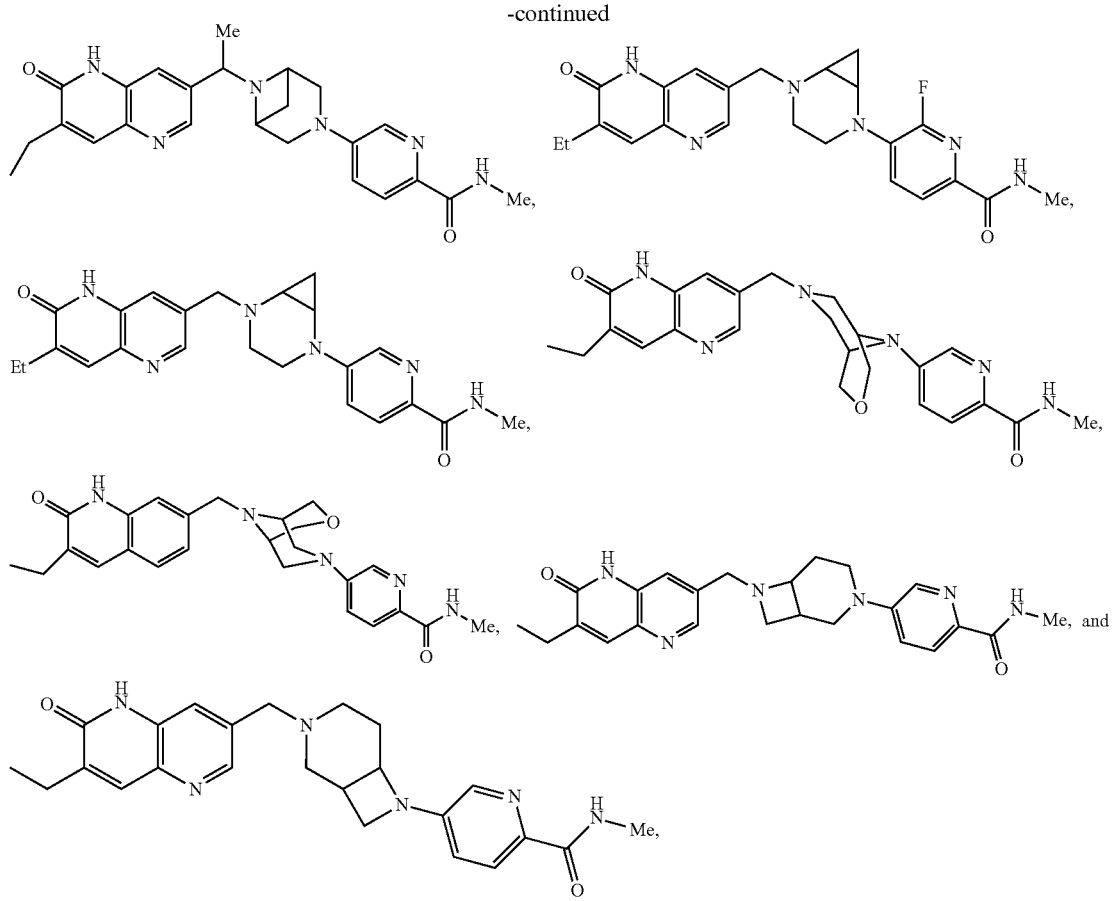
or a pharmaceutically acceptable salt, solvate, or stereoisomer thereof.
In some embodiments, the compound is selected from the group consisting of:
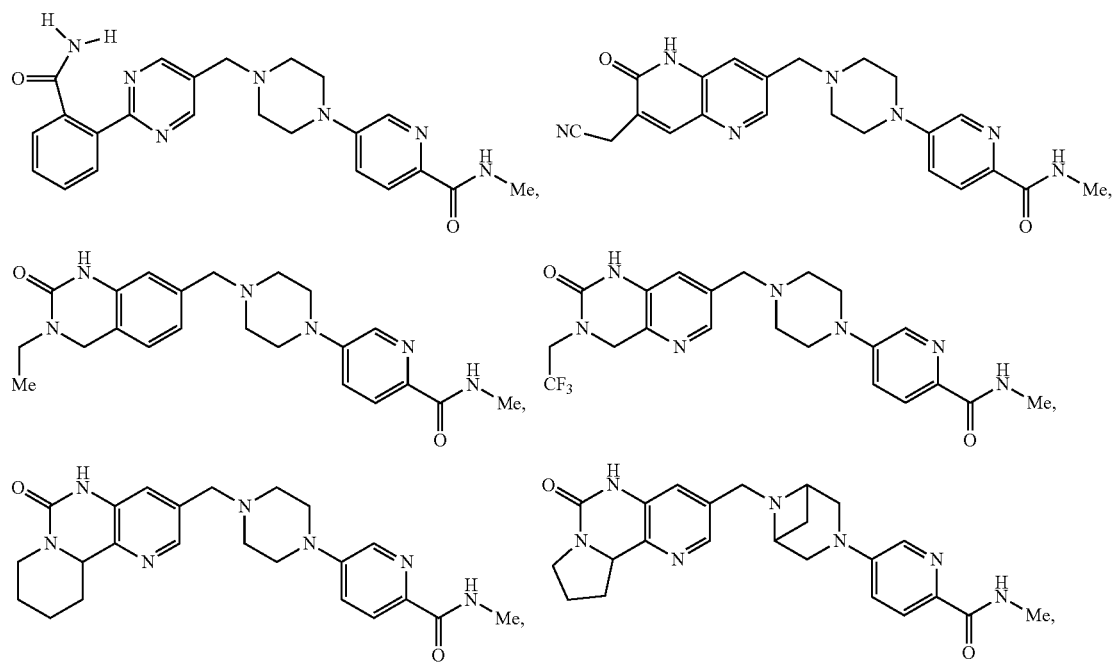

137                                 138
-continued
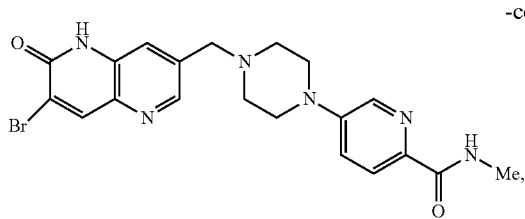
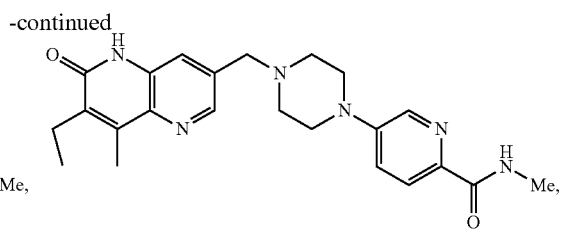
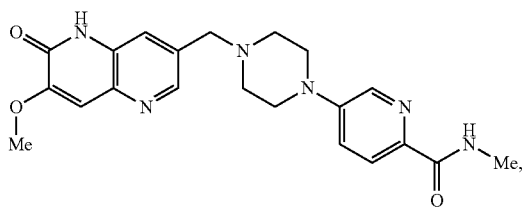
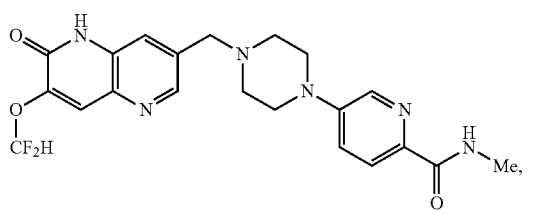
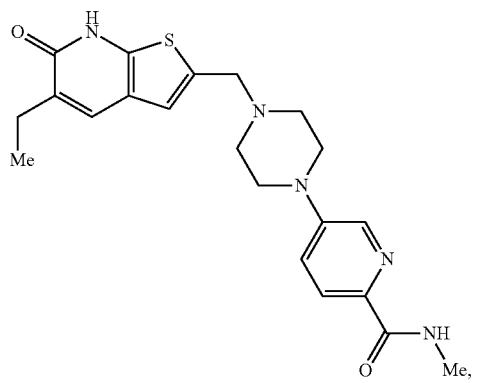
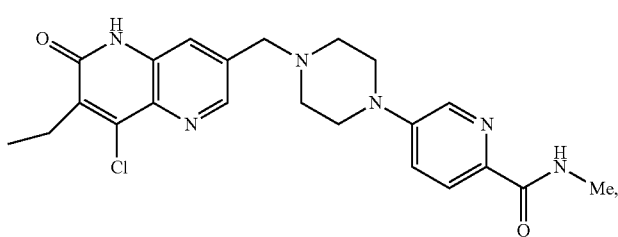
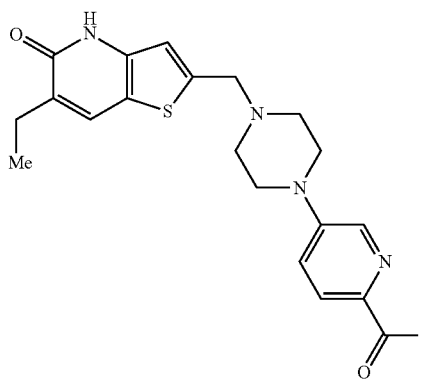
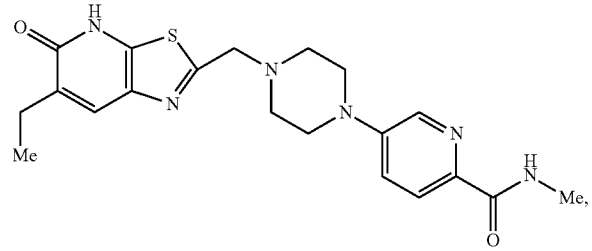
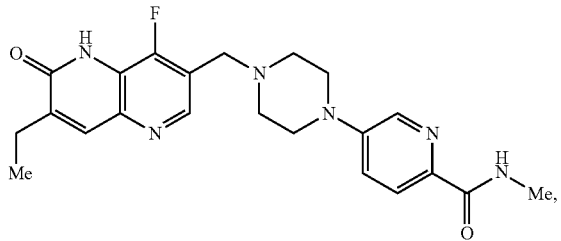
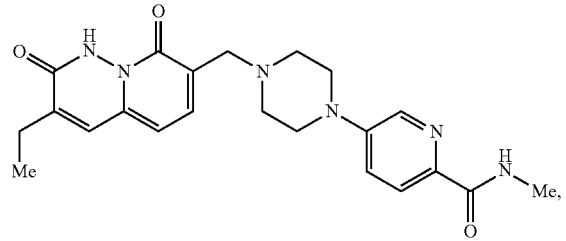

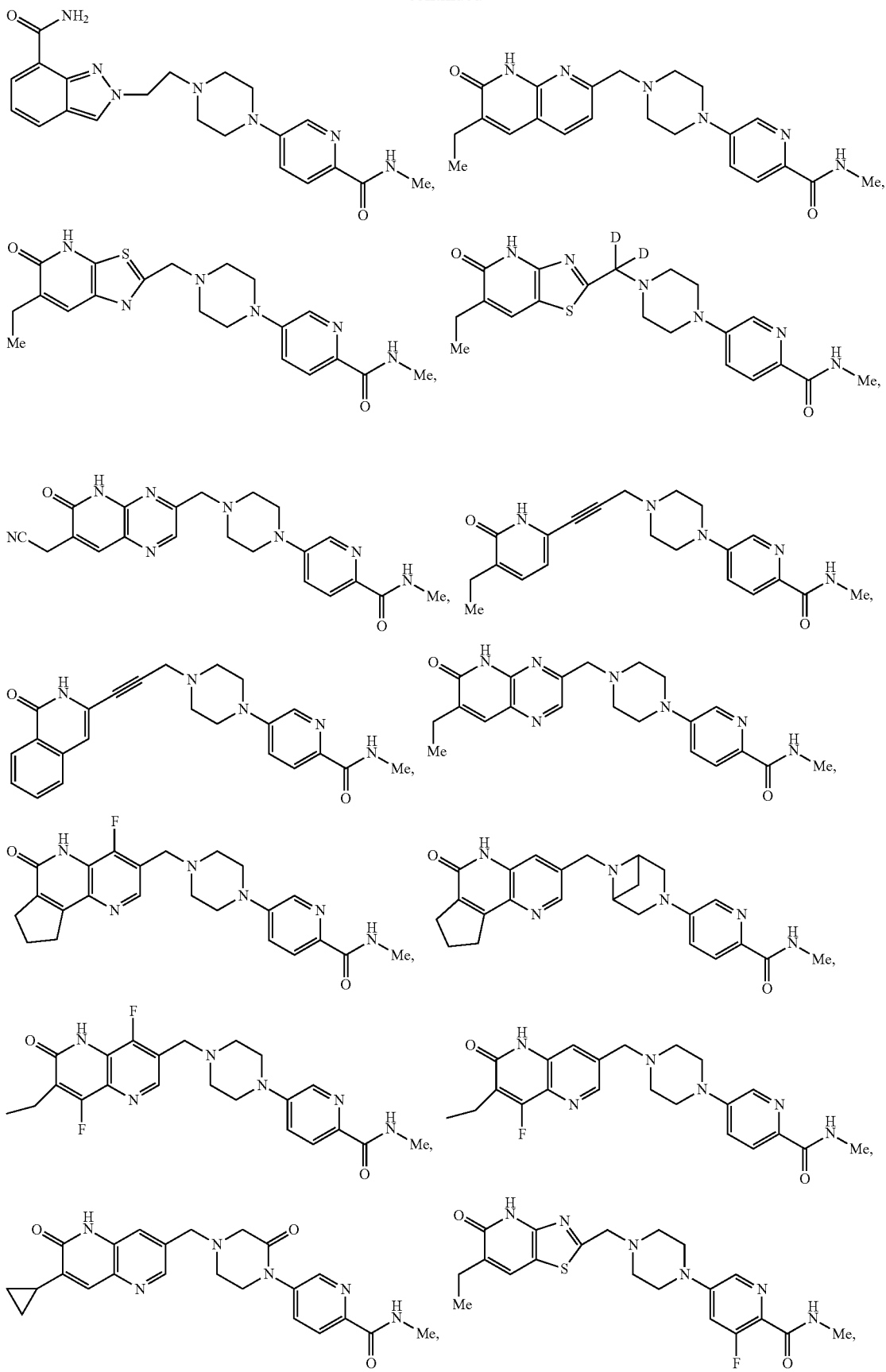

141
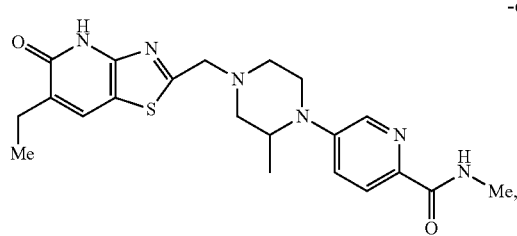
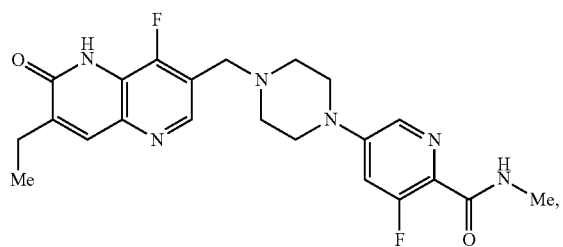
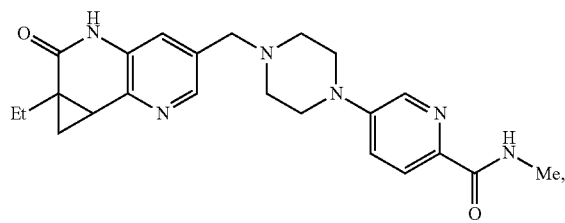
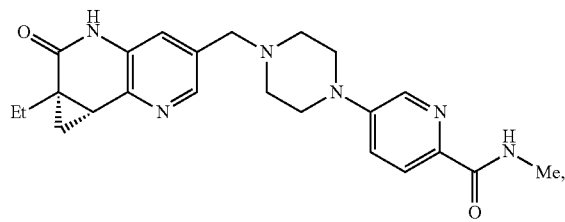
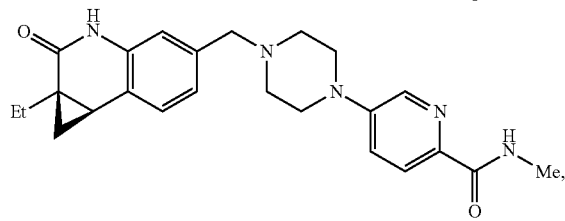
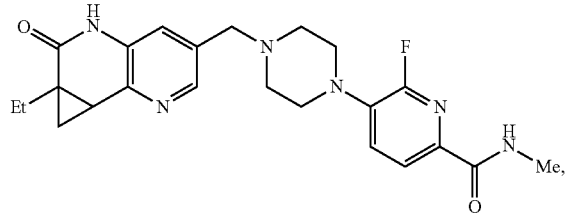
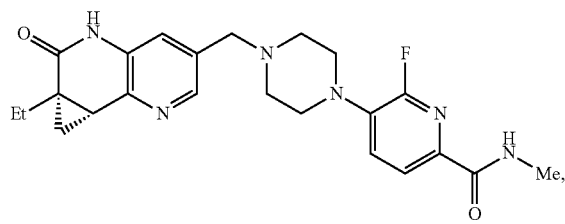
142
-continued
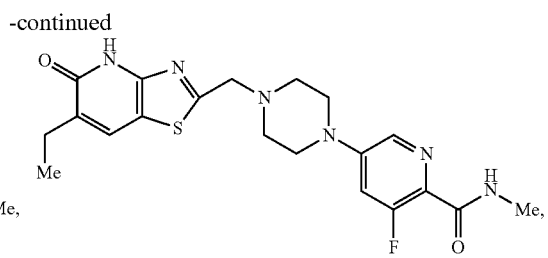
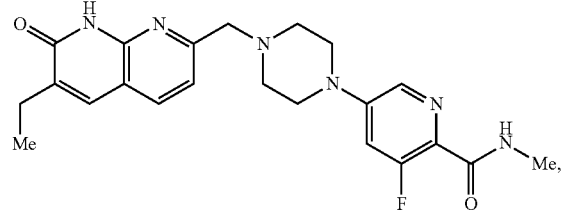
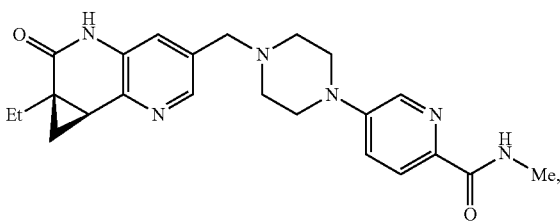
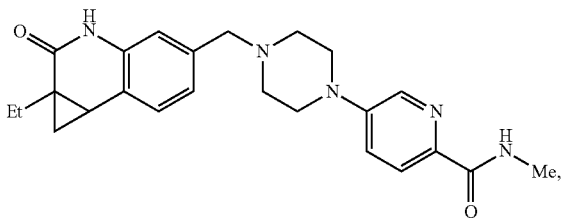
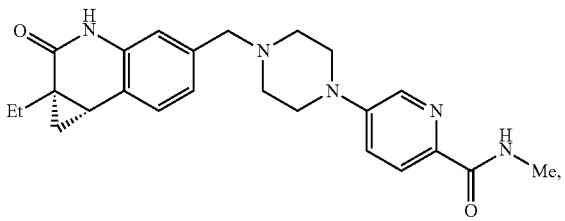
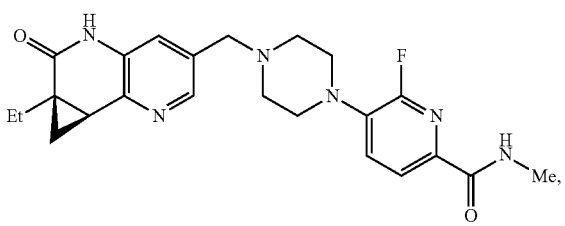
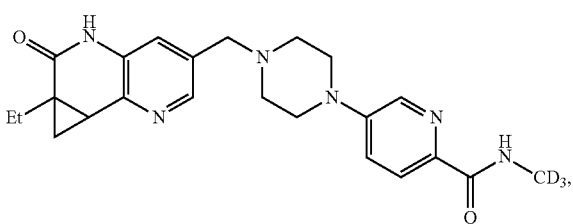

-continued
| 143 | 144 |
|---|---|
| 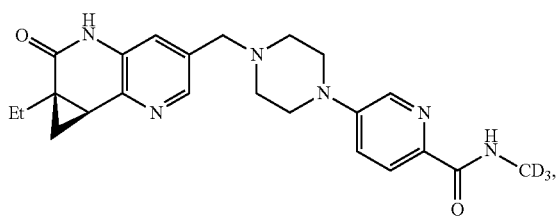 | 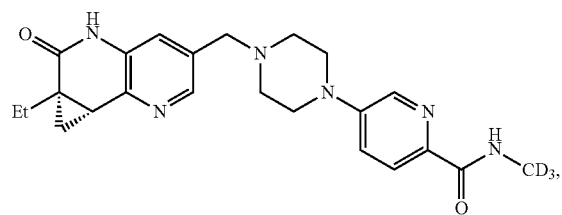 |
| 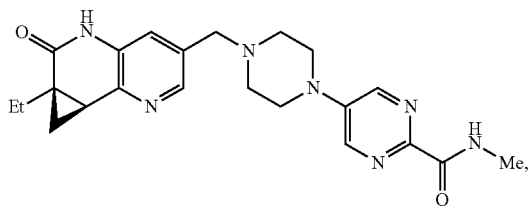 | 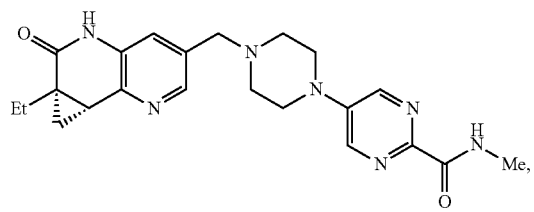 |
| 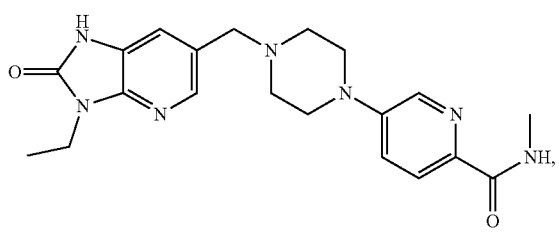 | 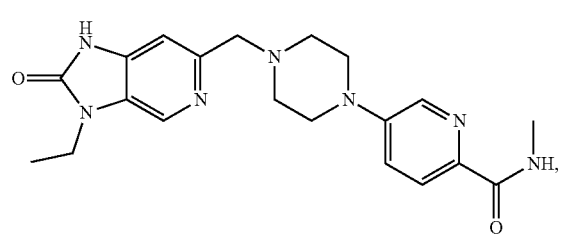 |
| 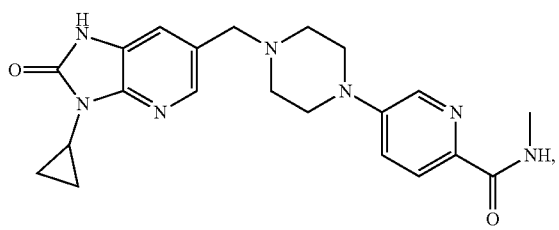 | 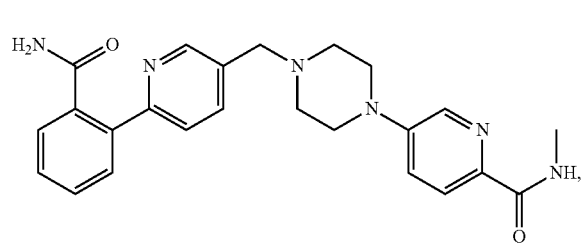 |
| 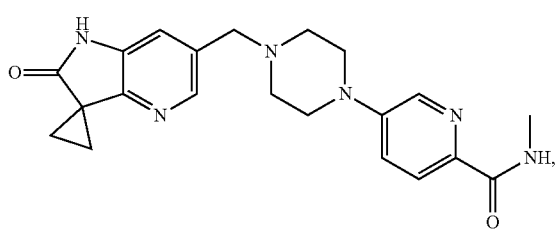 | 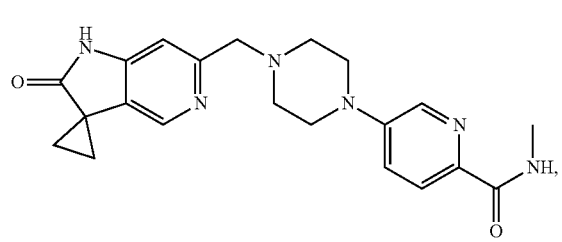 |
| 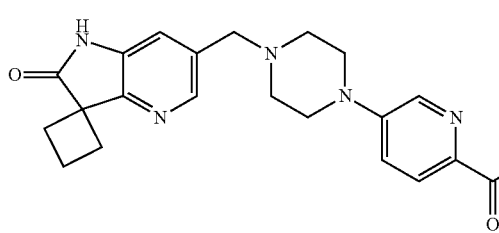 | 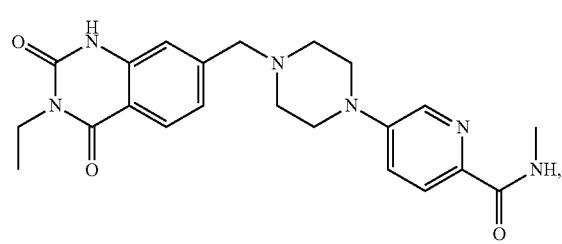 |

-continued
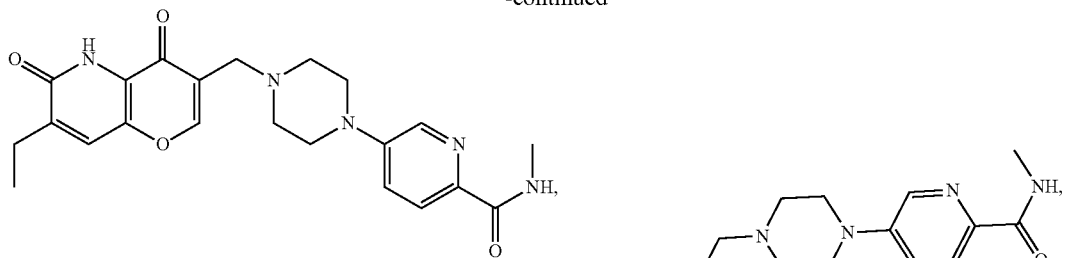
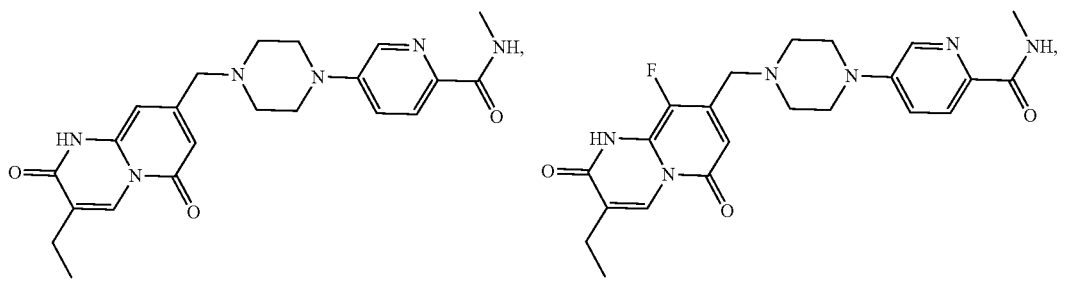
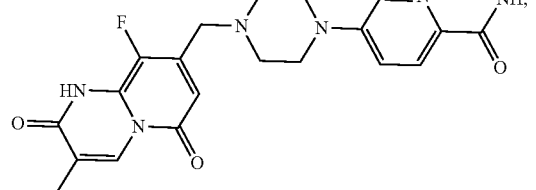
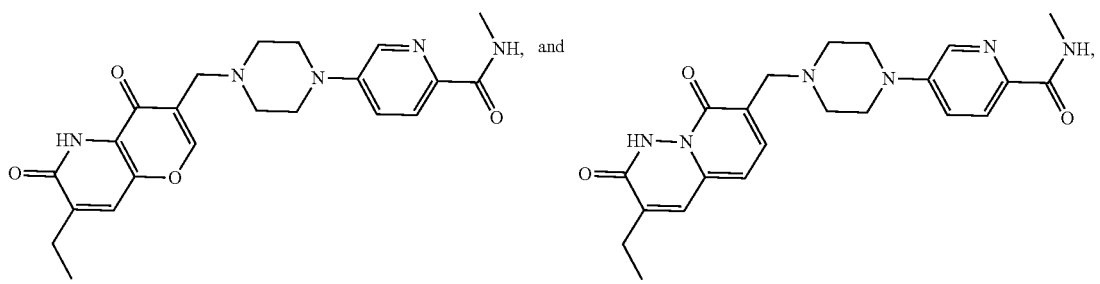
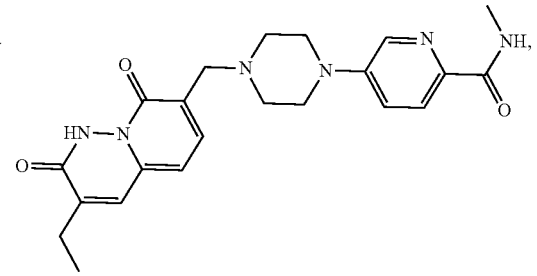
or a pharmaceutically acceptable salt, solvate, or stereoisomer thereof.
In some embodiments, the compound is selected from the group consisting of:
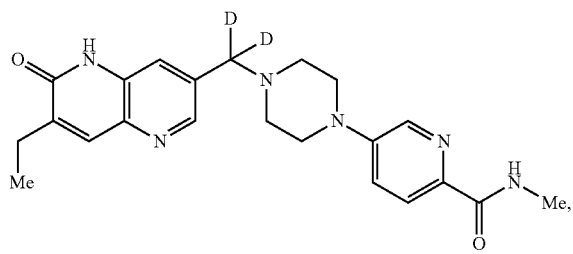
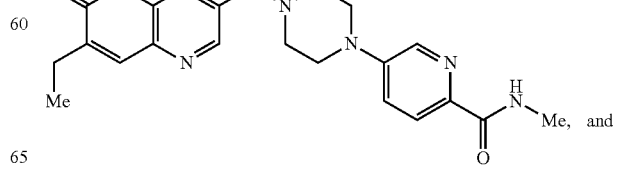
-continued

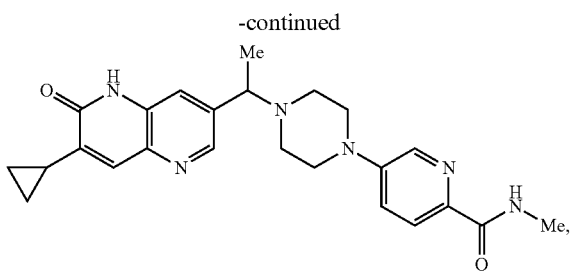

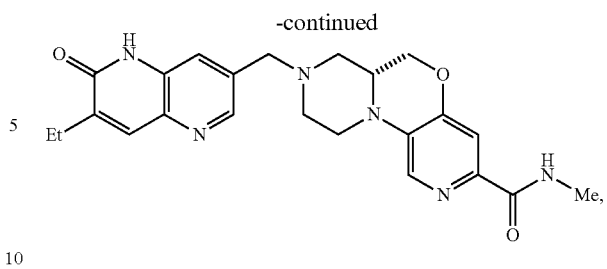

or a pharmaceutically acceptable salt, solvate, or stereoisomer thereof.

In some embodiments, the compound is selected from the group consisting of:

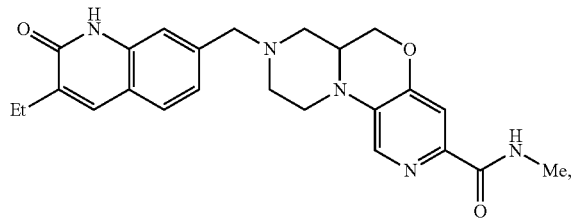

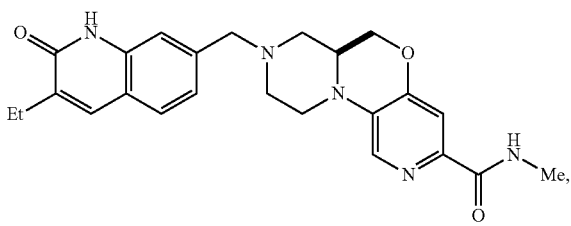

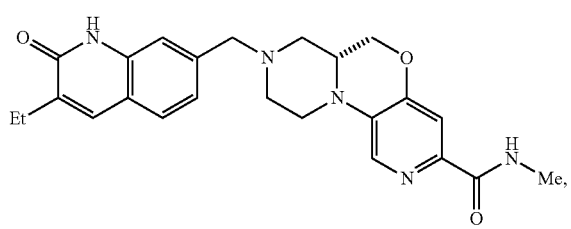

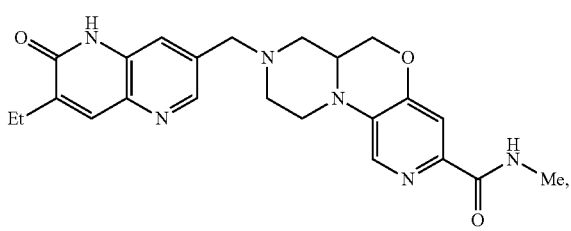

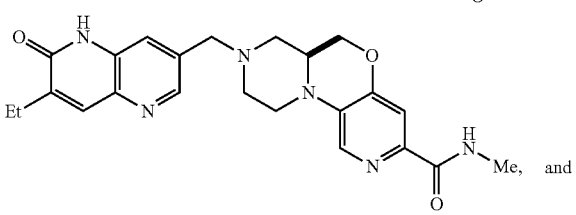

or a pharmaceutically acceptable salt, solvate, or stereoisomer thereof.

Further Forms of Compounds Disclosed Herein

Isomers Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as 3H and $^{14}$C are incorporated, are useful in drug and/or substrate tissue distribution assays. Tritiated, i.e., 3H and carbon-14, i.e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4} alkyl)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment Disclosed herein are methods of treatment of a disease in which inhibition of PARP is beneficial, the method comprising administering a compound disclosed herein. Also disclosed herein are methods of treatment of a disease in which inhibition of PARP1 is beneficial, the method comprising administering a compound disclosed herein. In some embodiments, the disease is cancer. In some embodiments, the cancer is breast cancer, ovarian cancer, pancreatic cancer, prostate cancer, a hematological cancer, a gastrointestinal cancer such as gastric cancer and colorectal cancer, or lung cancer. In some embodiments, the cancer is breast cancer, ovarian cancer, pancreatic cancer, or prostate cancer. In some embodiment, the cancer is leukemia, colon cancer, glioblastoma, lymphoma, melanoma, or cervical cancer.

In some embodiments, the cancer comprises a BRCA1 and/or a BRCA2 mutation.

In some embodiments, the cancer comprising a BRCA1 and/or a BRCA2 mutation is bladder cancer, brain & CNS cancers, breast cancer, cervical cancer, colorectal cancer, esophagus cancer, Hodgkin lymphoma, non-Hodgkin lymphoma, kidney cancer, leukemia, lung cancer, melanoma, myeloma, oral cavity cancer, ovarian cancer, pancreatic cancer, prostate cancer, skin cancer, stomach cancer, thyroid cancer, or uterus cancer.

In some embodiments, the cancer is a cancer deficient in Flomologous Recombination (FIR) dependent DNA DSB repair activity. The FIR dependent DNA DSB repair pathway repairs double-strand breaks (DSBs) in DNA via homologous mechanisms to reform a continuous DNA helix. The components of the FIR dependent DNA DSB repair pathway include, but are not limited to, ATM (NM_000051), RAD51 (NM_002875), RAD51 L1 (NM_002877), RAD51 C (NM_002876), RAD51 L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE1 1 A (NM_005590) and NBS1 (NM_002485). Other proteins involved in the FIR dependent DNA DSB repair pathway include regulatory factors such as EMSY. In some embodiments, the cancer which is deficient in FIR dependent DNA DSB repair comprises one or more cancer cells which have a reduced or abrogated ability to repair DNA DSBs through that pathway, relative to normal cells i.e. the activity of the FIR dependent DNA DSB repair pathway may be reduced or abolished in the one or more cancer cells.

In some embodiments, the activity of one or more components of the FIR dependent DNA DSB repair pathway is abolished in the one or more cancer cells of an individual having a cancer which is deficient in FIR dependent DNA DSB repair.

In some embodiments, the cancer cells have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor. BRCA1 and BRCA2 are known tumor suppressors whose wild-type alleles are frequently lost in tumors of heterozygous carriers. Amplification of the EMSY gene, which encodes a BRCA2 binding factor, is also known to be associated with breast and ovarian cancer. Carriers of mutations in BRCA1 and/or BRCA2 are also at elevated risk of certain cancers, including breast cancer, ovarian cancer, pancreatic cancer, prostate cancer, a hematological cancer, gastrointestinal cancer, and lung cancer.

To minimize the risks of off-target effects, it is desirable for drug molecules to possess selectivity for a specific target.

Avoiding inhibition of PARP family isoforms beyond PARP1 may be important in minimizing toxicities that may arise from inhibition of non-PARP1 isoforms. The pharmacology of inhibiting PARP isoforms beyond PARP1 may drive toxicities that reduce the therapeutic index for agents that possess lower selectivity's for PARP1 against PARP isoforms. PARP3, like PARP1, plays a role in DNA damage but has also been found to be a key player in the integrity of the mitotic spindle and in telomerase integrity (Boehler, C., Gauthier, L R., Mortusewicz O. et al. Poly(ADP-ribose) polymerase 3 (PARP3), a newcomer in cellular response to DNA damage and mitotic progression. PNAS, Jan. 26, 2011, 108 (7) 2783-2788). PARP5A also known as Tankyrase 1, plays key roles in Wnt signaling and telomere length (Kulak, O., Chen, H., Holohan B. et al. Disruption of Wnt/β-Catenin Signaling and Telomeric Shortening Are Inextricable Consequences of Tankyrase Inhibition in Human Cells. Mol Cell Biol. 2015 July; 35(14), 2425-2435). PARP6 is an essential microtubule-regulatory gene in mice, germline mutations in PARP6 that abrogate the catalytic activity has negative effects on neuronal function in humans (Vermehren-Schmaedick, A., Huang J. Y., Levinson, M. et al. Characterization of PARP6 Function in Knockout Mice and Patients with Developmental Delay. Cells, 2021 June; 10(6), 1289). PARP7 catalytic inhibition causes hyper stimulatory effects on type one interferon producing an autoimmune phenotype (Gozgit, J. M., Vasbinder, M. M., Abo, R. P. et al. PARP7 negatively regulates the type I interferon response in cancer cells and its inhibition triggers antitumor immunity. Volume 39, Issue 9, 13 Sep. 2021, Pages 1214-1226). While the exact function of PARP8 has not been established, its knockout has been shown to induce mitotic and nuclear morphology defects and a decrease in cellular viability (Vyas, S., Chesarone-Cataldo, M., Todorova, T., et al. A Systematic Analysis of the PARP Protein Family Identifies New Functions Critical for Cell Physiology. Nat. Commun. 2013, 4 (1), 2240). PARP10 has been described as a MYC interacting protein with tumor suppressor activities (Yu, M., Schreek, S., Cerni, C. et al. PARP-10, a novel Myc-interacting protein with poly(ADP-ribose) polymerase activity, inhibits transformation. Oncogene, 2005 volume 24, pages 1982-1993).

In some embodiments, the compounds disclosed herein, or a pharmaceutically acceptable salt, solvate, or stereoisomer thereof, are PARP1 selective over other members of the PARP family including PARP2, PARP3, PARP6, PARP7, PARP8, PARP10, PARP11, PARP14, PARP15, TNKS1 (PARP5A), and TNKS2 (PARP5B). In some embodiments, the compounds disclosed herein, or a pharmaceutically acceptable salt, solvate, or stereoisomer thereof, are selective for PARP1 over PARP2. In some embodiments, the compounds disclosed herein, or a pharmaceutically acceptable salt, solvate, or stereoisomer thereof, are selective for PARP1 over PARP3. In some embodiments, the compounds disclosed herein, or a pharmaceutically acceptable salt, solvate, or stereoisomer thereof, are selective for PARP1 over PARP6. In some embodiments, the compounds disclosed herein, or a pharmaceutically acceptable salt, solvate, or stereoisomer thereof, are selective for PARP1 over PARP7. In some embodiments, the compounds disclosed herein, or a pharmaceutically acceptable salt, solvate, or stereoisomer thereof, have selective for PARP1 over PARP8. In some embodiments, the compounds disclosed herein, or a pharmaceutically acceptable salt, solvate, or stereoisomer thereof, are selective for PARP1 over PARP10. In some embodiments, the compounds disclosed herein, or a pharmaceutically acceptable salt, solvate, or stereoisomer thereof, are selective for PARP1 over PARP11. In some embodiments, the compounds disclosed herein, or a pharmaceutically acceptable salt, solvate, or stereoisomer thereof, are selective for PARP1 over PARP14. In some embodiments, the compounds disclosed herein, or a pharmaceutically acceptable salt, solvate, or stereoisomer thereof, are selective for PARP1 over PARP15. In some embodiments, the compounds disclosed herein, or a pharmaceutically acceptable salt, solvate, or stereoisomer thereof, are selective for PARP1 over TNKS1 (PARP5A). In some embodiments, the compounds disclosed herein, or a pharmaceutically acceptable salt, solvate, or stereoisomer thereof, are selective for PARP1 over TNKS2 (PARP5B).

In some embodiments, the compounds disclosed herein, or a pharmaceutically acceptable salt, solvate, or stereoisomer thereof, are more than 10000-fold more PARP1 selective over PARP2. In some embodiments, the compounds disclosed herein, or a pharmaceutically acceptable salt, solvate, or stereoisomer thereof, are more than 9000-fold more PARP1 selective over PARP2. In some embodiments, the compounds disclosed herein, or a pharmaceutically acceptable salt, solvate, or stereoisomer thereof, are more than 8000-fold more PARP1 selective over PARP2. In some embodiments, the compounds disclosed herein, or a pharmaceutically acceptable salt, solvate, or stereoisomer thereof, are more than 7000-fold more PARP1 selective over PARP2. In some embodiments, the compounds disclosed herein, or a pharmaceutically acceptable salt, solvate, or stereoisomer thereof, are more than 6000-fold more PARP1 selective over PARP2. In some embodiments, the compounds disclosed herein, or a pharmaceutically acceptable salt, solvate, or stereoisomer thereof, are more than 5000-fold more PARP1 selective over PARP2. In some embodiments, the compounds disclosed herein, or a pharmaceutically acceptable salt, solvate, or stereoisomer thereof, are more than 4000-fold more PARP1 selective over PARP2. In some embodiments, the compounds disclosed herein, or a pharmaceutically acceptable salt, solvate, or stereoisomer thereof, are more than 3000-fold more PARP1 selective over PARP2. In some embodiments, the compounds disclosed herein, or a pharmaceutically acceptable salt, solvate, or stereoisomer thereof, are more than 2000-fold more PARP1 selective over PARP2. In some embodiments, the compounds disclosed herein, or a pharmaceutically acceptable salt, solvate, or stereoisomer thereof, are more than 1000-fold more PARP1 selective over PARP2. In some embodiments, the compounds disclosed herein, or a pharmaceutically acceptable salt, solvate, or stereoisomer thereof, are more than 100-fold more PARP1 selective over PARP2. In some embodiments, the compounds disclosed herein has at least a 400- to 600-fold selectivity for PARP1 over PARP2. In some embodiments, the compounds disclosed herein, or a pharmaceutically acceptable salt, solvate, or stereoisomer thereof, have at least a 400-fold selectivity for PARP1 over PARP2. In some embodiments, the compounds disclosed herein, or a pharmaceutically acceptable salt, solvate, or stereoisomer thereof, have at least a 500-fold selectivity for PARP1 over PARP2.

In some embodiments, the compounds disclosed herein, or a pharmaceutically acceptable salt, solvate, or stereoisomer thereof, are more than 100-fold more PARP1 selective over PARP3. In some embodiments, the compounds disclosed herein, or a pharmaceutically acceptable salt, solvate, or stereoisomer thereof, are more than 200-fold more PARP1 selective over PARP3.

In some embodiments, the compounds disclosed herein, or a pharmaceutically acceptable salt, solvate, or stereoisomer thereof, have at least a 200- to 700-fold selectivity for PARP1 over PARP3. In some embodiments, the compounds disclosed herein, or a pharmaceutically acceptable salt, solvate, or stereoisomer thereof, have at least a 200-fold selectivity for PARP1 over PARP3. In some embodiments, the compounds disclosed herein, or a pharmaceutically acceptable salt, solvate, or stereoisomer thereof, have at least a 650-fold selectivity for PARP1 over PARP3.

In some embodiments, the compounds disclosed herein, or a pharmaceutically acceptable salt, solvate, or stereoisomer thereof, have more than 1000-fold more PARP1 selective over PARP6. In some embodiments, the compounds disclosed herein, or a pharmaceutically acceptable salt, solvate, or stereoisomer thereof, have at least a 2000- to 3000-fold selectivity for PARP1 over PARP6. In some embodiments, the compounds disclosed herein, or a pharmaceutically acceptable salt, solvate, or stereoisomer thereof, have at least a 2400-fold selectivity for PARP1 over PARP6. In some embodiments, the compounds disclosed herein, or a pharmaceutically acceptable salt, solvate, or stereoisomer thereof, have at least a 3000-fold selectivity for PARP1 over PARP6.

In some embodiments, the compounds disclosed herein, or a pharmaceutically acceptable salt, solvate, or stereoisomer thereof, have more than 500-fold more PARP1 selective over PARP7. In some embodiments, the compounds disclosed herein, or a pharmaceutically acceptable salt, solvate, or stereoisomer thereof, have at least a 600- to 900-fold selectivity for PARP1 over PARP7. In some embodiments, the compounds disclosed herein, or a pharmaceutically acceptable salt, solvate, or stereoisomer thereof, have at least a 600-fold selectivity for PARP1 over PARP7. In some embodiments, the compounds disclosed herein, or a pharmaceutically acceptable salt, solvate, or stereoisomer thereof, have at least a 800-fold selectivity for PARP1 over PARP7.

In some embodiments, the compounds disclosed herein, or a pharmaceutically acceptable salt, solvate, or stereoisomer thereof, have more than 3000-fold more PARP1 selective over PARP8. In some embodiments, the compounds disclosed herein, or a pharmaceutically acceptable salt, solvate, or stereoisomer thereof, have at least a 5000- to 9000-fold selectivity for PARP1 over PARP8. In some embodiments, the compounds disclosed herein, or a pharmaceutically acceptable salt, solvate, or stereoisomer thereof, have at least a 8000-fold selectivity for PARP1 over PARP8. In some embodiments, the compounds disclosed herein, or a pharmaceutically acceptable salt, solvate, or stereoisomer thereof, have at least a 5000-fold selectivity for PARP1 over PARP8.

In some embodiments, the compounds disclosed herein, or a pharmaceutically acceptable salt, solvate, or stereoisomer thereof, have more than 200-fold more PARP1 selective over PARP10. In some embodiments, the compounds disclosed herein, or a pharmaceutically acceptable salt, solvate, or stereoisomer thereof, have at least a 300- to 400-fold selectivity for PARP1 over PARP10. In some embodiments, the compounds disclosed herein, or a pharmaceutically acceptable salt, solvate, or stereoisomer thereof, have at least a 350-fold selectivity for PARP1 over PARP10. In some embodiments, the compounds disclosed herein, or a pharmaceutically acceptable salt, solvate, or stereoisomer thereof, have at least a 300-fold selectivity for PARP1 over PARP10.

In some embodiments, the compounds disclosed herein, or a pharmaceutically acceptable salt, solvate, or stereoisomer thereof, have more than 5-fold more PARP1 selective over PARP11. In some embodiments, the compounds disclosed herein, or a pharmaceutically acceptable salt, solvate, or stereoisomer thereof, have at least a 5- to 270-fold selectivity for PARP1 over PARP11. In some embodiments, the compounds disclosed herein, or a pharmaceutically acceptable salt, solvate, or stereoisomer thereof, have at least a 6-fold selectivity for PARP1 over PARP11. In some embodiments, the compounds disclosed herein, or a pharmaceutically acceptable salt, solvate, or stereoisomer thereof, have at least a 270-fold selectivity for PARP1 over PARP11.

In some embodiments, the compounds disclosed herein, or a pharmaceutically acceptable salt, solvate, or stereoisomer thereof, have more than 2000-fold more PARP1 selective over PARP14. In some embodiments, the compounds disclosed herein, or a pharmaceutically acceptable salt, solvate, or stereoisomer thereof, have at least a 1400- to 2600-fold selectivity for PARP1 over PARP14. In some embodiments, the compounds disclosed herein, or a pharmaceutically acceptable salt, solvate, or stereoisomer thereof, have at least a 1400-fold selectivity for PARP1 over PARP14. In some embodiments, the compounds disclosed herein, or a pharmaceutically acceptable salt, solvate, or stereoisomer thereof, have at least a 2600-fold selectivity for PARP1 over PARP14.

In some embodiments, the compounds disclosed herein, or a pharmaceutically acceptable salt, solvate, or stereoisomer thereof, have more than 1000-fold more PARP1 selective over PARP15. In some embodiments, the compounds disclosed herein, or a pharmaceutically acceptable salt, solvate, or stereoisomer thereof, have at least a 1600-fold selectivity for PARP1 over PARP15.

In some embodiments, the compounds disclosed herein, or a pharmaceutically acceptable salt, solvate, or stereoisomer thereof, have more than 100-fold more PARP1 selective over TNKS1 (PARP5A). In some embodiments, the compounds disclosed herein, or a pharmaceutically acceptable salt, solvate, or stereoisomer thereof, have at least a 100- to 250-fold selectivity for PARP1 over TNKS1 (PARP5A). In some embodiments, the compounds disclosed herein, or a pharmaceutically acceptable salt, solvate, or stereoisomer thereof, have at least a 100-fold selectivity for PARP1 over TNKS1 (PARP5A). In some embodiments, the compounds disclosed herein, or a pharmaceutically acceptable salt, solvate, or stereoisomer thereof, have at least a 230-fold selectivity for PARP1 over TNKS1 (PARP5A).

In some embodiments, the compounds disclosed herein, or a pharmaceutically acceptable salt, solvate, or stereoisomer thereof, have more than 100-fold more PARP1 selective over TNKS2 (PARP5B). In some embodiments, the compounds disclosed herein, or a pharmaceutically acceptable salt, solvate, or stereoisomer thereof, have at least a 100- to 150-fold selectivity for PARP1 over TNKS2 (PARP5B). In some embodiments, the compounds disclosed herein, or a pharmaceutically acceptable salt, solvate, or stereoisomer thereof, have at least a 140-fold selectivity for PARP1 over TNKS2 (PARP5B). In some embodiments, the compounds disclosed herein, or a pharmaceutically acceptable salt, solvate, or stereoisomer thereof, have at least a 130-fold selectivity for PARP1 over TNKS2 (PARP5B).

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are methods of treating cancer using a compound disclosed herein, or a pharmaceutically acceptable salt, solvate, or stereoisomer thereof, in combination with an additional therapeutic agent.

In some embodiments, the additional therapeutic agent is an anticancer agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

EXAMPLES

Example 1

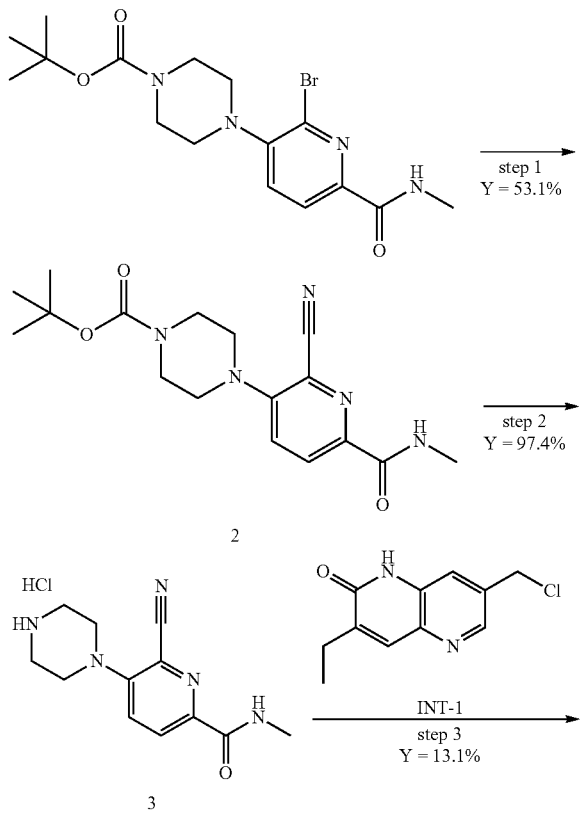

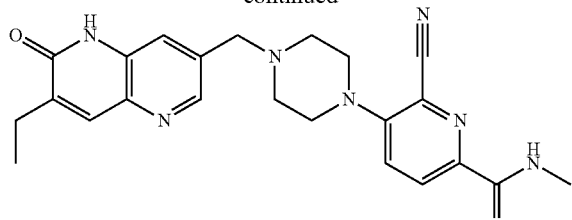

Example 1

Step 1: Preparation of tert-butyl 4-[2-cyano-6-(methylcarbamoyl)pyridin-3-yl]piperazine-1-carboxylate To a stirred solution of tert-butyl 4-[2-bromo-6-(methylcarbamoyl)pyridin-3-yl]piperazine-1-carboxylate (1.00 g, 2.50 mmol, 1.00 equiv.) and Zn(CN)$_2$ (0.44 g, 3.76 mmol, 1.50 equiv.) in DMF (10 mL) were added Pd(PPh$_3$)$_4$ (0.29 g, 0.25 mmol, 0.10 equiv.) at room temperature under N$_2$ atmosphere. The resulting mixture was stirred for 3 h at 120° C. under N$_2$ atmosphere. The reaction was monitored by LCMS. The resulting mixture was diluted with H$_2$O (50 mL). The resulting mixture was extracted with EtOAc (3×100 mL). The combined organic layers were washed with brine (3×30 mL), dried over anhydrous Na$_2$SO$_4$. After filtration, the filtrate was concentrated under reduced pressure. The residue was purified by silica gel column chromatography. The pure fraction was concentrated under vacuum to afford tert-butyl 4-[2-cyano-6-(methylcarbamoyl)pyridin-3-yl]piperazine-1-carboxylate (460 mg, 53.1%) as a white solid. LC-MS: (ES+H, m/z): [M+H]$^+$=346.2.

1H NMR (300 MHz, DMSO-d6) δ 8.60 (q, 1H), 8.13 (d, 1H), 7.76 (d, 1H), 3.52 (dd, 4H), 3.33 (d, 4H), 2.80 (d, 3H), 1.43 (s, 9H).

Step 2: Preparation of 6-cyano-N-methyl-5-(piperazin-1-yl)pyridine-2-carboxamide, HCl Salt To a stirred solution of tert-butyl 4-[2-cyano-6-(methylcarbamoyl)pyridin-3-yl]piperazine-1-carboxylate (260 mg, 0.75 mmol, 1.00 equiv.) in dioxane (2 ml) was added HCl (gas) in 1,4-dioxane (2 mL, 4M in 1,4-dioxane) dropwise at ice bath. The resulting mixture was stirred for 1 h at room temperature. The reaction was monitored by LCMS. The resulting mixture was concentrated under reduced pressure to afford 6-cyano-N-methyl-5-(piperazin-1-yl)pyridine-2-carboxamide, HCl salt (180 mg, 97.4%) The crude product was used in the next step directly without further purification.

LC-MS: (M+H, m/z): [M+H]$^+$=245.9. 1H NMR (300 MHz, DMSO-d6) δ 9.32 (brs, 2H), 8.65 (d, 1H), 8.16 (d, 1H), 7.86 (d, 1H), 3.58 (dd, 4H), 3.29 (s, 4H), 2.80 (d, 3H).

Step 3: Preparation of 6-cyano-5-{4-[(7-ethyl-6-oxo-5H-1,5-naphthyridin-3-yl)methyl]piperazin-1-yl}-N-methylpyridine-2-carboxamide To a stirred solution of 7-(chloromethyl)-3-ethyl-1H-1,5-naphthyridin-2-one (50 mg, 0.22 mmol, 1.00 equiv.) and 6-cyano-N-methyl-5-(piperazin-1-yl)pyridine-2-carboxamide (60 mg, 0.25 mmol, 1.10 equiv.) and KI (7 mg, 0.04 mmol, 0.20 equiv.) in MeCN (3 mL) were added DIEA (145 mg, 1.12 mmol, 5.00 equiv.) dropwise at room temperature under N$_2$ atmosphere. The resulting mixture was stirred for 2 h at 80° C. under N$_2$ atmosphere. The reaction was monitored by LCMS. The resulting mixture was concentrated under reduced pressure. The residue was dissolved in DMSO (3 mL). The crude product was purified by Prep-HPLC. The pure fraction was concentrated and lyophilized to afford 6-cyano-5-{4-[(7-ethyl-6-oxo-5H-1,5-naphthyridin-3-yl)methyl]piperazin-1-yl}-N-methylpyridine-2-carboxamide (12.9 mg, 13.11%) as a white solid. LC-MS: (ES+H, m/z): [M+H]$^+$=431.9. 1H NMR (300 MHz, DMSO-d6) δ 11.87 (s, 1H), 8.58 (d, 1H), 8.42 (s, 1H), 8.11 (d, 1H), 7.74 (d, 2H), 7.62 (s, 1H), 3.68 (s, 2H), 3.37 (d, 4H), 2.79 (d, 3H), 2.60-2.56 (m, 6H), 1.19 (t, 3H).

The following examples were made using similar procedures shown for example 1.

| Ex | NMR | LCMS (ESI) m/z |
|---|---|---|
| 37 | $^1$H NMR (400 MHz, DMSO-d6) δ 11.88 (s, 1H), 8.57 (q, 1H), 8.41 (d, 1H), 8.11 (d, 1H), 7.83 (s, 1H), 7.74 (d, 1H), 7.62 (d, 1H), 3.68 (s, 2H), 3.37 (m, 4H), 2.79 (d, 3H), 2.61 (m, 4H), 2.14 (d, 3H). | [M + H]$^+$ = 418.25 |
| 97 | $^1$H NMR (300 MHz, DMSO-d6) δ 11.90 (s, 1H), 8.58 (d, 1H), 8.40 (d, 1H), 8.11 (d, 1H) 7.75 (d, 1H), 7.60 (s, 1H), 7.43 (s, 1H), 3.67 (s, 2H), 3.41 – 3.35 (m, 4H), 2.79 (d, 3H), 2.61 (t, 4H), 2.18 – 2.11 (m, 1H), 1.03 – 0.93 (m, 2H), 0.84-0.81 (m, 2H). | [M + H]$^+$ = 444.2 |

Example 2

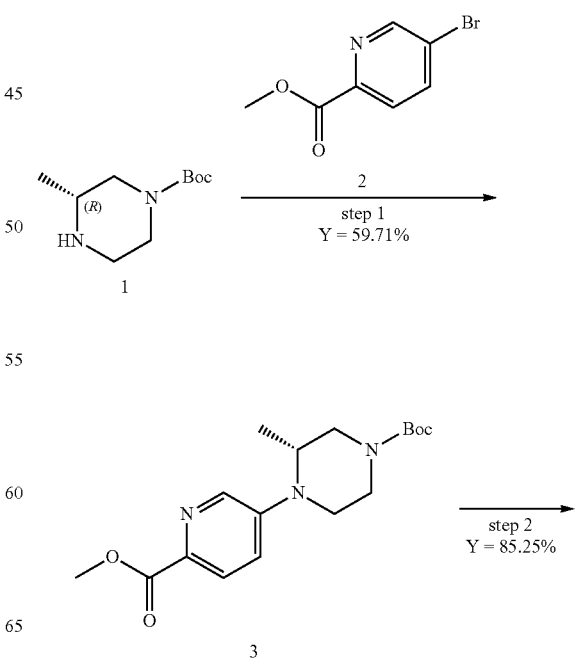

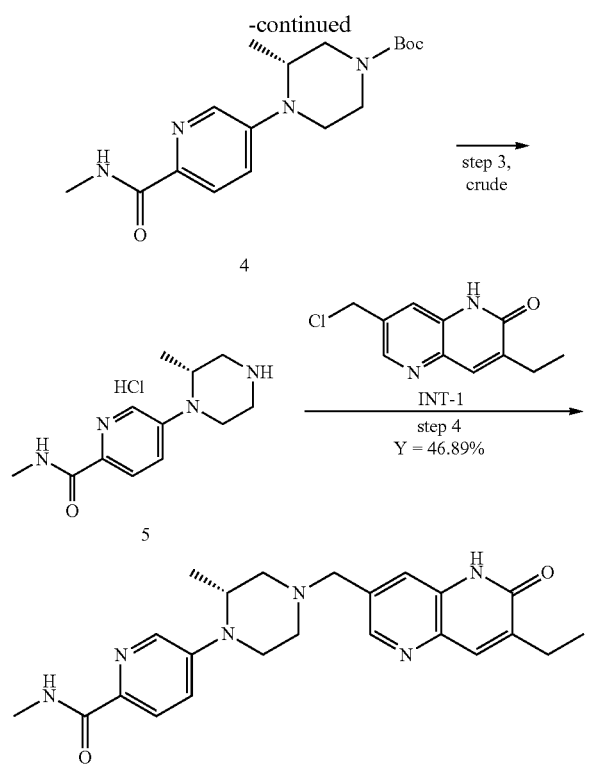

Example 2

Step 1: Preparation of tert-butyl (3R)-4-[6-(methoxycarbonyl)pyridin-3-yl]-3-methylpiperazine-1-carboxylate A mixture of tert-butyl (3R)-3-methylpiperazine-1-carboxylate (5.00 g, 24.96 mmol, 1.00 equiv, $[\alpha]^{26}D$ (c=1.0, CHCl$_3$): +14.75), methyl 5-bromopyridine-2-carboxylate (5.66 g, 26.21 mmol, 1.05 equiv), Cs$_2$CO$_3$ (16.27 g, 49.93 mmol, 2.00 equiv) and RuPhos Palladacycle Gen.3 (1.04 g, 1.25 mmol, 0.05 equiv) in 1,4-dioxane (50 mL) was stirred overnight at 120° C. under nitrogen atmosphere. The reaction was monitored by LCMS. The mixture was allowed to cool down to room temperature. The resulting mixture was diluted with water (100 mL), and then was extracted with EtOAc (2×100 mL). The combined organic layers were washed with brine (2×50 mL), dried over anhydrous Na$_2$SO$_4$. After filtration, the filtrate was concentrated under reduced pressure. The residue was purified by silica gel column chromatography to afford tert-butyl (3R)-4-[6-(methoxycarbonyl)pyridin-3-yl]-3-methylpiperazine-1-carboxylate (5.00 g, 59.71%) as a white solid. LC-MS: (ES+H, m/z): [M+H]$^+$=336.1.

Step 2: Preparation of tert-butyl (3R)-3-methyl-4-[6-(methylcarbamoyl)pyridin-3-yl]piperazine-1-carboxylate A solution of tert-butyl (3R)-4-[6-(methoxycarbonyl)pyridin-3-yl]-3-methylpiperazine-1-carboxylate (2.00 g, 5.96 mmol, 1.00 equiv) and methanamine (8 mL, 25-30 wt % solution in water) in CH$_3$OH (7 mL) was stirred for 3 h at room temperature under nitrogen atmosphere. The reaction was monitored by LCMS. The reaction was quenched with sat. NH$_4$Cl (30 mL) at room temperature. The resulting mixture was extracted with CH$_2$Cl$_2$ (3×50 mL). The combined organic layers were washed with brine (2×50 mL), dried over anhydrous Na$_2$SO$_4$. After filtration, the filtrate was concentrated under reduced pressure to afford tert-butyl (3R)-3-methyl-4-[6-(methylcarbamoyl)pyridin-3-yl]piperazine-1-carboxylate (1.70 g, 85.25%) as a light yellow oil. LC-MS: (ES+H, m/z): [M+H]$^+$=335.3.

Step 3: Preparation of N-methyl-5-[(2R)-2-methylpiperazin-1-yl]pyridine-2-carboxamide, HCl Salt A mixture of tert-butyl (3R)-3-methyl-4-[6-(methylcarbamoyl)pyridin-3-yl]piperazine-1-carboxylate (500 mg, 1.50 mmol, 1.00 equiv) and HCl (gas) in 1,4-dioxane (3.7 mL, 14.95 mmol, 10.00 equiv, 4.0 M) was stirred for 2 h at room temperature under nitrogen atmosphere. The reaction was monitored by LCMS. The resulting mixture was concentrated under reduced pressure to afford N-methyl-5-[(2R)-2-methylpiperazin-1-yl]pyridine-2-carboxamide, HCl salt (400 mg, crude) as a yellow solid. The crude product was used in the next step directly without further purification. LC-MS: (ES+H, m/z): [M+H]$^+$=234.9.

Step 4: Preparation of 5-[(2R)-4-[(7-ethyl-6-oxo-5H-1,5-naphthyridin-3-yl)methyl]-2-methylpiperazin-1-yl]-N-methylpyridine-2-carboxamide A mixture of N-methyl-5-[(2R)-2-methylpiperazin-1-yl]pyridine-2-carboxamide, HCl salt (128 mg, crude), 7-(chloromethyl)-3-ethyl-1H-1,5-naphthyridin-2-one (100 mg, 0.45 mmol, 1.00 equiv) and KI (15 mg, 0.09 mmol, 0.20 equiv) and DIEA (290 mg, 2.24 mmol, 5.00 equiv) in MeCN (10 mL) was stirred for 3 h at 80° C. under nitrogen atmosphere. The reaction was monitored by LCMS. The mixture was allowed to cool down to room temperature. The resulting mixture was extracted with EtOAc (2×30 mL). The combined organic layers were washed with brine (2×20 mL), dried over anhydrous Na$_2$SO$_4$. After filtration, the filtrate was concentrated under reduced pressure. The residue was purified by silica gel column chromatography to afford a crude product. The crude product was further purified by Prep-HPLC. The pure fraction was concentrated under reduced pressure and lyophilized to afford 5-[(2R)-4-[(7-ethyl-6-oxo-5H-1,5-naphthyridin-3-yl)methyl]-2-methylpiperazin-1-yl]-N-methylpyridine-2-carboxamide (90 mg, 46.89%) as a white solid. LC-MS: (ES+H, m/z): [M+H]$^+$=421.2. H NMR (400 MHz, DMSO-d$_6$) δ 11.90 (s, 1H), 8.42 (d, 1H), 8.37 (d, 1H), 8.21 (d, 1H), 7.82 (d, 1H), 7.76 (s, 1H), 7.67 (d, 1H), 7.33 (dd, 1H), 4.23 (s, 1H), 3.71 (d, 1H), 3.65-3.52 (m, 2H), 3.14-3.03 (m, 1H), 2.93 (d, 1H), 2.78 (d, 3H), 2.72 (d, 1H), 2.58-2.53 (m, 2H), 2.33 (dd, 1H), 2.29-2.15 (m, 1H), 1.19 (t, 3H), 1.13 (d, 3H).

The following examples were made using similar procedures shown for example 2.

| Ex | NMR | LCMS (ESI) m/z |
|---|---|---|
| 27 | $^1$H NMR (300 MHz, DMSO-d6) δ 11.91 (s, 1H), 8.42 (d, 1H), 8.38 (d, 1H), 8.21 (d, 1H), 7.83 (d, 1H), 7.76 (s, 1H), 7.69 (s, 1H), 7.33 (dd, 1H), 4.22 (brs, 1H), 3.72 (d, 1H), 3.65 – 3.53 (m, 2H), 3.15-3.03 (m, 1H), 2.94 (d, 1H), 2.78 | [M + H]$^+$ = 420.95 |

-continued

| Ex | NMR | LCMS (ESI) m/z |
|---|---|---|
|  | (d, 3H), 2.72 (d, 1H), 2.60 – 2.53 (m, 2H), 2.34-2.22 (m, 2H), 1.26 – 1.04 (m, 6H). | |
| 30 | $^1$H NMR (300 MHz, DMSO-d$_6$) δ 11.85 (s, 1H), 8.43 – 8.35 (m, 2H), 7.75 (s, 1H), 7.62 (d, 1H), 7.13 (s, 1H), 3.66 (s, 2H), 3.24-3.20 (m, 4H), 2.74 (d, 3H), 2.61-2.52 (m, 6H), 1.19 (t, 3H). | [M + H]$^+$ = 413.25 |
| 33 | $^1$H NMR (400 MHz, DMSO-d6) δ 11.87 (s, 1H), 8.44 – 8.36 (m, 2H), 8.27 (d, 1H), 7.85 – 7.80 (m, 2H), 7.62 (s, 1H), 7.39 (dd, 1H), 3.65 (s, 2H), 2.56 (t, 4H), 2.78 (d, 3H), 2.56 (t, 4H), 2.14 (d, 3H). | [M + H]$^+$ = 393.2 |
| 34 | 1H NMR (300 MHz, DMSO-d6) δ 11.89 (s, 1H), 8.45-8.36 (m, 2H), 7.84 (dd, J =8.0, 1.5 Hz, 1H), 7.62-7.52 (m, 2H), 7.42 (s, 1H), 3.64 (s, 2H), 3.31-3.13 (m, 4H), 2.76 (d, J = 4.8 Hz, 3H), 2.61-2.53 (m, 4H), 2.20-2.07 (m, 1H), 1.03-0.91 (m, 2H), 0.87-0.75 (m, 2H).<br>19F NMR (282 MHz, DMSO-d6) δ-72.53. | [M + H]$^+$ = 437.15. |
| 35 | $^1$H NMR (300 MHz, DMSO-d6) δ 11.87 (s, 1H), 8.41 (d, 1H), 8.27 (q, 1H), 8.13 (s, 1H) 7.76 (s, 1H), 7.62 (d, 1H), 7.22 (dd, 1H), 3.39 (m, 4H), 2.75 (d 3H), 2.60 – 2.52 (m, 6H), 1.19 (t, 3H).<br>$^{19}$F NMR (282 MHz, DMSO) δ-120.39. | [M + H]$^+$ = 427.15 |
| 38 | $^1$H NMR (300 MHz, DMSO-d6) δ 11.88 (s, 1H), 8.47-8.45 (m, 2H), 8.12 (d, 1H), 8.03 (q, 1H), 7.84 (s, 1H), 7.62 (s, 1H), 7.20 (d, 1H), 3.68 (s, 2H), 3.34-3.29 (m, 4H), 2.77 (s, 3H), 2.66-2.58 (m, 4H), 2.15 (s, 3H). | [M + H]$^+$ = 417.25 |
| 39 | $^1$H NMR (300 MHz, DMSO-d6, D$_2$O exchange) δ8.41 (s, 1H), 8.18 (br s), 8.02 (s, 1H), 7.78 (s, 1H), 7.73 (s, 1H), 7.04 (dd, 1H), 4.23 – 4.08 (m, 1H), 3.71 (d, 1H), 3.56 (d, 2H), 3.16 – 3.05 (m, 1H), 2.95 – 2.82 (m, 1H), 2.73 – 2.64 (m, 4H), 2.57 – 2.50 (m, 2H), 2.35 – 2.11 (m, 2H), 1.22 – 1.05 (m, 6H).<br>$^{19}$F NMR (282 MHz, DMSO) δ-120.36. | [M + H]$^+$ = 439.1 |
| 51 | $^1$H NMR (400 MHz, DMSO-d6) δ 11.93 (s, 1H), 8.45 – 8.41 (m, 2H), 7.92 (s, 1H), 7.77 (s, 1H), 7.66 (s, 1H), 6.75 (d, 1H), 4.81 – 3.41 (m, 6H), 2.75 (d, 3H), 2.61 – 2.50 (m, 6H), 1.19 (t, 3H).<br>$^{19}$F NMR (282 MHz, DMSO) δ-73.47. | [M + H]$^+$ = 425.2 |
| 61 | $^1$H NMR (300 MHz, DMSO-d6) δ 11.85 (s, 1H), 8.78 (d, 1H), 8.41 (d, 1H), 7.83 (d, 1H), 7.75 (s, 1H), 7.63 (s, 1H), 7.34 (d, 1H), 3.73 – 3.69 (m, 4H), 3.66 (s, 2H), 2.81 (d, 3H), 2.58 – 2.52 (m, 6H), 1.18 (t, 3H). | [M + H]$^+$ = 408.15 |
| 63 | $^1$H NMR (400 MHz, DMSO-d6) δ 11.88 (s, 1H), 8.42-8.33 (m, 2H), 8.23 (d, 1H), 7.85-7.80 (m, 2H), 7.62 (s, 1H), 7.39 (dd, 1H), 3.65(s, 2H), 3.34-3.31 (m, 4H), 2.89-2.80 (m, 1H), 2.55 (m, 4H), 2.14 (s 3H), 0.70-0.58 (m, 4H). | [M + H]$^+$ = 419.10 |
| 66 | $^1$H NMR (300 MHz, DMSO-d6) δ 11.91 (s, 1H), 8.60 (s, 1H), 8.41 (d, 1H), 8.12 (d, 1H), 7.86 – 7.78 (m, 2H), 7.65 (s, 1H), 4.02 (s, 1H), 3.65 (q, 2H), 3.47 (m, 1H), 3.22 (m, 1H), 2.90 – 2.76 (m, 4H), 2.55 (m, 2H), 2.42 (m, 1H), 2.14 (d, 3H), 1.13 (d, 3H). | [M + H]$^+$ = 432.2 |
| 67 | $^1$H NMR (300 MHz, DMSO-d6) δ 11.89 (s, 1H), 8.38 – 8.22 (m, 3H), 7.83 (d, 1H), 7.61 (s, 1H), 7.39 (m, 2H), 3.64 (s, 2H),3.32 – 3.24 (m, 4H), 2.53 – 2.43 (m, 4H), 2.25 – 2.10 (m, 1H),1.08 – 0.90 (m, 2H), 0.89 – 0.73 (m, 2H). | [M + H]$^+$ = 422.2 |
| 68 | $^1$H NMR (400 MHz, DMSO-d6) δ 11.88 (s, 1H), 8.44 – 8.33 (m, 2H), 8.27 (d, 1H), 7.81 (d, 1H), 7.76 (s, 1H), 7.64 (d, 1H), 7.39 (dd, 1H), 4.77 (dd, 1H), 4.65 (dd, 1H), 4.51 (s, 1H), 3.76 – 3.63 (m, 2H), 3.59 (d, 1H), 3.26 – 3.14 (m, 1H) 2.92 (t, 2H), 2.78 (d, 3H), 2.59 – 2.53 (m, 2H), 2.38 – 2.15 (m, 2H), 1.19 (t, 3H).<br>$^{19}$F NMR (377 MHz, DMSO) δ-223.51. | [M + H]$^+$ = 439.15 |
| 74 | $^1$H NMR (400 MHz, DMSO-d6) δ 11.94 (s, 1H), 8.41 – 8.35 (m, 2H), 8.20 (d, 1H), 7.82 (d, 1H), 7.65 (s, 1H), 7.42 (s, 1H), 7.33 (dd, 1H), 4.26 – 4.17 (m, 1H), 3.70 (d, 1H), 3.64 – 3.51 (m, 2H), 3.08 (td, 1H), 2.93 (d, 1H), 2.78 (d, 3H), 2.71 (d, 1H), 2.32 (dd, 1H), 2.28 – 2.09 (m, 2H), 1.12 (d, 3H), 1.01 – 0.93 (m, 2H), 0.85 – 0.78 (m, 2H). | [M + H]$^+$ = 433.30 |
| 79 | $^1$H NMR (400 MHz, DMSO-d6) δ 11.91 (s, 1H), 9.06 (d, 1H), 8.42 (d, 1H), 8.24 (d, 1H), 7.82 (d, 1H), 7.76 (s, 1H), 7.70-7.65 (m, 1H), 7.34 (dd, 1H), 5.08-4.95 (m, 1H), 4.75-4.68 (m, 4H), 4.30-4.24 (m, 1H), 3.75-3.54 (m, 3H), .14-3.04 (m, 1H), 2.95-2.92 (m, 1H), 2.74-2.71 (m, 1H), 2.58-2.53 (m, 2H), 2.37-2.19 (m, 2H), 1.26-1.11 (m, 6H). | [M + H]$^+$ = 463.10 |
| 93 | $^1$H NMR (300 MHz, DMSO-d6) δ 11.90 (s, 1H), 8.57 (s, 1H), 8.42 (d, 1H), 8.12 (d, 1H), 7.85 – 7.72 (m, 2H), 7.65 (d, 1H), 4.09 – 3.94 (m, 1H), 3.76 – 3.55 (m, 2H), 3.43-3.23 (m, 2H), 2.78 (m, 1H), 2.60 – 2.52 (m, 4H), 2.42 (t, 1H), 1.24 – 1.09 (m, 6H). | [M + H]$^+$ = 449.2 |
| 100 | $^1$H NMR (300 MHz, DMSO-d6) δ 11.88 (s, 1H), 8.38 (d, 1H), 8.26 (dd, 1H), 8.12 (s, 1H), 7.60 (d, 1H), 7.42 (s, 1H), 7.21 (dd, 1H), 3.63 (s, 2H), 3.41-3.35 (m, 4H), 2.74 (d, 3H), 2.56-2.52 (m, 4H), 2.19-2.09 (m, 1H), 1.01-0.94 (m, 2H), 0.85-0.79 (m, 2H).<br>$^{19}$F NMR (282 MHz, DMSO) δ-120.40. | [M + H]$^+$ = 437.25 |
| 105 | $^1$H NMR (300 MHz, DMSO-d6) δ 11.86 (s, 1H), 8.40 (d, 1H), 8.25 (d, 1H), 8.11 (s, 1H), 7.76 (s, 1H), 7.62 (d, 1H), 7.22 (dd, 1H), 3.65 (s, 2H), 3.41-3.35 (m, 4H), 2.85 – 2.74 (m, 1H), 2.60 – 2.52 (m, 6H), 1.19 (t, 3H), 0.72-0.62 (m, 2H), 0.54-0.61 (m, 2H).<br>$^{19}$F NMR (282 MHz, DMSO) δ -120.46 | [M + H]$^+$ = 451.4 |
| 108 | $^1$H NMR (400 MHz, DMSO-d6) δ 11.88 (s, 1H), 8.39 (d, 1H), 8.25 (d, 1H), (m, 8.10 (t, 1H), 7.83 (d, 1H), 7.61 (d, 1H), 7.22 (dd, 1H), 3.65 (s, 2H), 3.41-3.34 (m, 4H), 2.86-2.74 (m, 1H), 2.57-2.51(m, 4H), 2.14 (d, 3H), 0.70-0.63 2H), 0.61-0.54 (m, 2H).<br>$^{19}$F NMR (282 MHz, DMSO) δ-120.46. | [M + H]$^+$ = 437.20 |

-continued

| Ex | NMR | LCMS (ESI) m/z |
|---|---|---|
| 115 | $^1$H NMR (300 MHz, DMSO-d6) δ 8.39 (d, 2H), 8.25 (s, 1H), 7.83 (d, 1H), 7.61 (s, 1H), 7.46-7.26 (m, 2H), 3.51-3.32 (m, 4H), 2.78 (d, 3H), 2.78-2.54 (m,4H),2.14-2.13 (m,1H), 0.97-0.96 (m, 2H), 0.87-0.76 (m, 2H). | $[M + H]^+ = 21.2$ |
| 116 | $^1$H NMR (400 MHz, DMSO-d6) δ 11.89 (s, 1H), 8.38-8.36 (m, 2H), 8.26 (d, 1H), 7.83 (d, 1H), 7.60 (d, 1H), 7.44-7.35 (m, 2H), 3.36-3.30 (m, 4H), 2.55-2.53 (m, 4H), 2.15-2.13 (m, 1H), 1.00-0.94 (m, 2H), 0.86-0.78 (m, 2H) | $[M + H]^+ = 424.25$ |
| 117 | $^1$H NMR (400 MHz, DMSO-d6) δ 11.90 (s, 1H), 8.37 (dd, 2H), 8.23 (d, 1H), 7.83 (d, 1H), 7.60 (d, 1H), 7.45-7.35 (m, 2H), 3.33-3.26 (m, 4H), 2.90-2.80 (m, 1H), 2.61-2.52 (m, 4H), 2.20-2.09 (m, 1H), 1.04-0.91 (m, 2H), 0.88-0.77 (m, 2H), 0.70-0.56 (m, 4H). | $[M + H]^+ = 447.30$ |
| 119 | $^1$H NMR (400 MHz, DMSO-d6) δ 11.88 (s, 1H), 8.39 (d, 2H), 8.26 (d, 1H), 7.83 (d, 1H), 7.61 (d, 1H), 7.45 – 7.34 (m, 2H), 3.64 (s, 2H), 3.41 – 3.32 (m 4H), 2.59 – 2.52 (m, 4H), 2.19 – 2.10 (m, 1H), 1.01 – 0.93 (m, 2H), 0.85 – 0.79 (m, 2H). | $[M + H]^+ = 438.15$. |
| 134 | $^1$H NMR (300 MHz, DMSO-d6) δ 11.86 (s, 1H), 8.40 (d, 1H), 7.85 (t, 1H), 7.76 (s, 1H), 7.62 (d, 1H), 7.48 (t, 1H), 6.81 – 6.69 (m, 2H), 3.64 (s, 2H), 3.28 (d, 4H), 2.80 (tt, 1H), 2.56 (dd, 6H), 1.19 (t, 3H), 0.66 (td, 2H), 0.56 – 0.49 (m, 2H).<br>$^{19}$F NMR (282 MHz, DMSO) δ-111.70. | $[M + H]^+ = 450.15$ |
| 137 | $^1$H NMR (300 MHz, DMSO-d6) δ 11.88 (s, 1H), 8.43 – 8.39 (m, 2H), 8.26 (d, 1H), 7.83 (d, 1H), 7.61 (d, 1H), 7.42 – 7.37 (m, 2H), 3.64 (s, 2H), 3.33 – 3.29 (m, 2H), 3.27 – 3.24 (m, 4H), 2.56 (s, 4H), 2.20 – 2.10 (m, 1H), 1.10 (t, 3H), 1.00 – 0.94 (m, 2H), 0.85 (d, 2H). | $[M + H]^+ = 433.15$ |
| 139 | $^1$H NMR (300 MHz, DMSO-d6) δ 11.86 (s, 1H), 8.55 (d, 1H), 8.42 (d, 1H), 8.10 (d, 1H), 7.74 (d, 2H), 7.62 (d, 1H), 3.69 (s, 2H), 3.42 – 3.33 (m, 4H) 2.93-2.81 (m, 1H), 2.64 – 2.51 (m, 6H), 1.19 (t, 3H), 0.73 – 0.64 (m, 4H). | $[M + H]^+ = 458.20$ |
| 145 | $^1$H NMR (300 MHz, DMSO-d6) δ 11.86 (s, 1H), 8.45 – 8.36 (m, 1H), 8.18 (s, 1H), 7.89 – 7.74 (m, 2H), 7.62 (s, 1H), 7.00 (d, J = 8.9 Hz, 1H), 3.67 (s, 2H), 3.36-3.33 (m, 4H), 2.77 (d, J =4.5 Hz, 3H), 2.58-2.50 (m, 6H), 1.19 (t, J = 7.4 Hz, 3H).<br>$^{19}$F NMR (282 MHz, DMSO) δ -106.65. | $[M + H]^+ = 449.10$ |
| 158 | $^1$H NMR (300 MHz, DMSO-d6) δ 11.90 (s, 1H), 8.40-8.33 (m, 2H), 7.84 (d, J = 7.9 Hz, 1H), 7.63 – 7.51 (m, 2H), 7.42 (s, 1H), 3.64 (s, 2H), 3.19 – 3.14 (m, 4H), 2.87 – 2.84 (m, 1H), 2.59 – 2.54 (m, 4H), 2.17 – 2.14 (m, 1H), 0.99 – 0.95 (m, 2H), 0.86 – 0.77 (m, 2H), 0.69 – 0.62 (m, 4H).<br>$^{19}$F NMR (282 MHz, DMSO) δ -72.41. | $[M + H]^+ = 463.20$ |
| 161 | 1H NMR (300 MHz, DMSO-d6) δ 11.82 (s, 1H), 8.40-8.37 (m, 2H), 8.27 (d, 1H), 7.82 (d, 1H), 7.75 (s, 1H), 7.64 (s, 1H), 7.39 (dd, 1H), 4.11 (d, 1H), 3.71 (d, 1H), 3.60 (d, 1H), 3.41 – 3.36 (m, 1H) 2.96 (t, 1H), 2.84 – 2.70 (m, 5H), 2.64 – 2.53 (m, 3H), 2.28 (t, 1H), 1.25 – 1.09 (m, 6H). | $[M + H]^+ = 420.90$ |

Examples 3A and 3B

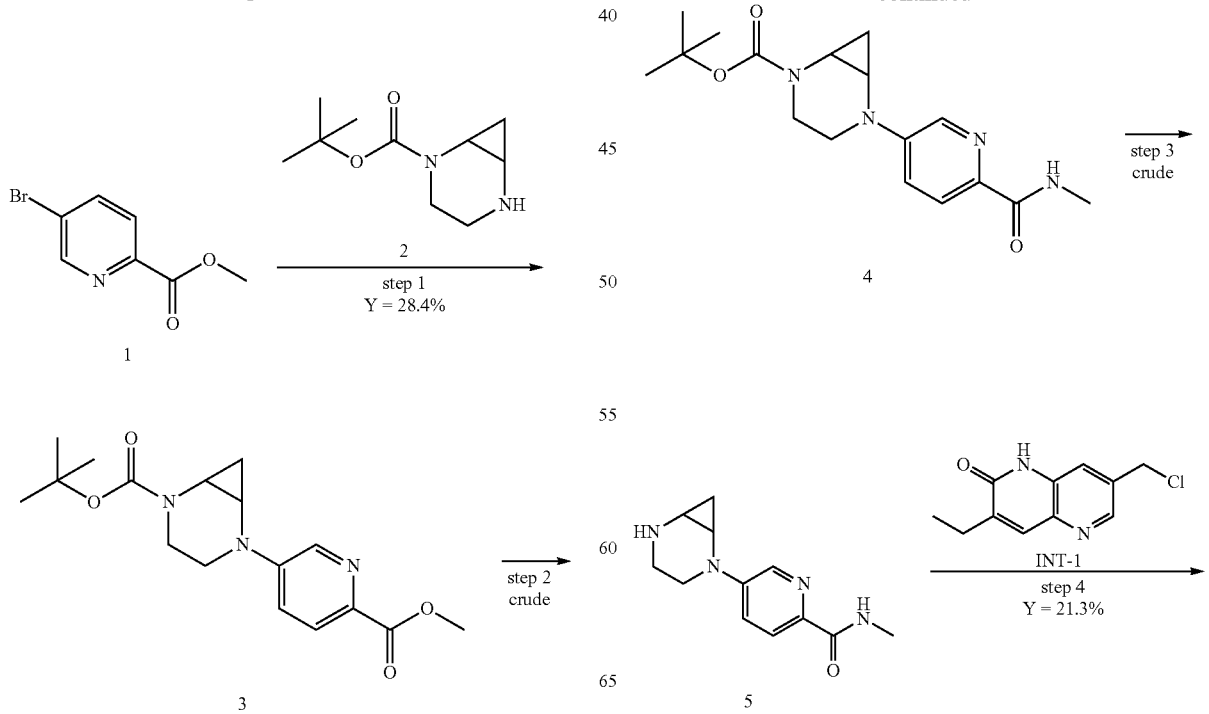

-continued

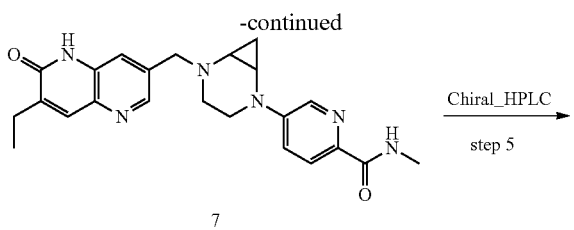

7

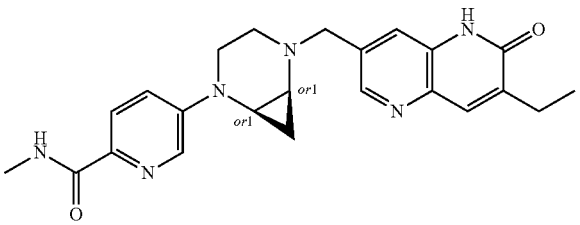

Example 3A
Y = 30.4%

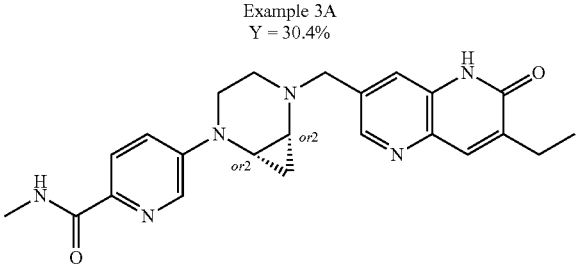

Example 3B
Y = 21.6%

Step 1: Preparation of tert-butyl 5-[6-(methoxycarbonyl)pyridin-3-yl]-2,5-diazabicyclo[4.1.0]heptane-2-carboxylate To a stirred mixture of methyl 5-bromopyridine-2-carboxylate (2.5 g, 11.57 mmol, 1 equiv) and tert-butyl 2,5-diazabicyclo[4.1.0]heptane-2-carboxylate (2.41 g, 12.15 mmol, 1.05 equiv) in dioxane (25 ml) were added RuPhos Palladacycle Gen.3 (0.48 g, 0.57 mmol, 0.05 equiv) and Cs$_2$CO$_3$ (7.54 g, 23.14 mmol, 2.00 equiv) at room temperature under nitrogen atmosphere. The resulting mixture was stirred for overnight at 110° C. under nitrogen atmosphere. The reaction was monitored by LCMS. The resulting mixture was diluted with water (200 mL). The resulting mixture was extracted with EtOAc (3×400 mL). The combined organic layers were washed with sat. NaCl(aq) (200 mL), dried over anhydrous Na$_2$SO$_4$. After filtration, the filtrate was concentrated under reduced pressure. The residue was purified by silica gel column chromatography to afford tert-butyl 5-[6-(methoxycarbonyl)pyridin-3-yl]-2,5-diazabicyclo[4.1.0]heptane-2-carboxylate (1.1 g, Y=28.4%) as a yellow solid. LC-MS: (ES+H, m/z): [M+H]$^+$=334.1

Step 2: Preparation of tert-butyl 5-[6-(methylcarbamoyl)pyridin-3-yl]-2,5-diazabicyclo[4.1.0]heptane-2-carboxylate A mixture of tert-butyl 5-[6-(methoxycarbonyl)pyridin-3-yl]-2,5-diazabicyclo[4.1.0]heptane-2-carboxylate (1 g, 3.00 mmol, 1 equiv) and CH$_3$NH$_2$ (2.33 g, 75.03 mmol, 25.01 equiv 40% in H$_2$O) in MeOH (15 ml) was stirred for 3 h at room temperature under nitrogen atmosphere. The reaction was monitored by LCMS. The resulting mixture was diluted with water (40 mL). The mixture was acidified to pH 6 with saturated NH$_4$Cl (aq.). The resulting mixture was extracted with CH$_2$Cl$_2$ (3×100 mL). The combined organic layers were washed with brine (50 mL), dried over anhydrous Na$_2$SO$_4$. After filtration, the filtrate was concentrated under reduced pressure to afford tert-butyl 5-[6-(methylcarbamoyl)pyridin-3-yl]-2,5-diazabicyclo[4.1.0]heptane-2-carboxylate (1.2 g, crude) as a yellow crude oil. LC-MS: (ES+H, m/z): [M+H]$^+$=333.1

Step 3: Preparation of 5-{2,5-diazabicyclo[4.1.0]heptan-2-yl}-N-methylpyridine-2-carboxamide To a stirred mixture of tert-butyl 5-[6-(methylcarbamoyl)pyridin-3-yl]-2,5-diazabicyclo[4.1.0]heptane-2-carboxylate (1.2 g, 3.61 mmol, 1 equiv) in MeOH (10 ml) was added HCl(gas) in 1,4-dioxane (6 mL) dropwise at room temperature under nitrogen atmosphere. The resulting mixture was stirred for 2 h at room temperature under nitrogen atmosphere. The reaction was monitored by LCMS. The resulting mixture was concentrated under reduced pressure. The residue was purified by trituration with diethyl ether (40 mL). The resulting mixture was concentrated under reduced pressure to afford 5-{2,5-diazabicyclo[4.1.0]heptan-2-yl}-N-methylpyridine-2-carboxamide (1 g, crude) as a yellow crude oil. LC-MS: (ES+H, m/z): [M+H]$^+$=232.9

Step 4: Preparation of 5-{5-[(7-ethyl-6-oxo-5H-1,5-naphthyridin-3-yl)methyl]-2,5-diazabicyclo[4.1.0]heptan-2-yl}-N-methylpyridine-2-carboxamide To a stirred mixture of 5-{2,5-diazabicyclo[4.1.0]heptan-2-yl}-N-methylpyridine-2-carboxamide (547.67 mg, 2.35 mmol, 1.5 equiv) and 7-(chloromethyl)-3-ethyl-1H-1,5-naphthyridin-2-one (350 mg, 1.57 mmol, 1.00 equiv) in acetonitrile (5 ml) were added KI (52.19 mg, 0.31 mmol, 0.20 equiv) at room temperature under nitrogen atmosphere. The resulting mixture was stirred for 2 h at 80° C. under nitrogen atmosphere. The reaction was monitored by LCMS. The resulting mixture was concentrated under reduced pressure. The residue was purified by silica gel column chromatography to afford 5-{5-[(7-ethyl-6-oxo-5H-1,5-naphthyridin-3-yl)methyl]-2,5-diazabicyclo[4.1.0]heptan-2-yl}-N-methylpyridine-2-carboxamide (180 mg, Y=21.3%) as a white solid. LC-MS: (ES+H, m/z): [M+H]$^+$=419.0

Step 5: Preparation of rel-5-[(1R,6S)-5-[(7-ethyl-6-oxo-5H-1,5-naphthyridin-3-yl)methyl]-2,5-diazabicyclo[4.1.0]heptan-2-yl]-N-methylpyridine-2-carboxamide (Example 3A) and rel-5-[(1R,6S)-5-[(7-ethyl-6-oxo-5H-1,5-naphthyridin-3-yl)methyl]-2,5-diazabicyclo[4.1.0]heptan-2-yl]-N-methylpyridine-2-carboxamide (Example 3B)

rel-5-[(1R,6S)-5-[(7-ethyl-6-oxo-5H-1,5-naphthyridin-3-yl)methyl]-2,5-diazabicyclo[4.1.0]heptan-2-yl]-N-methylpyridine-2-carboxamide was purified by PREP_CHIRAL_HPLC to afford rel-5-[(1R,6S)-5-[(7-ethyl-6-oxo-5H-1,5-naphthyridin-3-yl)methyl]-2,5-diazabicyclo[4.1.0]heptan-2-yl]-N-methylpyridine-2-carboxamide (Example 3A, 54.8 mg, Y=30.4%, ee=99.28%) and rel-5-[(1R,6S)-5-[(7-ethyl-6-oxo-5H-1,5-naphthyridin-3-yl)methyl]-2,5-diazabicyclo[4.1.0]heptan-2-yl]-N-methylpyridine-2-carboxamide (Example 3B, 39.0 mg, Y=21.6%, ee=98.42%). Note: The stereochemical assignments of examples 3A and 3B are arbitrary.

Example 3A

LC-MS: (ES+H, m/z): [M+H]⁺=419.2. 1H NMR (400 MHz, DMSO-d6) δ 11.83 (s, 1H), 8.44 (d, 1H), 8.37-8.32 (m, 1H), 8.19 (d, 1H), 7.85 (d, 1H), 7.75 (s, 1H), 7.69-7.65 (m, 1H), 7.27 (dd, 1H), 3.89 (q, 2H), 3.54-3.46 (m, 1H), 3.24-3.16 (m, 1H), 2.81-2.69 (m, 5H), 2.57-2.52 (m, 4H), 1.18 (t, 3H), 0.83-0.74 (m, 1H), 0.44-0.34 (m, 1H).

Example 3B

LC-MS: (ES+H, m/z): [M+H]⁺=419.1. 1H NMR (400 MHz, DMSO-d6) δ 11.83 (s, 1H), 8.46-8.40 (m, 1H), 8.38-8.31 (m, 1H), 8.19 (d, 1H), 7.85 (d, 1H), 7.75 (s, 1H), 7.67 (s, 1H), 7.27 (dd, 1H), 3.99-3.81 (m, 2H), 3.56-3.47 (m, 1H), 3.24-3.18 (m, 1H), 2.85-2.70 (m, 5H), 2.58-2.52 (m, 4H), 1.18 (t, 3H), 0.83-0.74 (m, 1H), 0.44-0.34 (m, 1H). The following examples in Table 3 were made using similar procedures shown for example 3A and 3B.

TABLE 3

| Ex | NMR | LCMS (ESI) m/z |
|---|---|---|
| 28 | ¹H NMR (400 MHz, DMSO-d₆) δ 11.83 (s, 1H), 8.43 (d, 1H), 8.35 (d, 1H), 8.19 (d, 1H), 7.85 (d, 1H), 7.75 (s, 1H), 7.66 (s, 1H), 7.27 (dd, 1H), 3.99 – 3.80 (m, 2H), 3.60 – 3.45 (m, 1H), 3.27 – 3.14 (m, 1H), 2.84 – 2.75 (m, 4H), 2.74 – 2.66 (m, 1H), 2.59 – 2.52 (m, 4H), 1.18 (t 3H), 0.84 – 0.69 (m, 1H), 0.49 – 0.28 (m, 1H). | [M + H]⁺ = 419.2 |
| 69 | ¹ NMR (300 MHz, DMSO-d6) δ 11.84 (s, 1H), 8.43 (d, 1H), 8.25 (q, 1H), 8.06 (t, 1H), 7.75 (q, 1H), 7.66 (d, 1H), 7.05 (dd, 1H), 3.97 – 3.80 (m, 2H), 3.60-3.45 (m, 1H), 3.26 – 3.15 (m, 1H), 2.83 – 2.69 (m, 5H), 2.57-2.52 (m, 4H), 1.18 (t, 3H), 0.79 (q, 1H), 0.41 (q, 1H). ¹⁹F NMR (282 MHz, DMSO) δ-120.44. | [M + H]⁺ = 437.20. |
| 88 | ¹ H NMR (400 MHz, DMSO-d6) δ 11.83 (s, 1H), 9.04 (d, 1H), 8.44 (d, 1H), 8.23 (d, 1H), 7.84 (d, 1H), 7.75 (s, 1H), 7.66 (d, 1H), 7.28 (dd, 1H), 5.01 (q, 1H), 4.79 – 4.57 (m, 4H), 3.97 – 3.81 (m, 2H), 3.56 – 3.47 (m, 1H), 3.27 – 3.19 (m, 1H), 2.84 – 2.70 (m, 2H), 2.58 – 2.52 (m, 4H), 1.18 (t, 3H), 0.78 (q, 1H), 0.38 (q, 1H). | [M + H]⁺ = 461.2 |
| 90 | ¹ H NMR (400 MHz, DMSO-d6) δ 11.83 (s, 1H), 8.44 (d, 1H), 8.33 (s, 1H), 8.19 (d, 1H), 7.85 (d, 1H), 7.76 (q, 1H), 7.69 – 7.64 (m, 1H), 7.27 (dd, 1H), 3.88 (q, 2H), 3.56 – 3.48 (m, 1H), 3.25 – 3.17 (m, 1H), 2.85 – 2.67 (m, 2H), 2.58 – 2.52 (m, 4H), 1.18 (t, 3H), 0.78 (q, 1H), 0.39 (q, 1H). | [M + H]⁺ = 422.1 |
| 96 | ¹ H NMR (400 MHz, DMSO-d6) δ 11.83 (s, 1H), 8.44 (d, 1H), 8.33 (s, 1H), 8.19 (d, 1H), 7.85 (d, 1H), 7.76 (q, 1H), 7.69 – 7.64 (m, 1H), 7.27 (dd, 1H) 3.88 (q, 2H), 3.56 – 3.48 (m, 1H), 3.25 – 3.17 (m, 1H), 2.85 – 2.67 (m, 2H), 2.58 – 2.52 (m, 4H), 1.18 (t, 3H), 0.78 (q, 1H), 0.39 (q, 1H). | [M + H]⁺ = 422.3 |
| 99 | ¹ H NMR (300 MHz, DMSO-d6) δ 11.92 (s, 1H), 8.55 – 8.37 (m, 2H), 8.26 (d, 1H), 7.98 – 7.88 (m, 2H), 7.66 (s, 1H), 7.34 (dd, 1H), 4.05 – 3.86 (m, 2H), 3.66 – 3.51 (m, 1H), 3.29 (td, 1H), 2.95 – 2.72 (m, 5H), 2.67-2.60 (m, 2H), 2.21 (d, 3H), 0.84 (q, 1H), 0.46 (q, 1H). | [M + H]⁺ = 405.35 |
| 107 | ¹ H NMR (300 MHz, DMSO-d6) δ 11.86 (s, 1H), 8.41 (d, 1H), 8.33 (s, 1H), 8.19 (d, 1H), 7.85 (d, 1H), 7.65 (d, 1H), 7.42 (s, 1H), 7.27 (dd, 1H), 3.96 – 3.80 (m, 2H), 3.51 (dd, 1H), 3.27 – 3.16 (m, 1H), 2.84 – 2.67 (m, 2H), 2.59 – 2.52 (m, 2H), 2.16-2.11 (m, 1H), 1.02 – 0.91 (m, 2H), 0.89 – 0.75 (m, 3H), 0.38 (q, 1H). | [M + H]⁺ = 434.25 |
| 109 | ¹ H NMR (300 MHz, DMSO-d6) δ 11.85 (s, 1H), 8.43 (d, 1H), 8.30 (d, 1H), 8.17 (d, 1H), 7.89 – 7.81 (m, 2H), 7.66 (d, 1H), 7.28 (dd, 1H), 3.98 – 3.81 (m, 2H), 3.57 – 3.44 (m, 1H), 3.28 – 3.16 (m, 1H), 2.89 – 2.68 (m, 3H), 2.60 – 2.49 (m, 2H), 2.14 (s, 3H), 0.77 (q, 1H), 0.70 – 0.59 (m, 4H), 0.38 (q, 1H). | [M + H]⁺ = 431.10 |
| 110 | ¹ H NMR (400 MHz, DMSO-d6) δ 11.85 (s, 1H), 8.41 (d, 1H), 8.34 (q, 1H), 8.18 (d, 1H), 7.85 (d, 1H), 7.64 (d, 1H), 7.42 (s, 1H), 7.27 (dd, 1H), 3.94 – 3.80 (m, 2H), 3.50 (td, 1H), 3.25 – 3.17 (m, 1H), 2.81 – 2.68 (m, 5H), 2.57 – 2.51 (m, 2H), 2.14 (tt, 1H), 1.00 – 0.91 (m, 2H), 0.86 – 0.73 (m, 3H), 0.38 (q, 1H). | [M + H]⁺ = 431.25 |
| 111 | ¹ H NMR (300 MHz, DMSO-d6) δ 11.83 (s, 1H), 8.43 (d, 1H), 8.29 (d, 1H), 8.16 (d, 1H), 7.85 (d, 1H), 7.75 (s, 1H), 7.66 (s, 1H), 7.27-7.24 (m, 1H), 3.99 – 3.78 (m, 2H), 3.57 – 3.42 (m, 1H), 3.27 – 3.13 (m, 1H), 2.91 – 2.64 (m, 3H), 2.57-2.51 (m, 4H), 1.18 (t, 3H), 0.83 – 0.55 (m, 5H), 0.37 (q, 1H). | [M + H]⁺ = 445.15 |
| 112 | ¹ H NMR (400 MHz, DMSO-d6) δ 11.86 (s, 1H), 8.41 (d, 1H), 8.30 (d, 1H), 8.16 (d, 1H), 7.85 (d, 1H), 7.64 (d, 1H), 7.42 (s, 1H), 7.27 (dd, 1H), 3.95 – 3.77 (m, 2H), 3.53-3.43 (m, 1H), 3.25-3.14 (m, 1H), 2.90 – 2.64 (m, 3H), 2.58-2.52 (m, 2H), 2.19-2.08 (m, 1H), 1.04 – 0.92 (m, 2H), 0.86 – 0.57 (m, 7H), 0.36 (q, 1H). | [M + H]⁺ = 457.25 |
| 113 | ¹ H NMR (400 MHz, DMSO-d6) δ 11.85 (s, 1H), 8.41 (d, 1H), 8.24 (q, 1H), 8.06 – 8.05 (m, 1H), 7.63 (d, 1H), 7.42 (s, 1H), 7.04 (dd, 1H), 4.02 – 3.76 (m, 2H), 3.59 – 3.43 (m, 1H), 3.24-3.15 (m, 1H), 3.06 – 2.63 (m,5H), 2.59 – 2.51 (m, 2H), 2.21 – 2.11 (m, 1H), 1.02 – 0.91 (m, 2H), 0.87 – 0.74 (m, 3H), 0.40 (q, 1H). ¹⁹F NMR (282 MHz, DMSO-d₆) δ-120.45. | [M + H]⁺ = 449.20 |

Example 4

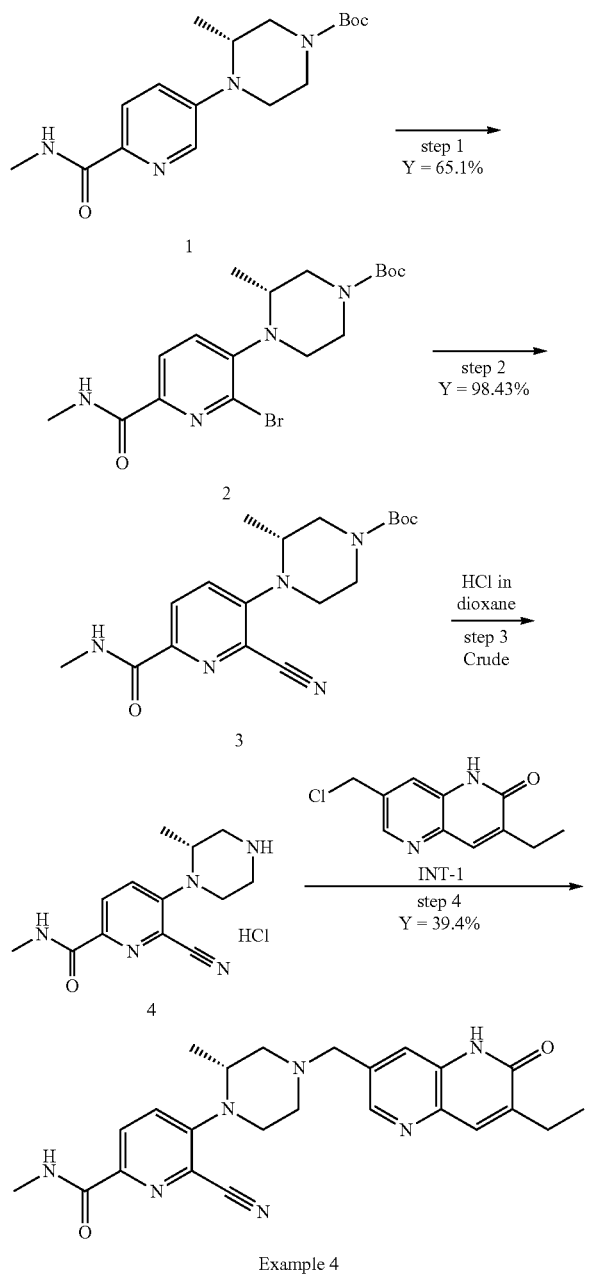

Example 4

Step 1: Preparation of tert-butyl (3R)-4-[2-bromo-6-(methylcarbamoyl)pyridin-3-yl]-3-methylpiperazine-1-carboxylate To a stirred solution of tert-butyl (3R)-3-methyl-4-[6-(methylcarbamoyl)pyridin-3-yl]piperazine-1-carboxylate (2.20 g, 6.58 mmol, 1.00 equiv) in DMF (30 mL) was added NBS (1.29 g, 7.24 mmol, 1.10 equiv) at 0° C. under nitrogen atmosphere. The resulting mixture was stirred for 3 h at room temperature under nitrogen atmosphere. Desired product could be detected by LCMS. The reaction was quenched by the addition of sat.NaHCO$_3$(aq) (30 mL) at 0° C. The resulting mixture was poured into water (100 mL), extracted with EtOAc (3×200 mL). The combined organic layers were washed with brine (3×150 mL), dried over anhydrous Na$_2$SO$_4$. After filtration, the filtrate was concentrated under reduced pressure. The residue was purified by silica gel flash chromatography to afford tert-butyl (3R)-4-[2-bromo-6-(methylcarbamoyl)pyridin-3-yl]-3-methylpiperazine-1-carboxylate (1.77 g, 65%) as a light yellow oil. LC-MS: (ES+H, m/z): [M+H]$^+$=413.0/415.0. $^1$H NMR (300 MHz, DMSO-d6) δ 8.47 (d, 1H), 7.97 (d, 1H), 7.75 (d, 1H), 3.66-3.48 (m, 4H), 3.27-3.18 (m, 2H), 2.80 (d, 3H), 2.73-2.60 (m, 1H), 1.43 (s, 9H), 0.84 (d, 3H).

Step 2: Preparation of tert-butyl (3R)-4-[2-cyano-6-(methylcarbamoyl)pyridin-3-yl]-3-methylpiperazine-1-carboxylate A mixture of tert-butyl (3R)-4-[2-bromo-6-(methylcarbamoyl)pyridin-3-yl]-3-methylpiperazine-1-carboxylate (500 mg, 1.21 mmol, 1.00 equiv), Zn(CN)2 (156 mg, 1.33 mmol, 1.10 equiv) and Pd(PPh3)4 (140 mg, 0.12 mmol, 0.10 equiv) in DMF (8 mL) was stirred overnight at 120° C. under nitrogen atmosphere. Desired product could be detected by LCMS. The mixture was allowed to cool down to room temperature. The resulting mixture was poured into water (100 mL), extracted with EtOAc (3×150 mL). The combined organic layers were washed with brine (2×100 mL), dried over anhydrous Na$_2$SO$_4$. After filtration, the filtrate was concentrated under reduced pressure. The residue was purified by silica gel chromatography to afford tert-butyl (3R)-4-[2-cyano-6-(methylcarbamoyl)pyridin-3-yl]-3-methylpiperazine-1-carboxylate (428 mg, 98%) as a yellow solid. LC-MS: (ES–H, m/z): [M–H]$^-$=358.1. $^1$H NMR (400 MHz, DMSO-d6) δ 8.60 (d, 1H), 8.12 (d, 1H), 7.81 (d, 1H), 3.41-3.33 (m, 4H), 3.21 (d, 2H), 2.80 (d, 3H), 2.52-2.51 (m, 1H), 1.43 (s, 9H), 1.02 (d, 3H).

Step 3: Preparation of 6-cyano-N-methyl-5-[(2R)-2-methylpiperazin-1-yl]pyridine-2-carboxamide, HCl Salt A solution of tert-butyl (3R)-4-[2-cyano-6-(methylcarbamoyl)pyridin-3-yl]-3-methylpiperazine-1-carboxylate (135 mg, 0.38 mmol, 1.00 equiv) and HCl(gas) in 1,4-dioxane (5 mL, 4M) in DCM (5 mL) was stirred for 3 h at room temperature under nitrogen atmosphere. Desired product could be detected by LCMS. The resulting mixture was concentrated under reduced pressure to afford 6-cyano-N-methyl-5-[(2R)-2-methylpiperazin-1-yl]pyridine-2-carboxamide, HCl salt (310 mg, crude) as a light yellow solid. The crude product was used in the next step directly without further purification. LC-MS: (ES+H, m/z): [M+H]$^+$=260.2

Step 4: Preparation of 6-cyano-5-[(2R)-4-[(7-ethyl-6-oxo-5H-1,5-naphthyridin-3-yl)methyl]-2-methylpiperazin-1-yl]-N-methylpyridine-2-carboxamide To a stirred mixture of 6-cyano-N-methyl-5-[(2R)-2-methylpiperazin-1-yl]pyridine-2-carboxamide, HCl salt (250 mg, crude) and DIEA (498 mg, 3.86 mmol, 5.00 equiv) in MeCN (8 mL) were added 7-(chloromethyl)-3-ethyl-1H-1,5-naphthyridin-2-one (172 mg, 0.77 mmol, 1.00 equiv) and KI (26 mg, 0.15 mmol, 0.20 equiv) at room temperature. The resulting mixture was stirred for 4 h at 80° C. under nitrogen atmosphere. Desired product could be detected by LCMS. The mixture was allowed to cool down to room temperature. The resulting mixture was concentrated under reduced pressure. The residue was purified by silica gel chromatography, the pure fraction was concentrated under reduced pressure to afford 6-cyano-5-[(2R)-4-[(7-ethyl-6-oxo-5H-1,5-naphthyridin-3-yl)methyl]-2-methylpiperazin-1-yl]-N-methylpyridine-2-carboxamide (135.4 mg, 39%, ee=97.6%) as a light yellow solid. LC-MS: (ES+H, m/z): [M+H]$^+$=446.1. $^1$H NMR (400 MHz, DMSO-d6) δ 11.89 (s, 1H), 8.58 (d, 1H), 8.42 (d, 1H), 8.12 (d, 1H), 7.81 (d, 1H), 7.75 (s, 1H), 7.65 (d, 1H), 4.02 (m, 1H), 3.74-3.58 (m, 2H), 3.47-3.39 (m, 1H), 3.28-3.20 (m, 1H) 2.79 (m, 4H), 2.58-2.53 (m, 4H), 2.42 (t, 1H), 1.19 (t, 3H), 1.13 (d, 3H).

Example 5

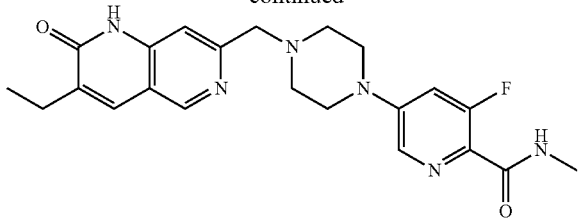

Example 5

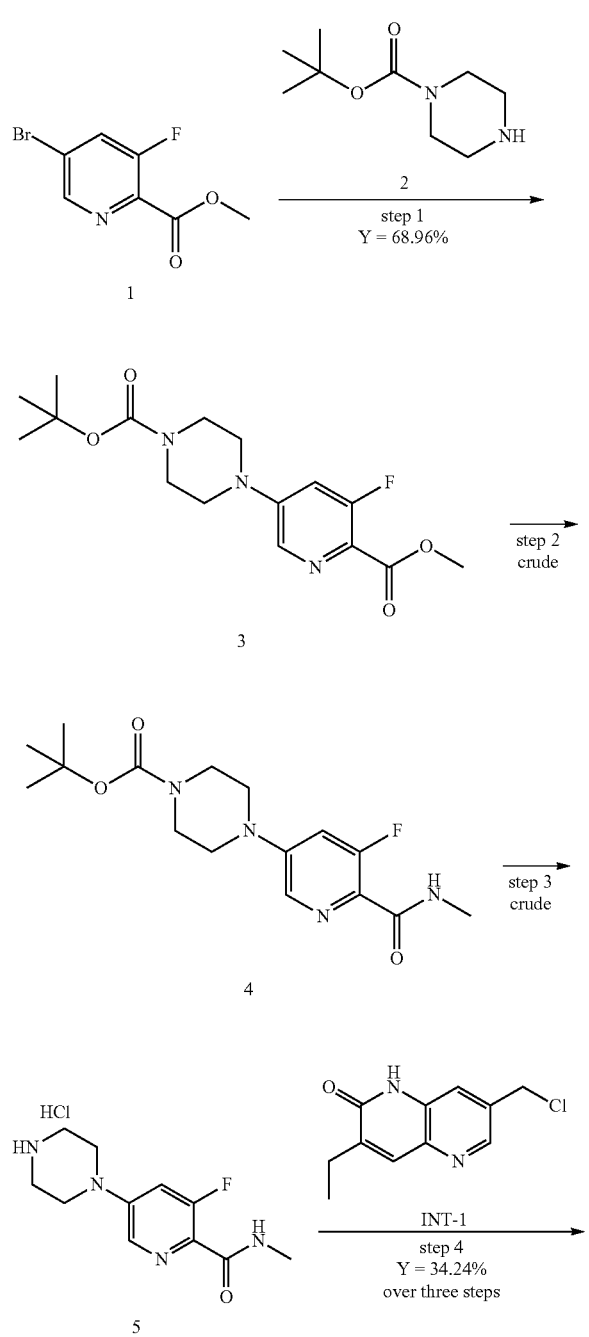

Step 1: Preparation of tert-butyl 4-(5-fluoro-6-(methoxycarbonyl)pyridin-3-yl)piperazine-1-carboxylate A mixture of methyl 5-bromo-3-fluoropyridine-2-carboxylate (1.00 g, 4.27 mmol, 1.00 equiv), tert-butyl piperazine-1-carboxylate (0.84 g, 4.48 mmol, 1.05 equiv), RuPhos Palladacycle Gen.3 (0.36 g, 0.43 mmol, 0.10 equiv) and Cs$_2$CO$_3$ (2.78 g, 8.55 mmol, 2.00 equiv) in 1,4-dioxane (16 mL) was stirred overnight at 110° C. under nitrogen atmosphere. The reaction was monitored by LCMS. The mixture was allowed to cool down to room temperature. The resulting mixture was concentrated under reduced pressure. The residue was purified by silica gel column chromatography to afford tert-butyl 4-[5-fluoro-6-(methoxycarbonyl)pyridin-3-yl]piperazine-1-carboxylate (1.00 g, 68.96%) as a white solid. LC-MS: (ES+H, m/z): [M+H]$^+$=339.9. $^1$H NMR (300 MHz, DMSO-d6) δ 8.24 (s, 1H), 7.23 (dd, 1H), 3.81 (s, 3H), 3.56-3.36 (m, 8H), 1.43 (s, 9H).

Step 2: Preparation of tert-butyl 4-(5-fluoro-6-(methylcarbamoyl)pyridin-3-yl)piperazine-1-carboxylate To a stirred solution of ethyl 4-[5-fluoro-6-(methoxycarbonyl)pyridin-3-yl]piperazine-1-carboxylate (1.20 g, 3.86 mmol, 1.00 equiv) in methanol (8 mL) was added CH$_3$NH$_2$ (8 mL, 25%-30% in water) at room temperature. The resulting mixture was stirred for 1 h at room temperature under nitrogen atmosphere. The reaction was monitored by LCMS. The reaction was quenched with sat. NH$_4$Cl (aq., 100 mL) at 0° C. The resulting mixture was extracted with CH$_2$Cl$_2$ (3×100 mL). The combined organic layers were dried over anhydrous Na$_2$SO$_4$. After filtration, the filtrate was concentrated under reduced pressure to afford crude product (1.22 g) as a white solid. The crude product was used in the next step directly without further purification. LC-MS: (ES+H, m/z): [M+H]$^+$=338.9. $^1$H NMR (400 MHz, DMSO-d6) δ 8.29 (q, 1H), 8.14 (d, 1H), 7.23 (d, 1H), 3.55-3.34 (m, 8H), 2.75 (d, 3H), 1.42 (s, 9H).

Step 3: Preparation of 3-fluoro-N-methyl-5-(piperazin-1-yl)picolinamide

To a stirred solution of 3-fluoro-N-methyl-5-(piperazin-1-yl)pyridine-2-carboxamide (1.22 g, 5.12 mmol, 1.00 equiv) in 1,4-dioxane (5 mL) was added HCl (gas) in 1,4-dioxane (10 mL, 4M) dropwise at 0° C. under nitrogen atmosphere. The resulting mixture was stirred for 1 h at room temperature under nitrogen atmosphere. The reaction was monitored by LCMS. The resulting mixture was concentrated under reduced pressure. The residue was purified by trituration with hexane:ether=1:1 (10 mL×3) to afford crude product (1.22 g, HCl salt) as a white solid. The crude product was used in the next step directly. LC-MS: (ES+H, m/z): [M+H]+=238.9.

Step 4: Preparation of 5-(4-((7-ethyl-6-oxo-5,6-dihydro-1,5-naphthyridin-3-yl)methyl)piperazin-1-yl)-3-fluoro-N-methylpicolinamide To a stirred solution of 3-fluoro-N-methyl-5-(piperazin-1-yl)pyridine-2-carboxamide (80 mg, assumed 100% yield, 0.34 mmol, 1.50 equiv) and 7-(chloromethyl)-3-ethyl-1H-1,5-naphthyridin-2-one (50 mg, 0.22 mmol, 1.00 equiv) in ACN (5 mL) was added KI (7 mg, 0.04 mmol, 0.20 equiv) and DIEA (145 mg, 1.12 mmol, 5.00 equiv) at room temperature. The resulting mixture was stirred for 3 h at 80° C. under nitrogen atmosphere. The reaction was monitored by LCMS. The mixture was allowed to cool down to r.t. The resulting mixture was concentrated under reduced pressure. The residue was purified by PREP_HPLC. The pure fractions were concentrated and lyophilized to afford 5-(4-((7-ethyl-6-oxo-5,6-dihydro-1,5-naphthyridin-3-yl)methyl)piperazin-1-yl)-3-fluoro-N-methylpicolinamide (34 mg, 34.24%, over three steps) as a white solid. LC-MS: (ES+H, m/z): [M+H]+=424.90. $^1$H NMR (400 MHz, DMSO-d6) δ 11.87 (s, 1H), 8.40 (s, 1H), 8.27 (q, 1H), 8.13 (s, 1H), 7.75 (s, 1H), 7.62 (s, 1H), 7.22 (dd, 1H), 3.65 (s, 2H), 3.45-3.34 (m, 4H), 2.74 (d, 3H), 2.58-2.51 (m, 6H), 1.18 (t, 3H). $^{19}$F NMR (377 MHz, DMSO) δ −120.40.

Example 6

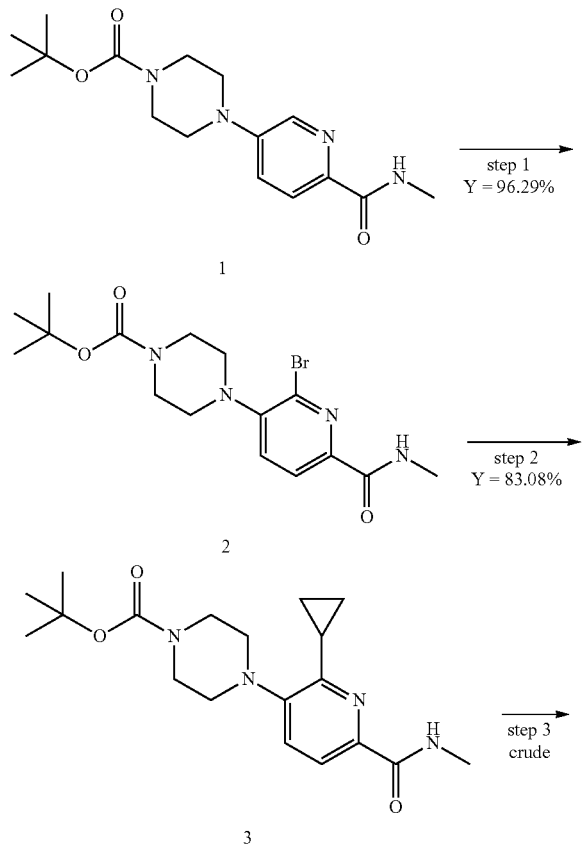

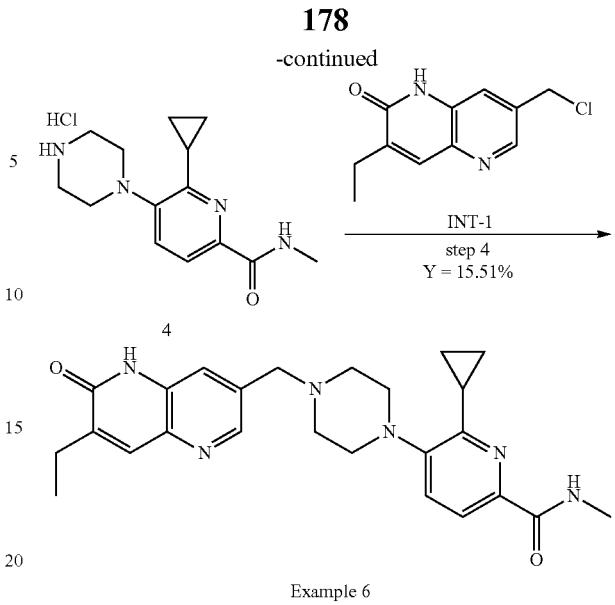

Example 6

Step 1: Preparation of tert-butyl 4-(2-bromo-6-(methylcarbamoyl)pyridin-3-yl)piperazine-1-carboxylate To a stirred solution of tert-butyl 4-[6-(methylcarbamoyl)pyridin-3-yl]piperazine-1-carboxylate (2.00 g, 6.24 mmol, 1.00 equiv) in DMF (10 ml) was added NBS (1.22 g, 6.87 mmol, 1.10 equiv) in portions at 0° C. under nitrogen atmosphere. The resulting mixture was stirred for 3 h at room temperature under nitrogen atmosphere. The reaction was monitored by LCMS. The reaction was quenched by the addition of sat. NaHCO$_3$(aq.) (5 mL) at 0° C. The resulting mixture was concentrated under vacuum. The residue was purified by silica gel column chromatography to afford tert-butyl 4-(2-bromo-6-(methylcarbamoyl)pyridin-3-yl) piperazine-1-carboxylate (2.40 g, 96.29%) as a colorless oil. LC-MS: (ES+H, m/z): [M+H]+=399.1/401.1. H NMR (400 MHz, DMSO-d6) δ 8.44 (q, 1H), 7.96 (d, 1H), 7.65 (d, 1H), 3.60-3.41 (m, 4H), 3.10-2.98 (m, 4H), 2.80 (d, 3H), 1.43 (s, 9H).

Step 2: Preparation of tert-butyl 4-(2-cyclopropyl-6-(methylcarbamoyl)pyridin-3-yl)piperazine-1-carboxylate A mixture of tert-butyl 4-[2-bromo-6-(methylcarbamoyl)pyridin-3-yl]piperazine-1-carboxylate (1.20 g, 3.00 mmol, 1.00 equiv), Pd(dppf)Cl$_2$ (0.22 g, 0.30 mmol, 0.10 equiv), Cs$_2$CO$_3$ (1.96 g, 6.01 mmol, 2.00 equiv) and cyclopropylboronic acid (0.26 g, 3.00 mmol, 1.00 equiv) in Toluene/H$_2$O (10 mL/1 mL) was stirred for 1.5 h at 100° C. under nitrogen atmosphere. The reaction was monitored by LCMS. The mixture was allowed to cool down to r.t. The resulting mixture was concentrated under vacuum. The residue was purified by silica gel column chromatography to afford tert-butyl 4-(2-cyclopropyl-6-(methylcarbamoyl)pyridin-3-yl)piperazine-1-carboxylate (900 mg, 83.08%) as a white solid. LC-MS: (ES+H, m/z): [M+H]+=361.1. $^1$H NMR (300 MHz, DMSO-d6) δ 8.28 (q, 1H), 7.71 (d, 1H), 7.44 (d, 1H), 3.64-3.43 (m, 4H), 3.06-2.89 (m, 4H), 2.80 (d, 3H), 2.45-2.32 (m, 1H), 1.43 (s, 9H), 1.22-1.13 (m, 2H), 1.07-0.88 (m, 2H).

Step 3: Preparation of 6-cyclopropyl-N-methyl-5-(piperazin-1-yl)picolinamide, HCl Salt To a stirred solution of tert-butyl 4-[2-cyclopropyl-6-(methylcarbamoyl)pyridin-3-yl]piperazine-1-carboxylate (900 mg, 2.50 mmol, 1.00 equiv) in 1,4-dioxane (3 ml) were added HCl(gas) in 1,4-dioxane (10.00 mL, 4 M) dropwise at 0° C. under nitrogen atmosphere. The resulting mixture was stirred for 2 h at room temperature under nitrogen atmosphere. The reaction was monitored by LCMS. The resulting mixture was concentrated under vacuum. The residue was purified by trituration with hexane:ether=1:1 (10 mL×3). to afford 6-cyclopropyl-N-methyl-5-(piperazin-1-yl)picolinamide, HCl salt (900 mg, crude) as a white solid. LC-MS: (ES+H, m/z): [M+H]⁺=261.2.

Step 4: Preparation of 6-cyclopropyl-5-(4-((7-ethyl-6-oxo-5,6-dihydro-1,5-naphthyridin-3-yl)methyl)piperazin-1-yl)-N-methylpicolinamide To a stirred mixture of 7-(chloromethyl)-3-ethyl-1H-1,5-naphthyridin-2-one (100 mg, 0.45 mmol, 1.00 equiv) and 6-cyclopropyl-N-methyl-5-(piperazin-1-yl)pyridine-2-carboxamide, HCl salt (200 mg, 0.67 mmol, 1.50 equiv) in MeCN (10 mL) were added KI (15 mg, 0.09 mmol, 0.20 equiv) and DIEA (290 mg, 2.25 mmol, 5.00 equiv) at room temperature. The resulting mixture was stirred for 2 h at 80° C. under nitrogen atmosphere. The reaction was monitored by LCMS. The mixture was allowed to cool down to r.t. The resulting mixture was concentrated under reduced pressure. The crude product was purified by Prep-HPLC. The pure fractions were concentrated and lyophilized to afford 6-cyclopropyl-5-(4-((7-ethyl-6-oxo-5,6-dihydro-1,5-naphthyridin-3-yl)methyl)piperazin-1-yl)-N-methylpicolinamide (31 mg, 15.51%) as a white solid. LC-MS: (ES+H, m/z): [M+H]⁺=447.0. ¹H NMR (400 MHz, DMSO-d6) δ 11.87 (s, 1H), 8.41 (d, 1H), 8.32-8.21 (m, 1H), 7.75 (s, 1H), 7.70 (d, 1H), 7.62 (s, 1H), 7.43 (d, 1H), 3.68 (s, 2H), 3.15-2.90 (m, 4H), 2.78 (d, 3H), 2.69-2.54 (m, 6H), 2.36-2.29 (m, 1H), 1.22-1.10 (m, 5H), 1.01-0.91 (m, 2H).

Example 7

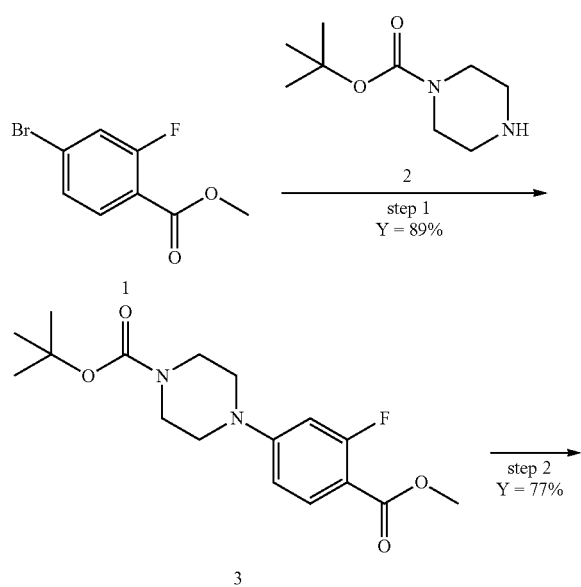

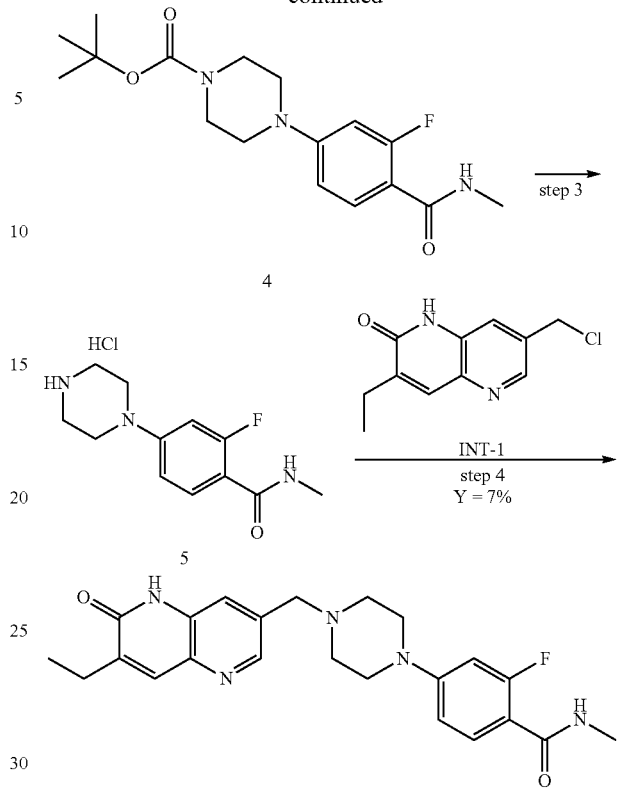

Example 7

Step 1: Preparation of tert-butyl 4-[3-fluoro-4-(methoxycarbonyl)phenyl]piperazine-1-carboxylate To a stirred mixture of methyl 4-bromo-2-fluorobenzoate (1.00 g, 4.29 mmol, 1.00 equiv) and tert-butyl piperazine-1-carboxylate (0.84 g, 4.51 mmol, 1.05 equiv) in dioxane (100 mL) were added Cs₂CO₃ (2.80 g, 8.58 mmol, 2.00 equiv) and RuPhos Palladacycle Gen.3 (0.18 g, 0.22 mmol, 0.05 equiv) at room temperature. The resulting mixture was stirred for 6 h at 120° C. under nitrogen atmosphere. The reaction was monitored by LCMS. The resulting mixture was filtered, the filter cake was washed with EtOAc (3×100 mL). The filtrate was concentrated under reduced pressure. The residue was purified by silica gel column chromatography to afford tert-butyl 4-[3-fluoro-4-(methoxycarbonyl)phenyl]piperazine-1-carboxylate (1.30 g, 89%) as a yellow solid. LC-MS: (ES+H, m/z): [M+H]⁺=339.2. ¹H NMR (300 MHz, DMSO-d6) δ 7.72 (t, 1H), 6.84-6.69 (m, 2H), 3.77 (s, 3H), 3.48-3.33 (m, 8H), 1.43 (s, 9H).

Step 2: Preparation of tert-butyl 4-[3-fluoro-4-(methylcarbamoyl)phenyl]piperazine-1-carboxylate A mixture of tert-butyl 4-[3-fluoro-4-(methoxycarbonyl)phenyl]piperazine-1-carboxylate (1.3 g, 3.84 mmol, 1.00 equiv) in MeOH (5 mL) was added Methylamine (3.5 mL, 25-30% wt in water) dropwise. And the mixture was stirred overnight at 50° C. under nitrogen atmosphere. The reaction was monitored by LCMS. The resulting mixture was diluted with water (100 mL). The resulting mixture was extracted with EtOAc (3×100 mL). The combined organic layers were dried over anhydrous Na₂SO₄. After filtration, the filtrate was concentrated under reduced pressure. The residue was purified by reversed combi-flash chromatography. The resulting mixture was concentrated under reduced pressure to afford tert-butyl 4-[3-fluoro-4-(methylcarbamoyl)phenyl]piperazine-1-carboxylate (1.00 g, 77%) as a white solid. LC-MS: (ES+H, m/z): [M+H]$^+$=338.2. $^1$H NMR (300 MHz, DMSO-d6) δ 7.78 (d, 1H), 7.58 (t, 1H), 6.85-6.68 (m, 2H), 3.45-3.40 (m, 4H), 3.27 (dd, 4H), 2.76 (d, 3H), 1.43 (s, 9H).

Step 3: Preparation of 2-fluoro-N-methyl-4-(piperazin-1-yl)benzamide, HCl Salt

To a stirred mixture of tert-butyl 4-[3-fluoro-4-(methylcarbamoyl)phenyl]piperazine-1-carboxylate (500 mg, 1.48 mmol, 1.00 equiv) in DCM (4 mL) was added HCl(gas) in 1,4-dioxane (2 mL, 4M) dropwise at room temperature under nitrogen atmosphere. The reaction was monitored by LCMS. The resulting mixture was concentrated under reduced pressure. The residue was purified by trituration with hexaneethyl ether:ethyl ether=1:1 (4 mL). The resulting mixture was concentrated under reduced pressure to afford 2-fluoro-N-methyl-4-(piperazin-1-yl)benzamide, HCl salt (500 mg, crude) as a white solid. LC-MS: (ES+H, m/z): [M+H]$^+$=237.9. $^1$H NMR (400 MHz, DMSO-d6) δ 9.46 (s, 2H), 7.92-7.79 (m, 1H), 7.60 (t, 1H), 6.91-6.72 (m, 2H), 3.54 (m, 4H), 3.17 (m, 4H), 2.75 (d, 3H).

Step 4: Preparation of 4-{4-[(7-ethyl-6-oxo-5H-1,5-naphthyridin-3-yl)methyl]piperazin-1-yl}-2-fluoro-N-methylbenzamide To a stirred mixture of 7-(chloromethyl)-3-ethyl-1H-1,5-naphthyridin-2-one, HCl salt (100 mg, 0.45 mmol, 1.00 equiv) and 2-fluoro-N-methyl-4-(piperazin-1-yl)benzamide hydrochloride (123 mg, 0.45 mmol, 1.00 equiv) in MeCN (5 mL) were added KI (15 mg, 0.09 mmol, 0.20 equiv) and DIEA (290 mg, 2.24 mmol, 5.00 equiv). The resulting mixture was stirred for 3 h at 80° C. under nitrogen atmosphere. The reaction was monitored by LCMS. The resulting mixture was concentrated under reduced pressure. The crude product was purified by Prep-HPLC, and the pure fractions were concentrated and lyophilized to afford 4-{4-[(7-ethyl-6-oxo-5H-1,5-naphthyridin-3-yl)methyl]piperazin-1-yl}-2-fluoro-N-methylbenzamide (14 mg, 7%) as an off-white solid. LC-MS: (ES+H, m/z): [M+H]$^+$=423.90. $^1$H NMR (400 MHz, DMSO-d6) δ 11.86 (s, 1H), 8.40 (d, 1H), 7.76 (d, 2H), 7.66-7.48 (m, 2H), 6.86-6.66 (m, 2H), 3.64 (s, 2H), 3.30 (d, 4H), 3.28 (d, 4H), 2.74 (d, 3H), 2.56-2.53 (m, 2H), 1.18 (t, 3H). $^{19}$F NMR (377 MHz, DMSO) δ −111.58.

Example 8

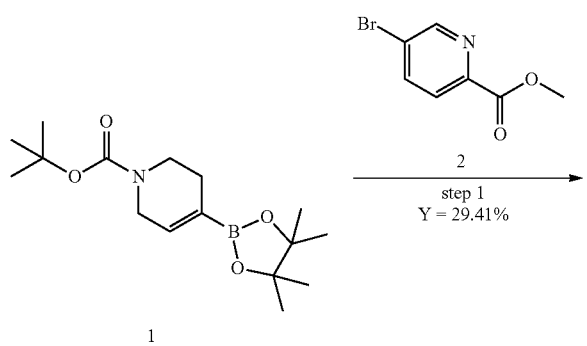

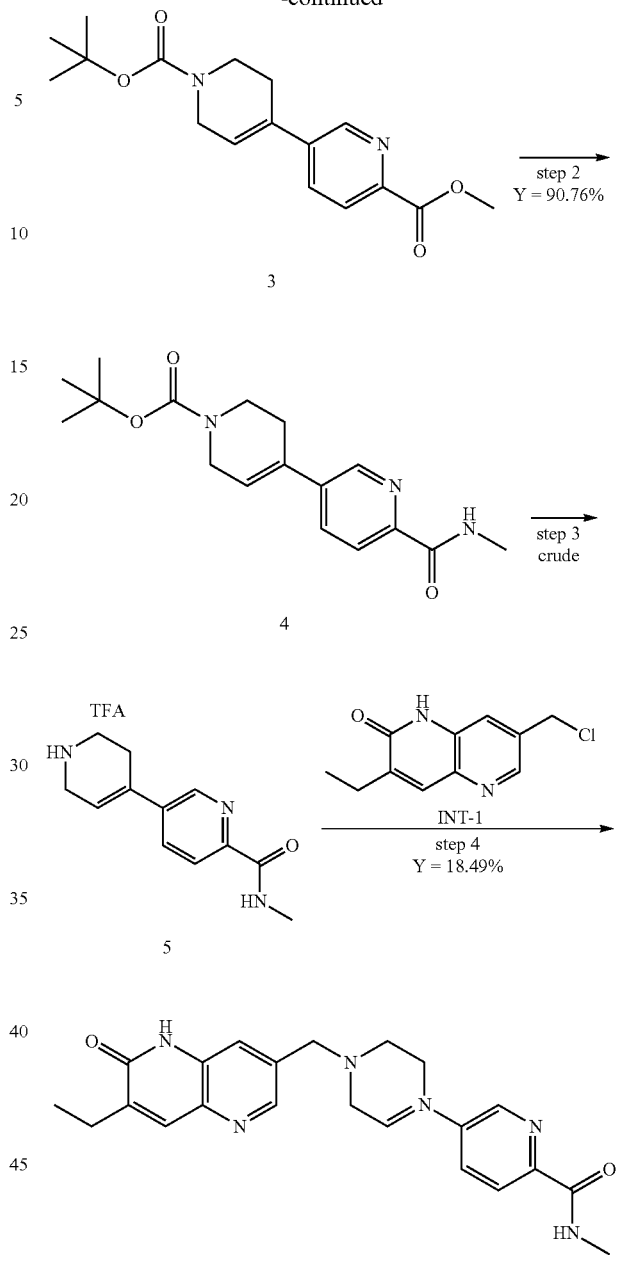

Example 8

Step 1: Preparation of 1'-(tert-butyl) 6-methyl 3',6'-dihydro-[3,4'-bipyridine]-1',6(2'H)-dicarboxylate A solution of tert-butyl 4-(4,4,5,5-tetramethyl-1,3,2-dioxaborolan-2-yl)-3,6-dihydro-2H-pyridine-1-carboxylate (859 mg, 2.78 mmol, 1.20 equiv), methyl 5-bromopyridine-2-carboxylate (500 mg, 2.31 mmol, 1.00 equiv), K$_2$CO$_3$ (640 mg, 4.63 mmol, 2.00 equiv) and Pd(dppf)Cl$_2$ (339 mg, 0.46 mmol, 0.2 equiv) in 1,4-dioxane (10 mL) and H$_2$O (2 mL) was stirred overnight at 80° C. under nitrogen atmosphere. The reaction was monitored by LCMS. The mixture was allowed to cool down to RT. The resulting mixture was diluted with H$_2$O (50 mL). The resulting mixture was extracted with EA (3×50 mL). The combined organic layers were washed with brine (50 mL), dried over anhydrous Na$_2$SO$_4$. After filtration, the filtrate was concentrated under reduced pressure. The residue was purified by silica gel column chromatography to afford 1'-(tert-butyl) 6-methyl 3',6'-dihydro-[3,4'-bipyridine]-1',6(2'H)-dicarboxylate (260 mg, 29.41%) as a yellow solid. LC-MS: (ES+H, m/z): [M+H]$^+$=319.1. $^1$H NMR (300 MHz, DMSO-d6) δ 8.82 (dd, 1H), 8.02 (t, 2H), 6.46 (s, 1H), 4.06 (d, 2H), 3.88 (s, 3H), 3.57 (t, 2H), 2.54 (s, 2H), 1.44 (s, 9H).

Step 2: Preparation of tert-butyl 6-(methylcarbamoyl)-3',6'-dihydro-[3,4'-bipyridine]-1'(2'H)-carboxylate To a stirred solution of 1'-(tert-butyl) 6-methyl 3',6'-dihydro-[3,4'-bipyridine]-1',6(2'H)-dicarboxylate (210 mg, 0.66 mmol, 1.00 equiv) in methanol (3 mL) was added CH$_3$NH$_2$ (3 mL, 25-30% wt in water) at room temperature. The resulting mixture was stirred for 1 h at room temperature under nitrogen atmosphere. The reaction was monitored by LCMS. The reaction was quenched by the addition of sat. NH$_4$Cl (aq.) (50 mL) at room temperature. The aqueous layer was extracted with EtOAc (3×50 mL). The combined organic layers were concentrated under reduced pressure to afford tert-butyl 6-(methylcarbamoyl)-3',6'-dihydro-[3,4'-bipyridine]-1'(2'H)-carboxylate (190 mg, 90.76%) as a purple solid. LC-MS: (ES+H, m/z): [M+H]$^+$=318.2. $^1$H NMR (400 MHz, DMSO-d6) δ 8.76-8.68 (m, 2H), 8.08-7.86 (m, 2H), 6.34 (d, 1H), 4.05 (d, 2H), 3.56 (t, 2H), 2.82 (d, 4H), 2.54 (d, 1H), 1.43 (s, 9H).

Step 3: Preparation of N-methyl-1',2',3',6'-tetrahydro-[3,4'-bipyridine]-6-carboxamide, TFA Salt To a stirred solution of tert-butyl 6-(methylcarbamoyl)-3',6'-dihydro-2'H-[3,4'-bipyridine]-1'-carboxylate (170 mg, 0.54 mmol, 1 equiv) in DCM (5 mL) was added TFA (1 mL) dropwise at room temperature under air atmosphere. The resulting mixture was stirred for 1 h at room temperature under nitrogen atmosphere. The reaction was monitored by LCMS. The resulting mixture was concentrated under reduced pressure. The crude product was used in the next step directly without further purification. LC-MS: (ES+H, m/z): [M+H]$^+$=218.1

Step 4: Preparation of 1'-((7-ethyl-6-oxo-5,6-dihydro-1,5-naphthyridin-3-yl)methyl)-N-methyl-1',2', 3',6'-tetrahydro-[3,4'-bipyridine]-6-carboxamide To a stirred mixture of N-methyl-1',2',3',6'-tetrahydro-[3, 4'-bipyridine]-6-carboxamide (101 mg, 0.50 mmol, 1.00 equiv) and 7-(chloromethyl)-3-ethyl-1,5-naphthyridin-2 (1H)-one (111 mg, 0.50 mmol, 1.00 equiv) in MeCN (5 mL) were added KI (17 mg, 0.10 mmol, 0.20 equiv) and DIEA (323 mg, 2.50 mmol, 5.00 equiv) at room temperature. The resulting mixture was stirred for 1 h at 80° C. under nitrogen atmosphere. The reaction was monitored by LCMS. The resulting mixture was concentrated under reduced pressure. The crude product was purified by Prep-HPLC. The pure fractions were concentrated and lyophilized to afford 1'-((7-ethyl-6-oxo-5,6-dihydro-1,5-naphthyridin-3-yl)methyl)-N-methyl-1',2',3',6'-tetrahydro-[3,4'-bipyridine]-6-carboxamide (39.6 mg, 18.49%, over two steps) as a light yellow solid. LC-MS: (ES+H, m/z): [M+H]$^+$=404.2. $^1$H NMR (400 MHz, DMSO-d6) δ 11.85 (s, 1H), 8.70 (t, 2H), 8.42 (s, 1H), 8.05-7.93 (m, 2H), 7.76 (s, 1H), 7.65 (s, 1H), 6.42 (s, 1H), 3.73 (s, 2H), 3.16 (s, 2H), 2.81 (d, 3H), 2.71 (s, 2H), 2.60-2.52 (m, 4H), 1.19 (t, 3H).

The following examples were made using similar procedures shown for example 8.

| Ex | NMR | LCMS (ESI) m/z |
|---|---|---|
| 64 | $^1$H NMR (300 MHz, DMSO-d6) δ 11.88 (s, 1H), 8.72 (d, 2H), 8.40 (d, 1H), 7.98 (s, 2H), 7.63 (s, 1H), 7.43 (s, 1H), 6.43 (s, 1H), 3.72 (s, 2H), 3.16 (d, 2H), 2.82 (d, 3H), 2.70 (d, 2H), 2.56 (m, 2H), 2.16 (dt, 1H), 1.03-0.93 (m, 2H), 0.85-0.82 (m, 2H). | M + H]$^+$ = 416.25 |

Example 9

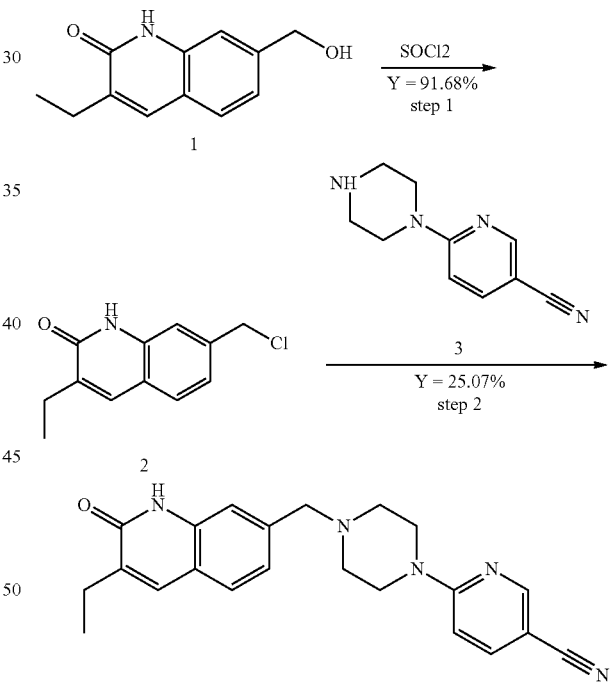

Example 9

Step 1: Preparation of 7-(chloromethyl)-3-ethyl-1H-quinolin-2-one

To a stirred mixture of 3-ethyl-7-(hydroxymethyl)-1H-quinolin-2-one (1.00 g, 4.92 mmol, 1.00 equiv) and DMF (18 mg, 0.25 mmol, 0.05 equiv) in DCM (20 mL) was added SOCl$_2$ (1.76 g, 14.76 mmol, 3.00 equiv) dropwise at 0° C. under nitrogen atmosphere. The resulting mixture was stirred for 2 h at room temperature under nitrogen atmosphere. The reaction was monitored by LCMS. The resulting mixture was concentrated under reduced pressure to afford 7-(chloromethyl)-3-ethyl-1H-quinolin-2-one (1.00 g, 91.68%) as an off-white solid. MS: (ES+H, m/z): [M+H]+ =222.1

Step 2: Preparation of 6-{4-[(3-ethyl-2-oxo-1H-quinolin-7-yl)methyl]piperazin-1-yl}pyridine-3-carbonitrile To a stirred mixture of 7-(chloromethyl)-3-ethyl-1H-quinolin-2-one (100 mg, 0.45 mmol, 1.20 equiv), 6-(piperazin-1-yl)pyridine-3-carbonitrile (71 mg, 0.38 mmol, 1.00 equiv) and KI (12 mg, 0.08 mmol, 0.20 equiv) in MeCN (5 mL) was added DIEA (243 mg, 1.88 mmol, 5.00 equiv) at room temperature. The resulting mixture was stirred for 2 h at 80° C. under nitrogen atmosphere. The reaction was monitored by LCMS. The resulting mixture was concentrated under reduced pressure. The crude product (100 mg) was purified by Prep-HPLC to afford 6-{4-[(3-ethyl-2-oxo-1H-quinolin-7-yl)methyl]piperazin-1-yl}pyridine-3-carbonitrile (35.2 mg, 25.07%) as an off-white solid. MS: (ES+H, m/z): [M+H]+=374.2. 1H NMR (300 MHz, DMSO-d6) δ 11.68 (s, 1H), 8.48 (d, 1H), 7.84 (dd, 1H), 7.70 (s, 1H), 7.57 (d, 1H), 7.27 (s, 1H), 7.13 (d, 1H), 6.92 (d, 1H), 3.67 (s, 4H), 3.57 (s, 2H), 2.50-2.47 (m, 6H), 1.16 (t, 3H).

Example 10

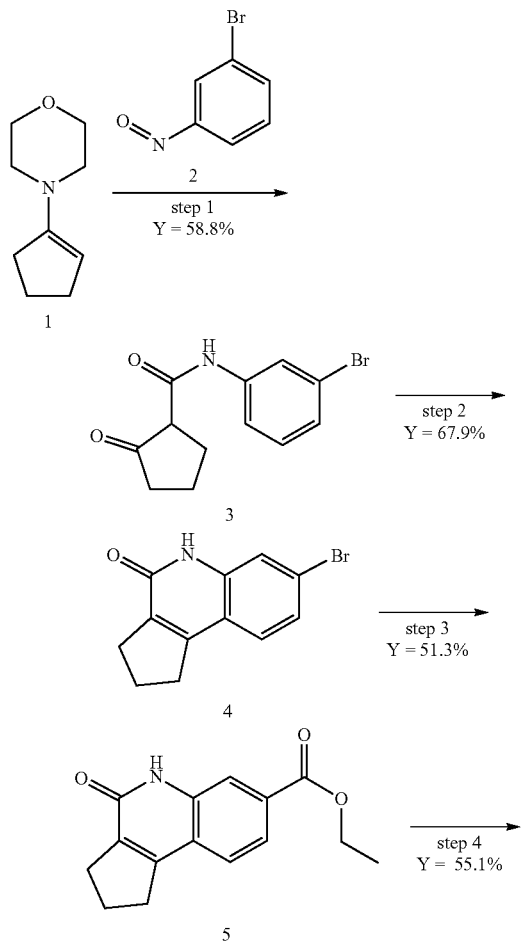

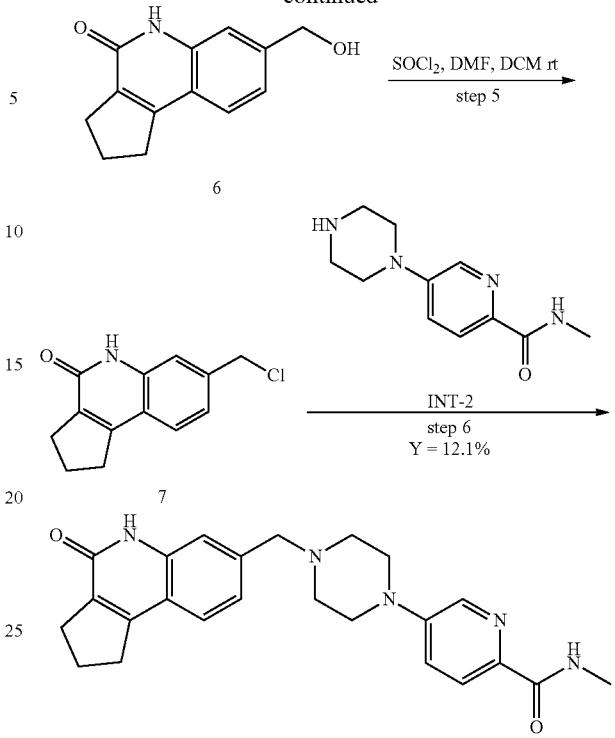

Example 10

Step 1: Preparation of N-(3-bromophenyl)-2-oxocyclopentane-1-carboxamide

A solution of 4-(cyclopent-1-en-1-yl) morpholine (3.60 g, 23.49 mmol, 1.00 equiv.) and 1-bromo-3-isocyanatobenzene (5.58 g, 28.19 mmol, 1.20 equiv.) in CHCl3 (100 mL) was stirred for 4 h at room temperature under nitrogen atmosphere. The reaction was monitored by LCMS. The resulting mixture was concentrated under vacuum. The residue was purified by silica gel column chromatography, the pure fraction was concentrated under vacuum to afford N-(3-bromophenyl)-2-oxocyclopentane-1-carboxamide (3.9 g, 58.8%) as a white solid. LC-MS: (ES+H, m/z): [M+H]+=281.9/283.9. 1H NMR (300 MHz, Chloroform-d) δ 8.83 (s, 1H), 7.84 (t, 1H), 7.45-7.41 (m, 1H), 7.29-7.15 (m, 2H), 3.20-3.11 (m, 1H), 2.51-2.33 (m, 4H), 2.17-2.05 (m, 1H), 1.96-1.83 (m, 1H).

Step 2: Preparation of 7-bromo-1H,2H,3H,5H-cyclopenta[c]quinolin-4-one

To a stirred solution of H2SO4 (10 mL) was added N-(3-bromophenyl)-2-oxocyclopentane-1-carboxamide (3.3 g, 11.69 mmol, 1.00 equiv.) slowly at 0° C. The resulting mixture was stirred for 4 h at room temperature. The reaction was monitored by LCMS. The mixture was basified with aq.Na2CO3 (200 mL) at 0° C. The resulting mixture was extracted with EtOAc (3×200 mL). The combined organic layers were washed with brine (3×200 mL), dried over anhydrous Na2SO4. After filtration, the filtrate was concentrated under reduced pressure to afford 7-bromo-1H,2H,3H, 5H-cyclopenta[c]quinolin-4-one (2.10 g, 67.9%) as a white solid. The crude product was used in the next step directly without further purification. LC-MS: (ES+H, m/z): [M+H]+

=264.0/266.0. $^1$H NMR (300 MHz, DMSO-d6) δ 11.66 (s, 1H), 7.52-7.43 (m, 2H), 7.33 (dd, 1H), 3.06 (t, 2H), 2.74 (t, 2H), 2.14-1.99 (m, 2H).

Step 3: Preparation of ethyl 4-oxo-1H,2H,3H,5H-cyclopenta[c]quinoline-7-carboxylate To a solution of 7-bromo-1H,2H,3H,5H-cyclopenta[c]quinolin-4-one (1.50 g, 5.67 mmol, 1.00 equiv.) and Et$_3$N (1.15 g, 11.35 mmol, 2.00 equiv.) in EtOH (20 mL) was added Pd(PPh$_3$)$_2$Cl$_2$ (797 mg, 1.13 mmol, 0.20 equiv.) in pressure tank. The mixture was purged with nitrogen for 3 min and then was pressurized to 40 atm with carbon monoxide at 120° C. for overnight. The reaction mixture was cooled to room temperature and filtered to remove insoluble solids. The residue was purified by silica gel column chromatography, the pure fraction was concentrated under vacuum to afford ethyl 4-oxo-1H,2H,3H,5H-cyclopenta[c]quinoline-7-carboxylate (750 mg, 51.33%) as a light yellow solid. LC-MS: (ES+H, m/z): [M+H]$^+$=258.2

Step 4: Preparation of 7-(hydroxymethyl)-1H,2H,3H,5H-cyclopenta[c]quinolin-4-one To a stirred solution of ethyl 4-oxo-1H,2H,3H,5H-cyclopenta[c]quinoline-7-carboxylate (650 mg, 2.52 mmol, 1.00 equiv.) in THF (3 mL) at 0° C. under nitrogen atmosphere. To the above mixture was added LiAlH$_4$ (2.02 mL, 5.05 mmol, 2.00 equiv., 2.5M in THF) dropwise over 3 min at 0° C. The resulting mixture was stirred for additional 2 h at room temperature. The reaction was monitored by LCMS. The reaction was quenched by the addition of H$_2$O (0.3 mL) at 0° C. Then added NaOH (15% wt, 1.4 mL) stirred for 10 min at room temperature. The reaction was added addition of H$_2$O (0.3 mL) and stirred for additional 10 min. The resulting mixture was filtered, the filter cake was washed with THF (3×5 mL), dried over anhydrous Na$_2$SO$_4$. The residue was purified by silica gel column chromatography, the pure fraction was concentrated under vacuum to afford 7-(hydroxymethyl)-1H,2H,3H,5H-cyclopenta[c]quinolin-4-one (300 mg, 55.1%) as a white solid. LC-MS: (ES+H, m/z): [M+H]$^+$=216.2. $^1$H NMR (400 MHz, DMSO-d6) δ 11.56 (s, 1H), 7.47 (d, 1H), 7.33 (s, 1H), 7.12-7.08 (m, 1H), 5.34 (t, 1H), 4.57 (d, 2H), 3.07 (t, 2H), 2.75 (t, 2H), 2.13-2.06 (m, 2H).

Step 5: Preparation of 7-(chloromethyl)-1H,2H,3H,5H-cyclopenta[c]quinolin-4-one

To a stirred solution of 7-(hydroxymethyl)-1H,2H,3H,5H-cyclopenta[c]quinolin-4-one (350 mg, 1.62 mmol, 1.00 equiv.) and DMF (12 mg, 0.16 mmol, 0.10 equiv.) in DCM (2 mL) was added SOCl$_2$ (967 mg, 8.13 mmol, 5.00 equiv.) dropwise at 0° C. The resulting mixture was stirred for 2 h at room temperature. The reaction was monitored by LCMS. The resulting mixture was washed with DCM (3×30 mL). The resulting mixture was concentrated under vacuum to afford 7-(chloromethyl)-3-ethyl-4-fluoro-1H-quinolin-2-one (390 mg, crude) as an orange solid. The crude product was used in the next step directly without further purification. LC-MS: (ES+H, m/z): [M+H]$^+$=234.0

Step 6: Preparation of N-methyl-5-[4-({4-oxo-1H,2H,3H,5H-cyclopenta[c]quinolin-7-yl}methyl)piperazin-1-yl]pyridine-2-carboxamide To a stirred solution of 7-(chloromethyl)-1H,2H,3H,5H-cyclopenta[c]quinolin-4-one (150 mg, 0.64 mmol, 1.00 equiv.) and N-methyl-5-(piperazin-1-yl)pyridine-2-carboxamide (148 mg, 0.67 mmol, 1.05 equiv.) in MeCN (3 mL) were added DIEA (415 mg, 3.21 mmol, 5.00 equiv.) dropwise at room temperature under nitrogen atmosphere. The resulting mixture was stirred for 2 h at room temperature under nitrogen atmosphere. The reaction was monitored by LCMS. The resulting mixture was concentrated under vacuum. The residue was purified by silica gel column chromatography, the pure fraction was concentrated under vacuum to afford N-methyl-5-[4-({4-oxo-1H,2H,3H,5H-cyclopenta[c]quinolin-7-yl}methyl)piperazin-1-yl]pyridine-2-carboxamide (34.1 mg, 12.1%) as a light brown solid. LC-MS: (ES+H, m/z): [M+H]$^+$=418.2. $^1$H NMR (300 MHz, DMSO-d6) δ 11.55 (s, 1H), 8.41 (d, 1H), 8.27 (d, 1H), 7.83 (d, 1H), 7.50 (d, 1H), 7.42-7.30 (m, 2H), 7.17 (d, 1H), 3.59 (s, 2H), 3.34-3.32 (m, 4H) 3.08 (t, 2H), 2.78-2.74 (m, 5H), 2.55-2.54 (d, 4H), 2.15-2.05 (m, 2H).

Example 11

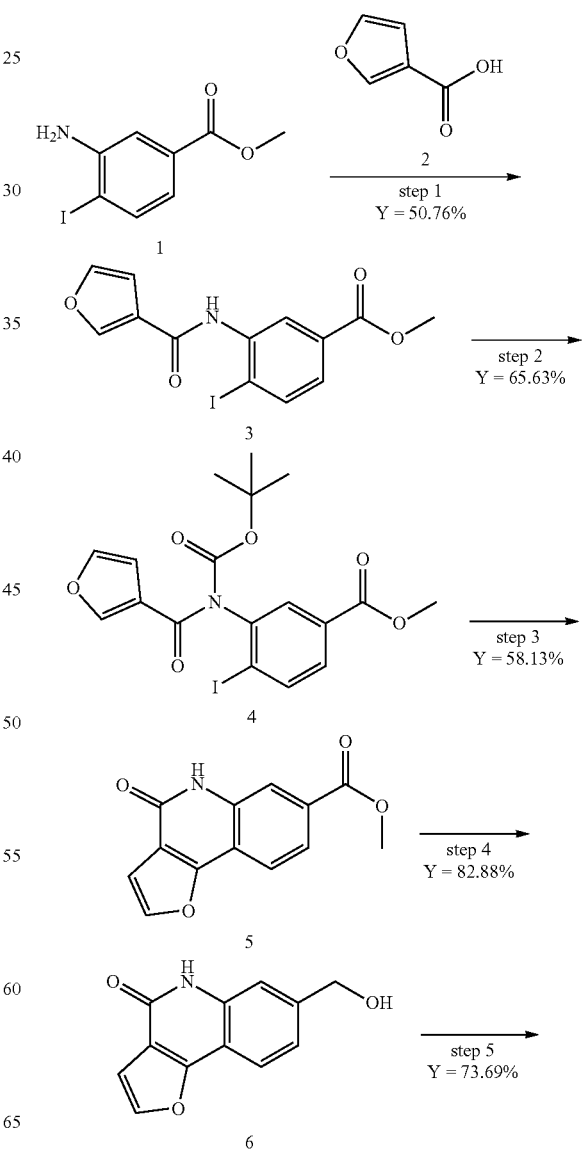

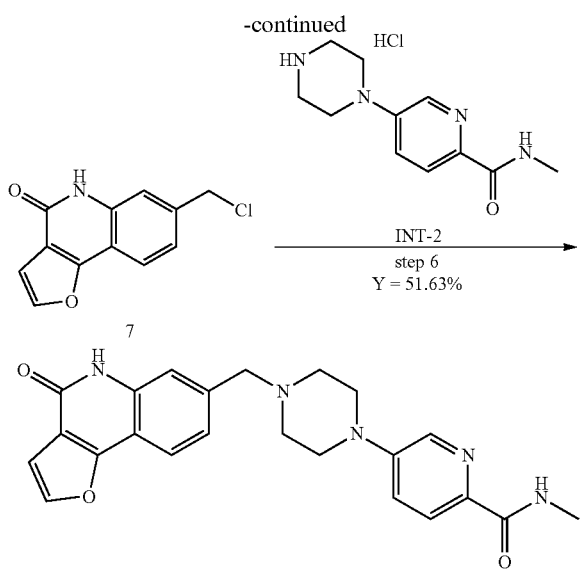

Example 11

Step 1: Preparation of methyl 3-(furan-3-amido)-4-iodobenzoate

A mixture of methyl 3-amino-4-iodobenzoate (10.00 g, 36.09 mmol, 1.00 equiv), 3-furoic acid (8.09 g, 72.18 mmol, 2.00 equiv), $T_3P$ (114.84 g, 180.46 mmol, 5.00 equiv, 50% wt in EA) and DIEA (23.32 g, 180.46 mmol, 5.00 equiv) in DCM (100 mL) was stirred overnight at 60° C. under nitrogen atmosphere. The mixture was allowed to cool down to room temperature. The reaction was monitored by LCMS. The resulting mixture was diluted with water (150 mL), and was extracted with EtOAc (3×150 mL). The combined organic layers were washed with brine (2×200 mL), dried over anhydrous $Na_2SO_4$. After filtration, the filtrate was concentrated under reduced pressure. The residue was purified by silica gel column chromatography to afford methyl 3-(furan-3-amido)-4-iodobenzoate (6.80 g, 50.76%) as a white solid. LC-MS: (ES+H, m/z): $[M+H]^+$=372.0.

Step 2: Preparation of methyl 3-[N-(tert-butoxycarbonyl)furan-3-amido]-4-iodobenzoate A solution of methyl 3-(furan-3-amido)-4-iodobenzoate (6.00 g, 16.167 mmol, 1.00 equiv), (Boc)2O (7.06 g, 32.34 mmol, 2.00 equiv) and DMAP (1.98 g, 16.17 mmol, 1.00 equiv) in DCE (100 mL) was stirred overnight at room temperature under nitrogen atmosphere. The reaction was monitored by LCMS. The resulting mixture was diluted with EtOAc (250 mL), and was washed with water (2×200 mL). The combined organic layers were washed with brine (2×200 mL), dried over anhydrous $Na_2SO_4$. After filtration, the filtrate was concentrated under reduced pressure. The residue was purified by silica gel column chromatography to afford methyl 3-[N-(tert-butoxycarbonyl)furan-3-amido]-4-iodobenzoate (5.00 g, 65.63%) as a white solid. $^1$H NMR (300 MHz, DMSO-d6) δ 8.31 (dd, 1H), 8.13 (d, 1H), 7.90 (d, 1H), 7.79 (t, 1H), 7.69 (dd, 1H), 6.79 (dd, 1H), 3.87 (s, 3H), 1.34 (s, 9H).

Step 3: Preparation of methyl 4-oxo-5H-furo[3,2-c]quinoline-7-carboxylate

To a mixture of methyl 3-[N-(tert-butoxycarbonyl)furan-3-amido]-4-iodobenzoate (400 mg, 0.85 mmol, 1.00 equiv) and $PCy_3$ (48 mg, 0.17 mmol, 0.20 equiv) in DMF (12 mL) were added $Pd(OAc)_2$ (38 mg, 0.17 mmol, 0.20 equiv) and $K_2CO_3$ (235 mg, 1.70 mmol, 2.00 equiv) at room temperature under nitrogen atmosphere. The final reaction mixture was irradiated with microwave radiation for 2 h at 100° C. The mixture was allowed to cool down to room temperature. The reaction was monitored by LCMS. The resulting mixture was diluted with EtOAc (50 mL). The resulting mixture was washed with water (2×25 mL). The combined organic layers were washed with brine (2×25 mL), dried over anhydrous $Na_2SO_4$. After filtration, the filtrate was concentrated under reduced pressure. The residue was purified by silica gel column chromatography to afford methyl 4-oxo-5H-furo[3,2-c]quinoline-7-carboxylate (120 mg, 58.13%) as a yellow solid. LC-MS: (ES+H, m/z): $[M+H]^+$=244.0.

Step 4: Preparation of 7-(hydroxymethyl)-5H-furo[3,2-c]quinolin-4-one

To a stirred mixture of methyl 4-oxo-5H-furo[3,2-c]quinoline-7-carboxylate (300 mg, 1.23 mmol, 1.00 equiv) in THF (2 mL) was added $LiAlH_4$ (0.99 mL, 2.47 mmol, 2.00 equiv, 2.5M in THF) dropwise at 0° C. under nitrogen atmosphere. The resulting mixture was stirred for 1 h at 0° C. under nitrogen atmosphere. The reaction was monitored by LCMS. The reaction was quenched by the addition of 1M aq HCl (1.2 mL) at 0° C. The residue was purified by silica gel column chromatography to afford 7-(hydroxymethyl)-5H-furo[3,2-c]quinolin-4-one (220 mg, 82.88%) as a yellow solid. LC-MS: (ES+H, m/z): $[M+H]^+$=216.1.

Step 5: Preparation of 7-(chloromethyl)-5H-furo[3,2-c]quinolin-4-one

To a stirred mixture of 7-(hydroxymethyl)-5H-furo[3,2-c]quinolin-4-one (300 mg, 1.39 mmol, 1.00 equiv) and DMF (10 mg, 0.14 mmol, 0.10 equiv) in DCM (5 mL) was added $SOCl_2$ (995 mg, 8.36 mmol, 6.00 equiv) dropwise at 0° C. under nitrogen atmosphere. The resulting mixture was stirred overnight at 0° C. under nitrogen atmosphere. The reaction was monitored by LCMS. The resulting mixture was concentrated under reduced pressure. The residue was purified by silica gel column chromatography to afford 7-(chloromethyl)-5H-furo[3,2-c]quinolin-4-one (240 mg, 73.69%) as a white solid. LC-MS: (ES+H, m/z): $[M+H]^+$=234.0.

Step 6: Preparation of N-methyl-5-[4-({4-oxo-5H-furo[3,2-c]quinolin-7-yl}methyl)piperazin-1-yl]pyridine-2-carboxamide A mixture of 7-(chloromethyl)-5H-furo[3,2-c]quinolin-4-one (100 mg, 0.43 mmol, 1.00 equiv), N-methyl-5-(piperazin-1-yl)picolinamide, HCl salt (110 mg, 0.43 mmol, 1.00 equiv), KI (14 mg, 0.09 mmol, 0.20 equiv) and DIEA (276 mg, 2.14 mmol, 5.00 equiv) in MeCN (10 mL) was stirred for 2 h at 80° C. under nitrogen atmosphere. The reaction was monitored by LCMS. The mixture was allowed to cool down to room temperature. The resulting mixture was concentrated under reduced pressure. The residue was purified by silica gel column chromatography to afford N-methyl-5-[4-({4-oxo-5H-furo[3,2-c]quinolin-7-yl}methyl)piperazin-1-yl]pyridine-2-carboxamide (95 mg, 51.63%) as a white solid. LC-MS: (ES+H, m/z): $[M+H]^+$=418.20. $^1$H NMR (400 MHz, DMSO-d6) δ 11.70 (s, 1H), 8.40 (q, 1H), 8.27 (d, 1H), 8.08 (d, 1H), 7.89 (d, 1H), 7.83 (d, 1H), 7.46 (s, 1H), 7.39 (dd, 1H), 7.28 (dd, 1H), 7.06 (d, 1H), 3.63 (s, 2H), 3.39-3.34 (m, 4H), 2.78 (d, 3H), 2.56 (m, 4H).

Example 12

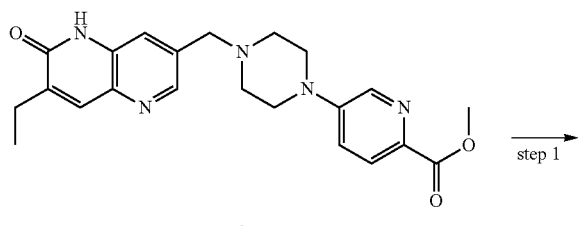

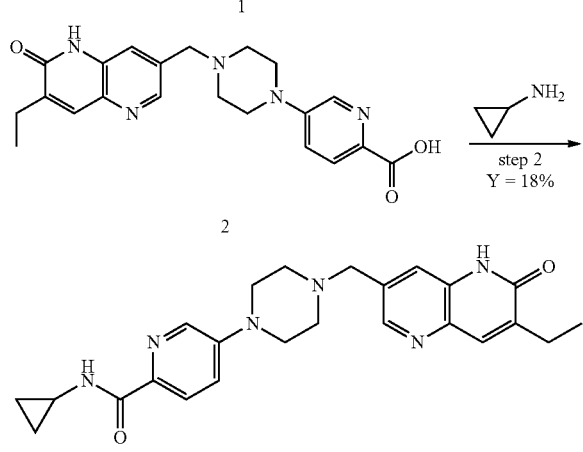

Example 12

Step 1: Preparation of 5-{4-[(7-ethyl-6-oxo-5H-1,5-naphthyridin-3-yl)methyl]piperazin-1-yl}pyridine-2-carboxylic acid To a stirred solution of methyl 5-{4-[(7-ethyl-6-oxo-5H-1,5-naphthyridin-3-yl)methyl]piperazin-1-yl}pyridine-2-carboxylate (120 mg, 0.29 mmol, 1.00 equiv) in EtOH/THF (1:1, 5 mL) was added aqueous NaOH (3.0 mL, 1N) at room temperature under nitrogen atmosphere. The resulting mixture was stirred for additional 1 h at room temperature. The reaction was monitored by LCMS. And then 1(N) aqueous HCl (3.0 mL) was added. The reaction was concentrated under reduced pressure to afford 5-{4-[(7-ethyl-6-oxo-5H-1,5-naphthyridin-3-yl)methyl]piperazin-1-yl}pyridine-2-carboxylic acid (150 mg) as a white solid. (used without further purification). LC-MS: (ES+H, m/z): [M+H]$^+$=394.2.

Step 2: Preparation of N-cyclopropyl-5-{4-[(7-ethyl-6-oxo-5H-1,5-naphthyridin-3-yl)methyl]piperazin-1-yl}pyridine-2-carboxamide To a stirred solution of 5-{4-[(7-ethyl-6-oxo-5H-1,5-naphthyridin-3-yl)methyl]piperazin-1-yl}pyridine-2-carboxylic acid (120 mg, 0.30 mmol, 1.00 equiv) and DIEA (158 mg, 1.22 mmol, 4.00 equiv) in DMF (4 mL) was added HATU (174 mg, 0.46 mmol, 1.50 equiv) at room temperature under nitrogen atmosphere. To the above mixture was added aminocyclopropane (35 mg, 0.61 mmol, 2.00 equiv) and stirred at room temperature overnight. The reaction was monitored by LCMS. The resulting mixture was diluted with water (10 mL). The resulting mixture was extracted with EtOAc (3×20 mL). The combined organic layers were washed with brine (1×5 mL), dried over anhydrous Na$_2$SO$_4$. After filtration, the filtrate was concentrated under reduced pressure. The residue was purified by reversed combi-flash chromatography, the pure fractions were concentrated and lyophilized to afford N-cyclopropyl-5-{4-[(7-ethyl-6-oxo-5H-1,5-naphthyridin-3-yl)methyl]piperazin-1-yl}pyridine-2-carboxamide (23.1 mg, 17%) as a white solid. LC-MS: (ES+H, m/z): [M+H]$^+$=433.2. $^1$H NMR (300 MHz, DMSO-d6) δ 11.85 (s, 1H), 8.41 (s, 1H), 8.35 (s, 1H), 8.24 (s, 1H), 7.83 (d, 1H), 7.75 (s, 1H), 7.63 (s, 1H), 7.40 (d, 1H), 3.65 (s, 2H), 3.30-3.14 (m, 6H), 2.85 (s, 1H), 2.65-2.53 (m, 4H), 1.18 (t, 3H), 0.69-0.57 (m, 4H).

Example 13

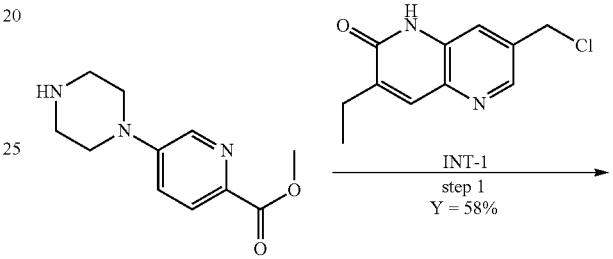

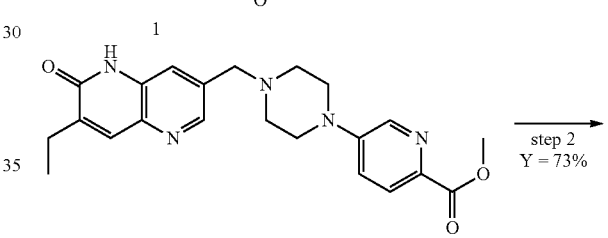

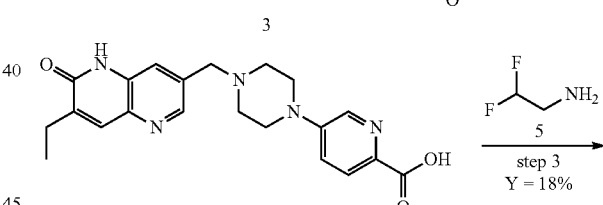

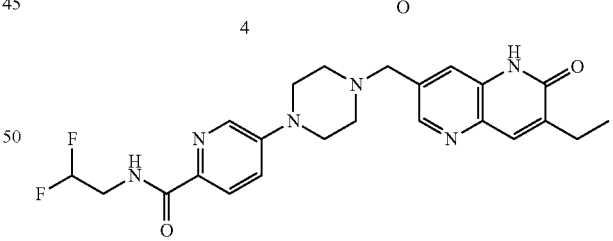

Example 13

Step 1: Preparation of methyl 5-{4-[(7-ethyl-6-oxo-5H-1,5-naphthyridin-3-yl)methyl]piperazin-1-yl}pyridine-2-carboxylate To a stirred mixture of methyl 5-(piperazin-1-yl)pyridine-2-carboxylate (280 mg, 1.26 mmol, 1.00 equiv) and DIEA (818 mg, 6.32 mmol, 5.00 equiv) in MeCN (6 mL) were added 7-(chloromethyl)-3-ethyl-1H-1,5-naphthyridin-2-one (282 mg, 1.26 mmol, 1.00 equiv) and KI (42 mg, 0.25 mmol, 0.20 equiv) at room temperature under nitrogen atmosphere.

The resulting mixture was stirred for 2 h at 80° C. under nitrogen atmosphere. The reaction was monitored by LCMS. The resulting mixture was concentrated under vacuum. The residue was purified by silica gel column chromatography to afford methyl 5-{4-[(7-ethyl-6-oxo-5H-1,5-naphthyridin-3-yl)methyl]piperazin-1-yl}pyridine-2-carboxylate (300 mg, 58%) as a white solid. LC-MS: (ES+H, m/z): [M+H]$^+$=408.1.

Step 2: Preparation of 5-(4-((7-ethyl-6-oxo-5,6-dihydro-1,5-naphthyridin-3-yl)methyl)piperazin-1-yl)picolinic acid To a stirred solution of methyl 5-{4-[(7-ethyl-6-oxo-5H-1,5-naphthyridin-3-yl)methyl]piperazin-1-yl}pyridine-2-carboxylate (200 mg, 0.49 mmol, 1.00 equiv) in EtOH/THF (5 mL/5 mL) was added 5.0 mL 1(N) aqueous NaOH at room temperature under nitrogen atmosphere. The resulting mixture was stirred for additional 2 hours at room temperature. The reaction solution was neutralized with 1 mol/l hydrochloric acid and the organic solvent was then distilled off under reduced pressure. After filtering off the obtained residue, it was washed with water and concentrated under reduced pressure to afford the title compound (140 mg, 73%) as a white solid. LC-MS: (ES+H, m/z): [M+H]$^+$=394.2.

Step 3: Preparation of N-(2,2-difluoroethyl)-5-{4-[(7-ethyl-6-oxo-5H-1,5-naphthyridin-3-yl) methyl] piperazin-1-yl} pyridine-2-carboxamide To a stirred solution of 5-{4-[(7-ethyl-6-oxo-5H-1,5-naphthyridin-3-yl) methyl]piperazin-1-yl}pyridine-2-carboxylic acid (220 mg, 0.56 mmol, 1.00 equiv) and DIEA (361 mg, 2.80 mmol, 5.00 equiv) in DMF (5 mL) ware added EDCI (536 mg, 2.80 mmol, 5.00 equiv) and HOBT (227 mg, 1.68 mmol, 3.00 equiv) at room temperature under nitrogen atmosphere. The resulting mixture was stirred for 2 h at 80° C. under nitrogen atmosphere. The reaction was monitored by LCMS. The resulting mixture was diluted with water (10 mL). The resulting mixture was extracted with EtOAc (3×20 mL). The combined organic layers were washed with brine (1×5 mL), dried over anhydrous Na$_2$SO$_4$. After filtration, the filtrate was concentrated under reduced pressure. The residue was purified by silica gel column chromatography to afford the title compound (80 mg, 94% purity) as a white solid. The crude was purified by reversed combi-flash chromatography and the pure fractions were concentrated and lyophilized to afford N-(2,2-difluoroethyl)-5-{4-[(7-ethyl-6-oxo-5H-1,5-naphthyridin-3-yl) methyl]piperazin-1-yl} pyridine-2-carboxamide (46 mg, 18%) as a white solid. LC-MS: (ES+H, m/z): [M+H]$^+$=457.2. $^1$H NMR (400 MHz, DMSO-d$_6$) δ 11.86 (s, 1H), 8.70 (t, 1H), 8.41 (s, 1H), 8.30 (d, 1H), 7.86 (d, 1H), 7.76 (s, 1H), 7.63 (s, 1H), 7.41 (dd, 1H), 6.25-5.97 (m, 1H), 3.73-3.60 (m, 4H), 3.37 (s, 4H), 2.61-2.52 (m, 6H), 1.18 (t, 3H).

The following examples were made using similar procedures shown for example 13.

| Ex | NMR | LCMS (ESI) m/z |
|---|---|---|
| 40 | $^1$H NMR (400 MHz, DMSO-d6) δ 11.86 (s, 1H), 8.58 (t, 1H), 8.41 (d, 1H), 8.28 (d, 1H) 7.83 (d, 1H), 7.76 (s, 1H), 7.63 (d, 1H), 7.40 (dd, 1H), 3.77-3.54 (m, 5H), 3.45 (dd, 1H), 3.45-3.26 (m, 4H), 3.26 (t, 2H), 2.59-2.51 (m, 7H), 1.95-1.82 (m, 1H), 1.58 (m, 1H), 1.26-1.10 (m, 3H) | [M + H]$^+$ = 477.35 |
| 41 | $^1$H NMR (300 MHz, DMSO-d$_6$) δ 11.86 (s, 1H), 8.58 (t, 1H), 8.41 (d, 1H), 8.28 (d, 1H), 7.84 (d, 1H), 7.76 (s, 1H), 7.63 (d, 1H), 7.40 (dd, 1H), 3.78-3.54 (m, 5H), 3.45 (dd, 1H), 3.41-3.34 (m, 4H), 3.30-3.22 (m, 2H), 2.65-2.52 (m, 6H), 2.49-2.42 (m, 1H), 1.97-1.80 (m, 1H), 1.66-1.52 (m, 1H), 1.23-1.14 (m, 3H). | [M + H]$^+$ = 477.3 |
| 42 | $^1$H NMR (300 MHz, DMSO-d$_6$) δ 11.86 (s, 1H), 8.45-8.25 (m, 3H), 7.84 (d, 1H), 7.77 (s, 1H),7.62 (s,1H), 7.40 (dd, 1H), 3.66 (s, 2H), 3.47-3.42 (m, 4H), 3.39-3.36 (m, 2H), 3.33-3.30 (m, 2H), 3.26 (s, 3H), 2.62-2.53 (m, 6H), 1.19 (t, 3H). | [M + H]$^+$ = 451.0 |
| 43 | $^1$H NMR (400 MHz, DMSO-d6) δ 11.86 (s, 1H), 8.41 (d, 1H), 8.27 (d, 1H), 8.08 (d, 1H), 7.83 (d, 1H), 7.75 (s, 1H), 7.63 (s, 1H), 7.40 (dd, 1H), 4.13-4.00 (m, 1H), 3.66 (s, 2H), 3.35 -3.32 (m, 4H), 2.60-2.51 (m, 6H), 1.26-1.13 (m, 9H) | [M + H]$^+$ = 434.9 |
| 44 | $^1$H NMR (300 MHz, DMSO-d6) δ 11.86 (s, 1H), 8.41 (d,1H), 8.30-8.23 (m, 2H), 7.84 (d,1H), 7.76 (s, 1H), 7.63 (s, 1H), 7.41 (dd, 1H), 4.06-3.92 (m, 1H), 3.91-3.80 (m, 2H), 3.66 (s, 2H), 3.44-3.34 (m, 6H), 2.61-2.52 (m, 6H), 1.77-1.57 (m, 4H), 1.19 (t, 3H). | [M + H]$^+$ = 477.20 |
| 45 | $^1$H NMR (300 MHz, DMSO-d6) δ 11.86 (s, 1H), 8.41 (d, 1H), 8.33 (d, 1H), 8.28 (d, 1H), 7.82 (d, 1H), 7.76 (s, 1H), 7.63 (s, 1H), 7.40 (dd, 1H), 4.93 (s, 1H), 4.02 (p, 1H), 3.66 (s, 2H), 3.35-3.33 (m, 4H) 2.64-2.53 (m, 6H), 2.25-2.39 (m, 2H), 2.19-2.01 (m, 2H), 1.28-1.11 (m, 6H). | [M + H]$^+$ = 477.3 |
| 46 | $^1$H NMR (300 MHz, DMSO-d6) δ 11.87 (s, 1H), 9.10 (d, 1H), 8.41 (s, 1H), 8.30 (d, 1H) 7.86-7.71 (m, 2H), 7.63 (s, 1H), 7.42-7.36 (m, 1H), 5.01 (q, 1H), 4.71-4.63 (m, 4H), 3.66 (s, 2H), 3.37-3.33 (m, 4H), 2.56 (m, 6H), 1.18 (t, 3H). | [M + H]$^+$ = 449.15 |
| 47 | $^1$H NMR (400 MHz, DMSO-d6) δ 11.85 (s, 1H), 8.40 (d, 1H), 8.36 (d, 1H), 8.27 (d, 1H), 7.83 (d, 1H), 7.75 (s, 1H), 7.63 (d, 1H), 7.40 (dd, 1H), 4.51-4.40 (m, 1H), 3.89-3.78 (m, 2H), 3.74-3.68 (m, 1H), 3.65 (s, 2H), 3.60-3.54 (m, 1H), 3.39-3.35 (m, 4H), 2.60-2.52 (m, 6H), 2.19-2.09 (m, 1H), 1.99-1.89 (m, 1H), 1.18 (t, 3H). | [M + H]$^+$ = 463.20 |
| 48 | $^1$H NMR(300 MHz, DMSO-d6) δ 11.87 (s, 1H), 8.45-8.33 (m, 2H), 8.28 (d, 1H), 7.84 (d, 1H), 7.76 (s, 1H), 7.63 (s, 1H), 7.41 (dd, 1H), 4.45 (m, 1H), 3.92-3.78 (m, 2H), 3.78-3.65 (m, 1H), 3.66 (s, 2H), 3.57 (dd, 1H), 3.39-3.36 (m, 4H),2.58-2.54 (m, 6H), 2.24-2.06 (m, 1H), 2.02-1.86 (m, 1H), 1.19 (t, 3H). | [M + H]$^+$ = 463.30 |

-continued

| Ex | NMR | LCMS (ESI) m/z |
|---|---|---|
| 49 | $^1$H NMR (300 MHz, DMSO-d6) δ 11.87 (s, 1H), 8.41 (s, 1H), 8.27 (s, 1H), 8.14 (d, 1H), 7.84 (d, 1H), 7.76 (s, 1H), 7.63 (s, 1H), 7.41 (d, 1H), 4.82 (d, 1H), 4.01-3.96 (m, 2H), 3.66 (s, 2H), 3.33-3.29 (m, 4H), 2.57-2.54 (m, 6H), 2.06-1.92 (m, 1H), 1.91-1.77 (m, 1H), 1.70-1.58 (m, 2H), 1.53-1.37 (m, 2H), 1.19 (t, 3H). | [M + H]$^+$ = 477.20 |
| 50 | $^1$H NMR (300 MHz, DMSO-d6) δ 11.94 (s, 1H), 8.84 (t, 1H), 8.48 (s, 1H), 8.37 (d, 1H), 7.92 (d, 1H), 7.83 (s, 1H), 7.70 (s, 1H), 7.48 (dd, 1H), 3.73 (s, 2H), 3.58 (d, 2H), 3.43-3.40 (m, 4H), 2.85 (t, 2H), 2.64 (m, 6H), 1.26 (t, 3H). | [M + H]$^+$ = 445.90 |
| 52 | $^1$H NMR (400 MHz, DMSO-d$_6$) δ 11.86 (s, 1H), 8.41 (d, 1H), 8.31 (d, 1H), 8.20 (t, 1H), 7.85 (d, 1H), 7.75 (s, 1H), 7.63 (s, 1H), 7.41 (dd, 1H), 4.68 (s, 1H), 3.65 (s, 2H), 3.36-3.34 (m, 4H), 3.25 (d, 2H), 2.58-2.56 (m, 6H), 1.19 (t, 3H), 1.09 (s, 6H). | [M + H]$^+$ = 465.2 |
| 53 | $^1$H NMR (300 MHz, DMSO-d$_6$) δ 11.87 (s, 1H), 8.41 (s, 1H), 8.29 (s, 1H), 8.21 (d, 1H), 7.84 (d, 1H), 7.76 (s, 1H), 7.63 (s, 1H), 7.41 (d, 1H), 3.93-3.87 (m, 1H), 3.76-3.63 (m, 4H), 3.40-3.32 (m, 6H), 2.61-2.52 (m, 6H), 1.87-1.83 (m, 1H), 1.75-1.49 (m, 3H), 1.19 (t, 3H). | [M + H]$^+$ = 477.3 |
| 54 | $^1$H NMR (300 MHz, DMSO-d$_6$) δ 11.87 (s, 1H), 8.41 (s, 1H), 8.29 (d, 1H), 8.22 (d, 1H) 7.84 (d, 1H), 7.75 (s, 1H), 7.63 (s, 1H), 7.41 (dd, 1H), 3.93-3.87 (m, 1H), 3.76-3.63 (m, 4H), 3.40-3.32 (m, 6H), 2.61-2.52 (m, 6H), 1.87-1.83 (m, 1H), 1.77-1.51 (m, 3H), 1.18 (t, 3H). | [M + H]$^+$ = 477.3 |
| 55 | $^1$H NMR (400 MHz, DMSO-d6) δ 11.86 (s, 1H), 8.41 (d, 1H), 8.32 (d, 1H), 8.28 (d, 1H), 7.81 (d, 1H), 7.76 (t, 1H), 7.63 (d, 1H), 7.39 (dd, 1H), 4.92 (s, 1H), 4.02-3.96 (m, 1H), 3.66 (s, 2H), 3.36-3.33 (m, 4H), 2.61-2.52 (m, 6H), 2.37-2.24 (m, 2H), 2.14-2.02 (m, 2H), 1.24 (s, 3H), 1.18 (t, 3H). | [M + H]$^+$ = 477.35 |
| 56 | 1H NMR (300 MHz, DMSO-d6) δ 11.86 (s, 1H), 8.41 (d, 1H), 8.28 (d, 1H), 8.13 (d, 1H), 7.84 (d, 1H), 7.76 (s, 1H), 7.63 (s, 1H), 7.41 (dd, 1H), 4.07-4.21 (m, 1H), 3.45 (s, 2H), 3.70-3.62 (m, 2H), 3.40-3.31 (m, 4H), 3.27 (s, 3H), 2.57-2.55 (m, 6H), 1.28-1.06 (m, 6H). | [M + H]$^+$ = 465.2 |
| 57 | $^1$H NMR (300 MHz, DMSO-d$_6$) δ 11.87 (s, 1H), 8.41 (d, 1H), 8.34-8.25 (m, 2H), 7.85 (d, 1H), 7.76 (s, 1H), 7.63 (d, 1H), 7.41 (dd, 1H), 4.84 (d, 1H), 3.85-3.71 (m, 1H), 3.66 (s, 2H), 3.40-3.16 (m, 1H) 3.34 - 3.27 (m, 4H), 3.21-3.04 (m, 1H), 2.65-2.53 (m, 6H), 1.19 (t, 3H), 1.05 (d, 3H). | [M + H]$^+$ = 451.2 |
| 58 | $^1$H NMR (300 MHz, DMSO-d6) δ 11.87 (s, 1H), 8.92 (d, 1H), 8.41 (d, 1H), 8.28 (d, 1H), 7.82 (d, 1H), 7.76 (s, 1H), 7.63 (d, 1H), 7.39 (dd, 1H), 4.53-4.46 (m, 1H), 3.66 (s, 2H), 3.40-3.36 (m, 4H), 3.12-2.94 (m, 1H), 2.61-2.53 (m, 10H), 1.19 (t, 3H). | [M + H]$^+$ = 472.15 |
| 59 | $^1$H NMR (400 MHz, DMSO-d6) δ 11.87 (s, 1H), 8.41 (d, 1H), 8.28 (d, 1H), 8.10 (d, 1H), 7.84 (d, 1H), 7.76 (s, 1H), 7.63 (d, 1H), 7.40 (dd, 1H), 4.85 (t, 1H), 3.99-3.95 (m, 1H), 3.65 (s, 2H), 3.46-3.40 (m, 2H), 3.34-3.45 (m, 4H), 2.57-2.49 (m, 6H), 1.21-1.11 (m, 6H). | [M + H]$^+$ = 451.2 |
| 60 | $^1$H NMR (300 MHz, DMSO-d$_6$) δ 11.84 (s, 1H), 8.41 (d, 1H), 8.33-8.22 (m, 2H), 7.84 (d, 1H), 7.75 (s, 1H), 7.63 (s, 1H), 7.40 (dd, 1H), 3.65 (s, 2H), 3.50-3.44 (m, 1H), 3.42-3.36 (m, 3H), 3.35-3.29 (m, 3H), 3.28 (s, 3H), 2.59-2.54 (m, 6H), 1.18 (t, 3H), 1.06 (d, 3H). | [M + H]$^+$ = 465.2 |
| 80 | $^1$H NMR (400 MHz, DMSO-d$_6$) δ 11.86 (s, 1H), 8.51 (dd, 1H), 8.39 (d, 1H), 7.83 (d, 1H), 7.60 (d, 1H), 7.53 (t, 1H), 6.83-6.71 (m, 2H), 5.01-4.90 (m, 1H), 4.76-4.71 (m, 2H), 4.58-4.51 (m, 2H), 3.64 (s, 2H), 3.32-3.27 (m, 4H), 2.55-2.51 (m, 4H), 2.14 (d, 3H). <br> $^{19}$F NMR (377 MHz, DMSO) δ-111.19. | [M + H]$^+$ = 452.05 |
| 81 | $^1$H NMR (300 MHz, DMSO-d6) δ 11.97 (s, 1H), 9.15 (d, 1H), 8.45 (d, 2H), 7.78 (d, 1H) 7.62 (d, 1H), 7.49 (d, 2H), 5.13-5.03 (m, 1H), 4.79-4.46 (m, 4H), 3.71 (s, 2H), 3.51-3.42 (m, 4H), 2.62-2.57 (m, 4H), 2.21-2.08 (m, 1H), 0.91-0.90 (m, 2H), 0.88-0.80 (m, 2H). | [M + H]$^+$ = 461.30 |

Example 14

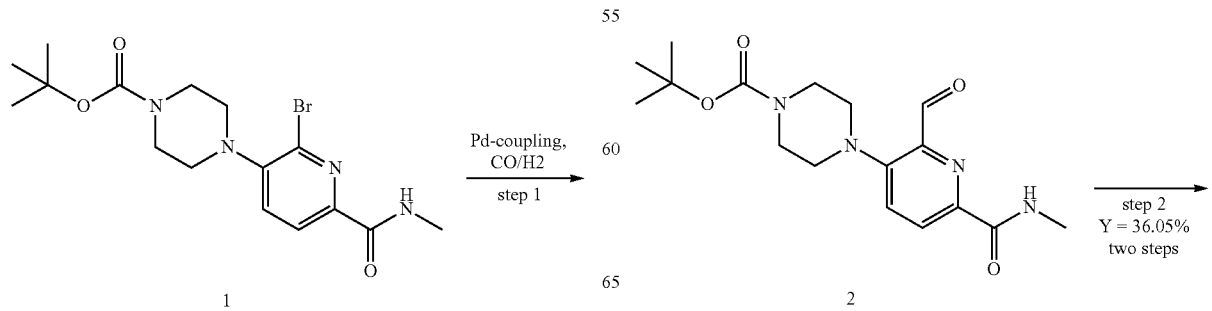

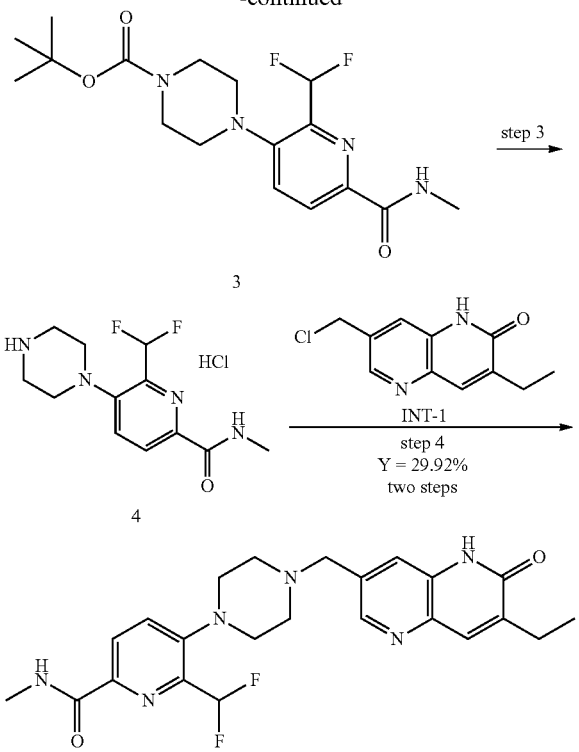

Example 14

Step 1: Preparation of tert-butyl 4-[2-formyl-6-(methylcarbamoyl)pyridin-3-yl]piperazine-1-carboxylate To a stirred solution of tert-butyl 4-[2-bromo-6-(methylcarbamoyl)pyridin-3-yl]piperazine-1-carboxylate (1.73 g, 4.33 mmol, 1.00 equiv) and TMEDA (604 mg, 5.20 mmol, 1.20 equiv) in toluene (60 ml) were added bis(adamantan-1-yl)(butyl)phosphane (311 mg, 0.87 mmol, 0.20 equiv) and Pd(OAc)$_2$ (97 mg, 0.43 mmol, 0.10 equiv) at room temperature under nitrogen atmosphere. The resulting mixture was stirred for overnight at 100° C. under CO/H$_2$ atmosphere (1:1, 30 atm). The reaction was monitored by LCMS. The mixture was allowed to cool down to room temperature. The resulting mixture was concentrated under vacuum. The residue was purified by silica gel column chromatography to afford tert-butyl 4-[2-formyl-6-(methylcarbamoyl)pyridin-3-yl]piperazine-1-carboxylate (1.50 g, crude) as a yellow solid. LC-MS: (ES−H, m/z): [M−H]$^-$=346.8.

Step 2: Preparation of tert-butyl 4-[2-(difluoromethyl)-6-(methylcarbamoyl)pyridin-3-yl]piperazine-1-carboxylate To a stirred solution of tert-butyl 4-[2-formyl-6-(methylcarbamoyl)pyridin-3-yl]piperazine-1-carboxylate (1.50 g, 4.29 mmol, 1.00 equiv) in DCM (8 mL) was added BAST (1.20 mL, 6.44 mmol, 1.50 equiv) at 0° C. under nitrogen atmosphere. The resulting mixture was stirred for 4 h at room temperature under nitrogen atmosphere. The reaction was monitored by LCMS. The reaction was quenched with ice-water (40 mL) at room temperature. The resulting mixture was extracted with CH$_2$Cl$_2$ (3×40 mL). The combined organic layers were washed with brine (3×20 mL), dried over anhydrous Na$_2$SO$_4$. After filtration, the filtrate was concentrated under reduced pressure. The residue was purified by silica gel column chromatography to afford tert-butyl 4-[2-(difluoromethyl)-6-(methylcarbamoyl)pyridin-3-yl]piperazine-1-carboxylate (580 mg, 36.05%, two steps) as an off-white solid. LC-MS: (ES+H, m/z): [M+H]$^+$=371.1. $^1$H NMR (300 MHz, Chloroform-d) δ 8.29 (d, 1H), 7.94 (d, 1H), 7.63 (d, 1H), 7.21-6.80 (m, 1H), 3.69-3.61 (m, 4H), 3.06 (d, 3H), 3.03-2.98 (m, 4H), 1.51 (s, 9H). $^{19}$F NMR (282 MHz, CDCl3) δ −116.99.

Step 3: Preparation of 6-(difluoromethyl)-N-methyl-5-(piperazin-1-yl)pyridine-2-carboxamide, HCl Salt To a stirred solution of tert-butyl 4-[2-(difluoromethyl)-6-(methylcarbamoyl)pyridin-3-yl]piperazine-1-carboxylate (570 mg, 1.54 mmol, 1.00 equiv) was added HCl(gas) in 1,4-dioxane (4 mL, 4M) at room temperature under nitrogen atmosphere. The resulting mixture was stirred for 30 min at room temperature under nitrogen atmosphere. The reaction was monitored by LCMS. The resulting mixture was concentrated under reduced pressure. This resulted in 6-(difluoromethyl)-N-methyl-5-(piperazin-1-yl)pyridine-2-carboxamide, HCl salt (610 mg, crude) as a red solid. LC-MS: (ES+H, m/z): [M+H]$^+$=270.9. $^1$H NMR (300 MHz, DMSO-d6) δ 9.39 (s, 2H), 8.50-8.40 (m, 1H), 8.14 (d, 1H), 7.93 (d, 1H), 7.52-7.06 (m, 1H), 3.31-3.27 (m, 4H), 3.22-3.18 (m, 4H), 2.84 (d, 3H).

Step 4: Preparation of 6-(difluoromethyl)-5-{4-[(7-ethyl-6-oxo-5H-1,5-naphthyridin-3-yl)methyl]piperazin-1-yl}-N-methylpyridine-2-carboxamide To a stirred solution of 6-(difluoromethyl)-N-methyl-5-(piperazin-1-yl)pyridine-2-carboxamide, HCl salt (250 mg, 0.82 mmol, 1.40 equiv) and 7-(chloromethyl)-3-ethyl-1H-1,5-naphthyridin-2-one (130 mg, 0.58 mmol, 1.00 equiv) in MeCN (5 mL) were added DIEA (377 mg, 2.92 mmol, 5.00 equiv) and KI (2 mg, 0.01 mmol, 0.02 equiv) at room temperature under nitrogen atmosphere. The resulting mixture was stirred for 1 h at 80° C. under nitrogen atmosphere. The reaction was monitored by LCMS. The resulting mixture was concentrated under reduced pressure. The crude product (366 mg) was purified by Prep-HPLC to afford 6-(difluoromethyl)-5-{4-[(7-ethyl-6-oxo-5H-1,5-naphthyridin-3-yl)methyl]piperazin-1-yl}-N-methylpyridine-2-carboxamide (76.0 mg, 29.92%, two steps) as an off-white solid. LC-MS: (ES+H, m/z): [M+H]$^+$=457.2. $^1$H NMR (400 MHz, DMSO-d6) δ 11.86 (s, 1H), 8.44-8.36 (m, 2H), 8.10 (d, 1H), 7.86 (d, 1H), 7.75 (s, 1H), 7.62 (d, 1H), 7.32-6.99 (m, 1H), 3.68 (s, 2H), 3.06-2.98 (m, 4H), 2.83 (d, 3H), 2.66-2.53 (m, 6H), 1.22-1.15 (m, 3H). $^{19}$F NMR (377 MHz, DMSO) δ −115.95.

Example 15

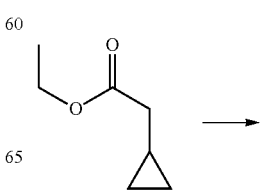

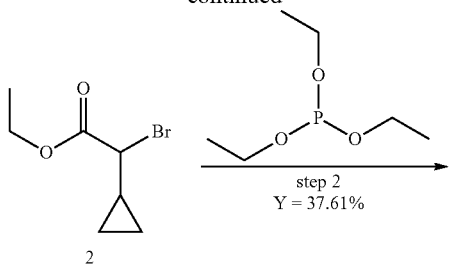

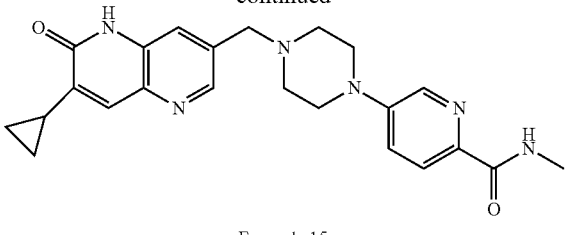

Example 15

Step 1: Preparation of ethyl 2-bromo-2-cyclopropylacetate

To a stirred solution of ethyl 2-cyclopropylacetate (10.00 g, 78.02 mmol, 1.00 equiv) in THF (100 mL) was added LDA (42.9 mL, 85.82 mmol, 1.10 equiv, 2.0 M in THF) dropwise at −78° C. under nitrogen atmosphere. The reaction was stirred for 1 hour then TMSCl (8.48 g, 78.02 mmol, 1.00 equiv) added dropwise and the reaction stirred for 3 hours as it warmed to room temperature. The reaction was cooled to −78° C. and NBS (15.28 g, 85.82 mmol, 1.10 equiv) in 50 mL THF added dropwise. The reaction was then stirred for 2 hours and allowed to warm to room temperature. The reaction was monitored by LCMS. The reaction was quenched by the addition of sat. NH$_4$Cl (aq.) (50 mL) at 0° C. The resulting mixture was extracted with Et$_2$O (3×200 mL). The combined organic layers were washed with brine (3×200 mL), dried over anhydrous Na$_2$SO$_4$. After filtration, the filtrate was concentrated under reduced pressure. The residue was purified by reversed combi-flash chromatography to afford ethyl 2-bromo-2-cyclopropylacetate (5.00 g, 30.95%) as a yellow liquid. $^1$H NMR (300 MHz, Chloroform-d) δ 4.25 (q, 2H), 3.58 (d, 1H), 1.65-1.55 (m, 1H), 1.31 (t, 3H), 0.92-0.76 (m, 2H), 0.61-0.53 (m, 1H), 0.48-0.40 (m, 1H).

Step 2: Preparation of ethyl 2-cyclopropyl-2-(diethoxyphosphoryl)acetate

A solution of ethyl 2-bromo-2-cyclopropylacetate (5.00 g, 24.14 mmol, 1.00 equiv) and triethyl phosphite (5.22 g, 31.39 mmol, 1.30 equiv) was stirred for 24 hours at 130° C. under nitrogen atmosphere. The residue was purified by reversed combi-flash chromatography to afford ethyl 2-cyclopropyl-2-(diethoxyphosphoryl)acetate (2.40 g, 37.61%) as a yellow liquid. $^1$H NMR (300 MHz, Chloroform-d) δ 4.26-4.07 (m, 6H), 2.19 (dd, 1H), 1.30 (dt, 10H), 0.71 (dddd, 1H), 0.60 (ddddd, 1H), 0.47-0.37 (m, 1H), 0.24 (ddtd, 1H).

Step 3: Preparation of methyl 6-[(1Z)-2-cyclopropyl-3-ethoxy-3-oxoprop-1-en-1-yl]-5-nitropyridine-3-carboxylate To a stirred mixture of NaH (0.29 g, 7.14 mmol, 1.50 equiv, 60% wt) in THF (20 mL) was added ethyl 2-cyclopropyl-2-(diethoxyphosphoryl)acetate (1.89 g, 7.14 mmol, 1.50 equiv) dropwise at 0° C. under nitrogen atmosphere. The resulting mixture was stirred for 10 min at 0° C. and then warmed to 40° C. stirred for 10 min under nitrogen atmosphere. The resulting mixture was cooled to −78° C. followed by the addition of methyl 6-formyl-5-nitropyridine-3-carboxylate (1.00 g, 4.76 mmol, 1.00 equiv) in THF (20 mL) dropwise. The resulting mixture was stirred for 30 min at −78° C. under nitrogen atmosphere. The reaction was

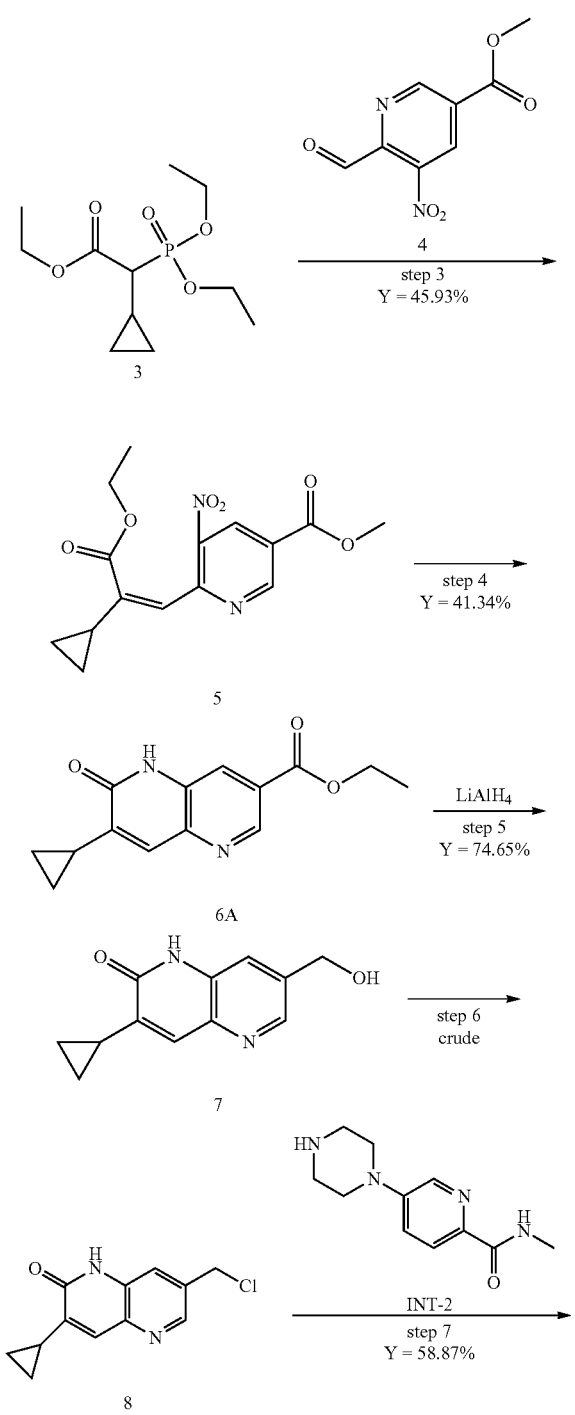

monitored by LCMS. The reaction was quenched by the addition of sat. NH₄Cl (aq.) (5 mL) at 0° C. The resulting mixture was added 20 mL water and extracted with EtOAc (3×20 mL). The combined organic layers were washed with brine (1×50 mL), dried over anhydrous Na₂SO₄. After filtration, the filtrate was concentrated under reduced pressure. The residue was purified by silica gel column chromatography to afford methyl 6-[(1Z)-2-cyclopropyl-3-ethoxy-3-oxoprop-1-en-1-yl]-5-nitropyridine-3-carboxylate (700 mg, 45.93%) as a brown oil. LC-MS: (ES+H, m/z): [M+H]⁺=320.8.

Step 4: Preparation of ethyl 7-cyclopropyl-6-oxo-5H-1,5-naphthyridine-3-carboxylate To a stirred mixture of methyl 6-[(1Z)-2-cyclopropyl-3-ethoxy-3-oxoprop-1-en-1-yl]-5-nitropyridine-3-carboxylate (600 mg, 1.87 mmol, 1.00 equiv) and Fe (1.04 g, 18.73 mmol, 10.00 equiv) in EtOH (10 mL) was added CaCl₂ (1.24 g, 11.24 mmol, 6.00 equiv) at room temperature under nitrogen atmosphere. The resulting mixture was stirred overnight at 90° C. under nitrogen atmosphere. The reaction was monitored by LCMS. The mixture was allowed to cool down to room temperature. The resulting mixture was filtered, the filter cake was washed with EtOAc (2×50 mL). The filtrate was concentrated under reduced pressure. The resulting mixture was added 50 mL water and extracted with EtOAc (2×50 mL). The combined organic layers were washed with brine (2×50 mL), dried over anhydrous Na₂SO₄. After filtration, the filtrate was concentrated under reduced pressure. The residue was purified by silica gel column chromatography to afford ethyl 7-cyclopropyl-6-oxo-5H-1,5-naphthyridine-3-carboxylate (200 mg, 41.34%) as a yellow solid. LC-MS: (ES+H, m/z): [M+H]⁺=259.0.

Step 5: Preparation of 3-cyclopropyl-7-(hydroxymethyl)-1H-1,5-naphthyridin-2-one To a stirred solution of ethyl 7-cyclopropyl-6-oxo-5H-1,5-naphthyridine-3-carboxylate (160 mg, 0.62 mmol, 1.00 equiv) was added LiAlH₄ (0.50 mL, 1.23 mmol, 2.00 equiv, 2.5M in THF) dropwise at 0° C. under nitrogen atmosphere. The resulting mixture was stirred for 1 h at 0° C. under nitrogen atmosphere. The reaction was monitored by LCMS. The reaction was quenched by the addition of 1M aq HCl (1 mL) at 0° C. The resulting mixture was concentrated under reduced pressure. The residue was purified by silica gel column chromatography to afford 3-cyclopropyl-7-(hydroxymethyl)-1H-1,5-naphthyridin-2-one (100 mg, 74.65%) as a light yellow solid. LC-MS: (ES+H, m/z): [M+H]⁺=217.2.

Step 6: Preparation of 7-(chloromethyl)-3-cyclopropyl-1H-1,5-naphthyridin-2-one

To a stirred mixture of 3-cyclopropyl-7-(hydroxymethyl)-1H-1,5-naphthyridin-2-one (80 mg, 0.37 mmol, 1.00 equiv) and DMF (3 mg, 0.04 mmol, 0.10 equiv) in DCM (10 mL) was added SOCl₂ (264 mg, 2.22 mmol, 6.00 equiv) dropwise at 0° C. under nitrogen atmosphere. The resulting mixture was stirred overnight at room temperature under nitrogen atmosphere. The reaction was monitored by LCMS. The resulting mixture was concentrated under reduced pressure to afford 7-(chloromethyl)-3-cyclopropyl-1H-1,5-naphthyridin-2-one as a yellow solid. The crude product was used in the next step directly without further purification. LC-MS: (ES+H, m/z): [M+H]⁺=235.0.

Step 7: Preparation of 5-{4-[(7-cyclopropyl-6-oxo-5H-1,5-naphthyridin-3-yl)methyl]piperazin-1-yl}-N-methylpyridine-2-carboxamide A mixture of 7-(chloromethyl)-3-cyclopropyl-1H-1,5-naphthyridin-2-one (80 mg, 0.34 mmol, 1.00 equiv), N-methyl-5-(piperazin-1-yl)pyridine-2-carboxamide (75 mg, 0.34 mmol, 1.00 equiv), KI (11 mg, 0.07 mmol, 0.20 equiv) and DIEA (220 mg, 1.71 mmol, 5.00 equiv) in MeCN (10 mL) was stirred for 2 hours at 80° C. under nitrogen atmosphere. The reaction was monitored by LCMS. The mixture was allowed to cool down to room temperature. The resulting mixture was diluted with water (50 mL), and was extracted with EtOAc (2×50 mL). The combined organic layers were washed with brine (2×50 mL), dried over anhydrous Na₂SO₄. After filtration, the filtrate was concentrated under reduced pressure. The residue was purified by silica gel column chromatography, to afford 5-{4-[(7-cyclopropyl-6-oxo-5H-1,5-naphthyridin-3-yl)methyl]piperazin-1-yl}-N-methylpyridine-2-carboxamide (85 mg, 58.57%) as a white solid. LC-MS: (ES+H, m/z): [M+H]⁺=419.3. ¹H NMR (300 MHz, DMSO-d₆) δ 11.89 (s, 1H), 8.43-8.36 (m, 2H), 8.26 (d, 1H), 7.83 (d, 1H), 7.61 (d, 1H), 7.44-7.35 (m, 2H), 3.64 (s, 2H), 3.34-3.28 (m, 4H), 2.78 (d, 3H), 2.56 (d, 4H), 2.21-2.07 (m, 1H), 0.97 (dt, 2H), 0.86-0.77 (m, 2H).

Example 16

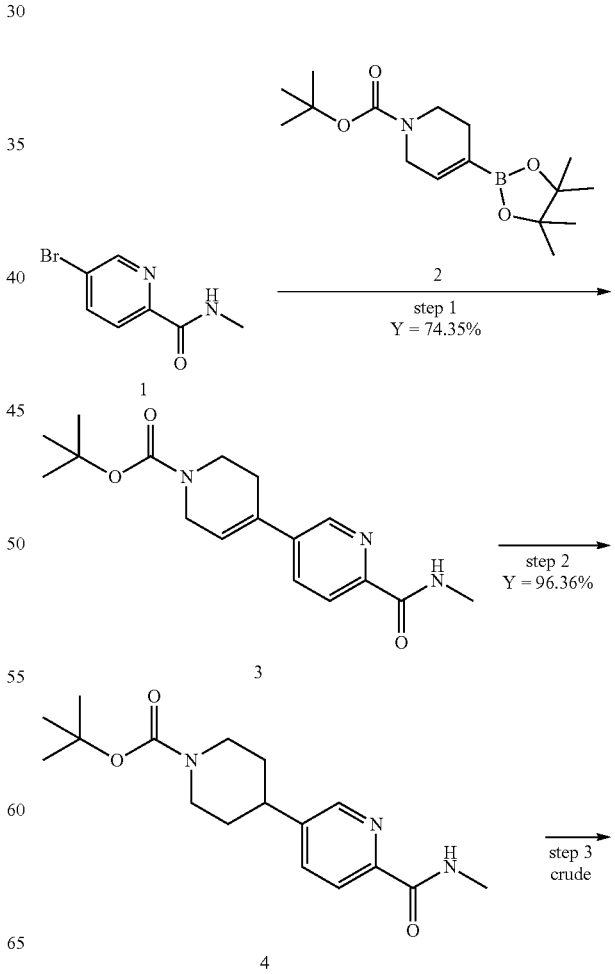

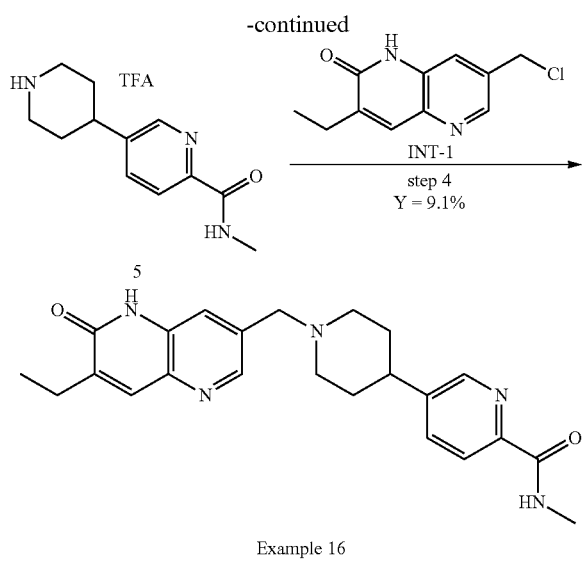

Example 16

Step 1: Preparation of tert-butyl 6-(methylcarbamoyl)-3',6'-dihydro-[3,4'-bipyridine]-1'(2'H)-carboxylate To a stirred mixture of 5-bromo-N-methylpyridine-2-carboxamide (300 mg, 1.40 mmol, 1.00 equiv) and tert-butyl 4-(4,4,5,5-tetramethyl-1,3,2-dioxaborolan-2-yl)-3,6-dihydro-2H-pyridine-1-carboxylate (518 mg, 1.67 mmol, 1.20 equiv) in 1,4-dioxane/H$_2$O (4/1, 5 mL) were added Pd(dppf)Cl$_2$ (102 mg, 0.14 mmol, 0.10 equiv) and K$_2$CO$_3$ (386 mg, 2.79 mmol, 2.00 equiv) at room temperature. The resulting mixture was stirred for 2 h at 80° C. under nitrogen atmosphere. The reaction was monitored by LCMS. The mixture was allowed to cool down to room temperature. The resulting mixture was concentrated under reduced pressure. The residue was purified by silica gel column chromatography to afford tert-butyl 6-(methylcarbamoyl)-3',6'-dihydro-[3,4'-bipyridine]-1'(2'H)-carboxylate (330 mg, 74.53%) as a white solid. LC-MS: (ES+H, m/z): [M+H]$^+$=318.2. $^1$H NMR (400 MHz, DMSO-d6) δ 8.75-8.67 (m, 2H), 8.04-7.95 (m, 2H), 6.41 (s, 1H), 4.08-4.00 (m, 2H), 3.56 (t, 2H), 2.82 (d, 3H), 2.53 (d, 2H), 1.43 (s, 9H).

Step 2: Preparation of tert-butyl 4-(6-(methylcarbamoyl)pyridin-3-yl)piperidine-1-carboxylate To a stirred solution of tert-butyl 6-(methylcarbamoyl)-3',6'-dihydro-[3,4'-bipyridine]-1'(2'H)-carboxylate (330 mg, 1.04 mmol, 1.00 equiv) in methanol (20 mL) was added Pd/C (33 mg, 10% wt) at room temperature under nitrogen atmosphere. The resulting mixture was stirred overnight at room temperature under hydrogen atmosphere. The reaction was monitored by LCMS. The resulting mixture was filtered, the filter cake was washed with MeOH (5×10 mL). The filtrate was concentrated under reduced pressure to afford tert-butyl 4-(6-(methylcarbamoyl)pyridin-3-yl)piperidine-1-carboxylate (320 mg, 96.36%) as a white solid. LC-MS: (ES+H, m/z): [M+H]$^+$=320.2. $^1$H NMR (400 MHz, DMSO-d6) δ 8.70 (d, 1H), 8.53 (d, 1H), 7.95 (d, 1H), 7.86 (dd, 1H), 4.09 (d, 2H), 2.81 (d, 6H), 1.78 (d, 2H), 1.55 (qd, 2H), 1.42 (s, 9H).

Step 3: Preparation of N-methyl-5-(piperidin-4-yl)picolinamide, TFA Salt

To a stirred solution of tert-butyl 4-(6-(methylcarbamoyl)pyridin-3-yl)piperidine-1-carboxylate (310 mg, 0.97 mmol, 1.00 equiv) in DCM (5 mL) was added TFA (2 mL) dropwise at 0° C. under nitrogen atmosphere. The resulting mixture was stirred for 1 h at room temperature under nitrogen atmosphere. The reaction was monitored by LCMS. The resulting mixture was concentrated under reduced pressure. The crude product N-methyl-5-(piperidin-4-yl)picolinamide, TFA salt (510 mg, crude) was used in the next step directly without further purification. LC-MS: (ES+H, m/z): [M+H]$^+$=220.2.

Step 4: Preparation of 5-(1-((7-ethyl-6-oxo-5,6-dihydro-1,5-naphthyridin-3-yl)methyl)piperidin-4-yl)-N-methylpicolinamide To a stirred mixture of N-methyl-5-(piperidin-4-yl)pyridine-2-carboxamide, TFA salt (294 mg, assumed 50% yield, 1.35 mmol, 2.00 eq) and 7-(chloromethyl)-3-ethyl-1H-1,5-naphthyridin-2-one (150 mg, 0.67 mmol, 1.00 equiv) in MeCN (3 mL) were added KI (112 mg, 0.67 mmol, 1.00 equiv) and DIEA (435 mg, 3.37 mmol, 5.00 equiv) at room temperature under nitrogen atmosphere. The resulting mixture was stirred for 2 h at 80° C. under nitrogen atmosphere. The reaction was monitored by LCMS. The resulting mixture was concentrated under reduced pressure. The crude product was purified by Prep-HPLC. The pure fractions were concentrated and lyophilized to afford 5-{1-[(7-ethyl-6-oxo-5H-1,5-naphthyridin-3-yl)methyl]piperidin-4-yl}-N-methylpyridine-2-carboxamide (24.6 mg, 9.01%) as a white solid. LC-MS: (ES+H, m/z): [M+H]$^+$=406.2. $^1$H NMR (400 MHz, DMSO-d6) δ 11.84 (s, 1H), 8.69 (d, 1H), 8.53 (d, 1H), 8.40 (d, 1H), 7.95 (d, 1H), 7.86 (dd, 1H), 7.75 (s, 1H), 7.61 (s, 1H), 3.62 (s, 2H), 2.94 (d, 2H), 2.81 (d, 3H), 2.68 (m, 1H), 2.59-2.53 (m, 2H), 2.13 (m, 2H), 1.82-1.68 (m, 4H), 1.18 (t, 3H).

Example 17

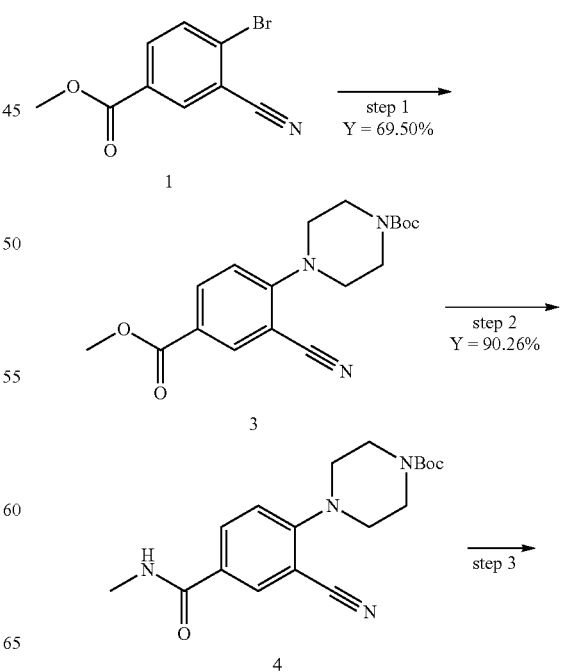

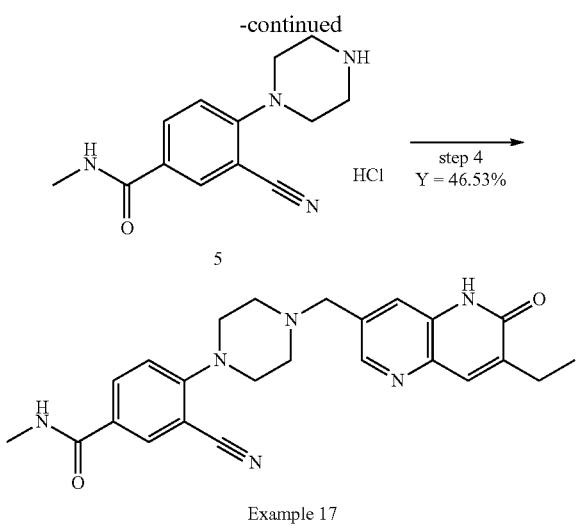

Example 17

Step 1: Preparation of tert-butyl 4-[2-cyano-4-(methoxycarbonyl)phenyl]piperazine-1-carboxylate To a stirred solution of methyl 4-bromo-3-cyanobenzoate (1.00 g, 4.17 mmol, 1.00 equiv) and tert-butyl piperazine-1-carboxylate (770 mg, 4.17 mmol, 1.00 equiv) in dioxane (10 mL) was added $Cs_2CO_3$ (2.70 g, 8.33 mmol, 2.00 equiv) and RuPhos Palladacycle Gen.3 (350 mg, 0.42 mmol, 0.10 equiv) under nitrogen atmosphere. The resulting mixture was stirred overnight at 80° C. under nitrogen atmosphere. The reaction was monitored by LCMS. The mixture was allowed to cool down to room temperature. The resulting mixture was filtered, the filter cake was washed with ethyl acetate (5×100 ml). The filtrate was concentrated under reduced pressure. The residue was purified by silica gel column chromatography to afford tert-butyl 4-[2-cyano-4-(methoxycarbonyl)phenyl]piperazine-1-carboxylate (1.00 g, 69.50%) as a dark oil. LC-MS: (ES+H, m/z): [M+H−tBu]⁺=289.8. ¹H NMR (400 MHz, Chloroform-d) δ 8.24 (d, 1H), 8.11 (dd, 1H), 6.97 (d, 1H), 3.91 (s, 3H), 3.68-3.59 (m, 4H), 3.36-3.28 (m, 4H), 1.39 (s, 9H).

Step 2: Preparation of tert-butyl 4-[2-cyano-4-(methylcarbamoyl)phenyl]piperazine-1-carboxylate To a stirred solution of tert-butyl 4-[2-cyano-4-(methoxycarbonyl)phenyl]piperazine-1-carboxylate (1.00 g, 2.90 mmol, 1.00 equiv) and methylamine (5 mL, 25%-30% wt in water) in methanol (5 mL). The resulting mixture was stirred overnight at 50° C. under nitrogen atmosphere. The reaction was monitored by LCMS. The mixture was allowed to cool down to room temperature. The resulting mixture was concentrated under reduced pressure. The residue was purified by silica gel column chromatography to afford tert-butyl 4-[2-cyano-4-(methylcarbamoyl)phenyl]piperazine-1-carboxylate (900 mg, 90.26%) as a yellow solid. LC-MS: (ES+H, m/z): [M+H−tBu]⁺=288.9. ¹H NMR (300 MHz, Chloroform-d) δ 8.01 (d, 1H), 7.98-7.87 (m, 1H), 7.01 (d, 1H), 6.41 (s, 1H), 3.65 (t, 4H), 3.28 (t, 4H), 3.02 (d, 3H), 1.50 (s, 9H).

Step 3: Preparation of 3-cyano-N-methyl-4-(piperazin-1-yl)benzamide, HCl Salt To a stirred solution of tert-butyl 4-[2-cyano-4-(methylcarbamoyl)phenyl]piperazine-1-carboxylate (900 mg, 2.61 mmol, 1.00 equiv) in Dichloromethane (3 mL) was added HCl(gas) in 1,4-dioxane (7 mL) dropwise at 0° C. The resulting mixture was stirred for 3 h at room temperature under nitrogen atmosphere. The reaction was monitored by LCMS. The resulting mixture was concentrated under reduced pressure. The residue was purified by trituration with N-hexane and ether (1:1) (12 ml×3). The precipitated solids were collected by filtration and washed with ether (3×5 mL) to afford 3-cyano-N-methyl-4-(piperazin-1-yl)benzamide, HCl salt (580 mg) as a white solid. LC-MS: (ES+H, m/z): [M+H]⁺=244.9.

Step 4: Preparation of 3-cyano-4-{4-[(7-ethyl-6-oxo-5H-1,5-naphthyridin-3-yl)methyl]piperazin-1-yl}-N-methylbenzamide To a stirred solution of 3-cyano-N-methyl-4-(piperazin-1-yl)benzamide, HCl salt (150 mg, crude) and 7-(chloromethyl)-3-methyl-1H-1,5-naphthyridin-2-one (128 mg, 0.61 mmol, 1.00 equiv) in acetonitrile (8 mL) was added DIEA (238 mg, 1.84 mmol, 3.00 equiv) and KI (20 mg, 0.12 mmol, 0.20 equiv) under nitrogen atmosphere. The resulting mixture was stirred for 1.5 h at 80° C. under nitrogen atmosphere. The reaction was monitored by LCMS. The mixture was allowed to cool down to room temperature. The resulting mixture was concentrated under reduced pressure. The residue was purified by silica gel column chromatography. The residue was purified by trituration with MeOH (3 mL). The resulting mixture was stirred for 1 h at 50° C. under nitrogen atmosphere. The precipitated solids were collected by filtration and washed with MeOH (2×1 mL). The pure fraction was concentrated under vacuum to afford 3-cyano-4-{4-[(7-ethyl-6-oxo-5H-1,5-naphthyridin-3-yl)methyl]piperazin-1-yl}-N-methylbenzamide (125.5 mg, 46.53%) as a white solid. LC-MS: (ES+H, m/z): [M−H]⁺=431.30. H NMR (400 MHz, DMSO-d₆) δ 11.87 (s, 1H), 8.49-8.39 (m, 2H), 8.12 (d, 1H), 8.01 (dd, 1H), 7.75 (s, 1H), 7.62 (s, 1H), 7.19 (d, 1H), 3.68 (s, 2H), 3.29 (m, 4H), 2.77 (d, 3H), 2.61-2.51 (m, 6H), 1.18 (t, 3H).

Example 18

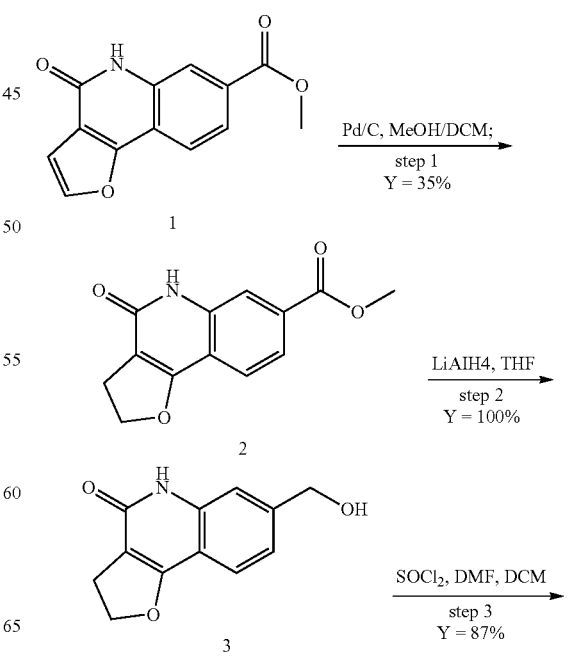

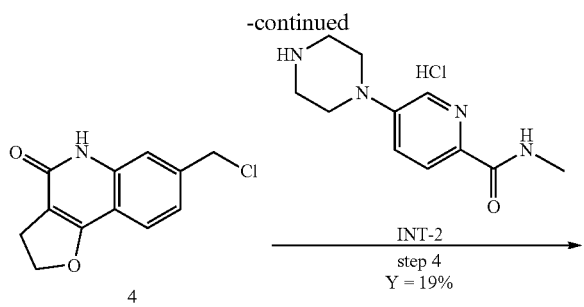

4

INT-2
step 4
Y = 19%

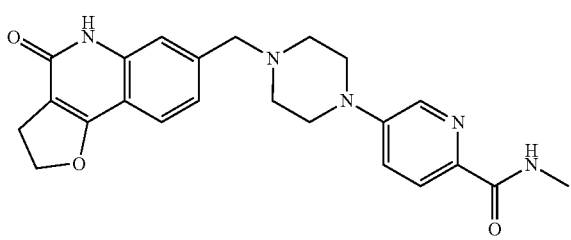

Example 18

Step 1: Preparation of methyl 4-oxo-2H,3H,5H-furo[3,2-c]quinoline-7-carboxylate

To a solution of methyl 4-oxo-5H-furo[3,2-c]quinoline-7-carboxylate (480 mg, 1.97 mmol, 1.00 equiv) in MeOH/DCM (80 mL/20 mL) was added Pd/C (200 mg, 10% wt) under nitrogen atmosphere. The mixture was hydrogenated at room temperature for 2 days under hydrogen atmosphere. The reaction was monitored by LCMS. The reaction mixture was filtered through a Celite pad and the filtrate was concentrated under reduced pressure. The residue was purified by reversed combi-flash chromatography to afford methyl 4-oxo-2H,3H,5H-furo[3,2-c]quinoline-7-carboxylate (170 mg, 35%) as a white solid. LC-MS: (ES+H, m/z): [M+H]$^+$=246.2.

Step 2: Preparation of 7-(hydroxymethyl)-2H,3H,5H-furo[3,2-c]quinolin-4-one

To a stirred solution of methyl 4-oxo-2H,3H,5H-furo[3,2-c]quinoline-7-carboxylate (170 mg, 0.69 mmol, 1.00 equiv) in THF (8 mL) was added LiAlH$_4$ (0.55 mL, 1.39 mmol, 2.00 equiv, 2.5M in THF) dropwise at 0° C. under nitrogen atmosphere. The resulting mixture was stirred for 2 h at 0° C. under nitrogen atmosphere. The reaction was monitored by LCMS. The reaction was quenched by the addition of 1M aq HCl (10 mL) at 0° C. The resulting mixture was concentrated under reduced pressure. The residue was purified by silica gel column chromatography to afford 7-(hydroxymethyl)-2H,3H,5H-furo[3,2-c]quinolin-4-one (150 mg, 100%) as a white solid. LC-MS: (ES+H, m/z): [M+H]$^+$=218.0. $^1$H NMR (400 MHz, DMSO-d$_6$) δ 11.38 (s, 1H), 7.53 (d, 1H), 7.34 (s, 1H), 7.09 (dd, 1H), 5.40-5.36 (m, 1H), 4.79 (t, 2H), 4.56 (s, 2H), 3.03 (t, 2H).

Step 3: Preparation of 7-(chloromethyl)-2H,3H,5H-furo[3,2-c]quinolin-4-one

To a stirred solution of 7-(hydroxymethyl)-2H,3H,5H-furo[3,2-c]quinolin-4-one (170 mg, 0.78 mmol, 1.00 equiv) and DMF (29 mg, 0.39 mmol, 0.50 equiv) in DCM (6 mL) was added thionyl chloride (744 mg, 6.26 mmol, 8.00 equiv) dropwise at 0° C. under nitrogen atmosphere. The resulting mixture was stirred overnight at room temperature under nitrogen atmosphere. The reaction was monitored by LCMS. The resulting mixture was concentrated under vacuum. The residue was purified by silica gel column chromatography to afford 7-(chloromethyl)-2H,3H,5H-furo[3,2-c]quinolin-4-one (160 mg, 87%) as a white solid. LC-MS: (ES+H, m/z): [M+H]$^+$=236.0.

Step 4: Preparation of N-methyl-5-[4-({4-oxo-2H,3H,5H-furo[3,2-c]quinolin-7-yl}methyl)piperazin-1-yl]pyridine-2-carboxamide To a stirred solution of N-methyl-5-(piperazin-1-yl)pyridine-2-carboxamide (200 mg, crude) and DIEA (351 mg, 2.72 mmol, 4.00 equiv) in MeCN (6 mL) were added 7-(chloromethyl)-2H,3H,5H-furo[3,2-c]quinolin-4-one (160 mg, 0.68 mmol, 1.00 equiv) and KI (22 mg, 0.14 mmol, 0.20 equiv) at room temperature under nitrogen atmosphere. The resulting mixture was stirred for 2 h at 80° C. under nitrogen atmosphere. The residue was purified by silica gel column chromatography to afford N-methyl-5-[4-({4-oxo-2H,3H,5H-furo[3,2-c]quinolin-7-yl}methyl)piperazin-1-yl]pyridine-2-carboxamide (56.5 mg, 19%) as a white solid. LC-MS: (ES+H, m/z): [M+H]$^+$=420.1. H NMR (400 MHz, DMSO-d$_6$) δ 11.36 (s, 1H), 8.40 (s, 1H), 8.27 (s, 1H), 7.83 (d, 1H), 7.56 (d, 1H), 7.43-7.28 (m, 2H), 7.16 (d, 1H), 4.79 (t, 2H), 3.60 (s, 2H), 3.43-3.31 (m, 4H), 3.05 (t, 2H), 2.84-2.73 (m, 3H), 2.61-2.52 (m, 4H).

The following examples were made using similar procedures shown for example 18.

| Ex | NMR | LCMS (ESI) m/z |
|---|---|---|
| 71 | $^1$H NMR (400 MHz, DMSO-d6) δ 11.37 (s, 1H), 8.27-8.12 (m, 2H), 8.56-8.19 (m, 4H), 4.79 (s, 2H), 3.65-3.61 (m, 2H), 3.53-3.35 (m, 4H), 3.13-2.95 (m, 2H), 2.75 (d, 3H), 2.56-2.52 (m, 4H). 19F NMR (282 MHz, DMSO) δ-120.38. | [M + H]$^+$ = 438.2 |
| 73 | $^1$H NMR (400 MHz, DMSO-d6) δ 11.46-11.36 (m, 1H), 8.37-8.26 (m, 2H), 7.90-7.83 (m, 1H), 7.56-7.06 (m, 4H), 4.92 (s, 2H), 3.72-3.55 (m, 2H), 3.30-3.16 (m, 4H), 3.10-2.95 (m, 2H), 2.70-2.52 (m, 4H). | [M + H]$^+$ = 423.2 |

Example 19

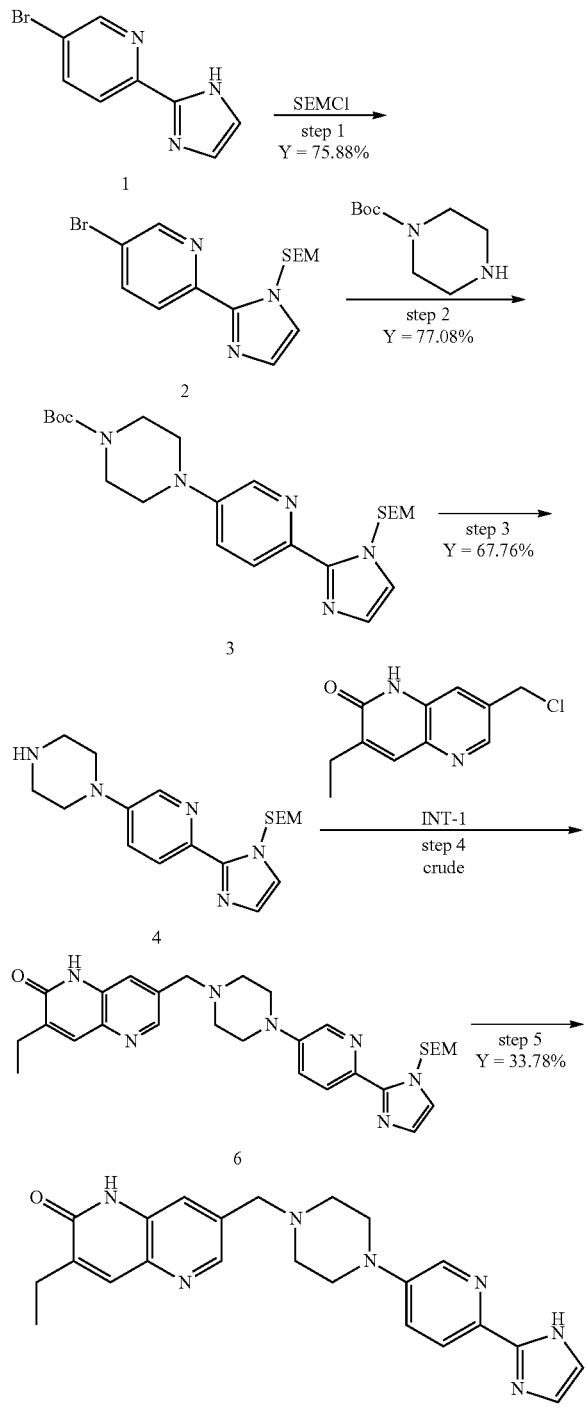

Example 19

Step 1: Preparation of 5-bromo-2-(1-{[2-(trimethylsilyl)ethoxy]methyl}imidazol-2-yl)pyridine A solution of 5-bromo-2-(1H-imidazol-2-yl)pyridine (1.00 g, 4.46 mmol, 1.00 equiv) and NaH (0.23 g, 5.80 mmol, 1.30 equiv, 60% wt) in DMF (10 mL) was stirred for 0.5 h at 0° C., and then to the above solution was added SEMCl (0.97 g, 5.80 mmol, 1.30 equiv) dropwise at room temperature. And the mixture was stirred for 2 h. The reaction was monitored by LCMS. The reaction was quenched with water (50 ml) at 0° C. The resulting mixture was extracted with EtOAc (3×100 mL). The combined organic layers were washed with water (3×50 mL) and dried over anhydrous $Na_2SO_4$. After filtration, the filtrate was concentrated under reduced pressure. The residue was purified by silica gel column chromatography to afford 5-bromo-2-(1-{[2-(trimethylsilyl)ethoxy]methyl}imidazol-2-yl)pyridine (1.20 g, 75.88%) as a brown oil. LC-MS: (ES+H, m/z): [M+H]+=353.8/355.8. $^1$H NMR (300 MHz, Chloroform-d) δ 8.65 (d, 1H), 8.14 (d, 1H), 7.91 (d, 1H), 7.24 (d, 1H), 7.20 (d, 1H), 6.01 (s, 2H), 3.59-3.53 (m, 2H), 0.93-0.87 (m, 2H), 0.00 (s, 9H).

Step 2: Preparation of tert-butyl 4-[6-(1-{[2-(trimethylsilyl)ethoxy]methyl}imidazol-2-yl)pyridin-3-yl]piperazine-1-carboxylate To a stirred solution of 5-bromo-2-(1-{[2-(trimethylsilyl)ethoxy]methyl}imidazol-2-yl)pyridine (900 mg, 2.54 mmol, 1.00 equiv) and tert-butyl piperazine-1-carboxylate (426 mg, 2.29 mmol, 1.00 equiv) in dioxane (10 mL) was added RuPhos Palladacycle Gen.3 (118 mg, 0.25 mmol, 0.10 equiv) and $Cs_2CO_3$ (1.66 g, 5.08 mmol, 2.00 equiv) at room temperature. The resulting mixture was stirred overnight at 100° C. under nitrogen atmosphere. The reaction was monitored by LCMS. The mixture was allowed to cool down to room temperature. The resulting mixture was filtered, the filter cake was washed with $CH_2Cl_2$/MeOH (3:1) (5×100 ml). The filtrate was concentrated under reduced pressure. The residue was purified by silica gel column chromatography to afford tert-butyl 4-[6-(1-{[2-(trimethylsilyl)ethoxy]methyl}imidazol-2-yl)pyridin-3-yl]piperazine-1-carboxylate (900 mg, 77.08%) as an orange oil. LC-MS: (ES+H, m/z): [M+H]+=460.2. $^1$H NMR (400 MHz, Chloroform-d) 68.33 (d, 1H), 8.15 (d, 1H), 7.37-7.34 (m, 1H), 7.24 (d, 1H), 7.21 (d, 1H), 6.08 (s, 2H), 3.74-3.64 (m, 4H), 3.63-3.57 (m, 2H), 3.32 (t, 4H), 1.58 (s, 9H), 0.99-0.92 (m, 2H), 0.00 (s, 9H).

Step 3: Preparation of 1-[6-(1-{[2-(trimethylsilyl)ethoxy]methyl}imidazol-2-yl)pyridin-3-yl]piperazine To a stirred solution of tert-butyl 4-[6-(1-{[2-(trimethylsilyl)ethoxy]methyl}imidazol-2-yl)pyridin-3-yl]piperazine-1-carboxylate (1.00 g, 2.17 mmol, 1.00 equiv) and DIEA (5.62 g, 43.50 mmol, 20.00 equiv) in dioxane (20 mL) was added TMSOTf (4.84 g, 21.75 mmol, 10.00 equiv) dropwise at 0° C. The resulting mixture was stirred for 2 h at room temperature under nitrogen atmosphere. The reaction was monitored by LCMS. The reaction was quenched by the addition of MeOH (3 mL) at room temperature. The residue was purified by silica gel column chromatography to afford 1-[6-(1-{[2-(trimethylsilyl)ethoxy]methyl}imidazol-2-yl)pyridin-3-yl]piperazine (530 mg, 67.76%) as an orange oil. LC-MS: (ES+H, m/z): [M+H]+=360.2. $^1$H NMR (300 MHz, Chloroform-d) 68.26 (d, 1H), 8.09-7.97 (m, 1H), 7.28 (d, 1H), 7.16 (d, 1H), 7.12 (d, 1H), 5.99 (s, 2H), 3.56-3.46 (m, 2H), 3.35-3.26 (m, 4H), 3.15-3.08 (m, 4H), 0.93-0.83 (m, 2H), 0.00 (s, 9H).

Step 4: Preparation of 3-ethyl-7-({4-[6-(1-{[2-(trimethylsilyl)ethoxy]methyl}imidazol-2-yl)pyridin-3-yl]piperazin-1-yl}methyl)-1H-1,5-naphthyridin-2-one To a stirred solution of 1-[6-(1-{[2-(trimethylsilyl)ethoxy]methyl}imidazol-2-yl)pyridin-3-yl]piperazine (160 mg, 0.44 mmol, 1.00 equiv) and 7-(chloromethyl)-3-ethyl-1H-1,5-naphthyridin-2-one (100 mg, 0.44 mmol, 1.00 equiv) in acetonitrile (8 mL) were added DIEA (172 mg, 1.34 mmol, 3.00 equiv) and potassium iodide (15 mg, 0.09 mmol, 0.20 equiv) at room temperature under nitrogen atmosphere. The resulting mixture was stirred for 1.5 h at 80° C. under nitrogen atmosphere. The reaction was monitored by LCMS. The mixture was allowed to cool down to room temperature. The resulting mixture was concentrated under reduced pressure. The residue was purified by silica gel column chromatography to afford 3-ethyl-7-({4-[6-(1-{[2-(trimethylsilyl)ethoxy]methyl}imidazol-2-yl)pyridin-3-yl]piperazin-1-yl}methyl)-1H-1,5-naphthyridin-2-one (300 mg, crude) as a brown solid. LC-MS: (ES+H, m/z): [M+H]$^+$=546.0.

Step 5: Preparation of 3-ethyl-7-({4-[6-(1H-imidazol-2-yl)pyridin-3-yl]piperazin-1-yl}methyl)-1H-1, 5-naphthyridin-2-one To a stirred solution of 3-ethyl-7-({4-[6-(1-{[2-(trimethylsilyl)ethoxy]methyl}imidazol-2-yl)pyridin-3-yl]piperazin-1-yl}methyl)-1H-1,5-naphthyridin-2-one (300 mg, 0.55 mmol, 1.00 equiv) in DCM (7 mL) was added TFA (3 mL) dropwise at 0° C. under nitrogen atmosphere. The resulting mixture was stirred for 3 h at room temperature under nitrogen atmosphere. The reaction was monitored by LCMS. The resulting mixture was concentrated under reduced pressure. The residue was purified by trituration with ether (10 mL×3). The residue was basified with NH4OH. The resulting mixture was concentrated under reduced pressure. The residue was purified by silica gel column chromatography. The pure fraction was concentrated under vacuum to afford 3-ethyl-7-({4-[6-(1H-imidazol-2-yl)pyridin-3-yl]piperazin-1-yl}methyl)-1H-1,5-naphthyridin-2-one (80.3 mg, 33.78%) as a white solid. LC-MS: (ES+H, m/z): [M+H]$^+$=416.30. $^1$H NMR (300 MHz, DMSO-d6) δ 12.45 (s, 1H), 11.87 (s, 1H), 8.42 (d, 1H), 8.27 (d, 1H), 7.87 (d, 1H), 7.76 (s, 1H), 7.64 (s, 1H), 7.44 (q, 1H), 7.05 (s, 2H), 3.66 (s, 2H), 3.34 (m, 4H), 2.59-2.51 (m, 6H), 1.23-1.17 (t, 3H).

Example 20 and Example 21

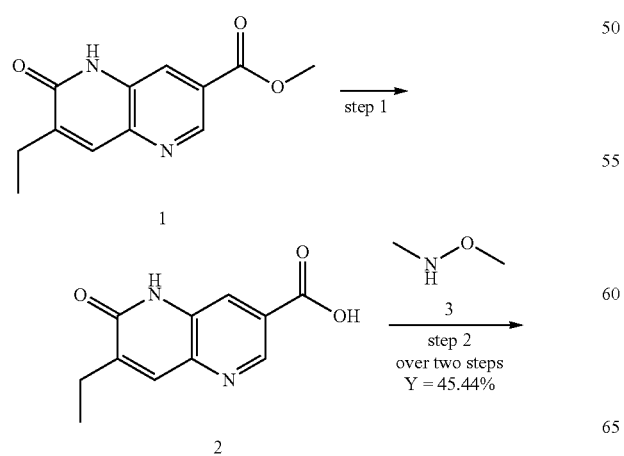

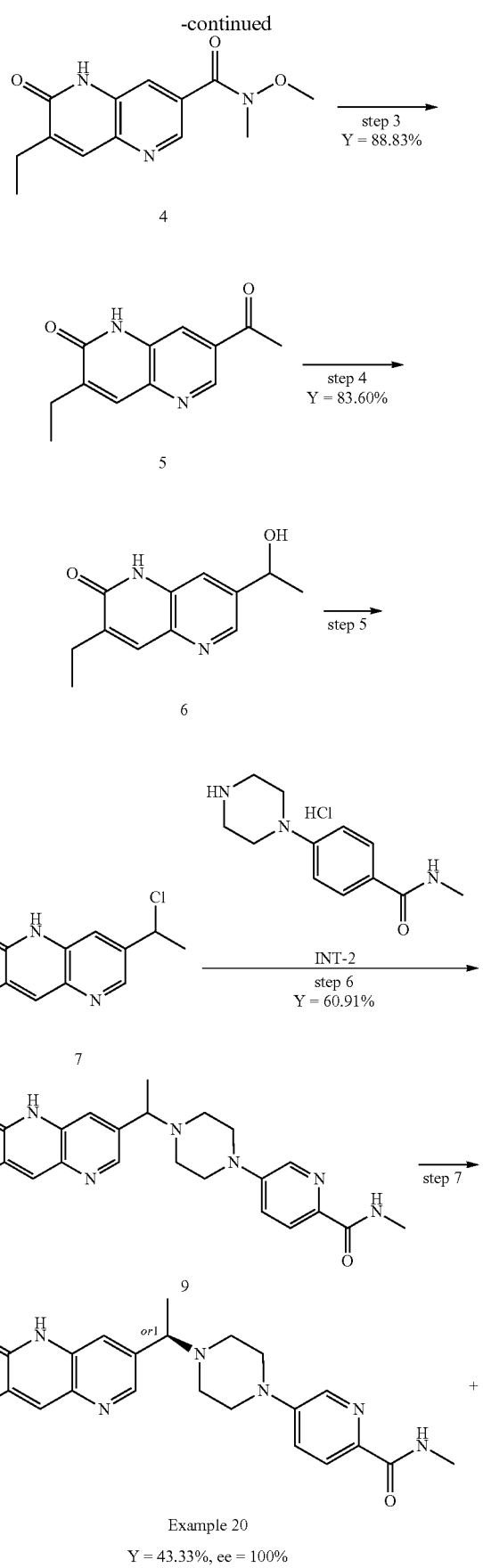

Example 20

Y = 43.33%, ee = 100%

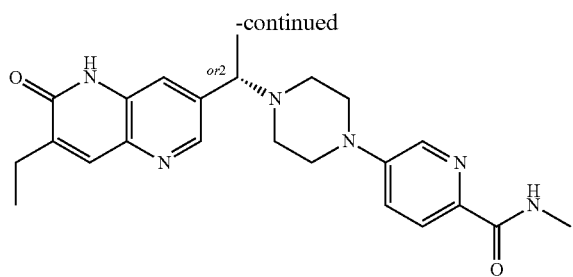

Example 21
Y = 40.80%, ee = 99.5%

Step 1: Preparation of 7-ethyl-6-oxo-5H-1,5-naphthyridine-3-carboxylic acid

To a solution of methyl 7-ethyl-6-oxo-5H-1,5-naphthyridine-3-carboxylate (1.15 g, 4.95 mmol, 1.00 equiv) in MeOH (15 mL) and $H_2O$ (3 mL) was added NaOH (0.59 g, 14.86 mmol, 3.00 equiv) in portions at room temperature. The resulting mixture was stirred for 1 h at room temperature. The reaction was monitored by LCMS. The resulting mixture was diluted with water (10 mL). The residue was acidified to pH 4 with 6N HCl (aq.). The resulting mixture was filtered, the solid was concentrated under reduced pressure to afford 7-ethyl-6-oxo-5H-1,5-naphthyridine-3-carboxylic acid (800.0 mg, crude) as a white solid. LC-MS: (ES+H, m/z): $[M+H]^+$=218.9.
$^1$H NMR (400 MHz, DMSO-$d_6$) δ 13.43 (s, 1H), 12.08 (s, 1H), 8.89 (d, 1H), 8.15 (d, 1H), 7.82 (s, 1H), 2.62-2.54 (m, 2H), 1.20 (t, 3H).

Step 2: Preparation of 7-ethyl-N-methoxy-N-methyl-6-oxo-5H-1,5-naphthyridine-3-carboxamide To a solution of 7-ethyl-6-oxo-5H-1,5-naphthyridine-3-carboxylic acid (800 mg, crude) and N,O-dimethylhydroxylamine (336 mg, 5.50 mmol, 1.50 equiv) in DMF (8 mL) was added EDCI (2.10 g, 11.00 mmol, 3.00 equiv) in portions at room temperature under nitrogen atmosphere. The resulting mixture was stirred for 2 h at room temperature under nitrogen atmosphere. The reaction was monitored by LCMS. The resulting mixture was diluted with water (20 mL). The resulting mixture was extracted with EtOAc (3×25 mL). The combined organic layers were washed with brine (3×50 mL), dried over anhydrous $Na_2SO_4$. After filtration, the filtrate was concentrated under reduced pressure. The residue was purified by silica gel column chromatography to afford 7-ethyl-N-methoxy-N-methyl-6-oxo-5H-1,5-naphthyridine-3-carboxamide (540 mg, 45.44%) as an off-white solid. LC-MS: (ES+H, m/z): $[M+H]^+$=262.1. $^1$H NMR (400 MHz, DMSO-$d_6$) δ 12.02 (s, 1H), 8.64 (d, 1H), 7.89 (dd, 1H), 7.80 (s, 1H), 3.58 (s, 3H), 3.31 (s, 3H), 2.57 (q, 2H), 1.20 (t, 3H).

Step 3: Preparation of 7-acetyl-3-ethyl-1H-1,5-naphthyridin-2-one

To a solution of 7-ethyl-N-methoxy-N-methyl-6-oxo-5H-1,5-naphthyridine-3-carboxamide (540 mg, 2.07 mmol, 1.00 equiv) in THF (5 mL) was added $CH_3MgBr$ (1.4 mL, 4.13 mmol, 2.00 equiv, 3M in THF) dropwise at 0° C. under nitrogen atmosphere. The resulting mixture was stirred for 1.5 h at room temperature under nitrogen atmosphere. The reaction was monitored by LCMS. The reaction was quenched with water at 0° C. The resulting mixture was diluted with water (15 mL). The resulting mixture was extracted with EtOAc (3×20 mL). The combined organic layers were washed with brine (2×60 mL), dried over anhydrous $Na_2SO_4$. After filtration, the filtrate was concentrated under reduced pressure. The residue was purified by silica gel column chromatography to afford 7-acetyl-3-ethyl-1H-1,5-naphthyridin-2-one (397 mg, 88.83%) as an off-white solid. LC-MS: (ES+H, m/z): $[M+H]^+$=217.1. $^1$H NMR (400 MHz, DMSO-$d_6$) δ 12.06 (s, 1H), 8.98 (s, 1H), 8.09 (d, 1H), 7.84 (d, 1H), 2.67 (s, 3H), 2.58 (q, 2H), 1.20 (t, 3H).

Step 4: Preparation of 3-ethyl-7-(1-hydroxyethyl)-1H-1,5-naphthyridin-2-one

To a solution of 7-acetyl-3-ethyl-1H-1,5-naphthyridin-2-one (398 mg, 1.84 mmol, 1.00 equiv) in MeOH (5 mL) was added $NaBH_4$ (174 mg, 4.59 mmol, 2.50 equiv) in portions at 0° C. under nitrogen atmosphere. The resulting mixture was stirred for 2 h at room temperature under nitrogen atmosphere. The reaction was monitored by LCMS. The reaction was quenched with sat. $NH_4Cl$ (aq.) at 0° C. The resulting mixture was diluted with water (15 mL). The resulting mixture was extracted with EtOAc (3×20 mL). The combined organic layers were washed with brine (3×50 mL), dried over anhydrous $Na_2SO_4$. After filtration, the filtrate was concentrated under reduced pressure. The residue was purified by silica gel column chromatography to afford 3-ethyl-7-(1-hydroxyethyl)-1H-1,5-naphthyridin-2-one (335.0 mg, 83.60%) as a brown solid. LC-MS: (ES+H, m/z): $[M+H]^+$=219.2.

Step 5: Preparation of 7-(1-chloroethyl)-3-ethyl-1H-1,5-naphthyridin-2-one

To a solution of 3-ethyl-7-(1-hydroxyethyl)-1H-1,5-naphthyridin-2-one (335 mg, 1.54 mmol, 1.00 equiv) in DCM (10 mL) was added $SOCl_2$ (457 mg, 3.84 mmol, 2.50 equiv) dropwise at 0° C. under nitrogen atmosphere. The resulting mixture was stirred for 4 h at room temperature under nitrogen atmosphere. The reaction was monitored by LCMS. The reaction mixture was concentrated under reduced pressure. The residue was used directly in the next step. LC-MS: (ES+H, m/z): $[M+H]^+$=237.0.

Step 6: Preparation of 5-{4-[1-(7-ethyl-6-oxo-5H-1,5-naphthyridin-3-yl)ethyl]piperazin-1-yl}-N-methylpyridine-2-carboxamide To a solution of 7-(1-chloroethyl)-3-ethyl-1H-1,5-naphthyridin-2-one (280 mg, 1.18 mmol, 1.00 equiv) and N-methyl-5-(piperazin-1-yl)pyridine-2-carboxamide (350 mg, crude) in MeCN (6 mL) was added KI (785 mg, 4.73 mmol, 4.00 equiv) and DIEA (917 mg, 7.10 mmol, 6.00 equiv) in portions at room temperature under nitrogen atmosphere. The resulting mixture was stirred for 2 h at 80° C. under nitrogen atmosphere. The reaction was monitored by LCMS. The mixture was allowed to cool down to room temperature. The resulting mixture was concentrated under reduced pressure. The residue was purified by silica gel column chromatography to afford 5-{4-[1-(7-ethyl-6-oxo-5H-1,5-naphthyridin-3-yl)ethyl]piperazin-1-yl}-N-methylpyridine-2-carboxamide (303.1 mg, 60.91%) as a white solid. LC-MS: (ES+H, m/z): $[M+H]^+$=421.2.

Step 7: Preparation of rel-5-{4-[(1R)-1-(7-ethyl-6-oxo-5H-1,5-naphthyridin-3-yl)ethyl]piperazin-1-yl}-N-methylpyridine-2-carboxamide (Example 20) & rel-5-{4-[(1R)-1-(7-ethyl-6-oxo-5H-1,5-naphthyridin-3-yl)ethyl]piperazin-1-yl}-N-methylpyridine-2-carboxamide (Example 21)

5-{4-[1-(7-ethyl-6-oxo-5H-1,5-naphthyridin-3-yl)ethyl]piperazin-1-yl}-N-methylpyridine-2-carboxamide (300 mg, 0.71 mmol, 1.00 equiv) was isolated by prep-Chiral HPLC. This resulted in rel-5-{4-[(1R)-1-(7-ethyl-6-oxo-5H-1,5-naphthyridin-3-yl)ethyl]piperazin-1-yl}-N-methylpyridine-2-carboxamide (Example 20, 130.0 mg, 43.33%, ee=100%) as a white solid and rel-5-(4-{[(1aR)-1a-ethyl-2-oxo-1H,3H,7bH-cyclopropa[c]quinolin-5-yl]methyl}piperazin-1-yl)-N-methylpyridine-2-carboxamide (Example 21, 122.4 mg, 40.80%, ee=99.5%) as a white solid. Note: The stereochemical assignments of examples 20 and 21 are arbitrary.

Example 20

LC-MS: (ES+H, m/z): [M+H]$^+$=421.3. $^1$H NMR (300 MHz, DMSO-d$_6$) δ 11.83 (s, 1H), 8.45 (s, 1H), 8.39 (q, 1H), 8.25 (d, 1H), 7.82 (d, 1H), 7.75 (s, 1H), 7.62 (s, 1H), 7.42-7.33 (m, 1H), 3.67-3.64 (m, 1H), 3.35-3.33 (m, 4H), 2.78 (dd, 3H), 2.63-2.59 (m, 4H), 2.55-2.50 (m, 2H), 1.38 (d, 3H), 1.18 (t, 3H).

Example 21

LC-MS: (ES+H, m/z): [M+H]$^+$=421.3. $^1$H NMR (300 MHz, DMSO-d$_6$) δ 11.83 (s, 1H), 8.45 (s, 1H), 8.39 (q, 1H), 8.25 (d, 1H), 7.82 (d, 1H), 7.75 (s, 1H), 7.62 (s, 1H), 7.42-7.33 (m, 1H), 3.67-3.64 (m, 1H), 3.35-3.33 (m, 4H), 2.78 (dd, 3H), 2.63-2.59 (m, 4H), 2.55-2.50 (m, 2H), 1.38 (d, 3H), 1.18 (t, 3H).

Example 22A

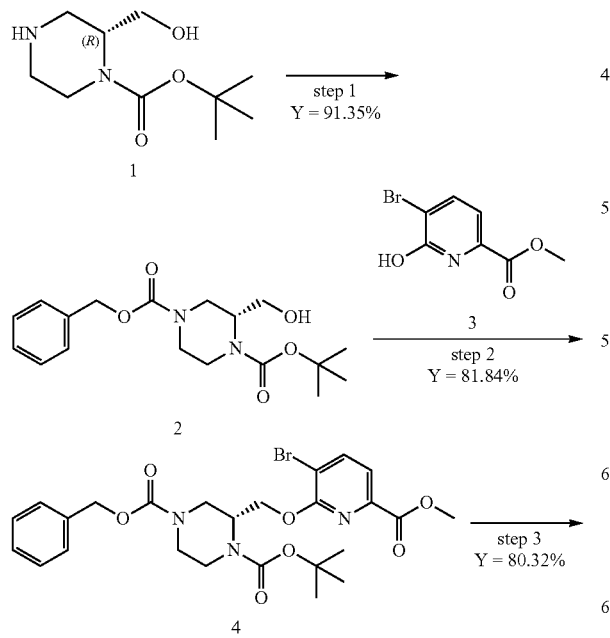

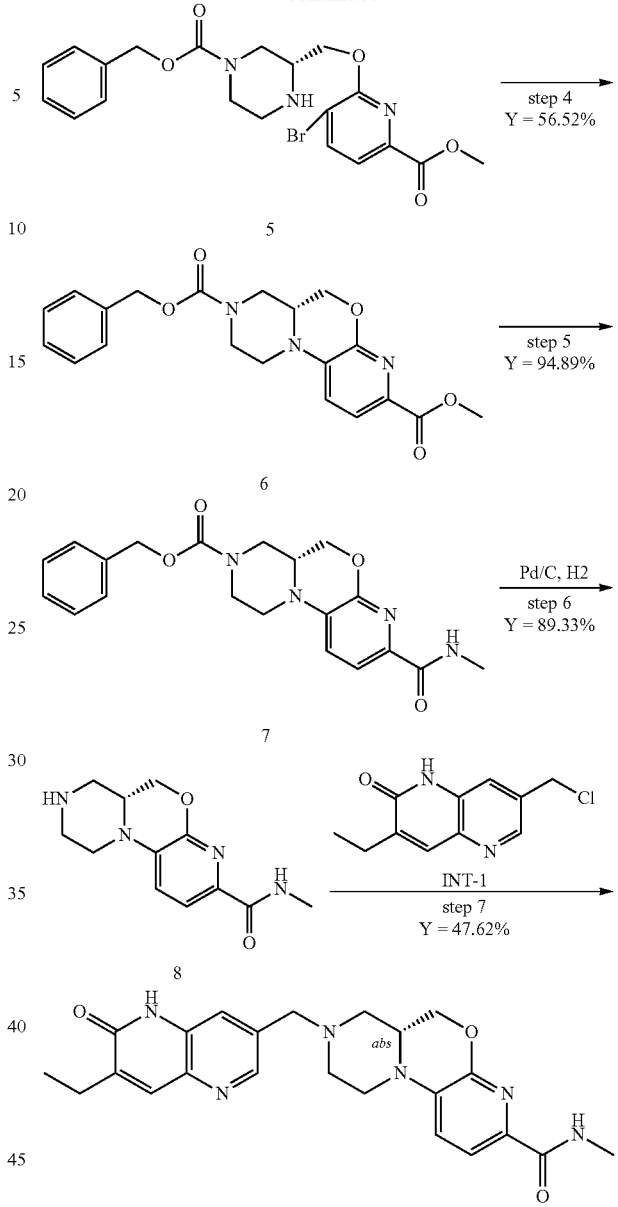

Example 22A

Step 1: Preparation of 4-benzyl 1-(tert-butyl) (R)-2-(hydroxymethyl)piperazine-1,4-dicarboxylate To a stirred mixture of tert-butyl (2R)-2-(hydroxymethyl)piperazine-1-carboxylate (5.00 g, 23.11 mmol, 1.00 equiv, [a]$^{26}$D (c=0.1, MeOH): +54.50) and Et$_3$N (7.02 g, 69.35 mmol, 3.00 equiv) in DCM (80 mL) was added Cbz-Cl (7.89 g, 46.23 mmol, 2.00 equiv) dropwise at 0° C. under nitrogen atmosphere. The resulting mixture was stirred overnight at room temperature. The reaction was quenched by the addition of water (100 mL) at room temperature. The resulting mixture was extracted with CH$_2$Cl$_2$ (3×150 mL). The combined organic layers were washed with brine (1×150 mL), dried over anhydrous Na$_2$SO$_4$. After filtration, the filtrate was concentrated under reduced pressure. The residue was purified by silica gel column chromatography, the pure fraction was concentrated under reduced pressure to afford 4-benzyl 1-(tert-butyl) (R)-2-(hydroxymethyl)piperazine-1,4-dicarboxylate (7.40 g, Y=91.35%) as a colorless oil. LC-MS: (ES+H, m/z): [M−(t−Bu)+H]⁺=294.9. ¹H NMR (300 MHz, DMSO-d₆) δ 7.44-7.26 (m, 5H), 5.09 (s, 2H), 4.80-4.70 (m, 1H), 4.18-3.85 (m, 2H), 3.80-3.60 (m, 2H), 3.50-3.35 (m, 2H), 3.15-2.75 (m, 3H), 1.41 (s, 9H).

Step 2: Preparation of 4-benzyl 1-(tert-butyl) (R)-2-(((3-bromo-6-(methoxycarbonyl)pyridin-2-yl)oxy)methyl)piperazine-1,4-dicarboxylate A mixture of PPh3 (19.76 g, 75.34 mmol, 6.00 equiv) and DEAD (10.93 g, 62.78 mmol, 5.00 equiv) in THF (200 mL) was stirred for 1 h at 0° C. under nitrogen atmosphere. The mixture was added to 4-benzyl 1-tert-butyl (2R)-2-(hydroxymethyl)piperazine-1,4-dicarboxylate (4.40 g, 12.55 mmol, 1.00 equiv) and methyl 5-bromo-6-hydroxypyridine-2-carboxylate (2.91 g, 12.55 mmol, 1.00 equiv) in THF (50 mL) dropwise over 10 min at 0° C. The resulting mixture was stirred for additional 2 h at room temperature. The reaction was monitored by LCMS. The resulting mixture was concentrated under reduced pressure. The residue was purified by silica gel column chromatography, the pure fraction was concentrated under reduced pressure to afford 4-benzyl 1-(tert-butyl) (R)-2-(((3-bromo-6-(methoxycarbonyl)pyridin-2-yl)oxy)methyl)piperazine-1,4-dicarboxylate (5.80 g, Y=81.84%) as a colorless oil. LC-MS: (ES+H, m/z): [M+Na]⁺=586.0/588.0.

Step 3: Preparation of benzyl (R)-3-(((3-bromo-6-(methoxycarbonyl)pyridin-2-yl)oxy)methyl)piperazine-1-carboxylate To a stirred mixture of 4-benzyl 1-tert-butyl 2-({[3-bromo-6-(methoxycarbonyl)pyridin-2-yl]oxy}methyl)piperazine-1,4-dicarboxylate (5.60 g, 9.62 mmol, 1.00 equiv) in DCM (100 mL) was added HCl(gas) in 1,4-dioxane (50 mL, 4M) in portions at room temperature under nitrogen atmosphere. The resulting mixture was stirred for 1 h at room temperature under nitrogen atmosphere. The reaction was monitored by LCMS. The resulting mixture was concentrated under reduced pressure. The residue was purified by trituration with hexane/diethyl ether (1/1, 3×50 mL). The precipitated solids were collected by filtration and washed with hexane (3×50 mL). The residue was basified to pH 8~9 with saturated Na2CO3 (aq.) and extracted with EtOAc (3×200 mL). The combined organic layers were washed with brine (1×200 mL), dried over anhydrous Na₂SO₄. After filtration, the filtrate was concentrated under reduced pressure. This resulted in benzyl (R)-3-(((3-bromo-6-(methoxycarbonyl)pyridin-2-yl)oxy)methyl)piperazine-1-carboxylate (3.7 g, Y=80.32%) as a light yellow oil. LC-MS: (ES+H, m/z): [M+H]⁺=463.9/465.9. ¹H NMR (300 MHz, DMSO-d₆) δ 8.23 (d, 1H), 7.60 (d, 1H), 7.45-7.25 (m, 5H), 5.08 (s, 2H), 4.45-3.99 (m, 4H), 3.92-3.68 (m, 4H), 3.04-2.54 (m, 4H).

Step 4: Preparation of 3-benzyl 8-methyl (R)-1,2,4a,5-tetrahydropyrazino[1,2-d]pyrido[2,3-b][1,4]oxazine-3,8(4H)-dicarboxylate To a stirred mixture of benzyl 3-({[3-bromo-6-(methoxycarbonyl)pyridin-2-yl]oxy}methyl)piperazine-1-carboxylate (1.20 g, 2.58 mmol, 1.00 equiv) and Cs₂CO₃ (2.53 g, 7.75 mmol, 3.00 equiv) in THF (60 mL) was added dichloro[bis(2-(diphenylphosphino)phenyl)ether]palladium(II) (740 mg, 1.03 mmol, 0.40 equiv) at room temperature under nitrogen atmosphere. The resulting mixture was stirred for 2 h at 80° C. under nitrogen atmosphere. The reaction was monitored by LCMS. The resulting mixture was cooled down to room temperature. The resulting mixture was concentrated under reduced pressure. The residue was purified by silica gel column chromatography, the pure fraction was concentrated under reduced pressure to afford 3-benzyl 8-methyl (R)-1,2,4a,5-tetrahydropyrazino[1,2-d]pyrido[2,3-b][1,4]oxazine-3,8(4H)-dicarboxylate (560 mg, Y=56.52%) as a light yellow oil. LC-MS: (ES+H, m/z): [M+H]⁺=384.1. 1H NMR (300 MHz, DMSO-d₆) δ 7.63 (d, 1H), 7.46-7.22 (m, 6H), 5.13 (s, 2H), 4.56-4.47 (m, 1H), 4.13-4.06 (m, 5H), 3.78 (s, 3H), 3.17 (d, 2H).

Step 5: Preparation of benzyl (R)-8-(methylcarbamoyl)-1,2,4a,5-tetrahydropyrazino[1,2-d]pyrido[2,3-b][1,4]oxazine-3(4H)-carboxylate To a stirred mixture of 3-benzyl 8-methyl (R)-1,2,4a,5-tetrahydropyrazino[1,2-d]pyrido[2,3-b][1,4]oxazine-3,8(4H)-dicarboxylate (560 mg, 1.46 mmol, 1.00 equiv) in MeOH (15 mL) was added methylamine (10 mL, 25-30% wt in water) dropwise at room temperature under nitrogen atmosphere. The resulting mixture was stirred overnight at room temperature. The reaction was monitored by LCMS. The resulting mixture was concentrated under reduced pressure. The resulting mixture was added saturated NH₄Cl (100 mL) and extracted with EtOAc (3×100 mL). The combined organic layers were washed with brine (1×100 mL) and dried over anhydrous Na₂SO₄. After filtration, the filtrate was concentrated under reduced pressure. This resulted in benzyl (R)-8-(methylcarbamoyl)-1,2,4a,5-tetrahydropyrazino[1,2-d]pyrido[2,3-b][1,4]oxazine-3(4H)-carboxylate (530 mg, Y=94.89%) as a white solid. LC-MS: (ES+H, m/z): [M+H]⁺=383.2.

Step 6: Preparation of (R)—N-methyl-1,2,3,4,4a,5-hexahydropyrazino[1,2-d]pyrido[2,3-b][1,4]oxazine-8-carboxamide To a stirred mixture of benzyl 5-(methylcarbamoyl)-8-oxa-1,6,12-triazatricyclo[8.4.0.0^{2,7}]tetradeca-2,4,6-triene-12-carboxylate (500 mg, 1.30 mmol, 1.00 equiv) and NH₃.H₂O (3 mL) in i-PrOH (15 mL) was added Pd/C (100 mg, 10% wt) at room temperature under hydrogen atmosphere. The resulting mixture was stirred for 1 h at room temperature under hydrogen atmosphere. The reaction was monitored by LCMS. The resulting mixture was filtered, the filter cake was washed with MeOH (5×50 mL). The filtrate was concentrated under reduced pressure. This resulted in (R)—N-methyl-1,2,3,4,4a,5-hexahydropyrazino[1,2-d]pyrido[2,3-b][1,4]oxazine-8-carboxamide (290 mg, Y=89.33%) as a white solid. LC-MS: (ES+H, m/z): [M+H]⁺=249.0.

Step 7: Preparation of (R)-3-((7-ethyl-6-oxo-5,6-dihydro-1,5-naphthyridin-3-yl)methyl)-N-methyl-1,2,3,4,4a,5-hexahydropyrazino[1,2-d]pyrido[2,3-b][1,4]oxazine-8-carboxamide To a stirred mixture of (R)—N-methyl-1,2,3,4,4a,5-hexahydropyrazino[1,2-d]pyrido[2,3-b][1,4]oxazine-8-carboxamide (123 mg, 0.49 mmol, 1.10 equiv) and 7-(chloromethyl)-3-ethyl-1H-1,5-naphthyridin-2-one (100 mg, 0.45 mmol, 1.00 equiv) in ACN (4 mL) were added DIEA (290 mg, 2.24 mmol, 5.00 equiv) and KI (7 mg, 0.04 mmol, 0.10 equiv) in portions at room temperature under nitrogen atmosphere. The resulting mixture was stirred for 2 h at 80° C. under nitrogen atmosphere. The reaction was monitored by LCMS. The resulting mixture was cooled down to room temperature. The reaction mixture was poured into Water (50 mL) at room temperature. The resulting mixture was extracted with EtOAc (3×50 mL). The combined organic layers were washed with brine (1×100 mL), dried over anhydrous $Na_2SO_4$. After filtration, the filtrate was concentrated under reduced pressure. The crude product was purified by PREP-HPLC, the pure fraction was concentrated under reduced pressure and lyophilized to afford (R)-3-((7-ethyl-6-oxo-5,6-dihydro-1,5-naphthyridin-3-yl)methyl)-N-methyl-1,2,3,4,4a,5-hexahydropyrazino[1,2-d]pyrido[2,3-b][1,4]oxazine-8-carboxamide (100 mg, ee %=99.17%, Y=47.62%) as a white solid. LC-MS: (ES+H, m/z): $[M+H]^+$=435.15. Optical Rotation: $[a]^{26}D$ (c=0.5, DMF): −3.38. $^1$H NMR (300 MHz, DMSO-$d_6$) δ 11.86 (s, 1H), 8.41 (d, 1H), 8.16 (d, 1H), 7.76 (s, 1H), 7.63 (d, 1H), 7.53 (d, 1H), 7.29 (d, 1H), 4.45-4.35 (m, 1H), 4.12-4.00 (m, 1H), 3.86-3.55 (m, 3H), 3.21-3.17 (m, 1H), 3.01-2.71 (m, 6H), 2.61-2.52 (m, 2H), 2.28-2.22 (m, 1H), 1.85-1.81 (m, 1H), 1.20 (t, 3H).

The following examples were made using similar procedures shown for example 22A.

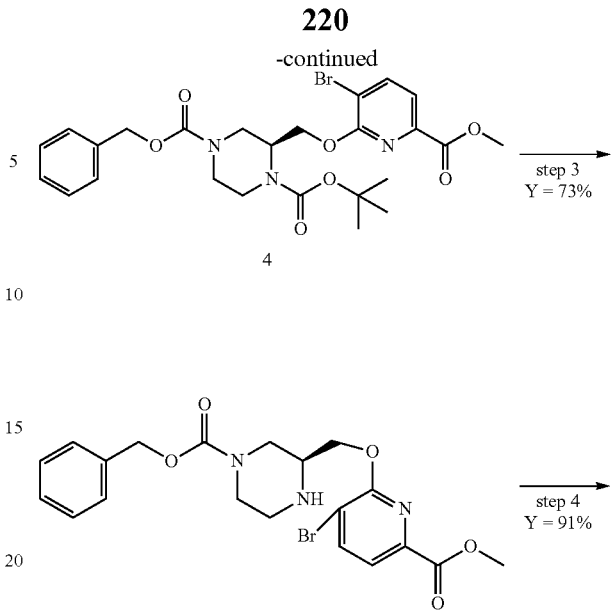

| Ex | NMR | LCMS (ESI) m/z |
|---|---|---|
| 77 | $^1$H NMR (400 MHz, DMSO-d6) δ 11.87 (s, 1H), 8.40 (d, 1H), 8.16 (s, 1H), 7.84 (s, 1H), 7.61 (s, 1H), 7.53 (d, 1H), 7.28 (d, 1H), 4.40 (dd, 1H), 4.10-4.01 (m, 1H), 3.79 (d, 1H), 3.75-3.71 (m, 1H), 3.65-3.61 (m, 1H), 3.21 (t, 1H), 2.98-2.88 (m, 2H), 2.84-2.78 (m, 1H), 2.74 (d, 3H), 2.29-2.16 (m, 1H), 2.16-2.12 (m, 3H), 1.83 (t, 1H). | $[M + H]^+$ = 421.1 |
| 78 | $^1$H NMR (400 MHz, DMSO-d6) δ 11.88 (s, 1H), 8.38 (d, 1H), 8.20-8.12 (m, 1H), 7.60 (d, 1H), 7.53 (d, 1H), 7.42 (s, 1H), 7.28 (d, 1H), 4.39 (dd, 1H), 4.10-4.02 (m, 1H), 3.79 (d, 1H), 3.70 (d, 1H), 3.60 (d, 1H), 3.25-3.15 (m, 1H), 2.96 (d, 1H), 2.89 (d, 1H), 2.83-2.77 (m, 1H), 2.75 (d, 3H), 2.29-2.20 (m, 1H) ,2.19-2.05 (m, 1H), 1.82 (t, 1H), 1.02-0.93 (m, 2H), 0.88-0.78 (m, 2H). | $[M + H]^+$ = 447.1 |
| 94 | MHz, DMSO-d6) δ 11.84 (s, 1H), 8.40 (d, 1H), 8.16 (d, 1H), 7.75 (s, 1H), 7.71-7.56 (m, 2H), 6.82 (d, 1H), 3.62 (s, 2H), 3.54-3.40 (m, 4H), 2.59-2.52 (m, 2H), 2.50-2.44 (m, 4H), 1.24-1.13 (m, 3H). | $[M + H]^+$ = 438.30 |

Example 22B

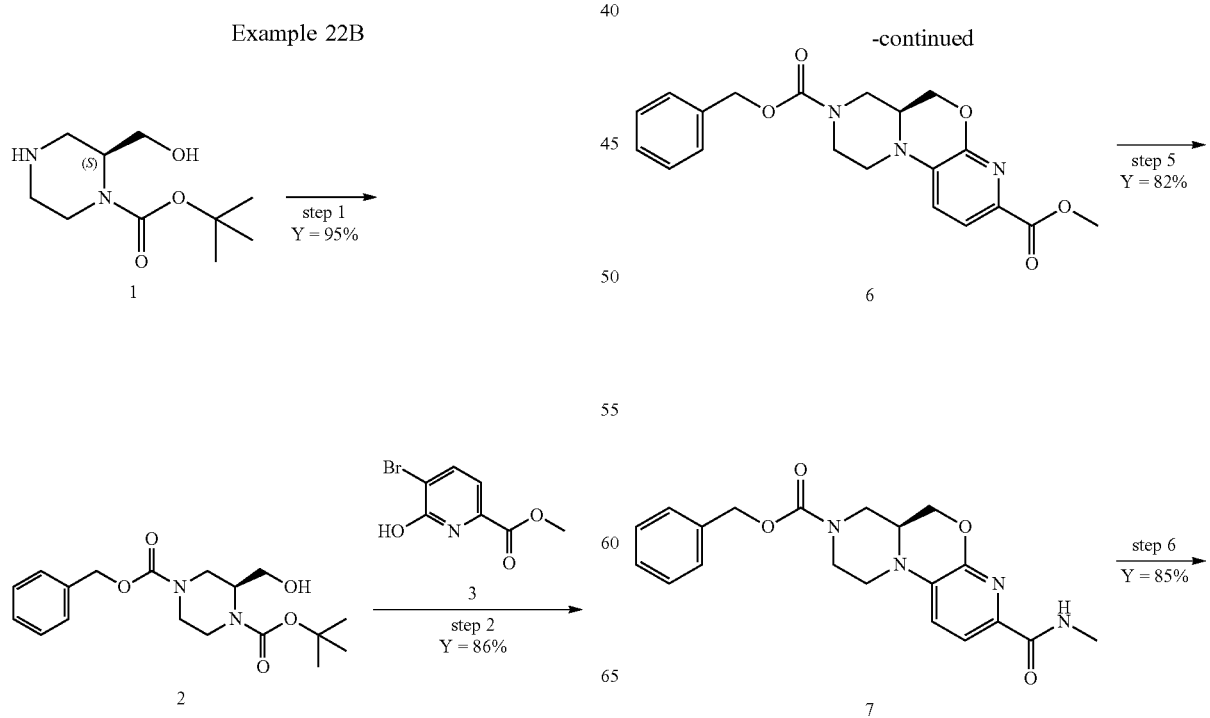

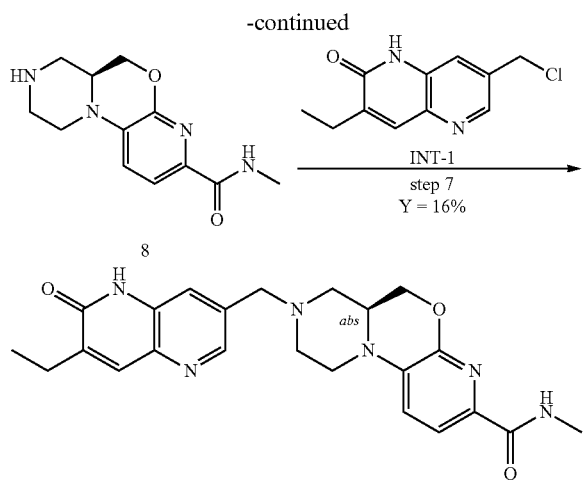

Example 22B

Step 1: Preparation of 4-benzyl 1-tert-butyl (2S)-2-(hydroxymethyl)piperazine-1,4-dicarboxylate A solution of tert-butyl (2S)-2-(hydroxymethyl)piperazine-1-carboxylate (5.00 g, 23.12 mmol, 1.00 equiv, $[a]^{26}_D$ (c=0.1, MeOH): −50.45) in DCM (100 mL) was treated with $NEt_3$ (7.02 g, 69.35 mmol, 3 equiv) for 10 min at 0° C. under nitrogen atmosphere followed by the addition of Cbz-Cl (5.92 g, 34.68 mmol, 1.50 equiv) dropwise at 0° C. The resulting mixture was stirred overnight at room temperature under nitrogen atmosphere. The reaction was monitored by LCMS. The resulting mixture was concentrated under reduced pressure. The resulting mixture was diluted with water (200 mL). The resulting mixture was extracted with EtOAc (3×200 mL). The combined organic layers were washed with brine (1×200 mL), dried over anhydrous $Na_2SO_4$. After filtration, the filtrate was concentrated under reduced pressure. The residue was purified by silica gel column chromatography to afford 4-benzyl 1-tert-butyl (2S)-2-(hydroxymethyl)piperazine-1,4-dicarboxylate (7.70 g, 95%) as a colorless oil. LC-MS: (ES+H, m/z): [M−tBu+H]$^+$=295. $^1$H NMR (400 MHz, DMSO-d6) δ 7.40-7.29 (m, 5H), 5.08 (s, 2H), 4.81 (s, 1H), 4.15-3.99 (m, 1H), 3.95 (m, 1H), 3.84 (m, 1H), 3.73 (m, 1H), 3.40 (m, 2H), 2.97 (m, 3H), 1.40 (s, 9H).

Step 2: Preparation of 4-benzyl 1-tert-butyl (2S)-2-({[3-bromo-6-(methoxycarbonyl)pyridin-2-yl]oxy}methyl)piperazine-1,4-dicarboxylate A mixture of PPh3 (11.23 g, 42.80 mmol, 6.00 equiv) and DEAD (6.21 g, 35.67 mmol, 5.00 equiv) in THF (100 mL) was stirred for 1 h at 0° C. under nitrogen atmosphere. The mixture was added to 4-benzyl 1-tert-butyl (2S)-2-(hydroxymethyl)piperazine-1,4-dicarboxylate (2.50 g, 7.13 mmol, 1.00 equiv) and methyl 5-bromo-6-hydroxypyridine-2-carboxylate (1.66 g, 7.13 mmol, 1.00 equiv) in THF (100 mL) dropwise over 10 min at 0° C. The resulting mixture was stirred for additional 2 h at room temperature. The reaction was monitored by LCMS. The resulting mixture was filtered. The filtrate was concentrated under reduced pressure. The residue was purified by silica gel column chromatography to afford 4-benzyl 1-tert-butyl (2S)-2-({[3-bromo-6-(methoxycarbonyl)pyridin-2-yl]oxy}methyl)piperazine-1,4-dicarboxylate (3.5 g, 86%) as a colorless oil. LC-MS: (ES+H, m/z): [M+H]$^+$=564.0/566.0

Step 3: Preparation of benzyl (3S)-3-({[3-bromo-6-(methoxycarbonyl)pyridin-2-yl]oxy}methyl)piperazine-1-carboxylate To a stirred mixture of 4-benzyl 1-tert-butyl (2S)-2-({[3-bromo-6-(methoxycarbonyl)pyridin-2-yl]oxy}methyl)piperazine-1,4-dicarboxylate (3.50 g, 6.20 mmol, 1.00 equiv) in DCM (100 mL) was added HCl(gas) in 1,4-dioxane (20 mL, 4M) in portions at room temperature under nitrogen atmosphere. The resulting mixture was stirred for 1 h at room temperature under nitrogen atmosphere. The reaction was monitored by LCMS. The resulting mixture was concentrated under reduced pressure. The residue was purified by trituration with hexane/diethyl ether (1/1, 3×20 mL). The precipitated solids were collected by filtration and washed with hexane (3×5 mL). The residue was basified to pH 8~9 with saturated Na2CO3 (aq.). The resulting mixture was added 200 mL water and extracted with EtOAc (3×200 mL). The combined organic layers were washed with brine (1×200 mL), dried over anhydrous $Na_2SO_4$. After filtration, the filtrate was concentrated under reduced pressure. This resulted in benzyl (3S)-3-({[3-bromo-6-(methoxycarbonyl)pyridin-2-yl]oxy}methyl)piperazine-1-carboxylate (2.1 g, 72.94%) as a light yellow oil. LC-MS: (ES+H, m/z): [M+H]$^+$=463.9/465.9. $^1$H NMR (400 MHz, DMSO-d6) δ 8.23 (d, 1H), 7.60 (d, 1H), 7.41-7.28 (m, 5H), 5.07 (s, 2H), 4.34 (dd, 1H), 4.28-4.15 (m, 1H), 4.07 (t, 1H), 3.86-3.80 (m, 4H), 3.01-2.75 (m, 4H), 2.68-2.56 (m, 2H).

Step 4: Preparation of 3-benzyl 8-methyl (S)-1,2,4a,5-tetrahydropyrazino[1,2-d]pyrido[2,3-b][1,4]oxazine-3,8(4H)-dicarboxylate To a stirred mixture of benzyl (3S)-3-({[3-bromo-6-(methoxycarbonyl)pyridin-2-yl]oxy}methyl)piperazine-1-carboxylate (2.00 g, 4.31 mmol, 1.00 equiv) and $Cs_2CO_3$ (4.21 g, 12.92 mmol, 3.00 equiv) in THF (100 mL) was added (II)/Dichloro[bis(2-(diphenylphosphino)phenyl)ether]palladium(II) (308 mg, 0.43 mmol, 0.10 equiv) at room temperature under nitrogen atmosphere. The resulting mixture was stirred for 2 h at 80° C. under nitrogen atmosphere. The reaction was monitored by LCMS. The resulting mixture was concentrated under reduced pressure. The residue was purified by flash chromatography. This resulted in 3-benzyl 8-methyl (S)-1,2,4a,5-tetrahydropyrazino[1,2-d]pyrido[2,3-b][1,4]oxazine-3,8(4H)-dicarboxylate (1.5 g, 91%) as a light yellow oil. LC-MS: (ES+H, m/z): [M+H]$^+$=384.1. $^1$H NMR (400 MHz, DMSO-d6) δ 7.63 (d, 1H), 7.42-7.28 (m, 6H), 5.13 (s, 2H), 4.52 (dd, 1H), 4.08 (q, 3H), 3.89 (d, 1H), 3.78 (s, 3H), 3.31-3.25 (m, 1H), 3.05 (s, 1H), 2.86-2.80 (m, 1H), 2.70-2.68 (m, 1H).

Step 5: Preparation of benzyl (S)-8-(methylcarbamoyl)-1,2,4a,5-tetrahydropyrazino[1,2-d]pyrido[2,3-b][1,4]oxazine-3(4H)-carboxylate A mixture of 3-benzyl 8-methyl (S)-1,2,4a,5-tetrahydropyrazino[1,2-d]pyrido[2,3-b][1,4]oxazine-3,8(4H)-dicarboxylate (500 mg, 1.30 mmol, 1.00 equiv) and methylamine water solution (5 mL, 25-30% wt in water) in MeOH (5 mL) was stirred overnight at room temperature under nitrogen atmosphere. The resulting mixture was concentrated under reduced pressure. The resulting mixture was added saturated $NH_4Cl$ (200 mL) and extracted with EtOAc (3×200 mL).

The combined organic layers were washed with brine (1×200 mL), dried over anhydrous Na$_2$SO$_4$. After filtration, the filtrate was concentrated under reduced pressure. This resulted in benzyl (S)-8-(methylcarbamoyl)-1,2,4a,5-tetrahydropyrazino[1,2-d]pyrido[2,3-b][1,4]oxazine-3(4H)-carboxylate (410 mg, 82%) as a white solid. LC-MS: (ES+H, m/z): [M+H]$^+$=383.1. $^1$H NMR (400 MHz, DMSO-d6) δ 8.19 (q, 1H), 7.54 (d, 1H), 7.41-7.30 (m, 6H), 5.13 (d, 2H), 4.52 (dd, 1H), 4.16-4.02 (m, 3H), 3.86 (d, 1H), 3.22 (td, 1H), 3.05 (s, 1H), 2.84-2.62 (m, 5H).

Step 6: Preparation of (10S)—N-methyl-8-oxa-1,6,12-triazatricyclo[8.4.0.0^{2,7}]tetradeca-2,4,6-triene-5-carboxamide To a stirred mixture of benzyl (10S)-5-(methylcarbamoyl)-8-oxa-1,6,12-triazatricyclo[8.4.0.0^{2,7}]tetradeca-2,4,6-triene-12-carboxylate (400 mg, 1.05 mmol, 1.00 equiv) in MeOH (10 mL) and HOAc (2 mL) was added Pd/C (40 mg) at room temperature under nitrogen atmosphere. The resulting mixture was stirred overnight at room temperature under hydrogen atmosphere. The reaction was monitored by LCMS. The resulting mixture was filtered, the filter cake was washed with MeOH (5×50 mL). The filtrate was concentrated under reduced pressure. This resulted in (10S)—N-methyl-8-oxa-1,6,12-triazatricyclo[8.4.0.0^{2,7}]tetradeca-2,4,6-triene-5-carboxamide (220 mg, 85%) as a white solid. LC-MS: (ES+H, m/z): [M+H]$^+$=249.0.

Step 7: Preparation of (10S)-12-[(7-ethyl-6-oxo-5H-1,5-naphthyridin-3-yl)methyl]-N-methyl-8-oxa-1,6,12-triazatricyclo[8.4.0.0^{2,7}]tetradeca-2,4,6-triene-5-carboxamide To a stirred mixture of (10S)—N-methyl-8-oxa-1,6,12-triazatricyclo[8.4.0.0^{2,7}]tetradeca-2,4,6-triene-5-carboxamide (200 mg, 0.81 mmol, 1.00 equiv) and 7-(chloromethyl)-3-ethyl-1H-1,5-naphthyridin-2-one (215 mg, 0.97 mmol, 1.20 equiv) in MeCN (10 mL) were added KI (27 mg, 0.16 mmol, 0.20 equiv) and DIEA (0.70 mL, 4.03 mmol, 5.00 equiv) at room temperature under nitrogen atmosphere. The resulting mixture was stirred for 2 h at 80° C. under nitrogen atmosphere. The reaction was monitored by LCMS. The resulting mixture was concentrated under reduced pressure. The residue was purified by flash chromatography. The resulting mixture was concentrated under reduced pressure. The residue was purified by trituration with MeOH (5 mL). This resulted in (10S)-12-[(7-ethyl-6-oxo-5H-1,5-naphthyridin-3-yl)methyl]-N-methyl-8-oxa-1,6,12-triazatricyclo[8.4.0.0^{2,7}]tetradeca-2,4,6-triene-5-carboxamide (55.6 mg, Y=16%, ee=100%) as a white solid. LC-MS: (ES+H, m/z): [M+H]$^+$=435.2. Optical Rotation: [a]$^{26}$D (c=0.5, DMF): +3.96. $^1$H NMR (400 MHz, DMSO-d6) δ 11.87 (s, 1H), 8.41 (d, 1H), 8.17 (q, 1H), 7.76 (s, 1H), 7.62 (d, 1H), 7.53 (d, 1H), 7.29 (d, 1H), 4.40 (dd, 1H), 4.05 (dd, 1H), 3.80 (d, 1H), 3.71 (d, 1H), 3.61 (d, 1H), 3.25-3.16 (m, 1H), 3.02-2.86 (m, 2H), 2.84-2.76 (m, 1H), 2.75 (d, 3H), 2.61-2.51 (m, 2H), 2.24 (td, 1H), 1.82 (t, 1H), 1.18 (t, 3H).

Example 23

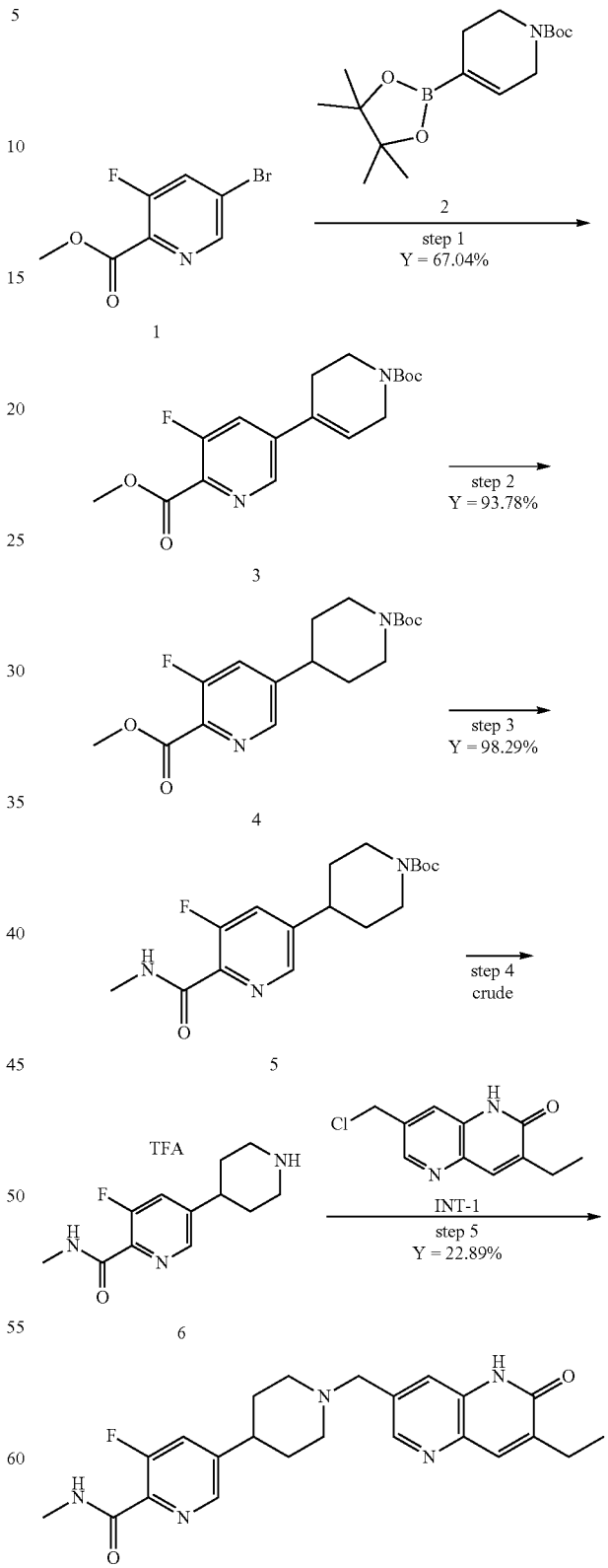

Example 23

Step 1: Preparation of 1'-tert-butyl 6-methyl 5-fluoro-3',6'-dihydro-2'H-[3,4'-bipyridine]-1',6-dicarboxylate A mixture of methyl 5-bromo-3-fluoropyridine-2-carboxylate (550 mg, 2.35 mmol, 1.00 equiv) and tert-butyl 4-(4,4,5,5-tetramethyl-1,3,2-dioxaborolan-2-yl)-3,6-dihydro-2H-pyridine-1-carboxylate (872 mg, 2.82 mmol, 1.20 equiv) and Pd(dppf)Cl$_2$ (171 mg, 0.23 mmol, 0.10 equiv) and K$_2$CO$_3$ (975 mg, 7.05 mmol, 3.00 equiv) in 1,4-dioxane (10 mL) and water (0.5 mL) was stirred for 2 h at 80° C. under nitrogen atmosphere. The reaction was monitored by LCMS. The mixture was allowed to cool down to room temperature. The resulting mixture was concentrated under reduced pressure. The residue was purified by silica gel column chromatography to afford 1'-tert-butyl 6-methyl 5-fluoro-3',6'-dihydro-2'H-[3,4'-bipyridine]-1',6-dicarboxylate (530 mg, 67.04%) as a colorless oil. LC-MS: (ES+H, m/z): [M+H]$^+$=337.2. $^1$H NMR (400 MHz, Chloroform-d) δ 8.52 (d, 1H), 7.40 (dd, 1H), 6.24 (s, 1H), 4.08 (m, 2H), 3.94 (s, 3H), 3.60 (t, 2H), 2.46 (brs, 2H), 1.42 (s, 9H).

Step 2: Preparation of methyl 5-[1-(tert-butoxycarbonyl)piperidin-4-yl]-3-fluoropyridine-2-carboxylate A solution of 1'-tert-butyl 6-methyl 5-fluoro-3',6'-dihydro-2'H-[3,4'-bipyridine]-1',6-dicarboxylate (530 mg, 1.57 mmol, 1.00 equiv) in EtOAc (10 ml) was add Pd/C (100 mg, 10% wt) at room temperature under nitrogen atmosphere. The mixture was stirred for 2 h at room temperature under hydrogen atmosphere. The reaction was monitored by LCMS. The resulting mixture was filtered, the filter cake was washed with EA (200 ml). The filtrate was concentrated under reduced pressure to afford methyl 5-[1-(tert-butoxycarbonyl)piperidin-4-yl]-3-fluoropyridine-2-carboxylate (500 mg, 93.78%) as a colorless oil. LC-MS: (ES+H, m/z): [M+H]$^+$=339.2. $^1$H NMR (400 MHz, Chloroform-d) δ 8.35 (d, 1H), 7.35-7.26 (dd, 1H), 4.35-4.09 (brs, 2H), 3.93 (s, 3H), 2.94-2.62 (m, 3H), 1.84-1.74 (m, 2H), 1.59-1.48 (m, 2H), 1.41 (s, 9H).

Step 3: Preparation of tert-butyl 4-[5-fluoro-6-(methylcarbamoyl)pyridin-3-yl]piperidine-1-carboxylate To a stirred solution of methyl 5-[1-(tert-butoxycarbonyl)piperidin-4-yl]-3-fluoropyridine-2-carboxylate (500 mg, 1.48 mmol, 1.00 equiv) in MeOH (5 ml) was added CH$_3$NH$_2$ (10 mL, 25-30% wt in water) dropwise at 0° C. under nitrogen atmosphere. The resulting mixture was stirred for additional 2 h at room temperature. The reaction was monitored by LCMS. The reaction was quenched by the addition of sat.NH$_4$Cl (50 mL) at 0° C. The aqueous layer was extracted with DCM (3×50 mL). The combined organic layers were dried over anhydrous Na$_2$SO$_4$. After filtration, the filtrate was concentrated under reduced pressure. This resulted in tert-butyl 4-[5-fluoro-6-(methylcarbamoyl)pyridin-3-yl]piperidine-1-carboxylate (490 mg, 98.29%) as a colorless oil. LC-MS: (ES+H, m/z): [M+H]$^+$=337.9. $^1$H NMR (400 MHz, DMSO-d6) δ 8.66-8.49 (m, 1H), 8.39 (d, 1H), 7.84-7.72 (m, 1H), 4.22-3.96 (m, 2H), 2.96-2.86 (m, 1H), 2.86-2.78 (m, 2H), 2.77 (d, 3H), 1.90-1.69 (m, 2H), 1.62-1.49 (m, 2H), 1.42 (s, 9H).

Step 4: Preparation of 3-fluoro-N-methyl-5-(piperidin-4-yl)pyridine-2-carboxamide, TFA Salt To a stirred solution of tert-butyl 4-[5-fluoro-6-(methylcarbamoyl)pyridin-3-yl]piperidine-1-carboxylate (460 mg, 1.36 mmol, 1.00 equiv) in DCM (10 ml) was added TFA (3 mL) dropwise at 0° C. under nitrogen atmosphere. The resulting mixture was stirred for 2 h at room temperature under nitrogen atmosphere. The reaction was monitored by LCMS. The resulting mixture was concentrated under reduced pressure. The residue was purified by trituration with hexane:ethyl ether=1:1 (2×5 mL). This resulted in 3-fluoro-N-methyl-5-(piperidin-4-yl)pyridine-2-carboxamide, TFA salt (450 mg, crude) as a colorless oil. LC-MS: (ES+H, m/z): [M+H]$^+$=238.3.

Step 5: Preparation of 5-{1-[(7-ethyl-6-oxo-5H-1,5-naphthyridin-3-yl)methyl]piperidin-4-yl}-3-fluoro-N-methylpyridine-2-carboxamide To a stirred mixture of 3-fluoro-N-methyl-5-(piperidin-4-yl)pyridine-2-carboxamide, TFA salt (200 mg, crude) and 7-(chloromethyl)-3-ethyl-1H-1,5-naphthyridin-2-one (150 mg, 0.67 mmol, 1.00 equiv) and KI (23 mg, 0.14 mmol, 0.20 equiv) in acetonitrile (5 ml) was added DIEA (435 mg, 3.37 mmol, 5.00 equiv) dropwise at room temperature under nitrogen atmosphere. The resulting mixture was stirred for 4 h at 80° C. under nitrogen atmosphere. The reaction was monitored by LCMS. The mixture was allowed to cool down to room temperature. The resulting mixture was concentrated under reduced pressure. The residue was purified by silica gel column chromatography to afford crude product (250 mg). The crude product was separated by Prep-HPLC, the pure fraction was concentrated under reduce pressure and lyophilized to afford 5-{1-[(7-ethyl-6-oxo-5H-1,5-naphthyridin-3-yl)methyl]piperidin-4-yl}-3-fluoro-N-methylpyridine-2-carboxamide (65.3 mg, 22.89%) as a white solid. LC-MS: (ES+H, m/z): [M+H]$^+$=423.95. $^1$H NMR (400 MHz, DMSO-d6) δ 11.86 (s, 1H), 8.57 (d, 1H), 8.40 (d, 2H), 7.79-7.71 (m, 2H), 7.60 (s, 1H), 3.62 (s, 2H), 2.98-2.87 (m, 2H), 2.77-2.64 (m, 4H), 2.59-2.53 (m, 2H), 2.19-2.02 (m, 2H), 1.90-1.59 (m, 4H), 1.18 (t, 3H).

Example 24

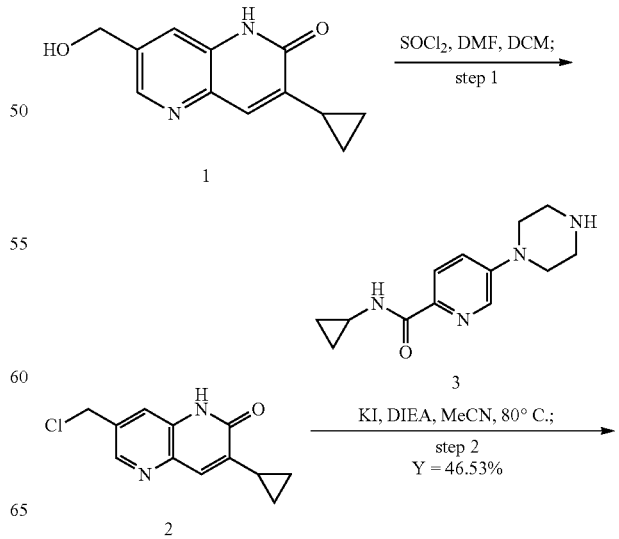

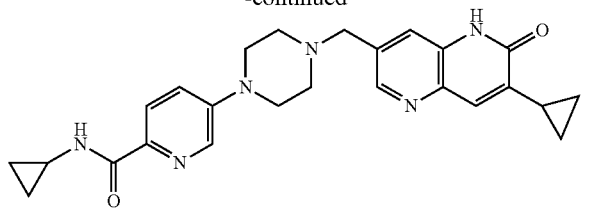

Example 24

Step 1: Preparation of 7-(chloromethyl)-3-cyclopropyl-1H-1,5-naphthyridin-2-one To a stirred mixture of 3-cyclopropyl-7-(hydroxymethyl)-1H-1,5-naphthyridin-2-one (1.00 g, 4.62 mmol, 1.00 equiv) and DMF (30 mg, 0.46 mmol, 0.10 equiv) in DCM (10 mL) were added $SOCl_2$ (3.30 g, 27.74 mmol, 6.00 equiv) dropwise at 0° C. under nitrogen atmosphere. The resulting mixture was stirred overnight at room temperature under nitrogen atmosphere. The reaction was monitored by LCMS. The resulting mixture was concentrated under reduced pressure to afford 7-(chloromethyl)-3-cyclopropyl-1H-1,5-naphthyridin-2-one (1.00 g, crude) as a yellow solid. The crude product was used in the next step directly without further purification. LC-MS: (ES+H, m/z): [M+H]⁺=235.0.

Step 2: Preparation of N-cyclopropyl-5-{4-[(7-cyclopropyl-6-oxo-5H-1,5-naphthyridin-3-yl)methyl]piperazin-1-yl}pyridine-2-carboxamide To a stirred mixture of N-cyclopropyl-5-(piperazin-1-yl)pyridine-2-carboxamide (115 mg, 0.47 mmol, 1.10 equiv) and DIEA (275 mg, 2.13 mmol, 5.00 equiv) in acetonitrile (5 mL) were added KI (14.15 mg, 0.09 mmol, 0.20 equiv) and 7-(chloromethyl)-3-cyclopropyl-1H-1,5-naphthyridin-2-one (100 mg, 0.43 mmol, 1.00 equiv) at room temperature under nitrogen atmosphere. The resulting mixture was stirred for 2 hours at 80° C. The reaction was monitored by LCMS. The mixture was allowed to cool down to room temperature. The resulting mixture was concentrated under reduced pressure. The residue was purified by silica gel column chromatography to afford N-cyclopropyl-5-{4-[(7-cyclopropyl-6-oxo-5H-1,5-naphthyridin-3-yl)methyl]piperazin-1-yl}pyridine-2-carboxamide (91.90 mg, 46.53%) as a white solid. LC-MS: (ES+H, m/z): [M+H]⁺=445.2. ¹H NMR (400 MHz, DMSO-$d_6$) δ 11.90 (s, 1H), 8.37 (dd, 2H), 8.23 (d, 1H), 7.83 (d, 1H), 7.60 (d, 1H), 7.43-7.36 (m, 2H), 3.64 (s, 2H), 3.32 (m, 4H), 2.86-2.82 (m, 1H), 2.55 (m, 4H), 2.14 (t, 1H), 1.01-0.93 (m, 2H), 0.85-0.78 (m, 2H), 0.69-0.59 (m, 4H).

Example 25

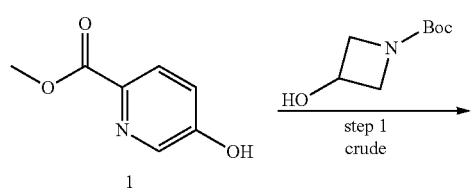

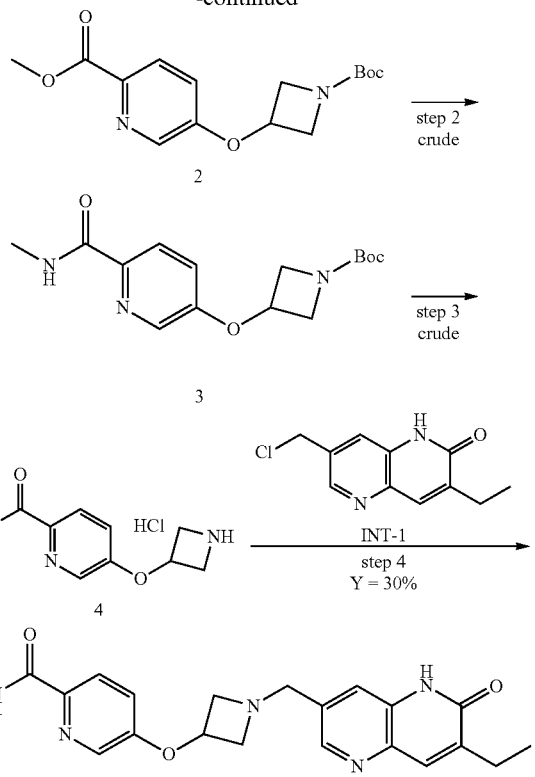

Example 25

Step 1: Preparation of methyl 5-{[1-(tert-butoxycarbonyl)azetidin-3-yl]oxy}pyridine-2-carboxylate A mixture of DEAD (5.69 g, 32.65 mmol, 5.00 equiv) and PPh3 (10.90 g, 39.18 mmol, 6.00 equiv) in THF (100 ml) was stirred for 1 h at 0° C. under nitrogen atmosphere. The mixture was added to methyl 5-hydroxypyridine-2-carboxylate (1.00 g, 6.53 mmol, 1.00 equiv) and tert-butyl 3-hydroxyazetidine-1-carboxylate (1.70 g, 9.79 mmol, 1.50 equiv) in THF (100 ml) dropwise at 0° C. under nitrogen atmosphere. The resulting mixture was stirred for additional 2 h at room temperature under nitrogen atmosphere. The reaction was monitored by LCMS. The resulting mixture was concentrated under reduced pressure. The residue was purified by silica gel column chromatography to afford methyl 5-{[1-(tert-butoxycarbonyl)azetidin-3-yl]oxy}pyridine-2-carboxylate (4.5 g, crude, contained TPPO) as a yellow solid. LC-MS: (ES+H, m/z): [M+H]⁺=309.1.

Step 2: Preparation of tert-butyl 3-{[6-(methylcarbamoyl)pyridin-3-yl]oxy}azetidine-1-carboxylate A mixture of methyl 5-{[1-(tert-butoxycarbonyl)azetidin-3-yl]oxy}pyridine-2-carboxylate (3.50 g, crude, contained TPPO) and $CH_3NH_2$ (20 mL, 25-30% wt in water) in MeOH (20 mL) was stirred for 2 h at room temperature under nitrogen atmosphere. The reaction was monitored by LCMS. The resulting mixture was concentrated under reduced pressure. The resulting mixture was added saturated $NH_4Cl$ (100 mL), and extracted with DCM (3×100 mL). The combined organic layers were washed with brine (1×100 mL), and dried over anhydrous $Na_2SO_4$. After filtration, the filtrate was concentrated under reduced pressure. This result in tert-butyl 3-{[6-(methylcarbamoyl)pyridin-3-yl]oxy}azetidine-1-carboxylate (3.3 g, crude, contained TPPO) as a yellow solid. LC-MS: (ES+H, m/z): [M+H]$^+$=308.1

Step 3: Preparation of 5-(azetidin-3-yloxy)-N-methylpyridine-2-carboxamide, HCl Salt A mixture of tert-butyl 3-{[6-(methylcarbamoyl)pyridin-3-yl]oxy}azetidine-1-carboxylate (3.30 g, crude, contained TPPO) in DCM (10 mL) was added HCl(gas) in 1,4-dioxane (10 mL, 4M in dioxane) in portions at room temperature under nitrogen atmosphere. The resulting mixture was stirred for 2 h at room temperature under nitrogen atmosphere. The reaction was monitored by LCMS. The resulting mixture was concentrated under reduced pressure. The residue was purified by trituration with EtOAc (3×20 mL). The precipitated solids were collected by filtration and concentrated under reduced pressure. This result in 5-(azetidin-3-yloxy)-N-methylpyridine-2-carboxamide, HCl salt (600 mg, crude) as a yellow solid. LC-MS: (ES+H, m/z): [M+H]$^+$=208.2.

Step 4: Preparation of 5-({1-[(7-ethyl-6-oxo-5H-1,5-naphthyridin-3-yl)methyl]azetidin-3-yl}oxy)-N-methylpyridine-2-carboxamide To a stirred mixture of 7-(chloromethyl)-3-ethyl-1H-1,5-naphthyridin-2-one (200 mg, 0.90 mmol, 1.00 equiv) and 5-(azetidin-3-yloxy)-N-methylpyridine-2-carboxamide, HCl salt (280 mg, crude) in MeCN (5 mL) were added KI (30 mg, 0.18 mmol, 0.20 equiv) and DIEA (580 mg, 4.49 mmol, 5.00 equiv) at room temperature under nitrogen atmosphere. The resulting mixture was stirred overnight at 80° C. under nitrogen atmosphere. The mixture was allowed to cool down to room temperature. The reaction was monitored by LCMS. The resulting mixture was concentrated under reduced pressure. The residue was purified by silica gel column chromatography. The pure fractions were concentrated and lyophilized to afford 5-({1-[(7-ethyl-6-oxo-5H-1,5-naphthyridin-3-yl)methyl]azetidin-3-yl}oxy)-N-methylpyridine-2-carboxamide (108 mg, 30%) as a white solid. LC-MS: (ES+H, m/z): [M+H]$^+$=394.20. $^1$H NMR (400 MHz, DMSO-d6) δ 11.85 (s, 1H), 8.56 (q, 1H), 8.37 (d, 1H), 8.23 (dd, 1H), 7.95 (dd, 1H), 7.73 (q, 1H), 7.57 (dd, 1H), 7.41 (dd, 1H), 5.02 (p, 1H), 3.78 (dt, 4H), 3.24-3.09 (m, 2H), 2.79 (d, 3H), 2.55 (dd, 2H), 1.18 (t, 3H).

Example 26

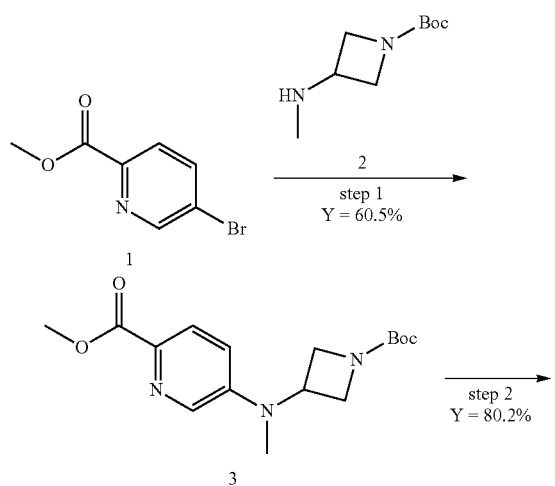

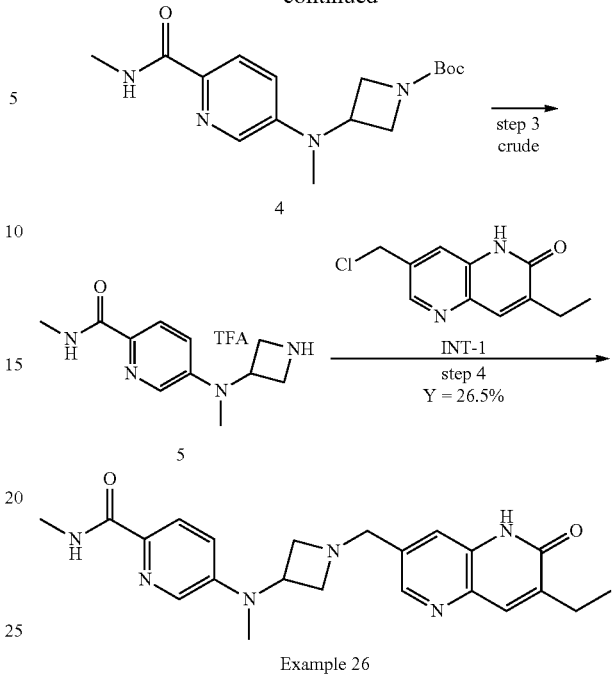

Example 26

Step 1: Preparation of methyl 5-{[1-(tert-butoxycarbonyl) azetidin-3-yl] (methyl)amino} pyridine-2-carboxylate To a solution of methyl 5-bromopyridine-2-carboxylate (2.00 g, 9.26 mmol, 1.00 equiv) and tert-butyl 3-(methylamino) azetidine-1-carboxylate (2.07 g, 11.11 mmol, 1.20 equiv) in 1,4-dioxane (20 mL) were added Cs$_2$CO$_3$ (9.05 g, 27.77 mmol, 3.00 equiv) and RuPhos Palladacycle Gen.3 (0.77 g, 0.93 mmol, 0.10 equiv) at room temperature. The resulting mixture was stirred overnight at 120° C. under nitrogen atmosphere. The reaction was monitored by LCMS. After cooled to rt, the resulting mixture was diluted with water (100 mL). The resulting mixture was extracted with EtOAc (3×100 mL). The combined organic layers were washed with brine (1×100 mL), dried over anhydrous Na$_2$SO$_4$. After filtration, the filtrate was concentrated under reduced pressure. The residue was purified by flash chromatography. This resulted in methyl 5-{[1-(tert-butoxycarbonyl) azetidin-3-yl] (methyl) amino} pyridine-2-carboxylate (1.8 g, 60.50%) as a brown oil. LC-MS: (ES+H, m/z): [M+H]$^+$=322.1. $^1$H NMR (300 MHz, DMSO-d6) δ 8.22 (d, 1H), 7.87 (d, 1H), 7.18 (dd, 1H), 4.85-4.76 (m, 1H), 4.18 (t, 2H), 3.93 (dd, 2H), 3.81 (s, 3H), 3.03 (s, 3H), 1.40 (s, 9H).

Step 2: Preparation of tert-butyl 3-{methyl[6-(methylcarbamoyl)pyridin-3-yl]amino}azetidine-1-carboxylate A solution of methyl 5-{[1-(tert-butoxycarbonyl) azetidin-3-yl] (methyl)amino} pyridine-2-carboxylate (1.00 g, 3.11 mmol, 1.00 equiv) and CH$_3$NH$_2$ (5 mL, 25-30% wt in water) in MeOH (5 mL) was stirred for 2 h at room temperature under nitrogen atmosphere. The reaction was monitored by LCMS. The resulting mixture was concentrated under reduced pressure. The resulting mixture was added saturated NH$_4$Cl (100 mL) and extracted with DCM (3×100 mL). The combined organic layers were washed with brine (1×100 mL) and dried over anhydrous Na$_2$SO$_4$. After filtration, the filtrate was concentrated under reduced pressure. This result in tert-butyl 3-{methyl[6-(methylcarbamoyl)pyridin-3-yl]amino}azetidine-1-carboxylate (800 mg, 80.2%) as a brown oil.

LC-MS: (ES+H, m/z): [M+H]$^+$=321.2. $^1$H NMR (300 MHz, DMSO-d6) δ 8.39 (d, 1H), 8.10 (d, 1H), 7.82 (d, 1H), 7.22 (dd, 1H), 4.77-4.68 (m, 1H), 4.43-4.20 (m, 2H), 3.94-3.89 (m, 2H), 3.00 (s, 3H), 2.78 (d, 3H), 1.40 (s, 9H).

Step 3: Preparation of 5-[azetidin-3-yl(methyl)amino]-N-methylpyridine-2-carboxamide, TFA Salt A solution of tert-butyl 3-{methyl[6-(methylcarbamoyl)pyridin-3-yl]amino}azetidine-1-carboxylate (800 mg, 2.50 mmol, 1.00 equiv) and TFA (10 mL) in DCM (10 mL) was stirred for 2 h at room temperature under nitrogen atmosphere. The reaction was monitored by LCMS. The resulting mixture was concentrated under reduced pressure. This resulted in 5-[azetidin-3-yl(methyl)amino]-N-methylpyridine-2-carboxamide, TFA salt (2 g, crude) as a brown oil. LC-MS: (ES+H, m/z): [M+H]$^+$=221.2

Step 4: Preparation of 5-({1-[(7-ethyl-6-oxo-5H-1,5-naphthyridin-3-yl) methyl] azetidin-3-yl}(methyl)amino)-N-methylpyridine-2-carboxamide To a stirred solution of 5-[azetidin-3-yl(methyl)amino]-N-methylpyridine-2-carboxamide, TFA salt (400 mg, crude) and DIEA (1.56 mL, 8.98 mmol, 10.00 equiv) in MeCN (10 mL) were added 7-(chloromethyl)-3-ethyl-1H-1,5-naphthyridin-2-one (200 mg, 0.90 mmol, 1.00 equiv) and KI (30 mg, 0.18 mmol, 0.20 equiv) at room temperature. The resulting mixture was stirred for 2 h at 50° C. under nitrogen atmosphere. The reaction was monitored by LCMS. The resulting mixture was diluted with water (100 mL). The resulting mixture was extracted with EtOAc (3×100 mL). The combined organic layers were washed with brine (1×100 mL), dried over anhydrous Na$_2$SO$_4$. After filtration, the filtrate was concentrated under reduced pressure. The crude product (200 mg) was purified by Prep-HPLC, the pure fraction was concentrated then lyophilized to afford 5-({1-[(7-ethyl-6-oxo-5H-1,5-naphthyridin-3-yl) methyl] azetidin-3-yl} (methyl)amino)-N-methylpyridine-2-carboxamide (97.0 mg, 26.57%) as a white solid. LC-MS: (ES+H, m/z): [M+H]$^+$=407.3. 1H NMR (300 MHz, DMSO-d6) δ 11.86 (s, 1H), 8.41-8.32 (m, 2H), 8.04 (d, 1H), 7.80 (d, 1H), 7.74 (s, 1H), 7.58 (d, 1H), 7.16 (dd, 1H), 4.45-4.29 (m, 1H), 3.78-3.63 (m, 4H), 3.13 (t, 2H), 2.98 (s, 3H), 2.78 (d, 3H), 2.60-2.52 (m, 2H), 1.20 (t, 3H).

Example 82

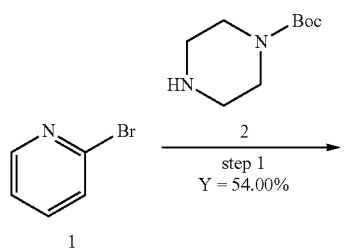

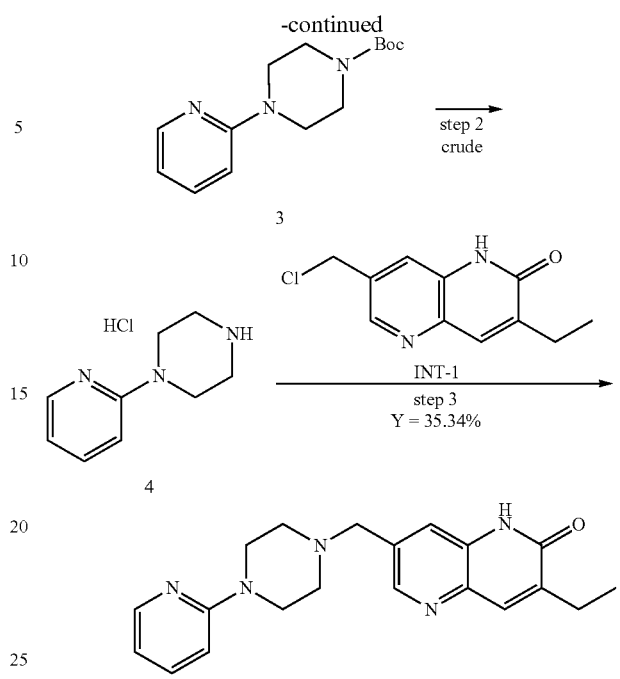

Example 82

Step 1: Preparation of tert-butyl 4-(pyridin-2-yl)piperazine-1-carboxylate

A mixture of 2-bromopyridine (500 mg, 3.16 mmol, 1.00 equiv), tert-butyl piperazine-1-carboxylate (589 mg, 3.16 mmol, 1.00 equiv), Cs$_2$CO$_3$ (2.06 g, 6.33 mmol, 2.00 equiv) and RuPhos Palladacycle Gen.3 (132 mg, 0.16 mmol, 0.05 equiv) in 1,4-dioxane (10 mL) was stirred for 2 h at 80° C. under nitrogen atmosphere. The reaction was monitored by LCMS. The mixture was allowed to cool down to room temperature. The resulting mixture was filtered, the filter cake was washed with CH$_2$Cl$_2$ (3×10 mL). The filtrate was concentrated under reduced pressure. The residue was purified by silica gel column chromatography to afford tert-butyl 4-(pyridin-2-yl)piperazine-1-carboxylate (450 mg, 54.00%) as a yellow oil. LC-MS: (ES+H, m/z): [M+H]$^+$=264.1. 1H NMR (300 MHz, DMSO-d$_6$) δ 8.13-8.11 (m, 1H), 7.58-7.52 (m, 1H), 6.83 (d, 1H), 6.74-6.61 (m, 1H), 3.50-3.44 (m, 8H), 1.43 (s, 9H).

Step 2: Preparation of Pyridinylpiperazine, HCl Salt

A mixture of tert-butyl 4-(pyridin-2-yl)piperazine-1-carboxylate (450 mg, 1.71 mmol, 1.00 equiv) in HCl(gas) in 1,4-dioxane (5 mL, 4M) was stirred for 30 min at room temperature. The reaction was monitored by LCMS. The resulting mixture was concentrated under vacuum to afford pyridinylpiperazine, HCl salt (300 mg, crude) as a yellow solid. LC-MS: (ES+H, m/z): [M+H]$^+$=164.25.

Step 3: Preparation of 3-ethyl-7-{[4-(pyridin-2-yl)piperazin-1-yl]methyl}-1H-1,5-naphthyridin-2-one To a stirred mixture of pyridinylpiperazine, HCl salt (150 mg, crude), 7-(chloromethyl)-3-ethyl-1H-1,5-naphthyridin-2-one (150 mg, 0.67 mmol, 1.00 equiv) and KI (22 mg, 0.14 mmol, 0.20 equiv) in ACN (5 mL) was added DIEA (261 mg, 2.02 mmol, 3.00 equiv) dropwise at room temperature under nitrogen atmosphere. The resulting mixture was stirred for 1 h at 80° C. The reaction was monitored by LCMS. The mixture was allowed to cool down to room temperature. The resulting mixture was diluted with water (20 mL). The aqueous layer was extracted with CH$_2$Cl$_2$ (3×20 mL). The combined organic layers were concentrated under reduced pressure. The crude product was purified by Prep-HPLC, the pure fraction was concentrated under reduced pressure then lyophilized to afford 3-ethyl-7-{[4-(pyridin-2-yl)piperazin-1-yl]methyl}-1H-1,5-naphthyridin-2-one (83.2 mg, 35.34%) as a white solid. LC-MS: (ES+H, m/z): [M+H]$^+$=350.20. $^1$H NMR (300 MHz, DMSO-d$_6$) δ 11.85 (s, 1H), 8.40 (d, 1H), 8.12-8.08 (m, 1H), 7.75 (s, 1H), 7.63 (d, 1H), 7.58-7.46 (m, 1H), 6.81 (d, 1H), 6.71-6.59 (m, 1H), 3.63 (s, 2H), 3.49 (t, 4H), 2.60-2.52 (m, 6H), 1.19 (t, 3H).

The following examples were made using similar procedures shown for example 82.

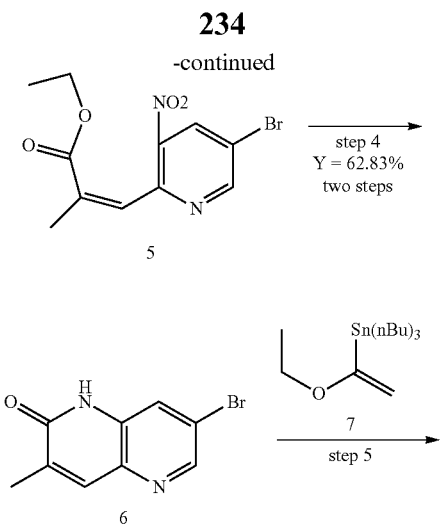

| Ex | NMR | LCMS (ESI) m/z |
|---|---|---|
| 132 | $^1$H NMR (300 MHz, DMSO-d6) δ 11.85 (s, 1H), 8.41 (s, 1H), 7.80-7.74 (m, 2H), 7.62 (s, 1H), 6.98-6.90 (m, 2H), 3.67 (s, 2H), 3.21 (s, 4H), 2.59-2.51 (m, 6H), 1.19 (t, 3H). $^{19}$F NMR (282 MHz, DMSO) δ -101.87. | [M + H]$^+$ = 392.15 |
| 136 | $^1$H NMR (300 MHz, DMSO-d6) δ 11.87 (s, 1H), 8.36 (d, 1H), 7.60 (d, 1H), 7.41 (s, 1H), 6.32 (d, 1H), 3.62 (s, 2H), 3.33 (s, 3H), 2.92 (t, 4H), 2.52-2.49 (m, 4H), 2.17-2.11 (m, 1H), 2.07 (s, 3H), 1.01-0.91 (m, 2H), 0.86-0.79 (m, 2H). | [M + H]$^+$ = 379.10 |

Examples 124 and 125

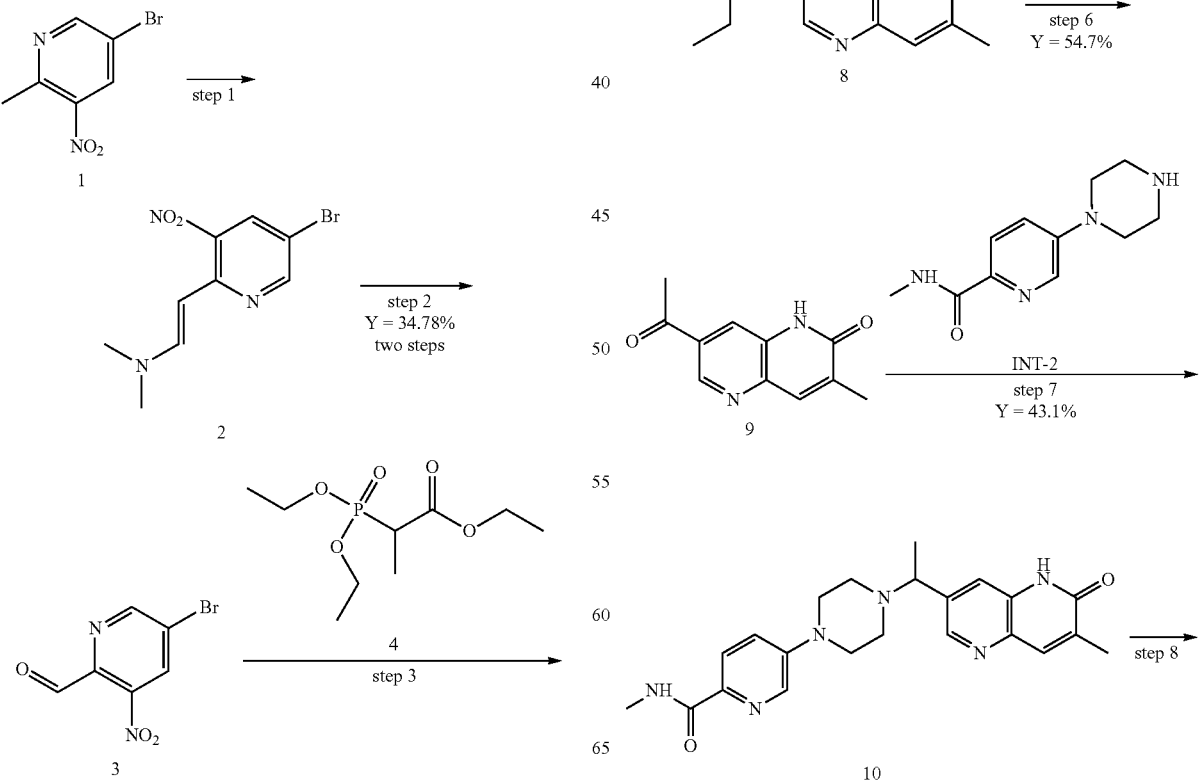

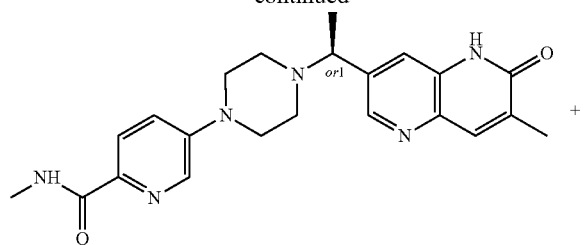

Example 124

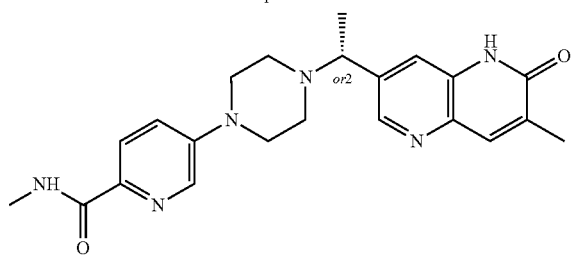

Example 125

Step 1: Preparation of (E)-2-(5-bromo-3-nitropyridin-2-yl)-N,N-dimethylethen-1-amine To a stirred solution of 5-bromo-2-methyl-3-nitropyridine (200 g, 921.57 mmol, 1.00 equiv) in NMP (1 L) was added DMF-DMA (219.6 g, 1843.13 mmol, 2.00 equiv) at room temperature. The resulting mixture was stirred overnight at 85° C. The reaction was monitored by TLC. The mixture was allowed to cool down to room temperature. The resulting mixture was concentrated under reduced pressure. The crude resulting mixture was used in the next step directly without further purification.

Step 2: Preparation of 5-bromo-3-nitropicolinaldehyde

A solution of NaIO4 (540 g, 2.52 mol, 2.50 equiv) in EtOH (1 L) and $H_2O$ (1.85 L) was treated for 30 min at room temperature under nitrogen atmosphere. The resulting mixture was added [(E)-2-(5-bromo-3-nitropyridin-2-yl)ethenyl]dimethylamine (200 g, 735.018 mmol, 1 equiv) in NMP (1 L) dropwise at room temperature. The resulting mixture was stirred overnight at room temperature under nitrogen atmosphere. The reaction was monitored by TLC. The resulting mixture was filtered; the filter cake was washed with EtOAc (3×1 L). The resulting mixture was diluted with water (5 L). The resulting mixture was extracted with EtOAc (3×2 L). The combined organic layers were washed with brine (5×5 L). After filtration, the filtrate was concentrated under reduced pressure. The residue was purified by silica gel column chromatography, the pure fraction was concentrated under reduced pressure to afford crude product as a yellow solid. The residue was purified by trituration with hexane (1.5 L). The precipitated solids were collected by filtration and washed with hexane (3×100 mL). This resulted in 5-bromo-3-nitropyridine-2-carbaldehyde (80 g, 47.12%, two steps) as a yellow solid. LC-MS: (ES+H, m/z): [M+H]$^+$=229.9/231.90. $^1$H NMR (300 MHz, DMSO-d6) δ 10.08 (d, 1H), 9.23 (d, 1H), 8.95 (d, 1H).

Step 3: Preparation of ethyl (Z)-3-(5-bromo-3-nitropyridin-2-yl)-2-methylacrylate A solution of LiCl (23.49 g, 554.10 mmol, 1.60 equiv) in Toluene (350 mL) and Pyridine (50 mL) was stirred for 1 h at 50° C. under nitrogen atmosphere. The mixture was allowed to cool down to room temperature. To the above mixture was added TEA (38.55 g, 380.94 mmol, 1.10 equiv). The resulting mixture was stirred for additional 15 min at 50° C. To the above mixture was added 5-bromo-3-nitropyridine-2-carbaldehyde (80 g, 346.31 mmol, 1.00 equiv) and ethyl 2-(diethoxyphosphoryl)propanoate (123.75 g, 519.47 mmol, 1.50 equiv) in Toluene (200 ml) dropwise over 2 h at 50° C. The resulting mixture was stirred for additional 30 min at 50° C. The reaction was monitored by LCMS. The mixture was allowed to cool down to room temperature. The resulting mixture was diluted with HCl (0.6N, 600 mL). The resulting mixture was extracted with EtOAc (3×500 mL). The combined organic layers were washed with brine (1×500 mL), dried over anhydrous $Na_2SO_4$. After filtration, the filtrate was concentrated under reduced pressure. The crude resulting mixture was used in the next step directly without further purification. LC-MS: (ES+H, m/z): [M+H]$^+$=315.0/317.0.

Step 4: Preparation of 7-bromo-3-methyl-1,5-naphthyridin-2(1H)-one

To a stirred solution of Fe (70.89 g, 1269.34 mmol, 5.00 equiv) in AcOH (500 mL) was added ethyl (2E)-3-(5-bromo-3-nitropyridin-2-yl)-2-methylprop-2-enoate (55 g, 174.54 mmol, 1.00 equiv, crude) dropwise at 80° C. under nitrogen atmosphere. The resulting mixture was stirred for additional 30 min at 75° C. The reaction was monitored by LCMS. The resulting mixture was filtered at 75° C., and the filter cake was washed with AcOH (3×200 mL). The filtrate was concentrated under reduced pressure. The resulting mixture was diluted with ice/water (800 mL). The precipitated solids were collected by filtration and washed with water (3×100 mL). The residue was purified by trituration with MTBE (500 mL). The precipitated solids were collected by filtration and washed with MTBE (3×100 mL). This resulted in 7-bromo-3-methyl-1H-1,5-naphthyridin-2-one (26 g, 62.83%, two steps) as a brown solid. LC-MS: (ES+H, m/z): [M+H]$^+$=238.85/240.85. $^1$H NMR (300 MHz, DMSO-d6) δ 11.94 (s, 1H), 8.50 (d, 1H), 7.81 (d, 1H), 7.79 (s, 1H), 2.12 (s, 3H).

Step 5: Preparation of 7-(1-ethoxyvinyl)-3-methyl-1,5-naphthyridin-2(1H)-one

To a stirred mixture of 7-bromo-3-methyl-1H-1,5-naphthyridin-2-one (3.00 g, 12.54 mmol, 1.00 equiv) and tributyl (1-ethoxyethenyl)stannane (13.60 g, 37.64 mmol, 3.00 equiv) in 1,4-dioxane (20 mL) were added Pd(PPh$_3$)$_2$Cl$_2$ (0.44 g, 0.62 mmol, 0.05 equiv) at room temperature. The resulting mixture was stirred for 2 h at 100° C. under nitrogen atmosphere. The reaction was monitored by LCMS. Desired product could be detected by LCMS. The resulting mixture was used in the next step directly without further purification. LC-MS: (ES+H, m/z): [M+H]$^+$=231.1

Step 6: Preparation of 7-acetyl-3-methyl-1,5-naphthyridin-2(1H)-one

To the resulting mixture from last step was allowed to cool down to room temperature and added conc. HCl (4 mL) dropwise at ice-bath. The resulting mixture was stirred for 1 h at room temperature. The reaction was monitored by LCMS. The mixture was basified to pH 8 with saturated NaHCO$_3$(aq.). The resulting mixture was diluted with water (100 mL). The resulting mixture was extracted with CH$_2$Cl$_2$ (3×200 mL). The combined organic layers were washed with brine (1×300 mL), dried over anhydrous Na$_2$SO$_4$. After filtration, the filtrate was concentrated under reduced pressure. The residue was purified by silica gel column chromatography to afford 7-acetyl-3-methyl-1,5-naphthyridin-2 (1H)-one (1.39 g, 54.7% over two steps) as a yellow solid. LC-MS: (ES+H, m/z): [M+H]$^+$=203.2.

Step 7: Preparation of N-methyl-5-{4-[1-(7-methyl-6-oxo-5H-1,5-naphthyridin-3-yl)ethyl]piperazin-1-yl}pyridine-2-carboxamide A mixture of N-methyl-5-(piperazin-1-yl)pyridine-2-carboxamide (743 mg, 2.23 mmol, 1.50 equiv) and 7-acetyl-3-methyl-1H-1,5-naphthyridin-2-one (300 mg, 1.48 mmol, 1.00 equiv) in DCM (2 mL) was stirred for 30 min at room temperature under nitrogen atmosphere. The resulting mixture was concentrated under reduced pressure. To the above mixture was added tetrakis(propan-2-yloxy)titanium (633 mg, 2.23 mmol, 1.5 equiv). The resulting mixture was stirred for additional 4 h at 80° C. The residue was dissolved in EtOH (2 mL). To the above mixture was added NaBH$_3$CN (187 mg, 2.97 mmol, 2.00 equiv) in portions at room temperature. The resulting mixture was stirred for 4 h at 80° C. under nitrogen atmosphere. The reaction was monitored by LCMS. The reaction was quenched by the addition of water (5 mL) at room temperature. The resulting mixture was filtered, the filter cake was washed with MeOH/DCM=1:1 (3×50 mL). The filtrate was concentrated under reduced pressure. The residue was purified by silica gel column chromatography to afford N-methyl-5-{4-[1-(7-methyl-6-oxo-5H-1,5-naphthyridin-3-yl)ethyl]piperazin-1-yl}pyridine-2-carboxamide (260 mg, 43.1%) as a white solid. LC-MS: (ES+H, m/z): [M+H]$^+$=407.3.

Step 8: Preparation of rel-N-methyl-5-{4-[(1R)-1-(7-methyl-6-oxo-5H-1,5-naphthyridin-3-yl)ethyl] piperazin-1-yl}pyridine-2-carboxamide and rel-N-methyl-5-{4-[(1R)-1-(7-methyl-6-oxo-5H-1,5-naphthyridin-3-yl)ethyl]piperazin-1-yl}pyridine-2-carboxamide The racemate N-methyl-5-{4-[1-(7-methyl-6-oxo-5H-1,5-naphthyridin-3-yl)ethyl]piperazin-1-yl}pyridine-2-carboxamide (240 mg) was separated by Prep-Chiral HPLC to afford rel-N-methyl-5-{4-[(1R)-1-(7-methyl-6-oxo-5H-1,5-naphthyridin-3-yl)ethyl]piperazin-1-yl}pyridine-2-carboxamide (Example 124, 93.9 mg, ee=100%) and rel-N-methyl-5-{4-[(1R)-1-(7-methyl-6-oxo-5H-1,5-naphthyridin-3-yl) ethyl]piperazin-1-yl}pyridine-2-carboxamide (Example 125, 66.0 mg, ee=100%).

Example 124: LC-MS: (ES+H, m/z): [M+H]$^+$=407.10. $^1$H NMR (300 MHz, DMSO-d$_6$) δ 11.84 (s, 1H), 8.42 (d, 2H), 8.25 (d, 1H), 7.82 (d, 2H), 7.62 (d, 1H), 7.37 (dd, 1H), 3.65 (d, 1H), 3.33-3.28 (m, 4H), 2.78 (d, 3H), 2.64-2.57 (m, 2H), 2.50-2.43 (m, 2H), 2.14 (d, 3H), 1.38 (d, 3H).

Example 125: LC-MS: (ES+H, m/z): [M+H]$^+$=407.25. $^1$H NMR (300 MHz, DMSO-d$_6$) δ 11.84 (s, 1H), 8.41 (d, 2H), 8.24 (d, 1H), 7.82 (d, 2H), 7.62 (s, 1H), 7.37 (dd, 1H), 3.65 (d, 1H), 3.34-3.31 (m, 4H), 2.78 (d, 3H), 2.67-2.57 (m, 2H), 2.49-2.41 (m, 2H), 2.14 (s, 3H), 1.37 (d, 3H).

The following examples were made using similar procedures shown for example 124 and 125.

| Ex | NMR | LCMS (ESI) m/z |
|---|---|---|
| 121 | $^1$H NMR (300 MHz, DMSO-d6) δ 11.90 (s, 1H), 8.44 (s, 1H), 8.36 (d, 1H), 8.18 (s, 1H), 7.82 (d, 2H), 7.65 (s, 1H), 7.32-7.29 (m, 1H), 4.14 (s, 1H), 3.65-3.59 (m, 2H), 3.13-3.10 (m, 2H), 2.78 (d, 3H), 2.62-2.58 (m, 1H), 2.28-2.14 (m, 5H), 1.37 (d, 3H), 1.08 (d, 3H). | [M + H]+ = 421.20 |
| 122 | $^1$H NMR (300 MHz, DMSO-d6) δ 11.85 (s, 1H), 8.47 (s, 1H), 8.36 (d, 1H), 8.18 (s, 1H), 7.83-7.80 (m, 2H), 7.67 (s, 1H), 7.33-7.29 (m, 1H), 4.24 (s, 1H), 3.68-3.66 (d, 1H), 3.52 (d, 1H), 3.04-2.97 (m, 1H), 2.88-2.84 (m, 5H), 2.37-2.34 (m, 1H), 2.21-2.14 (m, 4H), 1.36 (d, 3H), 1.17 (d, 3H). | [M + H]$^+$ = 421.15 |
| 126 | $^1$H NMR (400 MHz, DMSO-d6) δ 11.86 (s, 1H), 8.49 (d, 1H), 8.40 (d, 1H), 8.27 (d, 1H), 7.87 (d, 2H), 7.66 (d, 1H), 7.43 (dd, 1H), 3.71 (q, 1H), 3.38 (s, 4H), 2.90-2.87 (m, 1H), 2.67-2.64 (m, 2H), 2.56-2.51 (m, 2H), 2.19 (s, 3H), 1.43 (d, 3H), 0.74-0.68 (m, 4H). | [M + H]$^+$ = 433.25 |
| 127 | $^1$H NMR (400 MHz, DMSO-d6) δ 11.89 (s, 1H), 8.49 (d, 1H), 8.40 (d, 1H), 8.26 (d, 1H), 7.87 (d, 2H), 7.66 (d, 1H), 7.43 (q, 1H), 3.70 (q, 1H), 3.36 (d, 4H), 2.93-2.86 (m, 1H), 2.67-2.64 (m, 2H), 2.56-2.51 (m, 2H), 2.19 (d, 3H), 1.43 (d, 3H), 0.77-0.62 (m, 4H). | [M + H]$^+$ = 433.10 |

Example 128

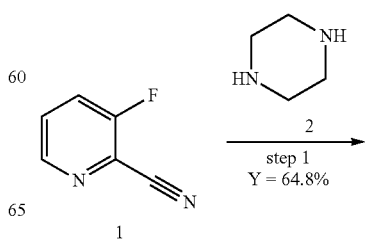

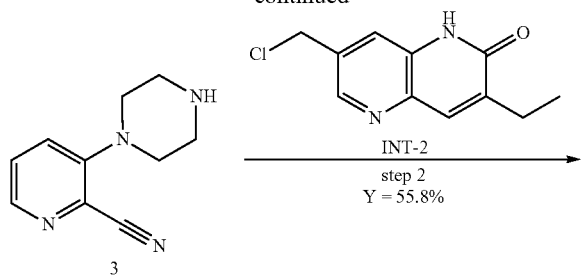

INT-2
step 2
Y = 55.8%

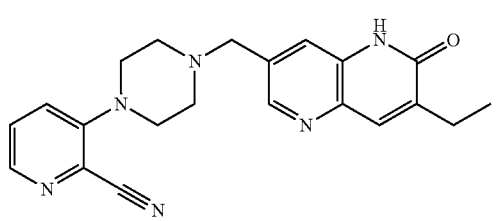

Example 128

Step 2: Preparation of 3-{4-[(7-ethyl-6-oxo-5H-1,5-naphthyridin-3-yl)methyl]piperazin-1-yl}pyridine-2-carbonitrile To a stirred solution of 3-(piperazin-1-yl)pyridine-2-carbonitrile (150 mg, 0.79 mmol, 1.00 equiv) and 7-(chloromethyl)-3-ethyl-1H-1,5-naphthyridin-2-one (266 mg, 1.19 mmol, 1.50 equiv) in MeCN (6 mL) were added DIEA (309 mg, 2.39 mmol, 3.00 equiv) and KI (26 mg, 0.15 mmol, 0.20 equiv) in portions at room temperature. The resulting mixture was stirred for 2 h at 80° C. under nitrogen atmosphere. The reaction was monitored by LCMS. The mixture was allowed to cool down to room temperature. The resulting mixture was filtered, the filter cake was washed with $CH_2Cl_2$/MeOH (10:1, 200 mL). The filtrate was concentrated under reduced pressure. The crude product (400 mg) was purified by HP-FLASH, the pure fraction was concentrated under vacuum then lyophilized to afford 3-{4-[(7-ethyl-6-oxo-5H-1,5-naphthyridin-3-yl)methyl]piperazin-1-yl}pyridine-2-carbonitrile (166.5 mg, Y=55.8%) as a white solid. LC-MS: (ES+H, m/z): $[M+H]^+$=375.25. $^1$H NMR (400 MHz, DMSO-d6) δ 11.86 (s, 1H), 8.41 (d, 1H), 8.28 (dd, 1H), 7.75 (s, 1H), 7.68-7.59 (m, 3H), 3.68 (s, 2H), 3.23 (t, 4H), 2.61 (t, 4H), 2.57-2.52 (m, 2H), 1.19 (t, 3H).

The following examples were made using similar procedures shown for example 128.

| Ex | NMR | LCMS (ESI) m/z |
|---|---|---|
| 83 | $^1$H NMR (300 MHz, DMSO-d6) δ 11.86 (s, 1H), 8.40 (d, 1H), 8.21 (d, 1H), 7.75 (s, 1H), 7.65-7.53 (m, 2H), 6.81 (d, 1H), 4.09 (s, 1H), 3.63 (s, 2H), 3.59-3.50 (m, 4H), 2.60-2.51(m, 3H), 2.49-2.43 (m, 3H), 1.18 (t, 3H). | $[M + H]^+$ = 374.05. |
| 106 | $^1$H NMR (300 MHz, DMSO-d6) δ 11.86 (s, 1H), 8.49 (s, 1H), 8.40 (d, 1H), 8.18 (d, 1H), 7.75 (s, 1H), 7.63 (d, 1H), 6.83 (dd, 1H), 3.62 (d, 6H), 2.61-2.43 (m, 6H), 1.19 (t, 3H). | $[M + H]^+$ = 351.25. |
| 118 | $^1$H NMR (400 MHz, DMSO-d6) δ 11.85 (s, 1H), 8.58 (s, 1H), 8.40-8.38 (m, 2H), 7.75 (s, 1H), 7.61 (s, 1H), 7.02 (d, 1H), 3.66 (s, 2H), 3.52 (t, 4H), 2.56-2.51 (m, 6H), 1.18 (t, 3H). | $[M + H]^+$ = 375.05 |
| 129 | $^1$H NMR (400 MHz, DMSO-d$_6$) δ 11.89 (s, 1H), 8.39 (d, 1H), 8.28 (dd, 1H), 7.67 (dd, 1H), 7.63-7.57 (m, 2H), 7.42 (s, 1H), 3.66 (s, 2H), 3.28-3.17 (m, 4H), 2.66-2.54 (m, 4H), 2.21-2.09 (m, 1H), 0.97 (dt, 2H), 0.83 (dt, 2H). | $[M + H]^+$ = 387.20. |
| 130 | $^1$H NMR (300 MHz, DMSO-d6) δ 11.87 (s, 1H), 8.42 (s, 1H), 7.76 (s, 1H), 7.74-7.67 (m, 1H) 7.63 (s, 1H), 7.61-7.55 (m, 1H), 7.26-7.14 (m, 1H), 7.15-7.00 (m, 1H), 3.68 (s, 2H), 3.25-3.10 (m, 4H), 2.70-2.58 (m, 4H), 2.58-2.53 (m, 2H), 1.19 (t, 3H). | $[M + H]^+$ = 374.10 |
| 131 | $^1$H NMR (400 MHz, DMSO-d6) δ 11.87 (s, 1H), 8.40 (d, 1H), 8.27 (dd, 1H), 7.83 (s, 1H), 7.71-7.55 (m, 3H), 3.67 (s, 2H), 3.29-3.16 (m, 4H), 2.66-2.55 (m, 4H), 2.14 (s, 3H). | $[M + H]^+$ = 361.05 |

Step 1: Preparation of 3-(piperazin-1-yl)pyridine-2-carbonitrile

A solution of 3-fluoropyridine-2-carbonitrile (2.00 g, 16.38 mmol, 1.00 equiv) and piperazine (4.50 g, 52.24 mmol, 3.20 equiv) in DMSO (20 mL) was stirred overnight at 50° C. under nitrogen atmosphere. The reaction was monitored by LCMS. The mixture was allowed to cool down to room temperature. The resulting mixture was diluted with brine (300 mL). The resulting mixture was extracted with EtOAc (3×500 mL). The combined organic layers were washed with brine (500 mL), dried over anhydrous $Na_2SO_4$. After filtration, the filtrate was concentrated under reduced pressure to afford 3-(piperazin-1-yl)pyridine-2-carbonitrile (2 g, Y=64.8%) as a yellow solid. LC-MS: (ES+H, m/z): $[M+H]^+$=189.00. $^1$H NMR (300 MHz, DMSO-d6) δ 8.26 (dd, 1H), 7.67-7.56 (m, 2H), 3.16-3.09 (m, 4H), 2.92-2.84 (m, 4H).

Example 138

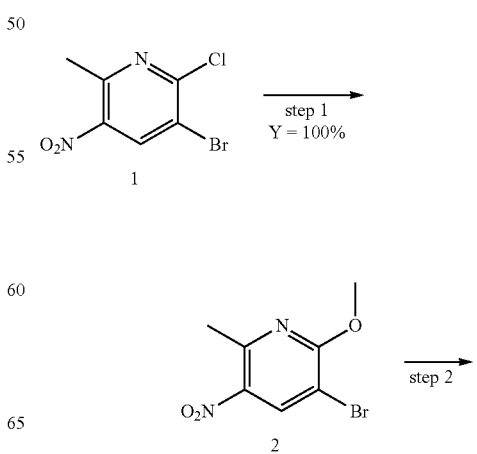

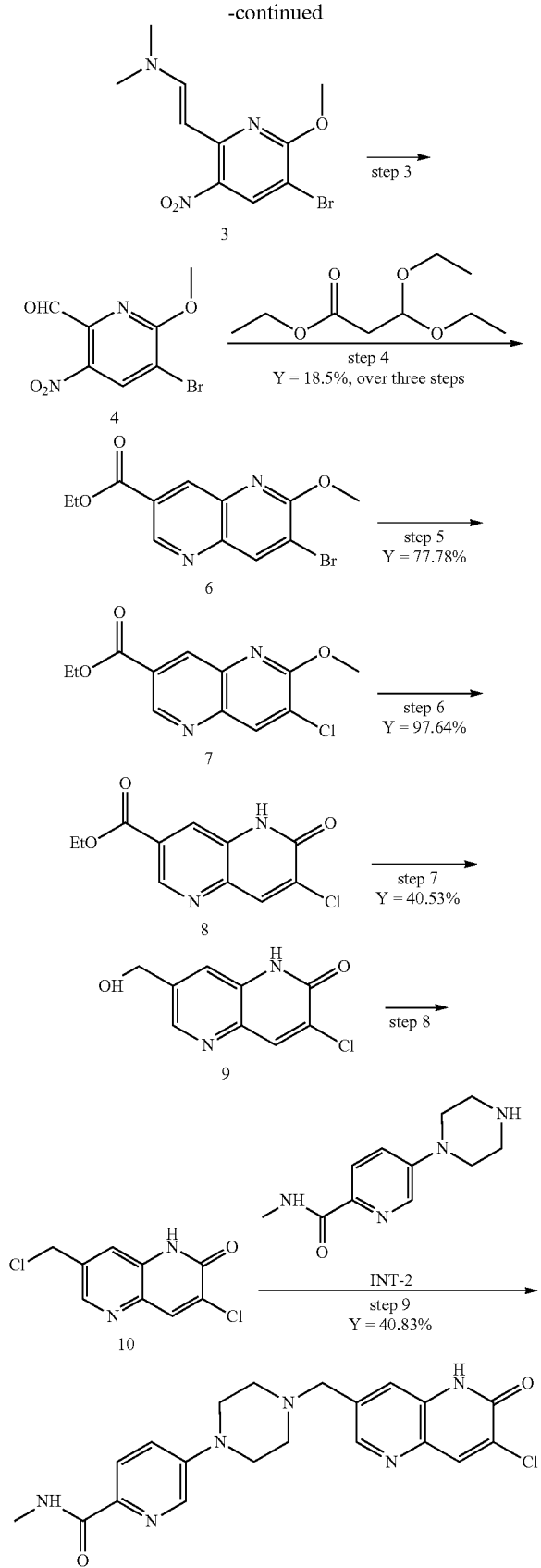

Example 138

Step 1: Preparation of
3-bromo-2-methoxy-6-methyl-5-nitropyridine

To a stirred mixture of 3-bromo-2-chloro-6-methyl-5-nitropyridine (20.00 g, 79.54 mmol, 1.00 equiv) in MeOH (50 mL) was added NaOMe (15.76 g, 87.49 mmol, 1.10 equiv, 30% wt) dropwise at 0° C. under nitrogen atmosphere. The resulting mixture was stirred overnight at room temperature under nitrogen atmosphere. The reaction was monitored by TLC. The resulting mixture was concentrated under reduced pressure and water (100 mL) was added. The resulting mixture was extracted with EtOAc (3×100 mL). The combined organic layers were washed with brine (1×200 mL), dried over anhydrous $Na_2SO_4$. After filtration, the filtrate was concentrated under reduced pressure to afford 3-bromo-2-methoxy-6-methyl-5-nitropyridine (20 g, Y=99%) as a yellow solid. $^1$H NMR (400 MHz, DMSO-$d_6$) δ 8.66 (s, 1H), 4.04 (s, 3H), 2.70 (s, 3H).

Step 2: Preparation of (E)-2-(5-bromo-6-methoxy-3-nitropyridin-2-yl)-N,N-dimethylethen-1-amine A mixture of 3-bromo-2-methoxy-6-methyl-5-nitropyridine (15.00 g, 60.72 mmol, 1.00 equiv) in DMF-DMA (100 mL) and DMF (100 mL) was stirred overnight at 100° C. under nitrogen atmosphere. The reaction was monitored by TLC. The mixture was allowed to cool down to room temperature. The resulting mixture was concentrated under reduced pressure. The crude product was used in the next step directly without further purification.

Step 3: Preparation of
5-bromo-6-methoxy-3-nitropicolinaldehyde

To a stirred mixture of (E)-2-(5-bromo-6-methoxy-3-nitropyridin-2-yl)ethenyl]dimethylamine (18.01 g, crude) in THF (100 mL) and $H_2O$ (100 mL) was added $NaIO_4$ (28.00 g, 131.07 mmol, 2.20 equiv) in portions at 0° C. under nitrogen atmosphere. The resulting mixture was stirred for 2 h at room temperature under nitrogen atmosphere. The reaction was monitored by TLC. The reaction was quenched by the addition of sat. sodium hyposulfite (aq.) (100 mL) at room temperature. The resulting mixture was extracted with EtOAc (3×100 mL). The combined organic layers were washed with brine (2×100 mL), dried over anhydrous $Na_2SO_4$. After filtration, the filtrate was concentrated under reduced pressure. The crude product was used in the next step directly without further purification. $^1$H NMR (400 MHz, DMSO-$d_6$) δ 10.16 (s, 1H), 8.87 (s, 1H), 4.10 (s, 3H).

Step 4: Preparation of ethyl
7-bromo-6-methoxy-1,5-naphthyridine-3-carboxylate

To a stirred mixture of 5-bromo-6-methoxy-3-nitropyridine-2-carbaldehyde (7.00 g, crude) and ethyl 3,3-diethoxypropanoate (20.40 g, 107.27 mmol, 4.00 equiv) in EtOH (100 mL) were added $SnCl_2$ (26.25 g, 134.09 mmol, 5.00 equiv) in portions at room temperature under nitrogen atmosphere. The resulting mixture was stirred overnight at 90° C. under nitrogen atmosphere. The reaction was monitored by LCMS. The mixture was allowed to cool down to room temperature. The resulting mixture was concentrated under reduced pressure. The crude mixture was poured into saturated sodium bicarbonate (100 mL). The resulting mixture was extracted with EtOAc (3×100 mL). The combined organic layers were concentrated under reduced pressure. The residue was purified by silica gel column chromatography to afford crude product as a white solid. The crude product was purified by trituration with hexane (50 mL) to afford ethyl 7-bromo-6-methoxy-1,5-naphthyridine-3-carboxylate (3.50 g, Y=18.5%, over three steps) as a white solid. LC-MS: (ES+H, m/z): [M+H]$^+$=311.0/313.0. $^1$H NMR (400 MHz, DMSO-d$_6$) δ 9.22 (s, 1H), 8.78 (s, 1H), 8.58 (s, 1H), 4.42 (q, 2H), 4.12 (s, 3H), 1.39 (t 3H).

Step 5: Preparation of ethyl 7-chloro-6-methoxy-1,5-naphthyridine-3-carboxylate

To a stirred mixture of ethyl 7-bromo-6-methoxy-1,5-naphthyridine-3-carboxylate (1.20 g, 3.85 mmol, 1.00 equiv) in DMF (10 mL) was added CuCl (0.57 g, 5.78 mmol, 1.50 equiv) at room temperature under nitrogen atmosphere. The resulting mixture was stirred overnight at 120° C. The reaction was monitored by LCMS. The mixture was allowed to cool down to room temperature. The resulting mixture was diluted with EtOAc (20 mL). The resulting mixture was washed with 3×30 mL of Water (10% NH$_3$.H$_2$O). The resulting mixture was concentrated under reduced pressure. The residue was purified by silica gel column chromatography to afford ethyl 7-chloro-6-methoxy-1,5-naphthyridine-3-carboxylate (800 mg, 77.78%) as a white solid. LC-MS: (ES+H, m/z): [M+H]$^+$=267.0. $^1$H NMR (300 MHz, DMSO-d6) δ 9.27 (d, 1H), 8.63 (d, 1H), 8.57 (s, 1H), 4.41 (q, 2H), 4.12 (s, 3H), 1.37 (t, 3H).

Step 6: Preparation of ethyl 7-chloro-6-oxo-5H-1,5-naphthyridine-3-carboxylate

To a stirred mixture of ethyl 7-chloro-6-methoxy-1,5-naphthyridine-3-carboxylate (800 mg, 3.00 mmol, 1.00 equiv) in CH$_3$CN (8 mL) was added TMSI (1.80 g, 9.00 mmol, 3.00 equiv) at room temperature under nitrogen atmosphere. The resulting mixture was stirred for 2 h at 50° C. The reaction was monitored by LCMS. The mixture was allowed to cool down to room temperature. The resulting mixture was diluted with EtOAc (50 mL). The aqueous layer was washed with 3×50 mL of water (10% Et$_3$N). The combined organic layers were washed with brine (50 mL), dried over anhydrous Na$_2$SO$_4$. After filtration, the filtrate was concentrated under reduced pressure. The residue was purified by silica gel column chromatography to afford ethyl 7-chloro-6-oxo-5H-1,5-naphthyridine-3-carboxylate (740 mg, 97.64%) as a white solid. LC-MS: (ES+H, m/z): [M+H]$^+$=252.9. $^1$H NMR (300 MHz, DMSO-d6) δ12.61 (s, 1H), 8.94 (d, 1H), 8.37 (d, 1H), 8.20 (s, 1H), 4.39 (q, 2H), 1.36 (t, 3H).

Step 7: Preparation of 3-chloro-7-(hydroxymethyl)-1H-1,5-naphthyridin-2-one

To a stirred mixture of ethyl 7-chloro-6-oxo-5H-1,5-naphthyridine-3-carboxylate (740 mg, 2.92 mmol, 1.00 equiv) in THF (6 mL) was added LiAlH$_4$ (2.5 mL, 5.85 mmol, 2.00 equiv) dropwise at 0° C. under nitrogen atmosphere. The resulting mixture was stirred for additional 2 h at 0° C. The reaction was monitored by LCMS. The mixture was acidified to pH 5 with 1 M HCl. The resulting mixture was concentrated under reduced pressure. The residue was purified by silica gel column chromatography to afford 3-chloro-7-(hydroxymethyl)-1H-1,5-naphthyridin-2-one (250 mg, 40.53%) as a white solid. LC-MS: (ES+H, m/z): [M+H]$^+$=211.00. $^1$H NMR (400 MHz, DMSO-d6) δ12.49 (s, 1H), 8.45 (d, 1H), 8.28 (s, 1H), 7.69 (d, 1H), 5.53 (t, 1H), 4.64 (d, 2H).

Step 8: Preparation of 3-chloro-7-(chloromethyl)-1H-1,5-naphthyridin-2-one

To a stirred mixture of 3-chloro-7-(hydroxymethyl)-1H-1,5-naphthyridin-2-one (250 mg, 1.18 mmol, 1.00 equiv) in CH$_2$Cl$_2$ (5 mL) was added SOCl$_2$ (423 mg, 3.56 mmol, 3.00 equiv) and DMF (8 mg, 0.11 mmol, 0.10 equiv) dropwise at room temperature under nitrogen atmosphere. The resulting mixture was stirred for 3 h at room temperature. The reaction was monitored by LCMS. The resulting mixture was concentrated under reduced pressure. This resulted in 3-chloro-7-(chloromethyl)-1H-1,5-naphthyridin-2-one (280 mg, crude) as a yellow solid. The crude product was used in the next step directly without further purification.
LC-MS: (ES+H, m/z): [M+H]$^+$=228.95.

Step 9: 5-{4-[(7-chloro-6-oxo-5H-1,5-naphthyridin-3-yl)methyl]piperazin-1-yl}-N-methylpyridine-2-carboxamide A solution of 3-chloro-7-(chloromethyl)-1H-1,5-naphthyridin-2-one (100 mg, 0.43 mmol, 1.00 equiv), KI (7 mg, 0.04 mmol, 0.10 equiv) and DIEA (225 mg, 1.74 mmol, 4.00 equiv) in acetonitrile (3 mL) was stirred for 1 h at 50° C. under nitrogen atmosphere. The mixture was allowed to cool down to room temperature. The reaction was monitored by LCMS. The resulting mixture was diluted with EtOAc (20 mL) then was washed with water (3×20 mL). The resulting mixture was concentrated under vacuum. The residue was purified by silica gel column chromatography to afford the crude product. The crude product was purified by Prep-HPLC, the pure fraction was concentrated then lyophilized to afford 5-{4-[(7-chloro-6-oxo-5H-1,5-naphthyridin-3-yl)methyl]piperazin-1-yl}-N-methylpyridine-2-carboxamide (73.6 mg, 40.83%) as a white solid. LC-MS: (ES+H, m/z): [M+H]$^+$=413.10. $^1$H NMR (300 MHz, DMSO-d$_6$) δ 12.45 (s, 1H), 8.49 (d, 1H), 8.43-8.36 (m, 1H), 8.29 (s, 1H), 8.27 (d, 1H), 7.83 (d, 1H), 7.70 (s, 1H), 7.40 (dd, 1H), 3.69 (s, 2H), 3.39-3.30 (m, 4H), 2.79 (d, 3H), 2.62-2.54 (m, 4H). The following examples were made using similar procedures shown for example 138.

| Ex | NMR | LCMS (ESI) m/z |
|---|---|---|
| 147 | $^1$H NMR (400 MHz, DMSO-d6) δ 12.45 (s, 1H), 8.49 (d, J = 1.8 Hz, 1H), 8.34 (d, J = 4.9 Hz, 1H), 8.29 (s, 1H), 8.24 (d, J = 2.9 Hz, 1H), 7.83 (d, J = 8.8 Hz, 1H), 7.69 (d, J = 1.9 Hz, 1H), 7.40 (dd, J = 8.8, 2.9 Hz, 1H), 3.68 (s, 2H), 3.37-3.33 (m, 4H), 2.89-2.79 (m, 1H), 2.62-2.52 (m, 4H), 0.71-0.57 (m, 4H). | [M + H]$^+$ = 439.10 |
| 152 | $^1$H NMR (300 MHz, DMSO-d6) δ 12.46 (s, 1H), 8.49 (d, J = 1.8 Hz, 1H), 8.36 (d, J = 5.0 Hz, 1H), 8.29 (s, 1H), 7.85 (dd, J = 8.1, 1.4 Hz, 1H), 7.69 (s, 1H), 7.57 (dd, J = 10.6, 8.0 Hz, 1H), 3.69 (s, 2H), 3.21-3.15 (m, 4H), 2.91-2.80 (m, 1H), 2.62-2.56 (m, 4H), 0.71-0.61 (m, 4H). $^{19}$F NMR (282 MHz, DMSO) δ-72.42. | [M + H]$^+$ = 457.10 |

| Ex | NMR | LCMS (ESI) m/z |
|---|---|---|
| 153 | $^1$H NMR (300 MHz, DMSO-d6) δ 12.42 (s, 1H), 8.62 (q, J = 4.7 Hz, 1H), 8.49 (d, J = 1.8 Hz, 1H), 8.28 (s, 1H), 8.08 (dd, J = 9.9, 7.7 Hz, 1H), 7.93 (dd, J = 7.7, 1.9 Hz, 1H), 7.72 (s, 1H), 6.25 (s, 1H), 3.75 (s, 2H), 3.23-3.18 (m, 2H), 2.80 (d, J = 4.8 Hz, 3H), 2.70 (t, J = 5.6 Hz, 2H), 2.50 (m, J = 2.1 Hz, 2H). $^{19}$F NMR (282 MHz, DMSO) δ-67.90, -68.25, -68.76. | [M + H]$^-$ = 426.00 |
| 160 | $^1$H NMR(400 MHz, DMSO-d6) δ 12.41 (s, 1H), 8.73-8.68 (m, 2H), 8.50 (d, J = 1.8 Hz, 1H), 8.29 (s, 1H), 8.02-7.95 (m, 2H), 7.71 (d, J = 1.8 Hz, 1H), 6.43 (s, 1H), 3.75 (s, 2H), 3.20-3.15 (m, 2H), 2.82 (d, J = 4.8 Hz, 3H), 2.75-2.68 (m, 2H), 2.56 (s, 2H). | [M + H]$^+$ = 410.10 |

Example 148

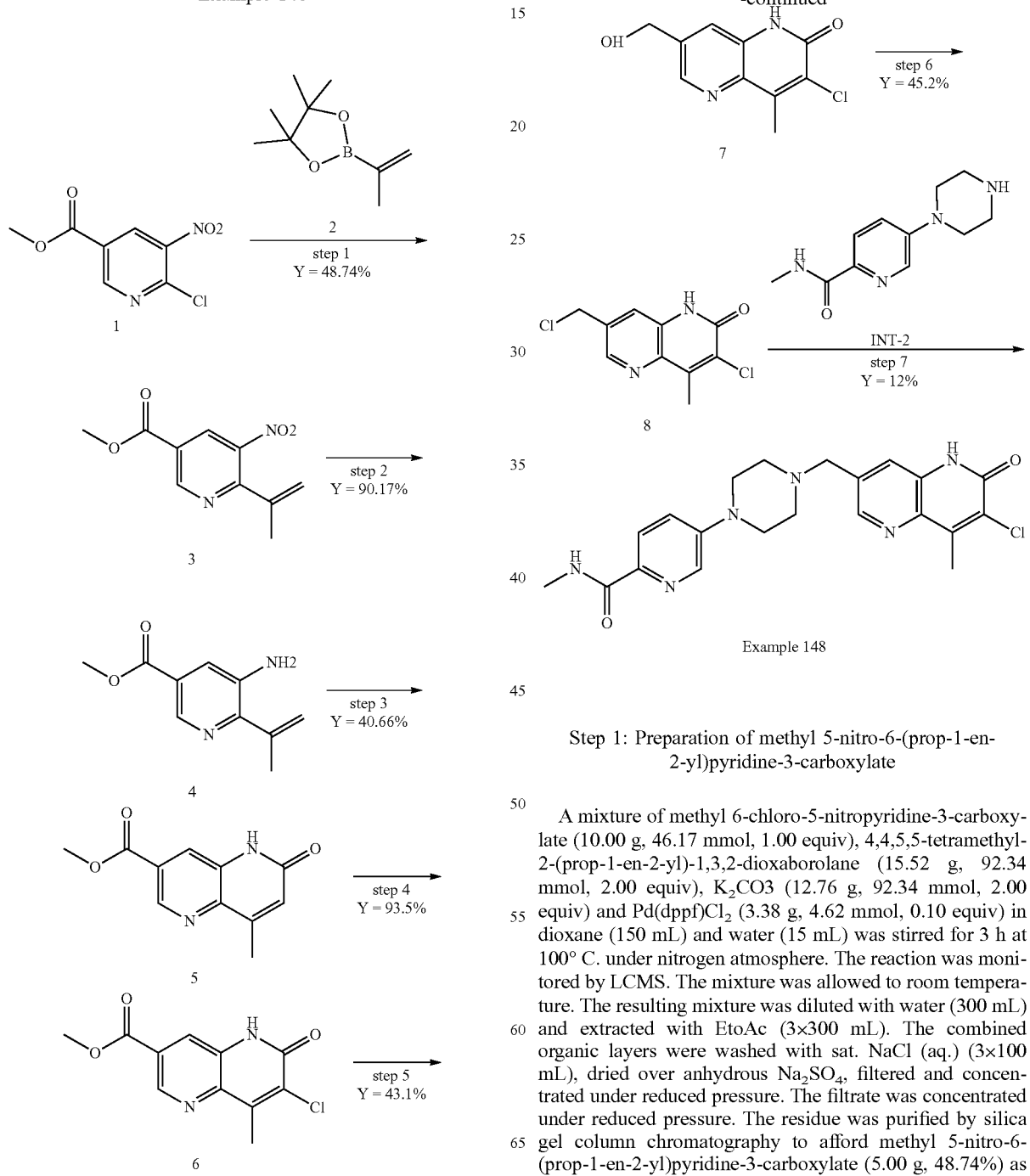

Example 148

Step 1: Preparation of methyl 5-nitro-6-(prop-1-en-2-yl)pyridine-3-carboxylate A mixture of methyl 6-chloro-5-nitropyridine-3-carboxylate (10.00 g, 46.17 mmol, 1.00 equiv), 4,4,5,5-tetramethyl-2-(prop-1-en-2-yl)-1,3,2-dioxaborolane (15.52 g, 92.34 mmol, 2.00 equiv), $K_2CO_3$ (12.76 g, 92.34 mmol, 2.00 equiv) and Pd(dppf)Cl$_2$ (3.38 g, 4.62 mmol, 0.10 equiv) in dioxane (150 mL) and water (15 mL) was stirred for 3 h at 100° C. under nitrogen atmosphere. The reaction was monitored by LCMS. The mixture was allowed to room temperature. The resulting mixture was diluted with water (300 mL) and extracted with EtOAc (3×300 mL). The combined organic layers were washed with sat. NaCl (aq.) (3×100 mL), dried over anhydrous Na$_2$SO$_4$, filtered and concentrated under reduced pressure. The filtrate was concentrated under reduced pressure. The residue was purified by silica gel column chromatography to afford methyl 5-nitro-6-(prop-1-en-2-yl)pyridine-3-carboxylate (5.00 g, 48.74%) as a light yellow oil. LC-MS: (ES+H, m/z): [M+H]$^+$=222.95.

1H NMR (300 MHz, DMSO-d6) δ 9.25 (d, 1H), 8.74 (d, 1H), 5.41-5.47 (m, 1H), 5.13-5.21 (m, 1H), 3.94 (s, 3H), 2.16 (dd, 3H).

Step 2: Preparation of methyl 5-nitro-6-(prop-1-en-2-yl)pyridine-3-carboxylate

To a stirred solution of methyl 5-nitro-6-(prop-1-en-2-yl)pyridine-3-carboxylate (5.00 g, 22.50 mmol, 1.00 equiv) in MeOH (100 mL) were added NH$_4$Cl (25 mL, sat. aq.) and Fe (5.03 g, 90.01 mmol, 4.00 equiv). The reaction was stirred at 80° C. for 4 h under nitrogen atmosphere. The reaction was monitored by LCMS. The mixture was allowed to room temperature then concentrated under reduced pressure. The residue was diluted with CH$_2$Cl$_2$/2-Propanol (5:1, 200 mL) and washed with water (250 mL) and brine (250 mL). The organic layers were dried over anhydrous Na$_2$SO$_4$, filtered and concentrated under reduced pressure. This resulted in methyl 5-amino-6-(prop-1-en-2-yl)pyridine-3-carboxylate (3.90 g, 90.17%) as a light yellow solid which was used directly without further purification. LC-MS: (ES+H, m/z): [M+H]+=193.15. 1H NMR (300 MHz, DMSO-d6) δ 8.29 (d, 1H), 7.60 (d, 1H), 5.51-5.47 (m, 1H), 5.41 (s, 2H), 5.39-5.36 (m, 1H), 3.84 (s, 3H), 2.08 (t, 3H).

Step 3: Preparation of methyl 8-methyl-6-oxo-5H-1,5-naphthyridine-3-carboxylate

A solution of triphosgene (1.54 g, 5.20 mmol, 0.50 equiv) in toluene (20 mL) was added to the solution of methyl 5-amino-6-(prop-1-en-2-yl)pyridine-3-carboxylate (3.90 g, 20.29 mmol, 1.00 equiv) and Et$_3$N (6.16 g, 60.87 mmol, 3.00 equiv) in toluene (40 mL) at 0° C. under nitrogen atmosphere. The resulting mixture was stirred overnight at 60° C. under nitrogen. The reaction was monitored by LCMS. The reaction was quenched with MeOH (30 mL) at 0° C. The resulting mixture was diluted with water (200 mL) and extracted with CH$_2$Cl$_2$/2-Propanol (5:1, 3×200 mL). The combined organic layers were washed with water (3×100 mL), dried over anhydrous Na$_2$SO$_4$, filtered and concentrated under reduced pressure. The residue was purified by silica gel column chromatography to afford methyl 8-methyl-6-oxo-5H-1,5-naphthyridine-3-carboxylate (1.80 g, 40.66%) as a light yellow solid. LC-MS: (ES+H, m/z): [M+H]$^+$=219.1. 1H NMR (400 MHz, DMSO-d6) δ 11.92 (s, 1H), 8.92 (d, 1H), 8.15 (d, 1H), 6.79 (s, 1H), 3.93 (s, 3H), 2.48 (s, 3H).

Step 4: Preparation of methyl 7-chloro-8-methyl-6-oxo-5H-1,5-naphthyridine-3-carboxylate To a solution of methyl 8-methyl-6-oxo-5H-1,5-naphthyridine-3-carboxylate (600 mg, 2.75 mmol, 1.00 equiv) and NCS (587 mg, 4.40 mmol, 1.60 equiv) in CH$_3$COOH (7 mL) was added 2,2-dichloroacetic acid (71 mg, 0.55 mmol, 0.20 equiv) dropwise at room temperature under nitrogen atmosphere. The resulting mixture was stirred overnight at 100° C. under nitrogen atmosphere. The reaction was monitored by LCMS. The mixture was allowed to cool down to room temperature. The resulting mixture was concentrated under reduced pressure. The residue was purified by silica gel column chromatography to afford methyl 7-chloro-8-methyl-6-oxo-5H-1,5-naphthyridine-3-carboxylate (650 mg, 93.5%) as a white solid. LC-MS: (ES+H, m/z): [M+H]$^+$=253.0. $^1$H NMR (300 MHz, DMSO-d6) δ 8.90 (d, 1H), 8.13 (d, 1H), 3.93 (s, 3H), 2.60 (s, 3H).

Step 5: Preparation of 3-chloro-7-(hydroxymethyl)-4-methyl-1H-1,5-naphthyridin-2-one To a stirred solution of methyl 7-chloro-8-methyl-6-oxo-5H-1,5-naphthyridine-3-carboxylate (600 mg, 2.38 mmol, 1.00 equiv) in THF (5 mL) was added LiAlH$_4$ (2 mL, 2.5 M in THF, 4.75 mmol, 2.00 equiv) dropwise at 0° C. under nitrogen atmosphere. The resulting mixture was stirred for 1 h at room temperature under nitrogen atmosphere. The reaction was monitored by LCMS. The reaction was quenched by the addition of HCl (1 mL, 12M) at 0° C. The resulting mixture was concentrated under reduced pressure. The residue was purified by silica gel column chromatography to afford 3-chloro-7-(hydroxymethyl)-4-methyl-1H-1,5-naphthyridin-2-one (230 mg, 43.1%) as a white solid. LC-MS: (ES+H, m/z): [M+H]$^+$=225.1. $^1$H NMR (300 MHz, DMSO-d6) δ 12.24 (br, 1H), 8.48 (d, 1H), 7.77 (d, 1H), 5.69 (s, 1H), 4.63 (s, 2H), 2.63 (s, 3H).

Step 6: Preparation of 3-chloro-7-(chloromethyl)-4-methyl-1H-1,5-naphthyridin-2-one To a stirred solution of 3-chloro-7-(hydroxymethyl)-4-methyl-1H-1,5-naphthyridin-2-one (200 mg, 0.89 mmol, 1.00 equiv) and DMF (7 mg, 0.09 mmol, 0.10 equiv) in DCM (10 mL) were added SOCl$_2$ (318 mg, 2.67 mmol, 3.00 equiv) dropwise at 0° C. under nitrogen atmosphere. The resulting mixture was stirred for 10 h at room temperature. The reaction was monitored by LCMS. The resulting mixture was concentrated under reduced pressure. The residue was purified by silica gel column chromatography to afford 3-chloro-7-(chloromethyl)-4-methyl-1H-1,5-naphthyridin-2-one (98 mg, 45.2%) as a white solid. LC-MS: (ES+H, m/z): [M+H]$^+$=243.0.

Step 7: Preparation of 5-{4-[(7-chloro-8-methyl-6-oxo-5H-1,5-naphthyridin-3-yl)methyl]piperazin-1-yl}-N-methylpyridine-2-carboxamide To a stirred mixture of 3-chloro-7-(chloromethyl)-4-methyl-1H-1,5-naphthyridin-2-one (120 mg, 0.49 mmol, 1.00 equiv), KI (16 mg, 0.09 mmol, 0.20 equiv) and N-methyl-5-(piperazin-1-yl)pyridine-2-carboxamide (97 mg, 0.44 mmol, 0.90 equiv) in MeCN (5 mL) was added DIEA (319 mg, 2.47 mmol, 5.00 equiv) dropwise at room temperature under nitrogen atmosphere. The resulting mixture was stirred for 5 h at 80° C. under nitrogen atmosphere. The reaction was monitored by LCMS. The mixture was allowed to cool down to room temperature. The resulting mixture was concentrated under reduced pressure. The crude product (120 mg) was purified by Prep-HPLC, the pure fraction was concentrated then lyophilized to afford 5-{4-[(7-chloro-8-methyl-6-oxo-5H-1,5-naphthyridin-3-yl)methyl]piperazin-1-yl}-N-methylpyridine-2-carboxamide (26.8 mg, 11.9%) as a yellow solid. LC-MS: (ES+H, m/z): [M+H]$^+$=427.15. $^1$H NMR (300 MHz, DMSO-d6) δ 12.31 (s, 1H), 8.53 (d, J=1.9 Hz, 1H), 8.46-8.33 (m, 1H), 8.28 (d, J=2.8 Hz, 1H), 7.83 (d, J=8.8 Hz, 1H), 7.70 (d, J=1.9 Hz, 1H), 7.40 (dd, J=8.8, 2.9 Hz, 1H), 3.70 (s, 2H), 3.38-3.33 (m, 4H), 2.78 (d, J=4.8 Hz, 3H), 2.66 (s, 3H), 2.60-2.54 (m, 4H).

The following examples were made using similar procedures shown for example 148.

| Ex | NMR | LCMS (ESI) m/z |
|---|---|---|
| 154 | $^1$H NMR (400 MHz, DMSO-d6) δ 8.49 (d, J = 1.9 Hz, 1H), 8.34 (d, J = 4.9 Hz, 1H), 8.23 (d, J = 2.9 Hz, 1H), 7.83 (d, J = 8.8 Hz, 1H), 7.67 (s, 1H), 7.39 (dd, J = 8.9, 2.8 Hz, 1H), 3.68 (s, 2H), 3.34-3.31 (m, 4H), 2.85-2.83 m, 1H), 2.65-2.62 (m, 3H), 2.50-2.49 (m, 4H), 0.67-0.62 (m, 4H). | [M + H]$^+$ = 453.10 |
| 156 | $^1$H NMR (400 MHz, DMSO-d6) δ 12.28 (s, 1H), 8.52 (d, J = 2.1 Hz, 1H), 8.38 (s, 1H), 7.84 (d, J = 7.8 Hz, 1H), 7.68 (d, J = 2.0 Hz, 1H), 7.61-7.46 (m, 1H), 3.77-3.57 (m, 2H), 3.19-3.11 (m, 4H), 2.76 (d, J = 4.9 Hz, 3H), 2.68-2.61 (m, 3H), 2.61-2.53 (m, 4H). | [M + H]$^+$ = 445.10 |

The following examples were made using similar procedures shown in the above examples.

| Ex | NMR | LCMS (ESI) m/z |
|---|---|---|
| 29 | $^1$H NMR (400 MHz, DMSO-d$_6$) δ 12.51 (brs, 1H), 8.47 (s, 2H), 8.36 (d, J = 5.0 Hz, 1H), 7.85 (d, J = 8.0 Hz, 1H), 7.68 (s, 1H), 7.56 (dd,J = 10.6, 8.0 Hz, 1H), 3.68 (s, 2H), 3.26-3.09 (m, 4H), 2.91-2.81 (m, 1H), 2.63-2.55 (m, 4H), 0.76-0.50 (m, 4H).<br>$^{19}$F NMR (377 MHz, DMSO-d$_6$) δ -72.40. | [M + H]$^+$ = 501.10/503.10 |
| 31 | $^1$H NMR (400 MHz, DMSO-d6) δ12.26 (s, 1H), 8.40 (q, 1H), 8.27 (d, 1H), 7.83 (d, 2H), 7.66 (d, 1H), 7.45-7.05 (m, 4H), 3.61 (s, 2H), 3.34 (m, 4H), 2.78 (d, 3H), 2.54 (t, 4H).<br>$^{19}$F NMR (377 MHz, DMSO) δ-82.20. | [M + H]$^+$ = 444.10 |
| 32 | $^1$H NMR (400 MHz, DMSO-d6) δ 11.85 (s, 1H), 8.97 (s, 2H), 8.41 (s, 1H), 7.76 (s, 1H), 7.63 (s, 1H), 7.50 (d, 2H), 7.07 (d, 2H), 3.65 (s, 2H), 3.26-3.18 (m, 4H), 2.60-2.53 (m, 6H), 1.18 (t, 3H). | [M + H]$^+$ = 416.2 |
| 36 | $^1$H NMR (300 MHz, DMSO-d6) δ 11.86 (s, 1H), 8.40 (d, 1H), 7.95 (q, 1H), 7.75 (s, 1H), 7.62 (d, 1H), 6.21 (s, 1H), 3.67 (m, 5H), 2.90 (m, 4H), 2.70 (d, 3H), 2.61-2.47 (m, 6H), 1.19 (t, 3H). | [M + H]$^+$ = 421.15 |
| 62 | | [M + H]$^+$ = 427.1 |
| 65 | $^1$H NMR (300 MHz, DMSO-d6) δ 11.85 (s, 1H), 9.49 (s, 1H), 8.40 (s, 1H), 8.21 (d,1H), 7.74 (s, 1H), 7.61 (s, 1H), 6.13 (d, 1H), 3.67 (s, 2H), 3.46 (s, 3H), 3.08-3.03 (m, 4H), 2.81 (d, 3H), 2.57-2.52 (m, 6H), 1.20 (t, 3H). | [M + H]$^+$ = 437.10 |
| 70 | $^1$H NMR (300 MHz, DMSO-d6) δ 12.16 (s, 1H), 11.86 (s, 1H), 8.41 (d, 1H), 7.87 (t, 1H) 7.78-7.60 (m, 3H), 7.32-7.24 (m, 1H), 6.87-6.68 (m, 2H), 3.64 (s, 2H), 3.20 (t, 4H), 2.64-2.52 (m, 6H), 1.19 (t, 3H).<br>19F NMR (282 MHz, DMSO) 6-113.73. | [M + H]$^+$ = 433.1 |
| 72 | $^1$H NMR (400 MHz, DMSO-d6) δ 11.92-11.85 (m, 1H), 8.56-8.34 (m, 2H), 8.23 (dd, 2H), 7.93-7.71 (m, 2H), 7.40 (dd, 1H), 7.13 (d, 1H), 3.69 (s, 2H), 3.62-3.35 (m, 4H), 2.78 (d, 3H), 2.58 (t, 4H). | [M + H]$^+$ = 419.1 |
| 75 | $^1$H NMR (400 MHz, DMSO-d6) δ 11.84 (s, 1H), 10.51 (s, 1H), 8.40 (d, 1H), 7.98 (d, 1H) 7.91 (d, 1H), 7.75 (s, 1H), 7.63 (d, 1H), 7.37 (dd, 1H), 3.64 (s, 2H), 3.20-3.14 (m, 4H), 2.60-2.55 (m, 6H), 2.0-1.94 (m, 1H), 1.25-1.15 (m, 3H), 0.85-0.76 (m, 4H). | [M + H]$^+$ = 433.2 |
| 76 | $^1$H NMR (400 MHz, DMSO-d6) δ 11.86 (s, 1H), 8.46-8.40 (m, 2H), 8.01 (d, 1H), 7.76 (s, 1H), 7.70-7.63 (m, 2H), 3.84 (q, 2H), 3.75-3.68 (m, 1H), 3.55-3.42 (m, 1H), 3.04-3.02 (m, 1H), 2.79-2.74 (m, 5H), 2.59-2.52 (m, 2H), 2.48-2.40 (m, 1H), 1.18 (t, 3H), 0.83-0.73 (m, 2H). | [M + H]$^+$ = 444.05 |
| 84 | $^1$H NMR (300 MHz, DMSO-d6) δ 11.69 (s, 1H), 8.45-8.36 (m, 2H), 8.26 (d, 1H), 7.83 (d, 1H), 7.65 (m, 1H), 7.38 (dd, 1H), 3.65 (s, 2H), 3.38-3.34 (m, 4H), 3.21-3.12 (m, 2H), 2.85-2.74 (m, 5H), 2.55 (t, 4H), 2.11 (p, 2H). | [M + H]$^+$ = 419.05 |
| 85 | $^1$H NMR (300 MHz, DMSO-d6) δ 11.82 (s, 1H), 8.52 (d, 1H), 8.36 (d, 1H), 8.19 (dd, 2H), 7.89-7.80 (m, 2H), 7.28 (dd, 1H), 7.13 (d, 1H), 4.02-3.85 (m, 2H), 3.59-3.47 (m, 1H), 3.29-3.17 (m, 1H), 2.87-2.68 (m, 5H), 2.57 (t, 2H), 0.81-0.74 (m, 1H), 0.41 (q, 1H). | [M + H]$^+$ = 431.15 |
| 86 | $^1$H NMR (300 MHz, DMSO-d6) δ 12.09 (s, 1H), 8.41 (d, 1H), 8.28 (d, 1H), 8.03 (s, 1H), 7.84 (d, 1H), 7.57-7.33 (m, 2H), 3.94 (s, 2H), 3.73-3.6 (m, 4H), 2.79 (s, 3H), 2.71-2.52 (m, 6H), 1.21 (t, 3H). | [M + H]$^+$ = 408.10 |
| 87 | $^1$H NMR (300 MHz, DMSO-d6) δ 12.44 (brs, 1H), 8.81 (s, 1H), 8.41 (q, 1H), 8.28 (d, 1H), 7.84 (d, 1H), 7.47-7.26 (m, 2H), 3.72 (s, 2H), 3.42-3.36 (m, 4H), 2.81-2.79 (m, 5H), 2.66-2.59 (m, 4H), 1.23 (t, 3H). | [M + H]$^+$ = 408.05 |
| 89 | $^1$H NMR (300 MHz, DMSO-d6) δ 11.69 (s, 1H), 9.51-9.46 (m, 1H), 8.22 (d, 1H), 7.70 (s, 1H), 7.57 (d, 1H), 7.27 (s, 1H), 7.12 (dd, 1H), 6.12 (d, 1H), 3.61 (s, 2H), 3.47 (s, 3H), 3.05 (t, 4H), 2.81 (d, 3H), 2.56-2.51 (m, 4H), 2.50-2.46 (m, 2H), 1.16 (t, 3H). | [M + H]$^+$ = 436.10 |
| 91 | $^1$H NMR (300 MHz, DMSO-d6) δ 12.41 (s, 1H), 8.47-8.37 (m, 2H), 8.28 (d, 1H), 7.83 (d, 1H), 7.66 (d, 1H), 7.40 (dd, 1H), 3.69 (s, 2H), 3.36 (m, 4H), 2.93-2.75 (m, 5H), 2.57 (m, 4H), 1.24 (t, 3H). | [M + H]$^+$ = 408.1 |
| 92 | $^1$H NMR (400 MHz, DMSO-d6) δ 11.87 (s, 1H), 8.47 (d, 1H), 8.41 (d, 1H), 8.13 (d, 1H), 7.80-7.69 (m, 3H), 7.64 (s, 1H), 7.57 (dd, 1H), 6.52-6.51 (m, 1H), 3.66 (s, 2H), 3.25-3.23 (m, 4H), 2.59-2.54 (m, 6H), 1.19 (t, 3H). | [M + H]$^+$ = 416.15 |

| Ex | NMR | LCMS (ESI) m/z |
|---|---|---|
| 95 | $^1$H NMR (400 MHz, DMSO-d6) δ 11.75 (s, 1H), 8.43-8.40 (m, 2H), 8.27 (d, 1H), 7.83 (d, 1H), 7.61 (d, 1H), 7.39 (dd, 1H), 3.66 (s, 2H), 3.35 (t, 4H), 2.78 (d, 3H), 2.56 (t, 4H), 2.49 (s, 3H), 2.14 (s, 3H). | [M + H]$^+$ = 407.3 |
| 98 | $^1$H NMR (300 MHz, DMSO-d6) δ 11.88 (s, 1H), 8.49-8.40 (m, 2H), 8.01 (d, 1H), 7.84 (d, 1H), 7.72-7.63 (m, 2H), 3.95-3.63 (m, 3H), 3.41-3.36 (m, 1H), 3.12-2.97 (m, 1H), 2.86-2.64 (m, 5H), 2.49-2.39 (m, 1H), 2.14 (s, 3H), 0.84-0.80 (m, 2H). | [M + H]$^+$ = 430.2 |
| 101 | $^1$H NMR (400 MHz, DMSO-d6) δ 11.85 (s, 1H), 8.89 (s, 1H), 8.40 (d, 1H), 7.92 (d, 1H), 7.75 (s, 1H), 7.69-7.57 (m, 2H), 7.35 (dd, 1H), 3.64 (s, 2H), 3.57 (t, 4H), 3.42 (t, 4H), 3.11 (t, 4H), 2.58-2.52 (m, 6H), 1.18 (t, 3H). | [M + H]$^+$ = 478.30 |
| 102 | $^1$H NMR (400 MHz, DMSO-d6) δ 11.85 (s, 1H), 10.08 (s, 1H), 8.40 (d, 1H), 7.96 (d, 1H), 7.75 (s, 1H), 7.65-7.56 (m, 2H), 7.41-7.38 (m, 1H), 5.44-5.34 (m, 1H), 4.80 (t, 2H), 4.56-4.43 (m, 2H), 3.64 (s, 2H), 3.18-3.09 (m, 4H), 2.60-2.53 (m, 6H), 1.18 (t, 3H). | [M + H]$^+$ = 465.3 |
| 103 | $^1$H NMR (300 MHz, DMSO-d6) δ 11.92 (s, 1H), 9.72 (s, 1H), 8.48 (d, 1H), 8.12-8.00 (m, 2H), 7.82 (s, 1H), 7.70 (d, 1H), 7.51 (dd, 1H), 5.21 (dd, 1H), 4.74-4.64 (m, 2H), 3.72 (s, 2H), 3.26-3.21 (m, 4H), 3.07-2.93 (m, 1H), 2.77-2.68 (m, 1H), 2.67-2.60 (m, 6H), 1.28-1.22 (m, 3H). | [M + H]$^+$ = 449.15 |
| 104 | $^1$H NMR (300 MHz, DMSO-d6) δ 11.82 (s, 1H), 8.45-8.34 (m, 2H), 8.27 (d, 1H), 7.83 (d, 1H), 7.72 (d, 1H), 7.62 (d, 1H), 7.43-7.35 (m, 1H), 3.65-3.60 (m, 3H), 3.38-3.31 (m, 4H), 2.78 (d, 3H), 2.62-2.52 (m, 4H), 2.35-2.22 (m, 2H), 2.16-1.92 (m, 3H), 1.87-1.71 (m, 1H). | [M + H]$^+$ = 433.10 |
| 114 | $^1$H NMR (400 MHz, DMSO-d6) δ 11.88 (s, 1H), 9.43 (d, 1H), 8.43 (d, 1H), 8.16 (d, 1H), 7.75 (s, 1H), 7.65 (d, 1H), 6.14 (d, 1H), 3.85-3.74 (m, 2H) 3.56 (s, 3H), 3.30-3.14 (m, 2H), 2.80 (d, 3H), 2.77-2.69 (m, 2H), 2.61-2.53 (m, 3H), 2.49-2.40 (m, 1H), 1.18 (t, 3H), 0.87 (q, 1H), 0.71 (q, 1H). | [M + H]$^+$ = 449.30 |
| 120 | $^1$H NMR (300 MHz, Methanol-d4/CDCl3 = 2:1) δ 8.81 (d, 1H), 8.48 (s, 1H), 7.89-7.58 (m, 2H), 7.17 (d, 1H), 3.75-3.69 (m, 6H), 2.88-2.50 (m, 6H), 1.29 (t, 3H). | [M + H]$^+$ = 376.20 |
| 123 | $^1$H NMR (300 MHz, DMSO-d6) δ 11.90 (s, 1H), 9.58 (s, 1H), 8.38 (d, 1H), 8.22 (d, 1H), 7.59 (s, 1H), 7.42 (s, 1H), 6.13 (d, 1H), 3.67 (s, 2H), 3.47 (s, 3H), 3.06-3.01 m, 4H), 2.62-6.58 (m, 4H), 2.20-2.08 (m, 1H), 1.03-0.93 (m, 2H), 0.88-0.74 (m, 2H). | [M + H]$^+$ = 468.20 |
| 133 | $^1$H NMR (300 MHz, DMSO-d6) δ 11.76 (s, 1H), 8.56 (d, 1H), 8.41 (d, 1H), 8.28 (d, 1H), 7.83 (d, 1H), 7.69 (d, 1H), 7.51-7.41 (m, 1H), 7.07 (t, 1H), 3.71 (s, 2H), 3.41-3.30 (m, 4H), 2.78 (d, 3H), 2.73 (s, 3H), 2.63-2.51 (m, 4H).<br>$^{19}$F NMR (282 MHz, DMSO) δ -115.49. | [M + H]$^+$ = 443.10 |
| 135 | $^1$H NMR (400 MHz, DMSO-d6) δ 12.18 (s, 1H), 8.48 (s, 1H), 8.39 (s, 1H), 8.27 (s, 1H), 8.16 (s, 1H), 7.83 (d, 1H), 7.65 (s, 1H), 7.39 (d, 1H), 4.52 (s, 1H), 3.68 (s, 2H), 3.34 (s, 4H), 2.78 (d, 3H), 2.57 (s, 4H). | [M + H]$^+$ = 403.25 |
| 140 | $^1$H NMR (400 MHz, DMSO-d6) δ 11.97 (s, 1H), 8.44 (s, 1H), 8.40-8.38 (m, 1H), 8.27-8.26 (m, 1H), 7.89 (s, 1H), 7.83 (d, J = 8.8 Hz, 1H), 7.66-7.65 (m, 1H), 7.39 (d, J = 8.8 Hz, 1H), 3.67 (s, 2H), 3.43-3.35 (m, 5H), 3.01-2.80 (m, 4H), 2.78 (d, J = 4.8 Hz, 3H), 2.57-2.55 (m, 4H).<br>$^{19}$F NMR (377 MHz, DMSO-d6) δ-81.12, -81.63, -95.62, 96.12. | [M + H]$^+$ = 469.10 |
| 141 | $^1$H NMR (400 MHz, DMSO-d6) δ 12.22 (s, 1H), 8.43-8.41 (m, 1H), 8.29 (s, 1H), 7.85-7.80 (m, 3H), 7.41 (d, J = 4.7 Hz, 1H), 3.81 (s, 2H), 3.36-3.33 (m, 4H), 2.78 (d, J = 4.7 Hz, 3H), 2.65-2.64 (m, 4H), 2.60-2.53 (m, 2H), 1.19 (t, 3H). | [M + H]$^+$ = 432.15 |
| 142 | $^1$H NMR (400 MHz, DMSO-d6) δ 11.83 (s, 1H), 8.48 (s, 1H), 8.34 (d, J = 4.8 Hz, 1H), 8.24 (d, J = 2.9 Hz, 1H), 8.18 (d, J = 2.0 Hz, 1H), 7.87-7.74 (m 2H), 7.40 (dd, 1H), 7.12 (d, J = 2.0 Hz, 1H), 3.70 (s, 2H), 3.39-3.30 (m, 4H), 2.89-2.80 (m, 1H), 2.58 (t, J = 5.0 Hz, 4H), 0.73-0.58 (m, 4H). | [M + H]$^+$ = 445.10 |
| 143 | $^1$H NMR (400 MHz, DMSO-d6) δ 12.10 (s, 1H), 8.45 (s, 1H), 8.40 (q, J = 4.9 Hz, 1H), 8.27 (d, J = 2.8 Hz, 1H), 7.87-7.80 (m, 2H), 7.67 (s, 1H), 7.39 (dd, J = 8.8, 2.9 Hz, 1H), 3.67 (s, 2H), 3.34 (t, J = 5.1 Hz, 4H), 3.02-2.92 (m, 1H), 2.78 (d, J = 4.8 Hz, 3H), 2.57 (t, J = 5.1 Hz, 4H), 2.26-2.14 (m, 1H), 2.05-1.93 (m, 1H).<br>19F NMR (377 MHz, DMSO) δ-125.18, -125.57, -141.46, -141.85. | [M + H]$^+$ = 455.10 |
| 144 | $^1$H NMR (400 MHz, DMSO-d6) δ 11.93 (s, 1H), 8.41 (q, J = 4.8 Hz, 1H), 8.28 (d, J = 2.9 Hz, 1H), 7.83 (d, J = 8.8 Hz, 1H), 7.76-7.73 (m, 1H), 7.41 (dd, J = 8.8, 2.9 Hz, 1H), 7.01 (s, 1H), 3.97 (s, 3H), 3.60 (s, 2H), 3.39-3.37 (m, 4H), 2.78 (d, J = 4.9 Hz, 3H), 2.66-2.64 (m, 4H), 2.50-2.47 (m, 2H), 1.15 (t, J = 7.5 Hz, 3H). | [M + H]$^+$ = 437.15 |
| 146 | $^1$H NMR (400 MHz, DMSO-d6) δ 11.86 (s, 1H), 8.67 (d, 1H), 8.42 (d, 2H), 7.88 (d, 1H), 7.75 (s, 1H), 7.63-7.51 (m, 2H), 3.75 (s, 2H), 3.09 (d, 2H), 2.79 (d, 3H), 2.54-2.40 (m, 4H), 1.90 (s, 2H), 1.18 (t, 4H). | [M + H]$^+$ = 404.1 |
| 149 | $^1$H NMR (400 MHz, DMSO-d6) δ 11.72 (s, 1H), 8.40 (q, J = 4.8 Hz, 1H), 8.28-8.21 (m, 2H) 7.83 (d, J = 8.7 Hz, 1H), 7.46 (s, 1H), 7.38 (dd, J = 8.9, 2.9 Hz, 1H), 6.41 (s, 1H), 4.08 (t, J = 7.3 Hz, 4H), 3.56 (s, 2H), 3.32 (m, 4H), 2.78 (d, J = 4.8 Hz, 3H), 2.53 (m, 4H), 2.27 (p, J = 7.3 Hz, 2H). | [M + H]$^+$ = 434.15 |
| 150 | $^1$H NMR (300 MHz, DMSO-d6) δ 12.05 (s, 1H), 8.39 (q, J = 4.9 Hz, 1H), 8.04 (d, J = 7.9 Hz, 1H), 7.85 (dd, J = 8.0, 1.5 Hz, 1H), 7.72 (s, 1H), 7.57 (dd, J = 10.6, 8.1 Hz, 1H), 7.33 (d, J = 7.9 Hz, 1H), 3.69 (s, 2H), 3.21-3.16 (m, 4H), 2.77 (d, J = 4.8 Hz, 3H), 2.66-2.59 (m, 4H), 2.54-2.48 (m, 2H), 1.16 (t, J = 7.4 Hz, 3H). | [M + H]$^+$ = 425.20 |

-continued

| Ex | NMR | LCMS (ESI) m/z |
|---|---|---|
| 151 | $^1$H NMR (300 MHz, DMSO-d6) δ 12.25 (s, 1H), 8.48 (d, J = 1.8 Hz, 1H), 8.40 (d, J = 5.0 Hz, 1H), 8.27 (d, J = 2.8 Hz, 1H), 7.83 (d, J = 8.8 Hz, 2H), 7.79-7.67 (m, 1H), 7.41-7.37 (m, 1H), 3.69 (s, 2H), 3.38-3.36 (m, 4H), 2.78 (d, J = 4.8 Hz, 3H), 2.57-2.50 (m, 4H), 2.08 (s, 3H). $^{19}$F NMR (282 MHz, DMSO) δ-117.71. | $[M + H]^+ = 443.10$ |
| 155 | $^1$H NMR (400 MHz, DMSO-d6) δ 12.39 (s, 1H), 8.48-8.46 (m, 2H), 8.32 (d, J = 4.9 Hz, 1H), 8.23 (d, J = 2.8 Hz, 1H), 7.83 (d, J = 8.8 Hz, 1H), 7.68 (d, J = 1.8 Hz, 1H), 7.39 (dd, J = 8.8, 2.9 Hz, 1H), 3.67 (s, 2H), 3.36-3.33 (m, 4H), 2.88-2.80 (m, 1H), 2.60-2.55 (m, 4H), 0.71-0.57 (m, 4H). | $[M + H]^+ = 483.05/485.05$ |
| 157 | $^1$H NMR (300 MHz, DMSO-d6) δ 12.40 (s, 1H), 8.43 (d, J = 1.8 Hz, 1H), 8.27 (s, 1H), 7.65 (s, 1H), 3.60 (s, 2H), 2.42-2.37 (m, 8H), 2.23-2.20 (m, 6H). | $[M + H]^+ = 370.05$ |
| 159 | $^1$H NMR (300 MHz, DMSO-d6) δ 12.60 (s, 1H), 8.56 (s, 1H), 8.41 (d, J = 4.6 Hz, 1H), 8.28 (d, J = 2.7 Hz, 1H), 7.83 (d, J = 8.8 Hz, 1H), 7.75 (s, 1H), 7.45-7.36 (m, 1H), 3.71 (s, 2H), 3.35 (m, 4H), 2.78 (d, J = 4.9 Hz, 3H), 2.58 (m, 4H). | $[M + H]^+ = 491.00/493.00$ |

Example A: Cell Growth Inhibition Assay

The objective of this study is to evaluate the effect of invention compounds on cell proliferation through the cell viability assay in DLD-1 BRCA2(−/−) and parental isogenic pair and MDA-MB-436 (mutated BRCA1) cell lines. The CellTiter-Glo (CTG) based cell viability assay is designed to determine the number of viable cells in the culture because of compound effect, by quantifying ATP, which indicates the presence of metabolically active cells.

DLD-1 BRCA2(−/−) and parental isogenic pair were cultured in RPMI 1640 supplemented with 10% fetal bovine serum (FBS), and MDA-MB-436 cells were cultured in DMEM supplemented with 10% FBS. Both are culture at 37° C. with 5% $CO_2$. Invention compounds were distributed to the 384 well plate (Corning, 3764) using Echo acoustic liquid handler to form a 1:3 serially diluted final concentration with top dose of 10 or 30 μM. The cells were seeded into the plate in the density of 50 cells/well (DLD-1 parental), 200 cells/well (DLD-1 BRCA2−/−), or 500 cells/well (MDA-MB-436). After a short spun, the cells were cultured in a well moisturized incubator at 37° C. with 5% $CO_2$ for 7 days without disturbance. The cell viability was measured by CellTiter Glo 2.0 assay kit (Promega, G9243), and growth inhibition rate was calculated and plotted against final compound concentration, and the data were fitted in Xfit to generate $IC_{50}$.

Example B: Biochemical (FP) Assay

Assays based on fluorescent polarization (FP) have been widely utilized in drug discovery due to the homogenous format, robust performance and lack of interference seen in other assays. To characterize our compounds, we utilized an assay measuring the displacement of a commercially available fluorescently labeled PARP 1/2 inhibitor (PARPi-FL, Tocris Biosciences, #6461) as exemplified in assays performed in WO2014/064149 and WO2021/013735A1. The assay was performed utilizing the following method:

Compounds were dissolved in DMSO an Echo550 liquid handler was utilized to make serial dilations in the desired concentration range in Optiplate-384F plates. 100% DMSO was used for the high (with protein) and low (without protein) control samples. 20 nL of compound or DMSO alone was added to individual assay plate wells.

PARP1 and PARP2 protein were expressed, purified and diluted in assay buffer containing 50 mM Tris pH 8.0, 0.001% Triton X-100, 10 mM $MgCl_2$, 150 mM NaCl to a final concentration of 20 nM. The PARPi-FL was then added at a final concentration of 3 nM.

The assay plate is centrifuged at 1000 rpm for 1 min and incubated for 4 h at room temperature.

The fluorescent polarization is read using an Envision plate reader using the following settings:
Excitation filter—FITC FP 480-Ex Slot 3
Emission filter—FITC FP P-pol 535-Em Slot 4
2nd Emission filter—FITC FP S-pol 535-Em Slot 3
Mirror module—FITC FP Dual Enh-Slot 1

The inhibition rate is calculated using the percentage of permuted Mahalanobis distances greater than the control samples (mP value) following the equation below:
$mP_C$: the mP value of compounds
$mP_L$: the mP value of Low controls
$mP_H$: the mP value of High controls $$\text{Inhibition}(\%) = \left(1 - \frac{mP_C - mP_L}{mP_H - mP_L}\right) \times 100\%$$

XLFit (equation 201) is used to calculate a reported IC50 for each compound.

The data from examples A and B are provided in Table 2.

TABLE 2

| Ex. | EC50 DLD-1 BRCA2(-/-) μM | EC50 DLD-1 parental μM | EC50 MDA-MB-436 μM | IC50 FP PARP1 μM | IC50 FP PARP2 μM |
|---|---|---|---|---|---|
| 1 | 0.0014 | 5000 | 0.00063 | 0.0073 | 3.7 |
| 2 | 0.0048 | >30 | 0.004 | 0.0036 | 2.9 |
| 3A | 0.23 | >30 | 0.024 | | |
| 3B | 0.0032 | 29 | 0.0015 | 0.0042 | 2.6 |
| 4 | 0.0016 | >30 | 0.00069 | 0.0066 | 2.6 |
| 5 | 0.0025 | 470 | 0.0014 | 0.0079 | 7 |
| 6 | 0.0028 | 11 | 0.0017 | 0.012 | 22 |
| 7 | 0.0031 | 300 | 0.0013 | 0.013 | 11 |
| 8 | 0.001 | 89 | 0.00025 | 0.0065 | 5.9 |
| 9 | 0.0035 | 13 | 0.0015 | 0.0077 | 9.4 |
| 10 | 0.0026 | 1400 | 0.00068 | 0.031 | 84 |
| 11 | 0.0028 | 440 | 0.0011 | 0.0066 | >100 |
| 12 | 0.0011 | 51 | 0.00062 | 0.006 | 2.6 |
| 13 | 0.001 | >30 | 0.00054 | | |
| 14 | 0.001 | >30 | 0.00053 | | |
| 15 | 0.0018 | >30 | 0.0013 | 0.0053 | 2.3 |
| 16 | 0.0042 | >30 | 0.0013 | | |
| 17 | 0.0021 | >30 | 0.0011 | | |
| 18 | 0.0051 | | 0.0023 | 0.0068 | >100 |
| 19 | 0.0037 | | 0.0018 | 0.009 | 6 |
| 20 | 0.0041 | | 0.0022 | 0.0022 | >100 |

TABLE 2-continued

| Ex. | EC50 DLD-1 BRCA2(-/-) μM | EC50 DLD-1 parental μM | EC50 MDA-MB-436 μM | IC50 FP PARP1 μM | IC50 FP PARP2 μM |
|---|---|---|---|---|---|
| 21 | 0.0017 | | 0.0009 | 0.0044 | 13 |
| 22A | 0.0015 | >30 | 0.001 | 0.0016 | 3 |
| 22B | 0.49 | | 0.16 | | |
| 23 | 0.006 | | 0.0022 | 0.011 | >100 |
| 24 | 0.0025 | >30 | 0.0014 | 0.0052 | 2.8 |
| 25 | 0.0087 | >30 | 0.0042 | 0.013 | >10 |
| 26 | 0.033 | | 0.039 | | |
| 27 | 0.0041 | 32 | 0.001 | | |
| 28 | 0.0032 | 33 | 0.0008 | 0.0059 | 4.8 |
| 30 | 0.22 | 40 | 0.058 | | |
| 31 | 0.048 | 56 | 0.015 | | |
| 32 | 0.077 | >30 | 0.015 | | |
| 33 | 0.0065 | >30 | 0.0031 | 0.0073 | 19 |
| 35 | 0.0023 | >30 | 0.0013 | 0.0097 | 0.62 |
| 36 | 0.11 | | 0.017 | | |
| 37 | 0.0014 | | 0.0005 | 0.012 | 33 |
| 38 | 0.0076 | | 0.0053 | 0.0064 | >100 |
| 39 | 0.0033 | | 0.0027 | 0.0062 | 4.2 |
| 40 | 0.0067 | | 0.0044 | 0.0051 | 9 |
| 41 | 0.0024 | | 0.0019 | 0.005 | 7.5 |
| 42 | 0.0033 | | 0.0041 | 0.0083 | 7.9 |
| 43 | 0.0024 | | 0.0032 | 0.0049 | >100 |
| 44 | 0.0074 | | 0.0053 | 0.0064 | 17 |
| 45 | 0.016 | | 0.0043 | | |
| 46 | 0.0037 | | 0.0012 | 0.0054 | 28 |
| 47 | 0.0077 | | 0.0033 | 0.0065 | 15 |
| 48 | 0.0027 | | 0.0017 | 0.0062 | 13 |
| 49 | 0.0055 | | 0.0024 | 0.0062 | 7.2 |
| 50 | 0.0045 | | 0.0021 | 0.0073 | 14 |
| 51 | 0.017 | | 0.0064 | | |
| 52 | 0.012 | | 0.004 | | |
| 53 | 0.0024 | | 0.00092 | 0.0035 | 14 |
| 54 | 0.0028 | | 0.001 | 0.0048 | 8 |
| 55 | 0.011 | | 0.0014 | 0.0051 | 6.1 |
| 56 | 0.0071 | | 0.0022 | 0.0085 | 33 |
| 57 | 0.011 | | 0.0036 | 0.0045 | 10 |
| 58 | 0.0035 | | 0.0009 | 0.0059 | 9.9 |
| 59 | 0.016 | | 0.0078 | | |
| 60 | 0.014 | | 0.005 | | |
| 61 | 0.0063 | | 0.0048 | 0.006 | 32 |
| 63 | 0.0093 | | 0.0032 | 0.0072 | >100 |
| 64 | 0.00092 | | 0.00064 | 0.0055 | 7 |
| 65 | 0.013 | | 0.0031 | 0.0083 | >10 |
| 66 | 0.0041 | | 0.0017 | 0.0074 | 15 |
| 67 | 0.0018 | | 0.0011 | 0.01 | 1.6 |
| 68 | 0.0041 | >30 | 0.0015 | 0.006 | 0.6 |
| 69 | 0.0073 | | 0.0044 | 0.0049 | 4.5 |
| 70 | 0.0055 | | 0.0026 | 0.006 | 95 |
| 71 | 0.013 | | 0.0059 | | |
| 72 | 0.0042 | >30 | 0.0025 | 0.015 | 8.8 |
| 73 | 0.0042 | | 0.0022 | 0.0072 | >100 |
| 74 | 0.0078 | | 0.0039 | 0.0066 | 3 |
| 75 | 0.0026 | | 0.0015 | 0.01 | 36 |
| 76 | 0.0016 | | 0.00098 | 0.0079 | 1 |
| 77 | 0.0085 | | 0.0058 | 0.0084 | 23 |
| 78 | 0.0028 | | 0.0018 | 0.007 | 1.5 |
| 79 | 0.0096 | | 0.0037 | | |
| 80 | 0.037 | | 0.0098 | | |
| 81 | 0.0059 | | 0.0045 | 0.0076 | 10 |
| 82 | 0.01 | | 0.0078 | 0.0071 | 46 |
| 83 | 0.0015 | | 0.0014 | 0.0057 | 0.77 |
| 84 | 0.0022 | | 0.002 | 0.0084 | 1.9 |
| 85 | 0.014 | | 0.013 | | |
| 86 | 0.006 | | 0.0061 | | |
| 87 | 0.0065 | | 0.0053 | 0.0072 | 26 |
| 88 | 0.0042 | | 0.0038 | 0.0089 | 4.7 |
| 89 | 0.0035 | | 0.0025 | 0.0053 | 8.2 |
| 90 | 0.0064 | | 0.0043 | 0.0076 | 6.6 |
| 91 | 0.013 | | 0.013 | 0.006 | 14 |
| 92 | 0.011 | | 0.01 | 0.012 | 16 |
| 93 | 0.0017 | | 0.00084 | 0.0034 | 1.2 |
| 94 | 0.039 | | 0.041 | 0.012 | >100 |
| 95 | 0.0039 | | 0.0029 | 0.0066 | 14 |
| 96 | 0.0029 | | 0.0017 | 0.0041 | 2.4 |
| 97 | 0.0015 | | 0.00071 | 0.0047 | 1 |
| 98 | 0.002 | | 0.0012 | 0.0053 | 6.2 |
| 99 | 0.016 | | 0.011 | 0.0051 | 13 |
| 100 | 0.0039 | | 0.0026 | 0.0036 | 1.5 |
| 101 | 0.017 | | 0.0098 | 0.0065 | 45 |
| 102 | 0.013 | | 0.018 | 0.012 | >100 |
| 103 | 0.0066 | | 0.0052 | 0.0043 | 16 |
| 104 | 0.0014 | | 0.0014 | 0.004 | 1.8 |
| 105 | 0.0032 | | 0.0018 | 0.0035 | 2.2 |
| 106 | 0.0057 | | 0.0066 | 0.0065 | 13 |
| 107 | 0.0091 | | 0.0025 | 0.0061 | 1.9 |
| 108 | 0.031 | | 0.014 | 0.009 | 31 |
| 109 | 0.037 | | 0.014 | 0.0053 | 25 |
| 110 | 0.0057 | | 0.0033 | 0.0046 | 1.4 |
| 111 | 0.0046 | | 0.0018 | 0.006 | 1.9 |
| 112 | 0.0078 | | 0.0033 | 0.0033 | 1.8 |
| 113 | 0.045 | | 0.02 | 0.0042 | 1.4 |
| 114 | 0.011 | | 0.0051 | 0.0085 | 52 |
| 115 | 0.0019 | | 0.0013 | 0.005 | 2.3 |
| 116 | 0.002 | | 0.0012 | 0.0059 | 2 |
| 117 | 0.0021 | | 0.0012 | 0.0051 | 2.5 |
| 118 | 0.0013 | | 0.00074 | 0.006 | 9.9 |
| 119 | 0.0018 | | 0.00099 | 0.0043 | 2.6 |
| 120 | 0.0027 | | 0.0017 | 0.0054 | 9.4 |
| 121 | 0.043 | | 0.035 | 0.0066 | >100 |
| 122 | 0.046 | | 0.011 | 0.0073 | >100 |
| 123 | 0.015 | | 0.0056 | 0.0074 | 18 |
| 124 | 0.0075 | | 0.017 | 0.0071 | 47 |
| 125 | 0.0085 | | 0.013 | >0.10 | 23 |
| 126 | 0.014 | | 0.0043 | 0.016 | >100 |
| 127 | 0.015 | | 0.0073 | 0.019 | 34 |
| 128 | 0.0048 | | 0.0042 | 0.0085 | 4 |
| 129 | 0.015 | | 0.007 | | |
| 130 | 0.0033 | | 0.0023 | | |
| 131 | 0.011 | | 0.0062 | | |
| 132 | 0.0067 | | 0.0044 | | |
| 133 | 0.001 | | 0.00087 | | |
| 134 | 0.0024 | | 0.0014 | | |
| 135 | 0.015 | | 0.024 | | |
| 136 | 0.002 | | 0.00093 | 0.0088 | 10 |
| 137 | 0.0021 | | 0.0013 | 0.0041 | 3.2 |
| 138 | 0.0027 | | 0.0021 | 0.0062 | >100 |
| 139 | 0.0015 | | 0.00077 | | |
| 140 | 0.0043 | | 0.0058 | | |
| 141 | 0.0064 | | 0.0041 | | |
| 142 | 0.0087 | | 0.004 | 0.011 | >100 |
| 143 | 0.013 | | 0.012 | | |
| 144 | 0.0041 | | 0.002 | | |
| 145 | 0.0019 | | 0.0011 | | |
| 146 | 0.32 | >30 | 0.0092 | | |
| 147 | 0.0029 | | 0.0013 | 0.0038 | >100 |
| 148 | 0.002 | | 0.0015 | | |
| 149 | 0.017 | | 0.0094 | | |
| 150 | 0.018 | | 0.009 | | |
| 151 | 0.016 | | 0.028 | | |
| 152 | 0.0011 | | 0.00051 | | |
| 153 | 0.00095 | | 0.00074 | | |
| 154 | 0.003 | | 0.0016 | | |
| 156 | 0.00068 | | 0.00039 | | |
| 157 | 0.061 | | 0.041 | | |
| 158 | 0.0021 | | 0.001 | | |
| 159 | 0.0017 | | 0.00072 | | |
| 160 | 0.0026 | | 0.0021 | | |
| 161 | 0.022 | >10 | | | |

Example C: In Vitro Human Hepatic Clearance in Cellular Relay Format

Working stocks of individual test articles were prepared at concentrations of 100 μM by diluting 10 mM stocks prepared in DMSO 100-fold (v:v) into ACN/1H$_2$O (50/50, v:v). Human cryopreserved hepatocytes were thawed in a 37° C. water bath in <2 min., suspended in thawing media, and then centrifuged at 100×g for 10 min. Thawing media was aspirated, and pelleted hepatocytes were resuspended into incubation media at 1.5E+06 cells/mL. Cell viability was determined using an Acridine Orange/Propidium Iodine stain, and hepatocytes were further diluted with incubation media to 0.5E+06 viable cells/mL. Hepatocyte aliquots of 495 μL were added to wells of a 24-well plate, and test article incubations were initiated by the addition of 5 μL of 100 μM working stocks. Plates were incubated at 37° C. in a 5% $CO_2$ atmosphere at 95% relative humidity on an orbital shaker at 300 rpm. Incubations were performed in duplicate. At time=0 and 4 hrs., aliquots of each incubation were extracted with 6 volumes ACN containing internal standards. After 4 hrs., hepatocytes were removed from the incubations via centrifugation, and supernatants were stored frozen until the following day at which point incubations were reinitiated by diluting thawed supernatants with freshly thawed hepatocytes in incubation media, again to a final concentration of 0.5E+06 viable cells/mL. These steps were repeated for a total of 5 incubations of 4 hrs. each covering 20 total hours of incubation. Incubational losses due to cellular uptake, nonspecific binding, and dilution at each relay step were corrected for. Supernatants of all incubation aliquots were diluted into ultrapure water prior to analysis via LC/MS/MS. In vitro intrinsic clearances ($CL_{int}$) in μL/min/1E+06 cells were determined for each incubation from calculated in vitro half-lives determined using a standard log-linear regression approach. In vitro $CL_{int}$ values were scaled up using the following physiological scaling factors: 99E+06 cells/g human liver and 25.7 g human liver/kg body weight. Scaled intrinsic clearance values were finally introduced to the well-stirred liver model for the purpose of calculating predicted human hepatic clearance ($CL_{hep,pred}$) in mL/min/kg assuming a human liver blood flow of 20.7 mL/min/kg and making no corrections for test article binding to red blood cells, plasma proteins, or components of the incubation system. S-Warfarin, Disopyramide and Diazepam were used as assay controls.

| Example | T1/2 (min) | $Cl_{hep,pred}$ (mL/min/kg) |
|---|---|---|
| AZD5305 | 1,911 | 1.69 |
| 1 | 1,947 | 1.67 |
| 2 | 1,891 | 1.71 |
| 5 | 6,531 | 0.53 |
| 15 | >3,727 | <0.9 |
| 24 | >3,727 | <0.9 |
| 56 | >3,727 | <0.9 |

Example D: PAPR and TNKS Broader Panel of Selectivity by FP

In general, all assays were carried out by following the BPS PARP and TNKS assay kit protocols with a few modifications.

The enzymatic reactions were conducted in duplicate at room temperature in 96 well plates coated with histone substrate. The incubation times were one hour for PARPs 3, 8, 10, 15 and TNKSs, and two hours for PARPs 6, 7, 11 and 14, respectively.

| Assay | Enzyme Used/ Reaction | Substrate Activated DNA |
|---|---|---|
| PARP3 | 80 ng | 25 μM $NAD^+$/2.5 μM $NAD^+$-Biotin 0.026 mg/ml |
| TNKS1 | 15 ng | 25 μM $NAD^+$/2.5 μM $NAD^+$-Biotin N/A |
| TNKS2 | 5 ng | 25 μM $NAD^+$/2.5 μM $NAD^+$-Biotin N/A |
| PARP6 | 200 ng | 12.5 μM $NAD^+$/12.5 μM $NAD^+$-Biotin N/A |
| PARP7 | 200 ng | 12.5 μM $NAD^+$/12.51 μM $NAD^+$-Biotin N/A |
| PARP8 | 400 ng | 50 μM $NAD^+$/5 μM $NAD^+$-Biotin N/A |
| PARP10 | 100 ng | 25 μM $NAD^+$/2.5 μM $NAD^+$-Biotin N/A |
| PARP11 | 300 ng | 12.5 μM NAD+/12.5 μM NAD+-Biotin N/A |
| PARP14 | 50 ng | 25 μM $NAD^+$/25 μM $NAD^+$-Biotin N/A |
| PARP15 | 50 ng | 25 μM NAD+/2.5 μM NAD+30-Biotin N/A |

The 50 μl reaction mixtures in PARP Assay Buffer containing: NAD+, biotinylated NAD+ enzymes, with test compounds or reference compounds, were incubated at room temperature for one or two hours. The wells were washed five times with PBST and was further incubated for 30 min with 50 μl Streptavidin-HRP (prepared with Blocking Buffer 3). The wells were washed again and 100 μl ELISA ECL substrate was added to each well.

Luminescence was measured using a BioTek Synergy™ 2 microplate reader.

Enzyme activity assays were performed in duplicates. The luminescence data were analyzed using the computer software, Graphpad Prism. In the absence of the compound, the luminescence (Lt) in each data set was defined as 100% activity. In the absence of the enzyme, the luminescence (Lb) in each data set was defined as 0% activity. The percent activity in the presence of each compound was calculated according to the following equation:

$$\% \text{ activity} = [(L-Lb)/(Lt-Lb)] \times 100;$$

where L=the luminescence in the presence of the compound, Lb=the luminescence in the absence of the enzyme, and Lt=the luminescence in the absence of the compound.

The percent inhibition was calculated according to the following equation:

$$\% \text{ inhibition} = 100 - \% \text{ activity}.$$

The values of % activity versus a series of compound concentrations were then plotted using non-linear regression analysis of Sigmoidal dose-response curve generated with the equation Y=B+(T−B)/1+10((Log EC50−X)×Hill Slope), where Y=percent activity, B=minimum percent activity, T=maximum percent activity, X=logarithm of compound and Hill Slope=slope factor or Hill coefficient. The $IC_{50}$ value was determined by the concentration causing a half-maximal percent activity.

| | $IC_{50}$ (μM) | | | | | |
|---|---|---|---|---|---|---|
| Ex. | PARP1 | PARP2 | PARP3 | PARP6 | PARP7 | PARP8 |
| AZD5305 | 0.0045 | 2.4 | 0.44 | 2.6 | 0.82 | 10 |
| 15 | 0.0053 | 2.3 | ~3.6 | ~13 | 3.3 | ~47 |
| 24 | 0.0052 | 2.8 | 1.1 | 16 | 4.4 | ~28 |

-continued

| Ex. | IC$_{50}$ (μM) | | | | | |
|---|---|---|---|---|---|---|
| | PARP10 | PARP11 | PARP14 | PARP15 | TNKS1 | TNKS2 |
| AZD5305 | 0.64 | 0.0076 | 6.5 | 2.4 | 0.23 | 0.25 |
| 15 | 1.9 | 0.035 | ~14 | 8.5 | 0.59 | 0.74 |
| 24 | 1.6 | 0.14 | 7.3 | 8.6 | 1.2 | 0.69 |

What is claimed is:

1. A compound of Formula (III), or a pharmaceutically acceptable salt, solvate, or stereoisomer thereof:

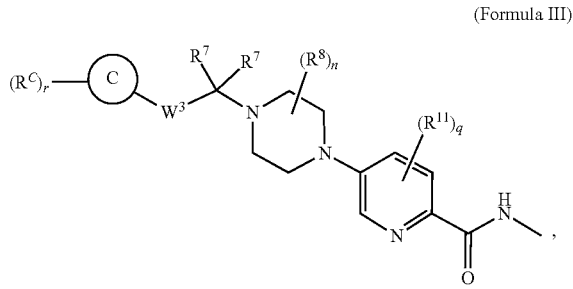

(Formula III)

wherein:

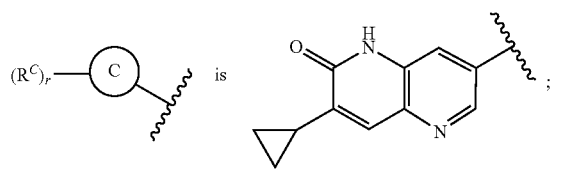 is

W$^3$ is absent;

each R$^7$ is independently hydrogen, deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

or two R$^7$ are taken together to form a cycloalkyl or a heterocycloalkyl; each optionally substituted with deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each R$^8$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^8$ on the same carbon are taken together to form an oxo;

or two R$^8$ on the same carbon, adjacent carbons, or opposite carbons are taken together to form a cycloalkyl or heterocycloalkyl; each optionally substituted with one or more deuterium, halogen, —CN, —OH, —OR$^a$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

n is 0-6;

each R$^{11}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

q is 0-3;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each R$^c$ and R$^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or R$^c$ and R$^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

2. The compound of claim 1, or a pharmaceutically acceptable salt, solvate, or stereoisomer thereof, wherein each R$^7$ is independently hydrogen, deuterium, halogen, C$_1$-C$_6$alkyl, or C$_1$-C$_6$haloalkyl.

3. The compound of claim 2, or a pharmaceutically acceptable salt, solvate, or stereoisomer thereof, wherein each R$^7$ is hydrogen.

4. The compound of claim 1, or a pharmaceutically acceptable salt, solvate, or stereoisomer thereof, wherein two R$^7$ are taken together to form a cycloalkyl.

5. The compound of claim 1, or a pharmaceutically acceptable salt, solvate, or stereoisomer thereof, wherein each R$^8$ is C$_1$-C$_6$alkyl; or two R$^8$ on the same carbon are taken together to form an oxo.

6. The compound of claim 5, or a pharmaceutically acceptable salt, solvate, or stereoisomer thereof, wherein each R$^8$ is C$_1$-C$_6$alkyl.

7. The compound of claim 1, or a pharmaceutically acceptable salt, solvate, or stereoisomer thereof, wherein two R$^8$ on opposite carbons are taken together to form a cycloalkyl.

8. The compound of claim 1, or a pharmaceutically acceptable salt, solvate, or stereoisomer thereof, wherein two R$^8$ on the same carbon are taken together to form a cycloalkyl.

9. The compound of claim 1, or a pharmaceutically acceptable salt, solvate, or stereoisomer thereof, wherein two R$^8$ on adjacent carbons are taken together to form a cycloalkyl.

10. The compound of claim 1, or a pharmaceutically acceptable salt, solvate, or stereoisomer thereof, wherein n is 0-3.

11. The compound of claim 10, or a pharmaceutically acceptable salt, solvate, or stereoisomer thereof, wherein n is 1 or 2.

12. The compound of claim 11, or a pharmaceutically acceptable salt, solvate, or stereoisomer thereof, wherein n is 1.

13. The compound of claim 1, or a pharmaceutically acceptable salt, solvate, or stereoisomer thereof, wherein each R$^{11}$ is independently deuterium, halogen, C$_1$-C$_6$alkyl, C$_1$-C$_6$haloalkyl, or C$_1$-C$_6$deuteroalkyl.

14. The compound of claim 13, or a pharmaceutically acceptable salt, solvate, or stereoisomer thereof, wherein each R$^{11}$ is independently halogen or C$_1$-C$_6$alkyl.

15. The compound of claim 14, or a pharmaceutically acceptable salt, solvate, or stereoisomer thereof, wherein each R$^{11}$ is independently halogen.

16. The compound of claim 1, or a pharmaceutically acceptable salt, solvate, or stereoisomer thereof, wherein q is 0 or 1.

17. The compound of claim 16, or a pharmaceutically acceptable salt, solvate, or stereoisomer thereof, wherein q is 1.

18. The compound of claim 1, wherein the compound is:

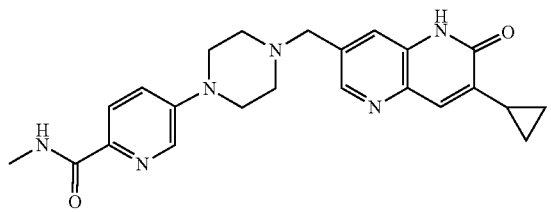 [SMILES: CNC(=O)c1ccc(N2CCN(Cc3cnc4cc(C5CC5)c(=O)[nH]c4c3)CC2)cn1]

or a pharmaceutically acceptable salt or solvate thereof.

19. The compound of claim 1, wherein the compound is:

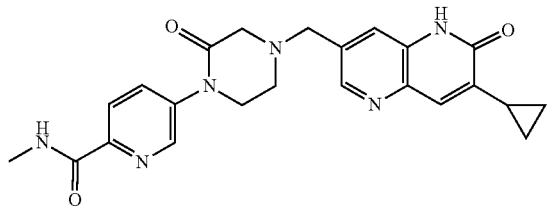 [SMILES: CNC(=O)c1ccc(N2CCN(Cc3cnc4cc(C5CC5)c(=O)[nH]c4c3)CC2=O)cn1]

or a pharmaceutically acceptable salt or solvate thereof.

20. A pharmaceutical composition comprising a compound of claim 1, or a pharmaceutically acceptable salt, solvate, or stereoisomer thereof, and a pharmaceutically acceptable excipient.

21. A method of treating cancer in a subject in need thereof, the method comprising administering a compound of any claim 1, or a pharmaceutically acceptable salt, solvate, or stereoisomer thereof; wherein the cancer is breast cancer, ovarian cancer, pancreatic cancer, prostate cancer, a hematological cancer, gastrointestinal cancer, or lung cancer.

* * * * *